US011072592B2

(12) United States Patent
Evseenko et al.

(10) Patent No.: US 11,072,592 B2
(45) Date of Patent: Jul. 27, 2021

(54) SMALL MOLECULES THAT ENABLE CARTILAGE REJUVENATION

(71) Applicant: The Regents of the University of California, Oakland, CA (US)

(72) Inventors: Denis Evseenko, Tarzana, CA (US); Benjamin J. Van Handel, Los Angeles, CA (US); Varghese John, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 69 days.

(21) Appl. No.: 15/553,353

(22) PCT Filed: Feb. 29, 2016

(86) PCT No.: PCT/US2016/020126
§ 371 (c)(1),
(2) Date: Aug. 24, 2017

(87) PCT Pub. No.: WO2016/138533
PCT Pub. Date: Sep. 1, 2016

(65) Prior Publication Data
US 2018/0244638 A1 Aug. 30, 2018

Related U.S. Application Data

(60) Provisional application No. 62/126,010, filed on Feb. 27, 2015.

(51) Int. Cl.
*C07D 277/42* (2006.01)
*C07D 417/04* (2006.01)

(52) U.S. Cl.
CPC ......... *C07D 277/42* (2013.01); *C07D 417/04* (2013.01)

(58) Field of Classification Search
None
See application file for complete search history.

(56) References Cited

U.S. PATENT DOCUMENTS

| | | | |
|---|---|---|---|
| 2011/0112073 A1* | 5/2011 | Thiele | A61K 31/415 514/217.04 |
| 2012/0283268 A1 | 11/2012 | Giordano et al. | |
| 2019/0169141 A1 | 6/2019 | Evseenko et al. | |

FOREIGN PATENT DOCUMENTS

| | | |
|---|---|---|
| CN | 103130792 A | 6/2013 |
| CN | 103130792 B | 6/2013 |
| JP | 2002-020286 A | 1/2002 |
| JP | 2003/525291 A | 8/2003 |
| WO | WO-01/64674 A1 | 9/2001 |
| WO | WO-03/015773 A2 | 2/2003 |

(Continued)

OTHER PUBLICATIONS

Millar, Heat Shock Proteins in Tendinopathy: Novel Molecular Regulators, Mediators of Inflammation, 2012, pp. 1-7. (Year: 2012).*

(Continued)

*Primary Examiner* — Savitha M Rao
*Assistant Examiner* — Andrew P Lee
(74) *Attorney, Agent, or Firm* — Mintz, Levin, Cohn, Ferris, Glovsky and Popeo, P.C.

(57) ABSTRACT

There are provided, inter alia, methods and compounds for activating a proliferative program in competent adult chondrocytes.

5 Claims, 50 Drawing Sheets

Specification includes a Sequence Listing.

(56) References Cited

FOREIGN PATENT DOCUMENTS

| | | | |
|---|---|---|---|
| WO | WO-03/015773 | A3 | 2/2003 |
| WO | WO-2004/110350 | A2 | 12/2004 |
| WO | WO-2004/110350 | A3 | 12/2004 |
| WO | WO-2005/033288 | A2 | 4/2005 |
| WO | WO-2005/033288 | A3 | 4/2005 |
| WO | WO-2006/122011 | A2 | 11/2006 |
| WO | WO-2006/122011 | A3 | 11/2006 |
| WO | WO-2006/135604 | A2 | 12/2006 |
| WO | WO-2006/135604 | A3 | 12/2006 |
| WO | WO-2007/031440 | A2 | 3/2007 |
| WO | WO-2007/031440 | A3 | 3/2007 |
| WO | WO-2008/147557 | A2 | 12/2008 |
| WO | WO-2008/147557 | A3 | 12/2008 |
| WO | WO-2013/056679 | A1 | 4/2013 |
| WO | WO-2014/113620 | A2 | 7/2014 |
| WO | WO-2014/113620 | A3 | 7/2014 |
| WO | WO-2015/021191 | A1 | 2/2015 |

OTHER PUBLICATIONS

Sharma, Tendon Injury and Tendinopathy: Healing and Repair, The Journal of Bone and Joint Surgery, 2005, 87(1), pp. 187-202 (Year: 2005).*

Simone, Oncology (Introduction), Textbook of Medicine, 1997, 20(1), pp. 1004-1010 (Year: 1997).*

Danziger, Automated site-directed drug design: a general algorithm for knowledge acquisition about hydrogen-bonding regions at protein surfaces, Proc. R. Soc. Lond. 1989, 236, pp. 10-113 (Year: 1989).*

Chemical Abstract Compound RN-61889-56-3 Entered STN Nov. 16, 1984, 1 page.

Kim, J-H. et al. (Jul. 28, 2015, e-published Jul. 13, 2015). "Matrix Cross-Linking-Mediated Mechanotransduction Promotes Post-traumatic Osteoarthritis," *PNAS USA* 112(30):9424-9429.

Makam, P. et al. (Nov. 24, 2014, e-published Sep. 30, 2014). "2-Aminothiazole derivatives as antimycobacterial agents: Synthesis, characterization, in vitro and in silico studies," *Eur J Med Chem* 87:643-656.

Metri, J. et al. (1982). "Synthesis of New Sulfamylanilino Substituted Thiazoles of Potential Biological Activity," *Egypt J Chem* 25(2):187-189.

Extended European Search Report dated Aug. 10, 2018, for EP Patent Application No. 16756554.8, 13 pages.

International Search Report dated Oct. 27, 2016, for PCT Application No. PCT/US2016/020126, filed Feb. 29, 2016, 5 pages.

Written Opinion dated Oct. 27, 2016, for PCT Application No. PCT/US2016/020126, filed Feb. 29, 2016, 8 pages.

* cited by examiner

FIG. 1D

| Pre-chondrocytes vs total limb cells at 5-6 weeks | |
|---|---|
| Gene Symbol | p-value |
| *Receptors and adhesion molecules* | |
| BMPR1B | 0.000134191 |
| PCDH10 | 0.000751492 |
| PTCH1 | 0.000635444 |
| CD44 | 0.0151098 |
| FGFR2 | 0.000195311 |
| FZD9 | 0.0148514 |
| ITGA10 | 0.0246543 |
| PCDH8 | 0.0396394 |
| FZD6 | 0.00291429 |
| FGFRL1 | 0.00167931 |
| SDC4 | 0.0224326 |
| *Growth factors/morphogens* | |
| GDF5 | 0.000129624 |
| PTHLH | 0.0020495 |
| WNT16 | 0.0171712 |
| SCRG1 | 0.00548691 |
| NOG | 0.00513526 |
| GDF10 | 0.0280791 |
| *Transcription factors* | |
| FOXC1 | 6.99E-07 |
| SOX5 | 6.69E-06 |
| SOX6 | 8.27E-06 |
| NKX3.2 | 3.91E-05 |
| SOX9 | 7.83E-07 |
| FOXC2 | 6.43E-05 |
| HOXA13 | 0.0476803 |
| GLI3 | 0.000145827 |
| FOXA3 | 0.0336405 |
| FOXP2 | 0.00180209 |
| HOXD11 | 0.0379312 |
| FOXP1 | 0.000117552 |
| GLI2 | 0.00126504 |
| GLI1 | 0.000173377 |

FIG. 2A
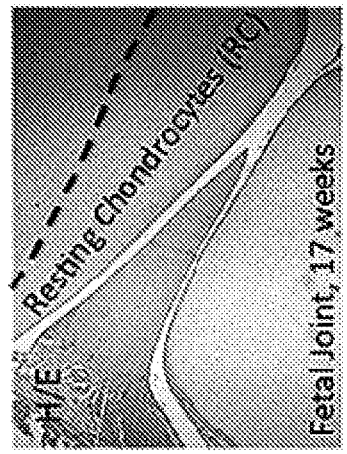
FIG. 2B
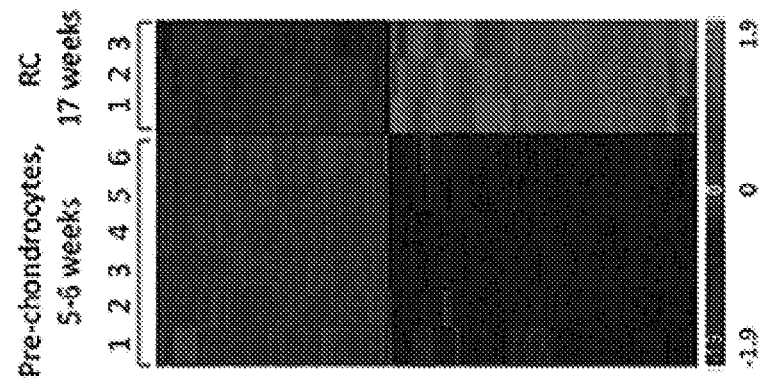
FIG. 2C
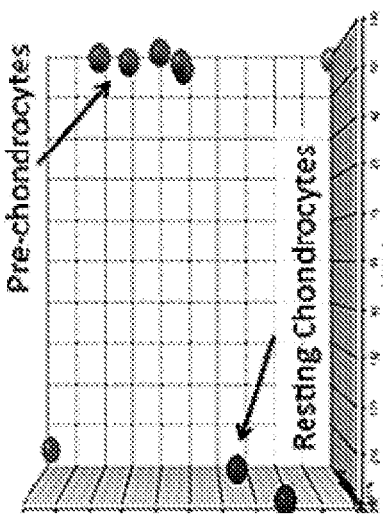
FIG. 2D
| Gene Symbol | P value | Fold change |
|---|---|---|
| Receptors and adhesion molecules | | |
| ICAM1 | 1.36E-07 | 181.3 |
| CD44 | 2.37E-07 | 82.7 |
| CD73/NT5E | 3.81E-07 | 72.4 |
| CD46 | 1.66E-07 | 24.2 |
| CD109 | 3.40E-06 | 19.3 |
| CD55 | 2.10E-06 | 18.6 |
| CD68 | 1.14E-08 | 16.2 |
| LIFR | 1.08E-08 | 17.2 |
| CD276 | 7.93E-09 | 15.4 |
| ITGA5 | 1.08E-06 | 13.8 |
| Growth factors/morphogens | | |
| LIF | 2.28E-09 | 76.8 |
| TGFB2 | 1.01E-07 | 37.2 |
| BMP6 | 3.56E-06 | 20.7 |
| NGF | 5.04E-09 | 16.7 |
| TGFB1 | 1.44E-06 | 7.1 |
| BMP2 | 9.14E-07 | 6.3 |

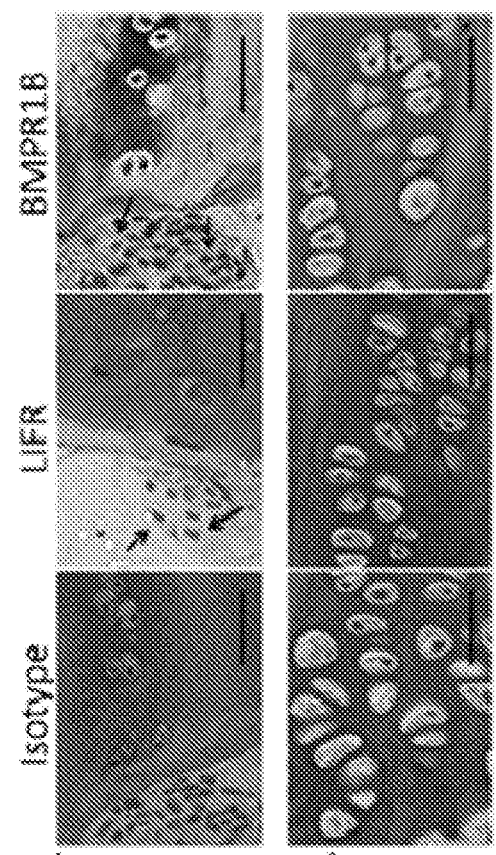
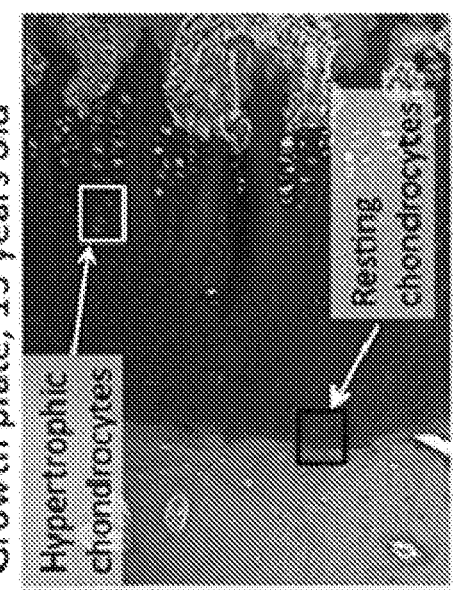
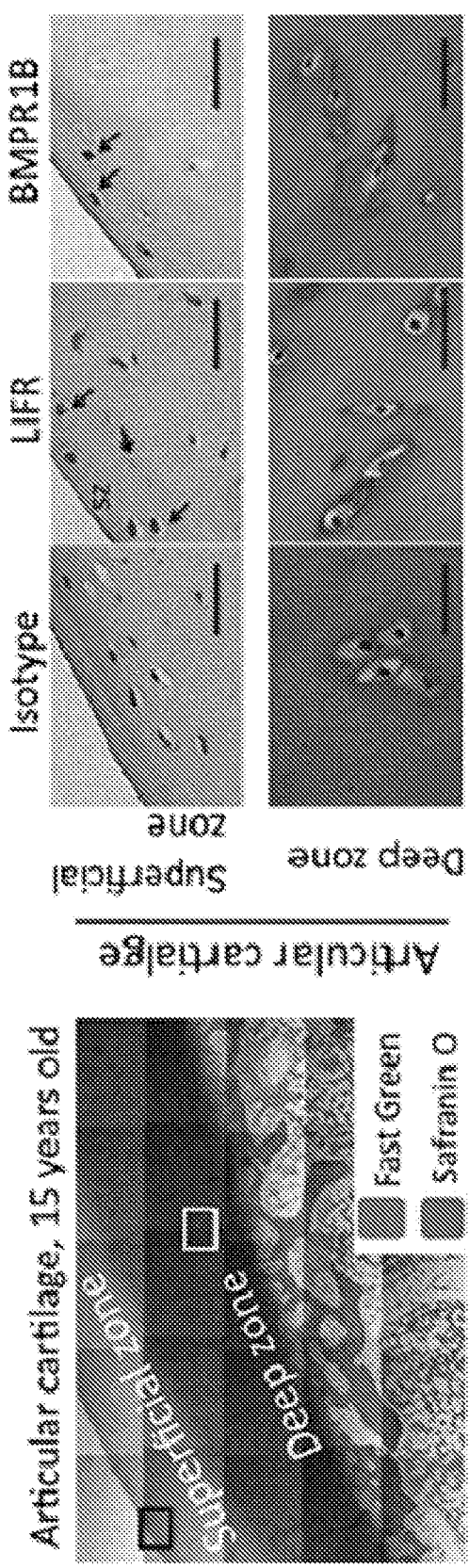
FIG. 3C Articular cartilage, 15 years old
FIG. 3D Growth plate, 15 years old

FIG. 3E

Articuar cartilage, 60 years old

BMPR1B    BMPR1B    LIFR

FIG. 3F

Synovial membrane, 60 years old

Isotype    LIF

FIG. 3G

SOX 9

Relative expression

LIFR+       LIFR neg
BMPR1B+     BMPR1B neg p<0.001

COL 10A1

LIFR+       LIFR neg
BMPR1B+     BMPR1B neg p<0.001

FIG. 8A
FIG. 8B
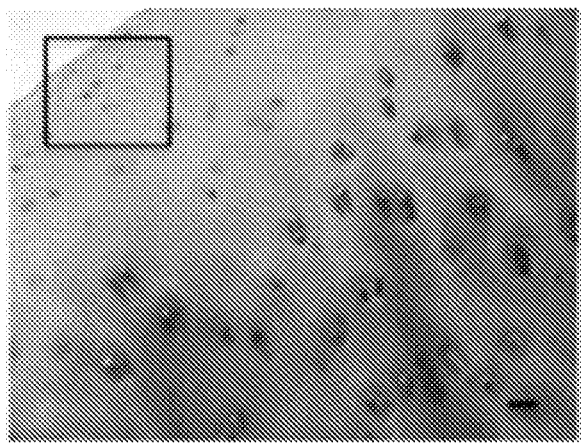
BMPR1B
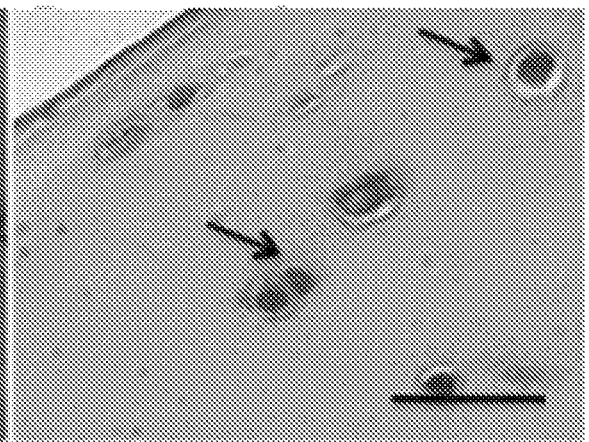
BMPR1B
FIG. 9A
FIG. 9B
Fig. 9C
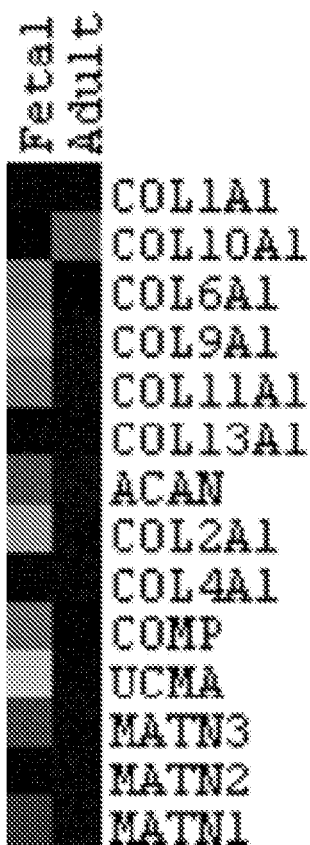
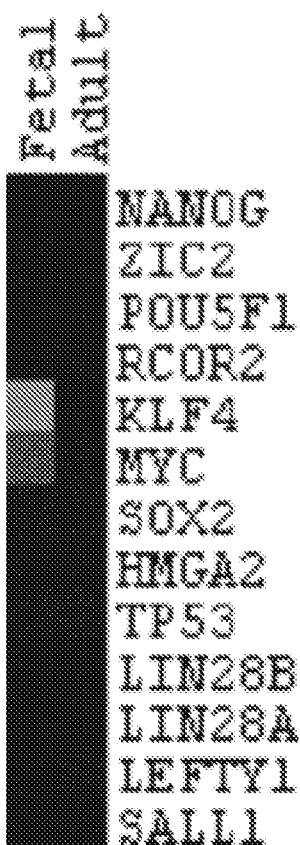
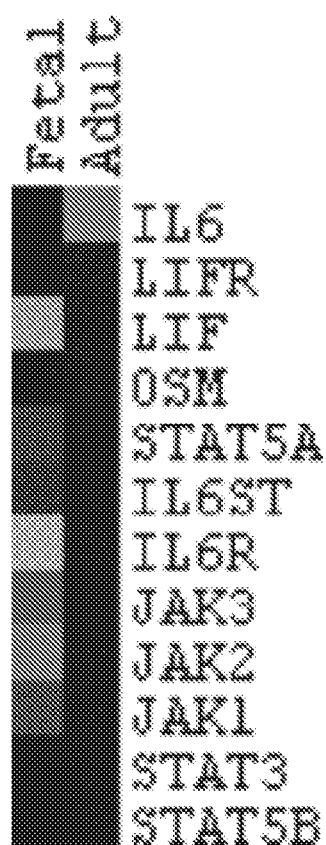

FIG. 24A

| No. | Stat+/Myc+ |
|---|---|
| 500 | (6-ethylthieno[3,2-e]pyrimidin-4-yl)-phenyl-ammonium chloride |
| 501 | 6-Ethyl-N-(4-methylphenyl)thieno[2,3-d]pyrimidin-4-amine hydrochloride (1:1) |
| 512 | 4-[(2,5,6-Trimethylthieno[2,3-d]pyrimidin-4-yl)amino]benzoic acid hydrochloride (1:1) |
| 513 | 6-Ethyl-N-(4-pyridinyl)thieno[2,3-d]pyrimidin-4-amine hydrochloride (1:1) |
| 515 | N-(4-Chlorophenyl)-6-ethylthieno[2,3-d]pyrimidin-4-amine |
| 398 | N'-(6-Ethyl-2-methylthieno[2,3-d]pyrimidin-4-yl)-N,N-dimethyl-1,4-benzenediamine |
| 623 | 6-Phenyl-4-[4-(2-pyrazinyl)-1-piperazinyl]thieno[2,3-d]pyrimidine |
|  |  |
| 600 | N-(4-Bromophenyl)-4-(3-pyridinyl)-1,3-thiazol-2-amine |
| 602 | 4-{[4-(4-Chlorophenyl)-1,3-thiazol-2-yl]amino}benzenesulfonamide hydrobromide (1:1) |
| 603 | 2-Anilino-4-[4-hydroxy-3,5-bis(2-methyl-2-propanyl)phenyl]-1,3-thiazol-3-ium bromide |
| 605 | N-(4-Chlorophenyl)-4-(4-iodophenyl)-1,3-thiazol-2-amine hydrobromide (1:1) |
| 609 | N,N-Dimethyl-N'-(4-phenyl-1,3-thiazol-2-yl)-1,4-benzenediamine |
| 611 | N-(4-Fluorophenyl)-4-[4-(methylsulfonyl)phenyl]-1,3-thiazol-2-amine |
| 612 | 4-(3,4-Dichlorophenyl)-N-phenyl-1,3-thiazol-2-amine |
| 619 | 2-(2-aminoethyl)-5,6-dimethyl-N-(3-(pyridin-4-yl)propyl)thieno[2,3-d]pyrimidin-4-amine |
| 624 | 1-[5-(thieno[3,2-e]pyrimidin-4-ylamino)indolin-1-yl]ethanone |
| 423 | N-(4-Bromophenyl)-4-phenyl-1,3-thiazol-2-amine |
| 522 | 4-(4-(4-chloro-phenyl)thiazol-2-ylamino)phenol |
| 519 | N-(4-Methoxyphenyl)-4-[4-(methylsulfonyl)phenyl]-1,3-thiazol-2-amine |

FIG. 24B

| No. | Stat-/Myc- |
|---|---|
| 503 | 6-Ethyl-N-(4-methoxyphenyl)thieno[2,3-d]pyrimidin-4-amine hydrochloride (1:1) |
| 504 | N-(3-Fluorophenyl)-6-methylthieno[2,3-d]pyrimidin-4-amine hydrochloride (1:1) |
| 505 | N-(4-Fluorophenyl)-6-methylthieno[2,3-d]pyrimidin-4-amine hydrochloride (1:1) |
| 506 | 3-[(6-Ethyl-2-methylthieno[2,3-d]pyrimidin-4-yl)amino]phenol hydrochloride (1:1) |
| 507 | N,N-Dimethyl-N'-(6-methylthieno[2,3-d]pyrimidin-4-yl)-1,4-benzenediamine |
| 510 | 6-Ethyl-2-methyl-4-[4-(2-pyridinyl)-1-piperazinyl]thieno[2,3-d]pyrimidine hydrochloride (1:1) |
| 626 | N-Benzyl-5,6-dimethylthieno[2,3-d]pyrimidin-4-amine |
|  |  |
| 601 | N-(2,4-Dibromophenyl)-4-(4-pyridinyl)-1,3-thiazol-2-amine |
| 613 | 5-Methyl-N,4-bis(4-methylphenyl)-1,3-thiazol-2-amine |
| 614 | N-(3-Chlorophenyl)-5-methyl-4-(4-methylphenyl)-1,3-thiazol-2-amine |
| 616 | 4-(4-bromophenyl)-N-(5-methylpyridin-2-yl)thiazol-2-amine |
| 617 | 2-Anilino-4-(4-bromophenyl)-3-(2-hydroxyethyl)-1,3-thiazol-3-ium |
| 518 | N-Ethyl-4-(4-fluorophenyl)-1,3-thiazol-2-amine |
| 523 | 1-(3-{[4-(4-Pyridinyl)-1,3-thiazol-2-yl]amino}phenyl)ethanone |
| 525 | N-(4-Chlorophenyl)-4-(3-pyridinyl)-1,3-thiazol-2-amine |
| 526 | 4-{[4-(3-Pyridinyl)-1,3-thiazol-2-yl]amino}benzoic acid |
| 527 | 4-(4-Chlorophenyl)-N-(4-phenoxyphenyl)-1,3-thiazol-2-amine hydrobromide (1:1) |
| 530 | 4-(2,5-Dimethylphenyl)-N-(4-phenoxyphenyl)-1,3-thiazol-2-amine hydrobromide (1:1) |

FIG. 24C

| No. | Stat-/Myc+ |
|---|---|
| 502 | 6-Methyl-N-phenylthieno[2,3-d]pyrimidin-4-amine hydrochloride (1:1) |
| 508 | N-(4-Bromophenyl)-6-ethylthieno[2,3-d]pyrimidin-4-amine hydrochloride (1:1) |
| 509 | N-(2-Fluorophenyl)-6-methylthieno[2,3-d]pyrimidin-4-amine hydrochloride (1:1) |
| 520 | 5-Bromo-N-[4-(4-ethylphenyl)-1,3-thiazol-2-yl]-2-pyridinamine |
| 524 | N-(2,4-Dibromophenyl)-4-(4-pyridinyl)-1,3-thiazol-2-amine |
| 529 | N-(4-Chlorophenyl)-4-(3,4-dimethylphenyl)-1,3-thiazol-2-amine hydrobromide (1:1) |
| 531 | 3-[(4-Phenyl-1,3-thiazol-2-yl)amino]benzoic acid |
| 532 | 4-(3,4-Dimethoxyphenyl)-N-(4-ethoxyphenyl)-1,3-thiazol-2-amine |
|  |  |
| 606 | 4-(3-fluoro-4-methoxyphenyl)-N-phenylthiazol-2-amine |
| 607 | N-(4-Bromophenyl)-4-(3,4-dimethylphenyl)-1,3-thiazol-2-amine hydrobromide (1:1) |
| 608 | N,4-Bis(3,4-dimethylphenyl)-1,3-thiazol-2-amine hydrobromide (1:1) |
| 610 | 4-[4-(Methylsulfonyl)phenyl]-N-phenyl-1,3-thiazol-2-amine |
| 618 | N-((1H-imidazol-2-yl)methyl)-N,5,6-trimethylthieno[2,3-d]pyrimidin-4-amine |
| 620 | 4-[[5-(4-methoxyphenyl)thieno[3,2-e]pyrimidin-4-yl]amino]-N-methyl-benzamide |
| 621 | 5,6-dimethyl-N-sec-butyl-thieno[3,2-e]pyrimidin-4-amine |
| 622 | 1-[(2-methyl-5,6,7,8-tetrahydrobenzothiopheno[3,2-e]pyrimidin-4-yl)amino]propan-2-ol |

FIG. 24D

| No. | Stat+/Myc- |
|---|---|
| 511 | 6-Ethyl-2-methyl-N-(3-pyridinylmethyl)thieno[2,3-d]pyrimidin-4-amine hydrochloride (1:1) |
| 514 | N-Benzyl-5,6-dimethylthieno[2,3-d]pyrimidin-4-amine |
| 516 | 6-Ethyl-N-phenylthieno[2,3-d]pyrimidin-4-amine |
| 517 | 6-Ethyl-N-(4-methoxyphenyl)thieno[2,3-d]pyrimidin-4-amine |
| 521 | 4-{[4-(4-Pyridinyl)-1,3-thiazol-2-yl]amino}phenol |
| 528 | 4-(3,4-Dimethylphenyl)-N-(2-methoxyphenyl)-1,3-thiazol-2-amine hydrobromide (1:1) |
|  |  |
| 604 | N-(3,4-Dimethylphenyl)-4-(4-iodophenyl)-1,3-thiazol-2-amine hydrobromide (1:1) |
| 625 | 6-Ethyl-4-(4-morpholinyl)thieno[2,3-d]pyrimidine hydrochloride (1:1) |

FIG. 25A

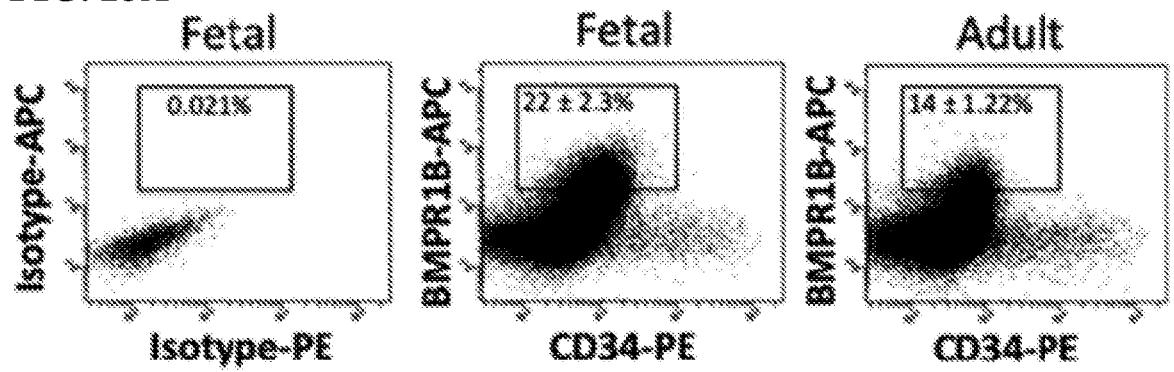

FIG. 25B
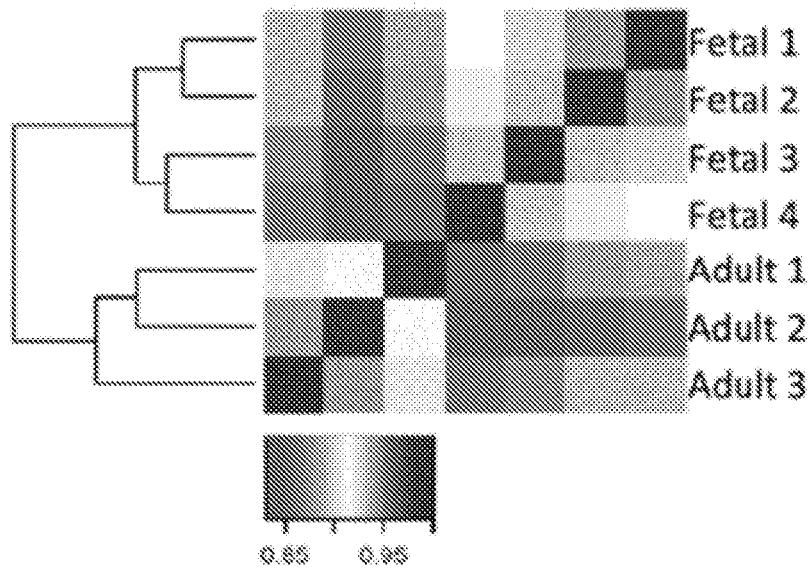
FIG. 25C
| GO Term | p value |
|---|---|
| Skeletal system development | 8.50E-06 |
| Cell adhesion | 2.16E-05 |
| Cholesterol biosynthetic process | 2.45E-05 |
| Chondrocyte development | 1.85E-04 |
| Cartilage development | 2.57E-04 |
| Ribosome biogenesis | 0.00101 |
| Extracellular matrix organization | 0.00184 |
| Collagen fibril organization | 0.00258 |
| Chromatin assembly or disassembly | 0.00409 |
| Cell morphogenesis | 0.01851 |
FIG. 25D
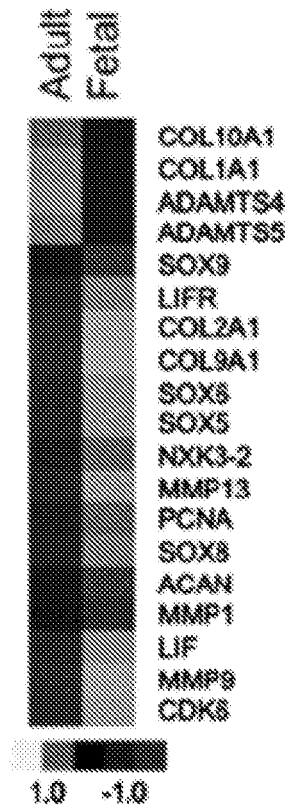

FIG. 28B
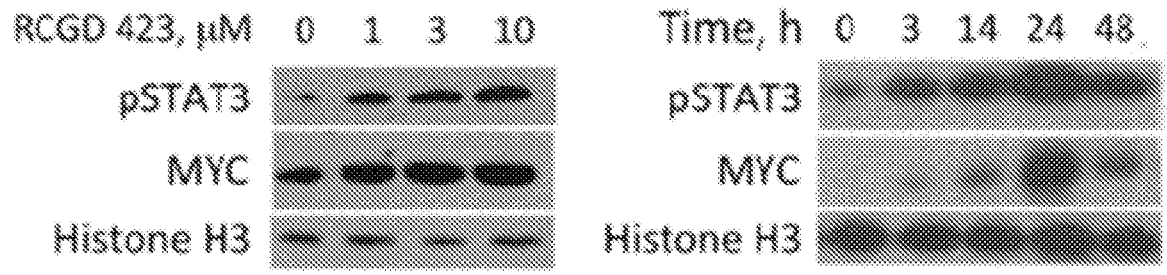
FIG 28C  FIG. 28D  FIG. 28E
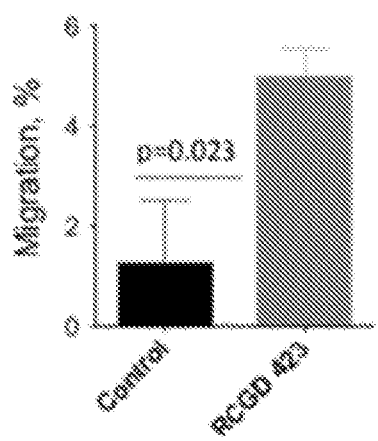 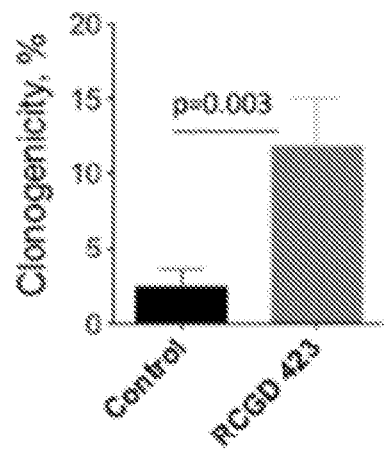 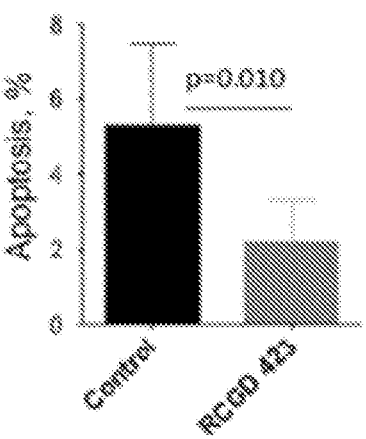
FIG. 28F
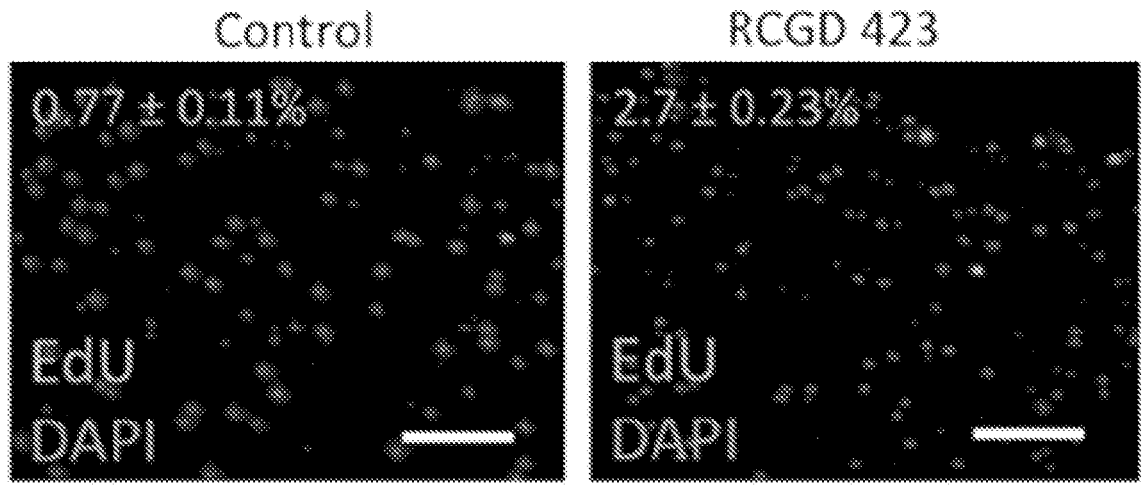

| GO Term | p value |
|---|---|
| M phase | 6.90E-06 |
| Regulation of response to external stimulus | 1.68E-05 |
| Cell division | 4.49E-05 |
| Intracellular signaling cascade | 6.30E-05 |
| Cell adhesion | 2.65E-04 |
| Regulation of cellular localization | 8.63E-04 |
| Phosphoinositide-mediated signaling | 0.00243 |
| Regulation of secretion | 0.00277 |
| Elevation of cytosolic calcium ion concentration | 0.00415 |
| Positive regulation of chemotaxis | 0.00513 |

FIG. 29C
Potential binding site 1 in the structure of gp130
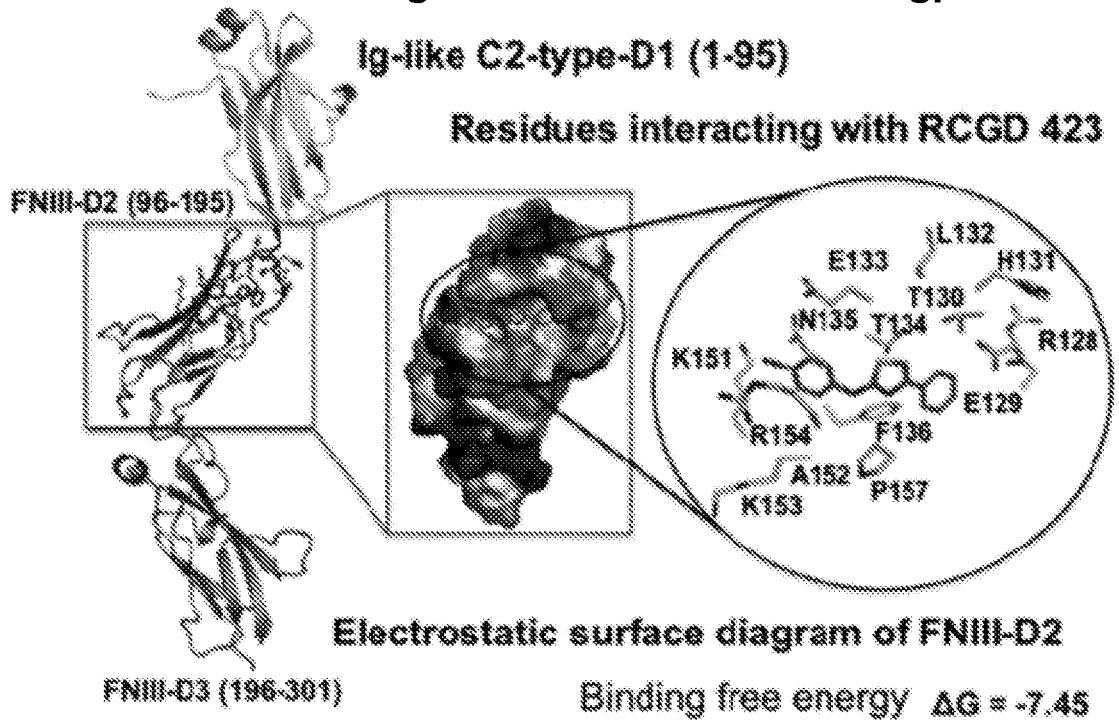
Potential binding site 2 in the structure of gp130
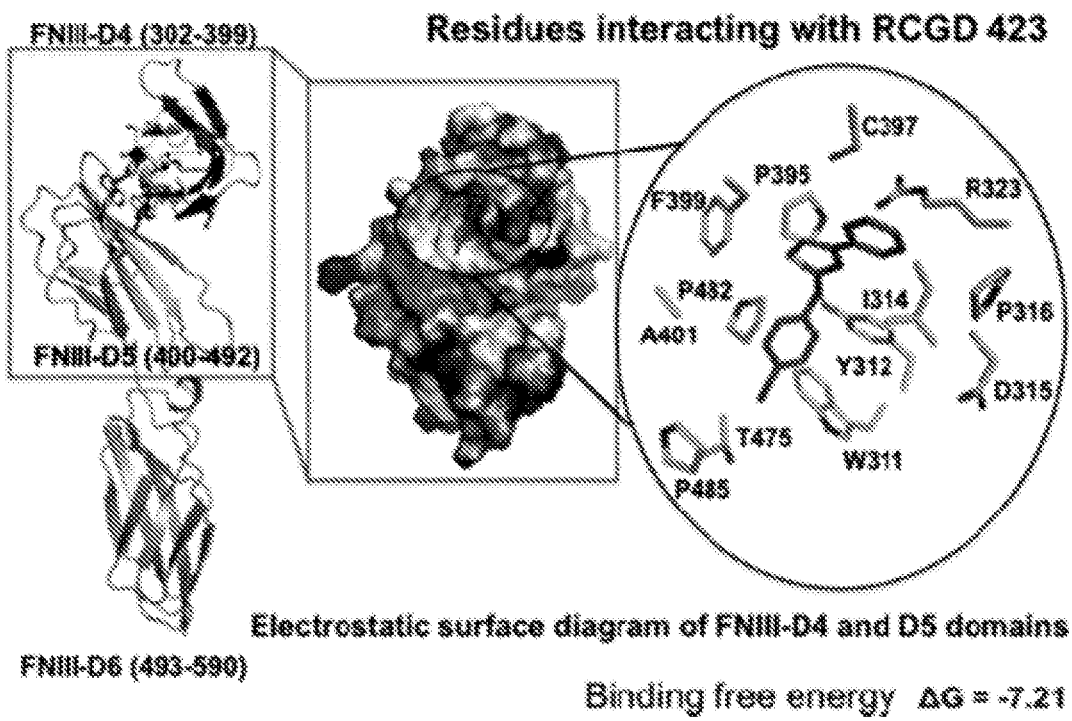

FIG. 30A
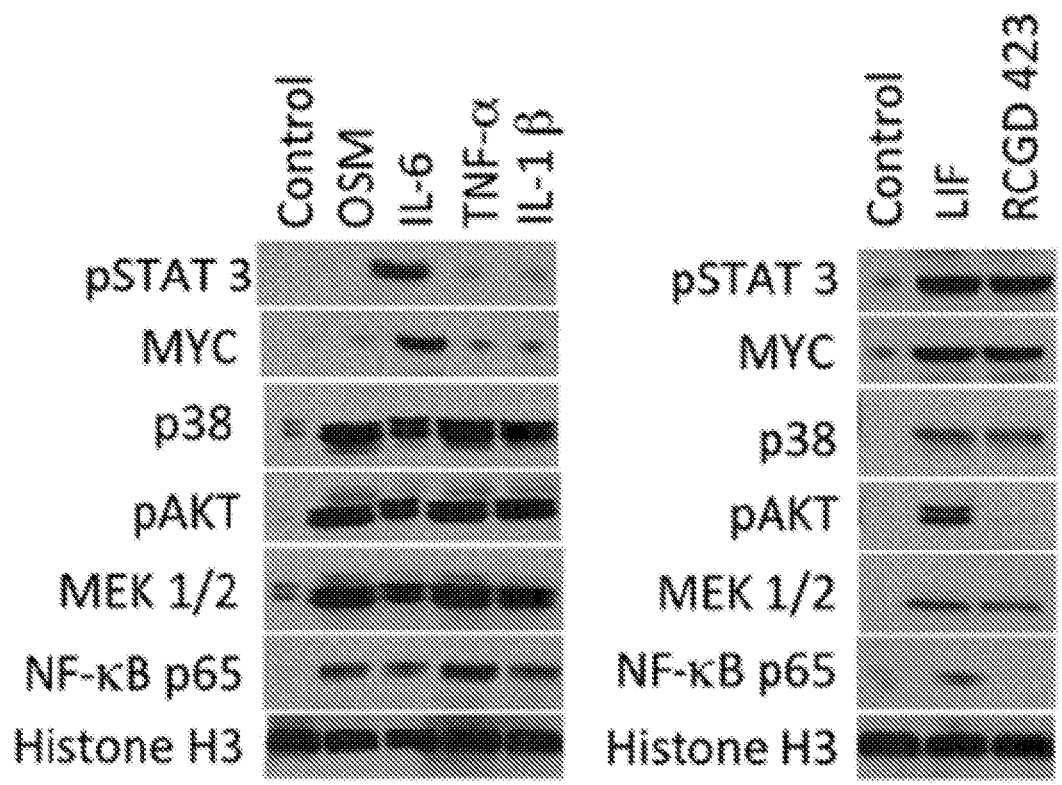
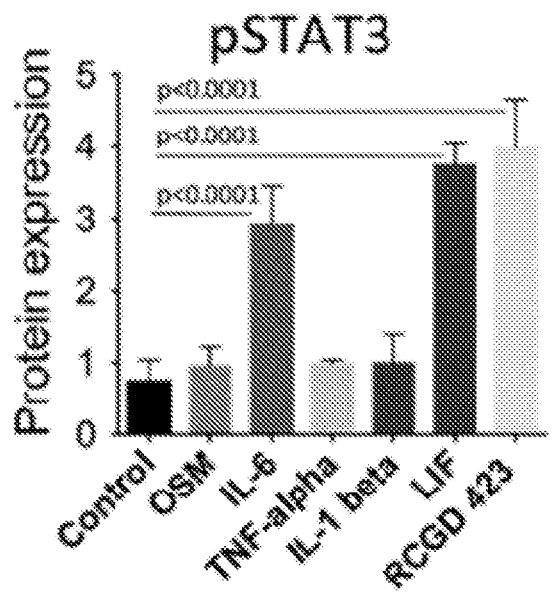
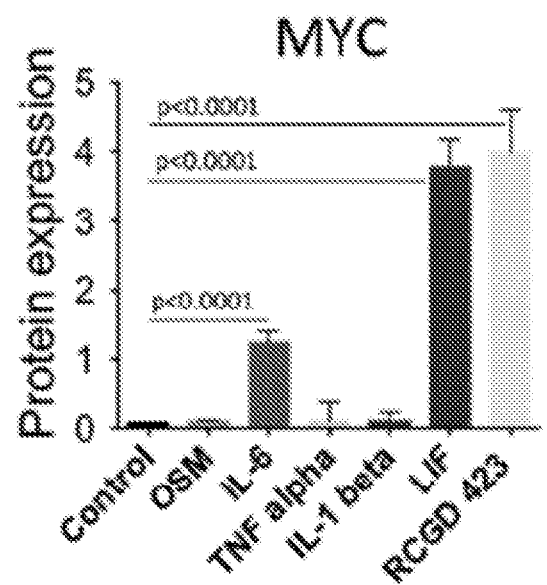

FIG. 32A

| GO Term | p value |
|---|---|
| Immune response | 1.01E-09 |
| Acute inflammatory response | 8.93E-06 |
| Lysosome organization | 2.40E-05 |
| Positive regulation of cell adhesion | 1.49E-04 |
| Oxygen and reactive oxygen species metabolic process | 1.62E-04 |
| Negative regulation of cell proliferation | 2.21E-04 |
| Death | 0.00128 |
| Regulation of osteoclast differentiation | 0.00966 |

FIG. 32B

| GSEA Gene Set | NES | p value | FDR |
|---|---|---|---|
| Hecker IFNB1 targets | 5.59 | 0 | 0 |
| Browne interferon responsive genes | 5.29 | 0 | 0 |
| Moserle IFNA response | 5.23 | 0 | 0 |
| Sana response to IFNG up | 5.22 | 0 | 0 |
| Sana TNF signaling up | 4.71 | 0 | 0 |

SEQUENCE LISTING

<160> NUMBER OF SEQ ID NOS: 4

<210> SEQ ID NO 1
<211> LENGTH: 918
<212> TYPE: PRT
<213> ORGANISM: Homo sapiens

<400> SEQUENCE: 1

```
Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205
```

```
Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
            275                 280                 285

Leu Lys Pro Phe Thr Glu Tyr Val Phe Arg Ile Arg Cys Met Lys Glu
        290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ala Ile Val Val Pro
    610                 615                 620
```

```
Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
        675                 680                 685

Thr Asp Val Ser Val Val Glu Ile Glu Ala Asn Asp Lys Lys Pro Phe
    690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Asp Glu Asn Glu Ser Ser Gln Asn
                740                 745                 750

Thr Ser Ser Thr Val Gln Tyr Ser Thr Val Val His Ser Gly Tyr Arg
            755                 760                 765

His Gln Val Pro Ser Val Gln Val Phe Ser Arg Ser Glu Ser Thr Gln
        770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
    850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
            900                 905                 910

Gly Gly Tyr Met Pro Gln
        915

<210> SEQ ID NO 2
<211> LENGTH: 8
<212> TYPE: PRT
<213> ORGANISM: Homo sapiens

<400> SEQUENCE: 2

Glu Thr His Leu Glu Thr Asn Phe
1               5

<210> SEQ ID NO 3
<211> LENGTH: 7
<212> TYPE: PRT
<213> ORGANISM: Homo sapiens

<400> SEQUENCE: 3

Lys Ala Lys Arg Asp Thr Pro
1               5
```

```
<210> SEQ ID NO 4
<211> LENGTH: 4
<212> TYPE: PRT
<213> ORGANISM: Homo sapiens
<400> SEQUENCE: 4
Lys Ala Lys Arg
1
```

SMALL MOLECULES THAT ENABLE CARTILAGE REJUVENATION

CROSS-REFERENCES TO RELATED APPLICATIONS

This application claims the benefit of U.S. Provisional Application No. 62/126,010, filed Feb. 27, 2015, which is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with Government support under Grant W81XWH-13-1-0465 awarded by the U.S. Army, Medical Research and Materiel Command. The government has certain rights in the present invention.

REFERENCE TO A "SEQUENCE LISTING," A TABLE, OR A COMPUTER PROGRAM LISTING APPENDIX SUBMITTED AS AN ASCII FILE

The Sequence Listing written in file 48539_516001 WO_ST25.TXT, created Feb. 29, 2016, 8,611 bytes, machine format IBM-PC, MS-Windows operating system, is hereby incorporated by reference.

BACKGROUND OF THE INVENTION

Articular cartilage is a highly specialized tissue formed from chondrocytes that protects the bones of diarthrodial joints from forces associated with load bearing and impact and allows nearly frictionless motion between articular surfaces. Cartilage injury and minimal regeneration often lead to osteoarthritis, characterized by degradation of joints, including both articular cartilage and subchondral bone. Osteoarthritis (OA) currently affects more than 25 million people in the United States alone, making joint surface restoration a major priority in modern medicine. Regeneration of tissues is a complex process that can occur via multiple mechanisms. In some tissues with high turnover, such as blood or skin, replacement of dying cells is achieved by constant output from stem cells. In other organs such as the liver, regeneration of damaged or diseased parenchymal cells requires de-differentiation of competent, highly specialized cells, re-acquisition of a progenitor-like phenotype, in situ expansion and re-differentiation. The cellular and molecular mechanisms of articular cartilage regeneration in physiological and pathological conditions are poorly understood. Although cartilage regeneration in humans is limited, recent clinical reports about cartilage healing in long term immobilized OA joints suggest that the regenerative potential of articular cartilage may be underestimated. A variety of options exist for the treatment of cartilage lesions, most with limited results. In the US, microfracture is one of the most commonly performed procedures, which involves the creation of channels in the subchondral bone to allow for stromal cells to migrate into the defect. This technique, only performed for smaller lesions, results in the formation of fibrocartilage that has inferior mechanical properties as compared to hyaline cartilage. For larger lesions, autologous or allogeneic osteochondral grafting remains the current standard of care. Clear limitations exist for these procedures, including limited supply of donor cartilage, as well as significant donor site morbidity. None of the current mesenchymal cell-based repair strategies including in vitro expanded adult mesenchymal stromal cells from bone marrow, adipose tissue, synovium or amniotic fluid have generated long-lasting hyaline articular cartilage. Thus, improvements to the current clinical management of, among other indications, arthritis and cartilage pathologies would have significant benefits for health and human disease. Provided herein are solutions to these and other problems in the art.

BRIEF SUMMARY OF THE INVENTION

In a first aspect, there is provided a compound of Formula (III):

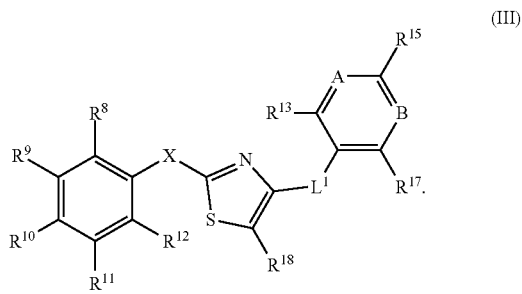

In the compound of Formula (III), A is $CR^{14}$ or N. B is $CR^{16}$ or N. X is O, $NR^{19}$ or S. $L^1$ is a bond or substituted or unsubstituted $C_1$-$C_3$ alkylene. $R^8$ is hydrogen, halogen, $-CX^{8.1}_3$, $-CHX^{8.1}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$ is hydrogen, halogen, $-CX^{9.1}_3$, $-CHX^{9.1}_2$, $-CH_2X^{9.1}$, $-CN$, $-SO_{n1}R^{9A}$, $-SO_{v1}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m1}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ is hydrogen, halogen, $-CX^{10.1}_3$, $-CHX^{10.1}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{11}$ is hydrogen, halogen, $-CX^{11.1}_3$, $-CHX^{11.1}_2$, $-CH_2X^{11.1}$, $-CN$, $-SO_{n1}R^{11A}$, $-SO_{v1}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, —N(O)$_{m1}$, —NR$^{11B}$R$^{11C}$, —C(O)R$^{11D}$, —C(O)OR$^{11D}$, —C(O)NR$^{11B}$R$^{11C}$, —OR$^{11A}$, —NR$^{11B}$SO$_2$R$^{11A}$, —NR$^{11B}$C(O)R$^{11D}$, —NR$^{11B}$C(O)OR$^{11D}$, —NR$^{11B}$OR$^{11D}$, —OCX$^{11.1}{}_3$, —OCHX$^{11.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{12}$ is hydrogen, halogen, —CX$^{12.1}{}_3$, —CHX$^{12.1}{}_2$, —CH$_2$X$^{12.1}$, —CN, —SO$_{n1}$R$^{12A}$, —SO$_{v1}$NR$^{12B}$R$^{12C}$, —NHNR$^{12B}$R$^{12C}$, —ONR$^{12B}$R$^{12C}$, —NHC(O)NHNR$^{12B}$R$^{12C}$, —NHC(O)NR$^{12B}$R$^{12C}$, —N(O)$_{m1}$, —NR$^{12B}$R$^{12C}$, —C(O)R$^{12D}$, —C(O)OR$^{12D}$, —C(O)NR$^{12B}$R$^{12C}$, —OR$^{12A}$, —NR$^{12B}$SO$_2$R$^{12A}$, —NR$^{12B}$C(O)R$^{12D}$, —NR$^{12B}$C(O)OR$^{12D}$, —NR$^{12B}$OR$^{12D}$, —OCX$^{12.1}{}_3$, —OCHX$^{12.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{13}$ is hydrogen, halogen, —CX$^{13.1}{}_3$, —CHX$^{13.1}{}_2$, —CH$_2$X$^{13.1}$, —CN, —SO$_{n1}$R$^{13A}$, —SO$_{v1}$NR$^{13B}$R$^{13C}$, —NHNR$^{13B}$R$^{13C}$, —ONR$^{13B}$R$^{13C}$, —NHC(O)NHNR$^{13B}$R$^{13C}$, —NHC(O)NR$^{13B}$R$^{13C}$, —N(O)$_{m1}$, —NR$^{13B}$R$^{13C}$, —C(O)R$^{13D}$, —C(O)OR$^{13D}$, —C(O)NR$^{13B}$R$^{13C}$, —OR$^{13A}$, —NR$^{13B}$SO$_2$R$^{13A}$, —NR$^{13B}$C(O)R$^{13D}$, —NR$^{13B}$C(O)OR$^{13D}$, —NR$^{13B}$OR$^{13D}$, —OCX$^{13.1}{}_3$, —OCHX$^{13.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{14}$ is hydrogen, halogen, —CX$^{14.1}{}_3$, —CHX$^{14.1}{}_2$, —CH$_2$X$^{14.1}$, —CN, —SO$_{n1}$R$^{14A}$, —SO$_{v1}$NR$^{14B}$R$^{14C}$, —NHNR$^{14B}$R$^{14C}$, —ONR$^{14B}$R$^{14C}$, —NHC(O)NHNR$^{14B}$R$^{14C}$, —NHC(O)NR$^{14B}$R$^{14C}$, —N(O)$_{m1}$, —NR$^{14B}$R$^{14C}$, —C(O)R$^{14D}$, —C(O)OR$^{14D}$, —C(O)NR$^{14B}$R$^{14C}$, —OR$^{14A}$, —NR$^{14B}$SO$_2$R$^{14A}$, —NR$^{14B}$C(O)R$^{14D}$, —NR$^{14B}$C(O)OR$^{14D}$, —NR$^{14B}$OR$^{14D}$, —OCX$^{14.1}{}_3$, —OCHX$^{14.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{15}$ is hydrogen, halogen, —CX$^{15.1}{}_3$, —CHX$^{15.1}{}_2$, —CH$_2$X$^{15.1}$, —CN, —SO$_{n1}$R$^{15A}$, —SO$_{v1}$NR$^{15B}$R$^{15C}$, —NHNR$^{15B}$R$^{15C}$, —ONR$^{15B}$R$^{15C}$, —NHC(O)NHNR$^{15B}$R$^{15C}$, —NHC(O)NR$^{15B}$R$^{15C}$, —N(O)$_{m1}$, —NR$^{15B}$R$^{15C}$, —C(O)R$^{15D}$, —C(O)OR$^{15D}$, —C(O)NR$^{15B}$R$^{15C}$, —OR$^{15A}$, —NR$^{15B}$SO$_2$R$^{15A}$, —NR$^{15B}$C(O)R$^{15D}$, —NR$^{15B}$C(O)OR$^{15D}$, —NR$^{15B}$OR$^{15D}$, —OCX$^{15.1}{}_3$, —OCHX$^{15.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{16}$ is hydrogen, halogen, —CX$^{16.1}{}_3$, —CHX$^{16.1}{}_2$, —CH$_2$X$^{16.1}$, —CN, —SO$_{n1}$R$^{16A}$, —SO$_{v1}$NR$^{16B}$R$^{16C}$, —NHNR$^{16B}$R$^{16C}$, —ONR$^{16B}$R$^{16C}$, —NHC(O)NHNR$^{16B}$R$^{16C}$, —NHC(O)NR$^{16B}$R$^{16C}$, —N(O)$_{m1}$, —NR$^{16B}$R$^{16C}$, —C(O)R$^{16D}$, —C(O)OR$^{16D}$, —C(O)NR$^{16B}$R$^{16C}$, —OR$^{16A}$, —NR$^{16B}$SO$_2$R$^{16A}$, —NR$^{16B}$C(O)R$^{16D}$, —NR$^{16B}$C(O)OR$^{16D}$, —NR$^{16B}$OR$^{16D}$, —OCX$^{16.1}{}_3$, —OCHX$^{16.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{17}$ is hydrogen, halogen, —CX$^{17.1}{}_3$, —CHX$^{17.1}{}_2$, —CH$_2$X$^{17.1}$, —CN, —SO$_{n1}$R$^{17A}$, —SO$_{v1}$NR$^{17B}$R$^{17C}$, —NHNR$^{17B}$R$^{17C}$, —ONR$^{17B}$R$^{17C}$, —NHC(O)NHNR$^{17B}$R$^{17C}$, —NHC(O)NR$^{17B}$R$^{17C}$, —N(O)$_{m1}$, —NR$^{17B}$R$^{17C}$, —C(O)R$^{17D}$, —C(O)OR$^{17D}$, —C(O)NR$^{17B}$R$^{17C}$, —OR$^{17A}$, —NR$^{17B}$SO$_2$R$^{17A}$, —NR$^{17B}$C(O)R$^{17D}$, —NR$^{17B}$C(O)OR$^{17D}$, —NR$^{17B}$OR$^{17D}$, —OCX$^{17.1}{}_3$, —OCHX$^{17.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{18}$ is hydrogen, halogen, —CX$^{18.1}{}_3$, —CHX$^{18.1}{}_2$, —CH$_2$X$^{18.1}$, —CN, —SO$_{n1}$R$^{18A}$, —SO$_{v1}$NR$^{18B}$R$^{18C}$, —NHNR$^{18B}$R$^{18C}$, —ONR$^{18B}$R$^{18C}$, —NHC(O)NHNR$^{18B}$R$^{18C}$, —NHC(O)NR$^{18B}$R$^{18C}$, —N(O)$_{m1}$, —NR$^{18B}$R$^{18C}$, —C(O)R$^{18D}$, —C(O)OR$^{18D}$, —C(O)NR$^{18B}$R$^{18C}$, —OR$^{18A}$, —NR$^{18B}$SO$_2$R$^{18A}$, —NR$^{18B}$C(O)R$^{18D}$, —NR$^{18B}$C(O)OR$^{18D}$, —NR$^{18B}$OR$^{18D}$, —OCX$^{18.1}{}_3$, —OCHX$^{18.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{19}$ is hydrogen, —COR$^{19D}$, —C(O)NHNR$^{19B}$R$^{19C}$, —C(O)OR$^{19D}$, —SO$_2$R$^{19A}$, C(O)NR$^{19B}$R$^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{11A}$, R$^{11B}$, R$^{11C}$, R$^{11D}$, R$^{12A}$, R$^{12B}$, R$^{12C}$, R$^{12D}$, R$^{13A}$, R$^{13B}$, R$^{13C}$, R$^{13D}$, R$^{14A}$, R$^{14B}$, R$^{14C}$, R$^{14D}$, R$^{15A}$, R$^{15B}$, R$^{15C}$, R$^{15D}$, R$^{16A}$, R$^{16B}$, R$^{16C}$, R$^{16D}$, R$^{17A}$, R$^{17B}$, R$^{17C}$, R$^{17D}$, R$^{18A}$, R$^{18B}$, R$^{18C}$ and R$^{18D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1B}$, R$^{1C}$, R$^{2B}$, R$^{2C}$, R$^{3B}$, R$^{3C}$, R$^{4B}$, R$^{4C}$, R$^{5B}$, R$^{5C}$, R$^{6B}$, R$^{6C}$, R$^{7B}$, R$^{7C}$, R$^{8B}$, R$^{8C}$, R$^{9B}$, R$^{9C}$, R$^{10B}$, R$^{10C}$, R$^{11B}$, R$^{11C}$, R$^{12B}$, R$^{12C}$, R$^{13B}$, R$^{13C}$, R$^{14B}$, R$^{14C}$, R$^{15B}$, R$^{15C}$, R$^{16B}$, R$^{16C}$, R$^{17B}$, R$^{17C}$, R$^{18B}$ and R$^{18C}$ substituents bonded to the same nitrogen atom may optionally be joined to form a substituted or unsubstituted heterocycloalkyl or substituted or unsubstituted heteroaryl. X$^{1.1}$, X$^{2.1}$, X$^{3.1}$, X$^{4.1}$, X$^{5.1}$, X$^{6.1}$, X$^{7.1}$, X$^{8.1}$, X$^{9.1}$, X$^{10.1}$, X$^{11.1}$, X$^{12.1}$, X$^{13.1}$, X$^{14.1}$, X$^{15.1}$, X$^{16.1}$, X$^{17.1}$ and X$^{18.1}$ are independently —Cl, —Br, —I or —F. The symbol n1 is 0, 1, 2, 3 or 4. The symbols m1 and v1 are independently 1 or 2.

In embodiments, when A is CR$^{14}$, then R$^{10}$ is not bromine. In embodiments, when B is CR$^{16}$, then R$^{10}$ is not bromine. In embodiments, when L$^1$ is bond, then R$^{10}$ is not bromine. In embodiments, when one of R$^8$, R$^9$, R$^{11}$, R$^{12}$, R$^{13}$, R$^{14}$, R$^{15}$, R$^{16}$, R$^{17}$, R$^{18}$ and R$^{19}$ is hydrogen, then R$^{10}$ is not bromine. In embodiments, when R$^8$, R$^9$, R$^{11}$, R$^{12}$, R$^{13}$, R$^{14}$, R$^{15}$, R$^{16}$, R$^{17}$, R$^{18}$ and R$^{19}$ are hydrogen, then R$^{10}$ is not bromine. In embodiments, when A is CR$^{14}$; B is CR$^{16}$; L$^1$ is bond; and R$^8$, R$^9$, R$^{11}$, R$^{12}$, R$^{13}$, R$^{14}$, R$^{15}$, R$^{16}$, R$^{17}$, R$^{18}$ and R$^{19}$ are hydrogen, then R$^{10}$ is not bromine. In embodiments, R$^{10}$ is not bromine.

In another aspect, there is provided a compound of Formula (IIIa):

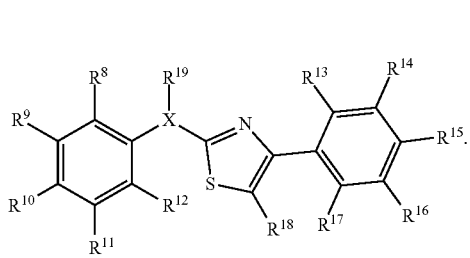

(IIIa)

In the compound of Formula (IIIa), $R^8$ is hydrogen, halogen, $-CX^{8.1}_3$, $-CHX^{8.1}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$ is hydrogen, halogen, $-CX^{9.1}_3$, $-CHX^{9.1}_2$, $-CH_2X^{9.1}$, $-CN$, $-SO_{n1}R^{9A}$, $-SO_{v1}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m1}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ is hydrogen, fluorine, chlorine or iodine, $-CX^{10.1}_3$, $-CHX^{10.1}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{11}$ is hydrogen, halogen, $-CX^{11.1}_3$, $-CHX^{11.1}_2$, $-CH_2X^{11.1}$, $-CN$, $-SO_{n1}R^{11A}$, $-SO_{v1}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, $-N(O)_{m1}$, $-NR^{11B}R^{11C}$, $-C(O)R^{11D}$, $-C(O)OR^{11D}$, $-C(O)NR^{11B}R^{11C}$, $-OR^{11A}$, $-NR^{11B}SO_2R^{11A}$, $-NR^{11B}C(O)R^{11D}$, $-NR^{11B}C(O)OR^{11D}$, $-NR^{11B}OR^{11D}$, $-OCX^{11.1}_3$, $-OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{12}$ is hydrogen, halogen, $-CX^{12.1}_3$, $-CHX^{12.1}_2$, $-CH_2X^{12.1}$, $-CN$, $-SO_{n1}R^{12A}$, $-SO_{v1}NR^{12B}R^{12C}$, $-NHNR^{12B}R^{12C}$, $-ONR^{12B}R^{12C}$, $-NHC(O)NHNR^{12B}R^{12C}$, $-NHC(O)NR^{12B}R^{12C}$, $-N(O)_{m1}$, $-NR^{12B}R^{12C}$, $-C(O)R^{12D}$, $-C(O)OR^{12D}$, $-C(O)NR^{12B}R^{12C}$, $-OR^{12A}$, $-NR^{12B}SO_2R^{12A}$, $-NR^{12B}C(O)R^{12D}$, $-NR^{12B}C(O)OR^{12D}$, $-NR^{12B}OR^{12D}$, $-OCX^{12.1}_3$, $-OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{13}$ is hydrogen, halogen, $-CX^{13.1}_3$, $-CHX^{13.1}_2$, $-CH_2X^{13.1}$, $-CN$, $-SO_{n1}R^{13A}$, $-SO_{v1}NR^{13B}R^{13C}$, $-NHNR^{13B}R^{13C}$, $-ONR^{13B}R^{13C}$, $-NHC(O)NHNR^{13B}R^{13C}$, $-NHC(O)NR^{13B}R^{13C}$, $-N(O)_{m1}$, $-NR^{13B}R^{13C}$, $-C(O)R^{13D}$, $-C(O)OR^{13D}$, $-C(O)NR^{13B}R^{13C}$, $-OR^{13A}$, $-NR^{13B}SO_2R^{13A}$, $-NR^{13B}C(O)R^{13D}$, $-NR^{13B}C(O)OR^{13D}$, $-NR^{13B}OR^{13D}$, $-OCX^{13.1}_3$, $-OCHX^{13.1}_2$, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{14}$ is hydrogen, halogen, $-CX^{14.1}_3$, $-CHX^{14.1}_2$, $-CH_2X^{14.1}$, $-CN$, $-SO_{n1}R^{14A}$, $-SO_{v1}NR^{14B}R^{14C}$, $-NHNR^{14B}R^{14C}$, $-ONR^{14B}R^{14C}$, $-NHC(O)NHNR^{14B}R^{14C}$, $-NHC(O)NR^{14B}R^{14C}$, $-N(O)_{m1}$, $-NR^{14B}R^{14C}$, $-C(O)R^{14D}$, $-C(O)OR^{14D}$, $-C(O)NR^{14B}R^{14C}$, $-OR^{14A}$, $-NR^{14B}SO_2R^{14A}$, $-NR^{14B}C(O)R^{14D}$, $-NR^{14B}C(O)OR^{14D}$, $-NR^{14B}OR^{14D}$, $-OCX^{14.1}_3$, $-OCHX^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{15}$ is hydrogen, halogen, $-CX^{15.1}_3$, $-CHX^{15.1}_2$, $-CH_2X^{15.1}$, $-CN$, $-SO_{n1}R^{15A}$, $-SO_{v1}NR^{15B}R^{15C}$, $-NHNR^{15B}R^{15C}$, $-ONR^{15B}R^{15C}$, $-NHC(O)NHNR^{15B}R^{15C}$, $-NHC(O)NR^{15B}R^{15C}$, $-N(O)_{m1}$, $-NR^{15B}R^{15C}$, $-C(O)R^{15D}$, $-C(O)OR^{15D}$, $-C(O)NR^{15B}R^{15C}$, $-OR^{15A}$, $-NR^{15B}SO_2R^{15A}$, $-NR^{15B}C(O)R^{15D}$, $-NR^{15B}C(O)OR^{15D}$, $-NR^{15B}OR^{15D}$, $-OCX^{15.1}_3$, $-OCHX^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{16}$ is hydrogen, halogen, $-CX^{16.1}_3$, $-CHX^{16.1}_2$, $-CH_2X^{16.1}$, $-CN$, $-SO_{n1}R^{16A}$, $-SO_{v1}NR^{16B}R^{16C}$, $-NHNR^{16B}R^{16C}$, $-ONR^{16B}R^{16C}$, $-NHC(O)NHNR^{16B}R^{16C}$, $-NHC(O)NR^{16B}R^{16C}$, $-N(O)_{m1}$, $-NR^{16B}R^{16C}$, $-C(O)R^{16D}$, $-C(O)OR^{16D}$, $-C(O)NR^{16B}R^{16C}$, $-OR^{16A}$, $-NR^{16B}SO_2R^{16A}$, $-NR^{16B}C(O)R^{16D}$, $-NR^{16B}C(O)OR^{16D}$, $-NR^{16B}OR^{16D}$, $-OCX^{16.1}_3$, $-OCHX^{16.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{17}$ is hydrogen, halogen, $-CX^{17.1}_3$, $-CHX^{17.1}_2$, $-CH_2X^{17.1}$, $-CN$, $-SO_{n1}R^{17A}$, $-SO_{v1}NR^{17B}R^{17C}$, $-NHNR^{17B}R^{17C}$, $-ONR^{17B}R^{17C}$, $-NHC(O)NHNR^{17B}R^{17C}$, $-NHC(O)NR^{17B}R^{17C}$, $-N(O)_{m1}$, $-NR^{17B}R^{17C}$, $-C(O)R^{17D}$, $-C(O)OR^{17D}$, $-C(O)NR^{17B}R^{17C}$, $-OR^{17A}$, $-NR^{17B}SO_2R^{17A}$, $-NR^{17B}C(O)R^{17D}$, $-NR^{17B}C(O)OR^{17D}$, $-NR^{17B}OR^{17D}$, $-OCX^{17.1}_3$, $-OCHX^{17.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{18}$ is hydrogen, halogen, $-CX^{18.1}_3$, $-CHX^{18.1}_2$, $-CH_2X^{18.1}$, $-CN$, $-SO_{n1}R^{18A}$, $-SO_{v1}NR^{18B}R^{18C}$, $-NHNR^{18B}R^{18C}$, $-ONR^{18B}R^{18C}$, $-NHC(O)NHNR^{18B}R^{18C}$, $-NHC(O)NR^{18B}R^{18C}$, $-N(O)_{m1}$, $-NR^{18B}R^{18C}$, $-C(O)R^{18D}$, $-C(O)OR^{18D}$, $-C(O)NR^{18B}R^{18C}$, $-OR^{18A}$, $-NR^{18B}SO_2R^{18A}$, $-NR^{18B}C(O)R^{18D}$, $-NR^{18B}C(O)OR^{18D}$, $-NR^{18B}OR^{18D}$, $-OCX^{18.1}_3$, $-OCHX^{18.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{19}$ is hydrogen, $-COR^{19D}$, $-C(O)NHNR^{19B}R^{19C}$, $-C(O)OR^{19D}$, —$SO_2R^{19A}$, $C(O)NR^{19B}R^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, RISC, $R^{15D}$, $R^{16A}$, $R^{16B}$, $R^{16C}$, $R^{16D}$, $R^{17A}$, $R^{17B}$, $R^{17C}$, $R^{17D}$, $R^{18B}$, $R^{18C}$ and $R^{18D}$ are independently hydrogen, halogen, —$CF_3$, —$CCl_3$, —$CBr_3$, —$CI_3$, —$OH$, —$NH_2$, —$COOH$, —$CONH_2$, —$NO_2$, —$SH$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)$—$OH$, —$NHOH$, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{11B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17C}$, $R^{18B}$ and $R^{18C}$ substituents bonded to the same nitrogen atom may optionally be joined to form a substituted or unsubstituted heterocycloalkyl or substituted or unsubstituted heteroaryl. $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$, $X^{12.1}$, $X^{13.1}$, $X^{14.1}$, $X^{15.1}$, $X^{16.1}$, $X^{17.1}$ and $X^{18.1}$ are independently —Cl, —Br, —I or —F. The symbol n1 is 0, 1, 2, 3 or 4. The symbols m1 and v1 are independently 1 or 2.

In another aspect, there is provided a compound of Formula (Mb):

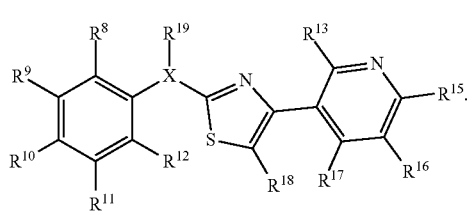

(IIIb)

In the compound of Formula (Mb), $R^8$ is hydrogen, halogen, —$CX^{8.1}_3$, —$CHX^{8.1}_2$, —$CH_2X^{8.1}$, —CN, —$SO_{n1}R^{8A}$, —$SO_{v1}NR^{8B}R^{8C}$, —$NHNR^{8B}R^{8C}$, —$ONR^{8B}R^{8C}$, —$NHC(O)NHNR^{8B}R^{8C}$, —$NHC(O)NR^{8B}R^{8C}$, —$N(O)_{m1}$, —$NR^{8B}R^{8C}$, —$C(O)R^{8D}$, —$C(O)OR^{8D}$, —$C(O)NR^{8B}R^{8C}$, —$OR^{8A}$, —$NR^{8B}SO_2R^{8A}$, —$NR^{8B}C(O)R^{8D}$, —$NR^{8B}C(O)OR^{8D}$, —$NR^{8B}OR^{8D}$, —$OCX^{8.1}_3$, —$OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$ is hydrogen, halogen, —$CX^{9.1}_3$, —$CHX^{9.1}_2$, —$CH_2X^{9.1}$, —CN, —$SO_{n1}R^{9A}$, —$SO_{v1}NR^{9B}R^{9C}$, —$NHNR^{9B}R^{9C}$, —$ONR^{9B}R^{9C}$, —$NHC(O)NHNR^{9B}R^{9C}$, —$NHC(O)NR^{9B}R^{9C}$, —$N(O)_{m1}$, —$NR^{9B}R^{9C}$, —$C(O)R^{9D}$, —$C(O)OR^{9D}$, —$C(O)NR^{9B}R^{9C}$, —$OR^{9A}$, —$NR^{9B}SO_2R^{9A}$, —$NR^{9B}C(O)R^{9D}$, —$NR^{9B}C(O)OR^{9D}$, —$NR^{9B}OR^{9D}$, —$OCX^{9.1}_3$, —$OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ is hydrogen, halogen, —$CX^{10.1}_3$, —$CHX^{10.1}_2$, —$CH_2X^{10.1}$, —CN, —$SO_{n1}R^{10A}$, —$SO_{v1}NR^{10B}R^{10C}$, —$NHNR^{10B}R^{10C}$, —$ONR^{10B}R^{10C}$, —$NHC(O)NHNR^{10B}R^{10C}$, —$NHC(O)NR^{10B}R^{10C}$, —$N(O)_{m1}$, —$NR^{10B}R^{10C}$, —$C(O)R^{10D}$, —$C(O)OR^{10D}$, —$C(O)NR^{10B}R^{10C}$, —$OR^{10A}$, —$NR^{10B}SO_2R^{10A}$, —$NR^{10B}C(O)R^{10D}$, —$NR^{10B}C(O)OR^{10D}$, —$NR^{10B}OR^{10D}$, —$OCX^{10.1}_3$, —$OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{11}$ is hydrogen, halogen, —$CX^{11.1}_3$, —$CHX^{11.1}_2$, —$CH_2X^{11.1}$, —CN, —$SO_{n1}R^{11A}$, —$SO_{v1}NR^{11B}R^{11C}$, —$NHNR^{11B}R^{11C}$, —$ONR^{11B}R^{11C}$, —$NHC(O)NHNR^{11B}R^{11C}$, —$NHC(O)NR^{11B}R^{11C}$, —$N(O)_{m1}$, —$NR^{11B}R^{11C}$, —$C(O)R^{11D}$, —$C(O)OR^{11D}$, —$C(O)NR^{11B}R^{11C}$, —$OR^{11A}$, —$NR^{11B}SO_2R^{11A}$, —$NR^{11B}C(O)R^{11D}$, —$NR^{11B}C(O)OR^{11D}$, —$NR^{11B}OR^{11D}$, —$OCX^{11.1}_3$, —$OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{12}$ is hydrogen, halogen, —$CX^{12.1}_3$, —$CHX^{12.1}_2$, —$CH_2X^{12.1}$, —CN, —$SO_{n1}R^{12A}$, —$SO_{v1}NR^{12B}R^{12C}$, —$NHNR^{12B}R^{12C}$, —$ONR^{12B}R^{12C}$, —$NHC(O)NHNR^{12B}R^{12C}$, —$NHC(O)NR^{12B}R^{12C}$, —$N(O)_{m1}$, —$NR^{12B}R^{12C}$, —$C(O)R^{12D}$, —$C(O)OR^{12D}$, —$C(O)NR^{12B}R^{12C}$, —$OR^{12A}$, —$NR^{12B}SO_2R^{12A}$, —$NR^{12B}C(O)R^{12D}$, —$NR^{12B}C(O)OR^{12D}$, —$NR^{12B}OR^{12D}$, —$OCX^{12.1}_3$, —$OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{13}$ is hydrogen, halogen, —$CX^{13.1}_3$, —$CHX^{13.1}_2$, —$CH_2X^{13.1}$, —CN, —$SO_{n1}R^{13A}$, —$SO_{v1}NR^{13B}R^{13C}$, —$NHNR^{13B}R^{13C}$, —$ONR^{13B}R^{13C}$, —$NHC(O)NHNR^{13B}R^{13C}$, —$NHC(O)NR^{13B}R^{13C}$, —$N(O)_{m1}$, —$NR^{13B}R^{13C}$, —$C(O)R^{13D}$, —$C(O)OR^{13D}$, —$C(O)NR^{13B}R^{13C}$, —$OR^{13A}$, —$NR^{13B}SO_2R^{13A}$, —$NR^{13B}C(O)R^{13D}$, —$NR^{13B}C(O)OR^{13D}$, —$NR^{13B}OR^{13D}$, —$OCX^{13.1}_3$, —$OCHX^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{15}$ is hydrogen, halogen, —$CX^{15.1}_3$, —$CHX^{15.1}_2$, —$CH_2X^{15.1}$, —CN, —$SO_{n1}R^{15A}$, —$SO_{v1}NR^{15B}R^{15C}$, —$NHNR^{15B}R^{15C}$, —$ONR^{15B}R^{15C}$, —$NHC(O)NHNR^{15B}R^{15C}$, —$NHC(O)NR^{15B}R^{15C}$, —$N(O)_{m1}$, —$NR^{15B}R^{15C}$, —$C(O)R^{15D}$, —$C(O)OR^{15D}$, —$C(O)NR^{15B}R^{15C}$, —$OR^{15A}$, —$NR^{15B}SO_2R^{15A}$, —$NR^{15B}C(O)R^{15D}$, —$NR^{15B}C(O)OR^{15D}$, —$NR^{15B}OR^{15D}$, —$OCX^{15.1}_3$, —$OCHX^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{16}$ is hydrogen, halogen, —$CX^{16.1}_3$, —$CHX^{16.1}_2$, —$CH_2X^{16.1}$, —CN, —$SO_{n1}R^{16A}$, —$SO_{v1}NR^{16B}R^{16C}$, —$NHNR^{16B}R^{16C}$, —$ONR^{16B}R^{16C}$, —$NHC(O)NHNR^{16B}R^{16C}$, —$NHC(O)NR^{16B}R^{16C}$, —$N(O)_{m1}$, —$NR^{16B}R^{16C}$, —$C(O)R^{16D}$, —$C(O)OR^{16D}$, —$C(O)NR^{16B}R^{16C}$, —$OR^{16A}$, —$NR^{16B}SO_2R^{16A}$, —$NR^{16B}C(O)R^{16D}$, —$NR^{16B}C(O)OR^{16D}$, —$NR^{16B}OR^{16D}$, —$OCX^{16.1}_3$, —$OCHX^{16.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{17}$ is hydrogen, halogen, $-CX^{17.1}_3$, $-CHX^{17.1}_2$, $-CH_2X^{17.1}$, $-CN$, $-SO_{n1}R^{17A}$, $-SO_{v1}NR^{17B}R^{17C}$, $-NHNR^{17B}R^{17C}$, $-ONR^{17B}R^{17C}$, $-NHC(O)NHNR^{17B}R^{17C}$, $-NHC(O)NR^{17B}R^{17C}$, $-N(O)_{m1}$, $-NR^{17B}R^{17C}$, $-C(O)R^{17D}$, $-C(O)OR^{17D}$, $-C(O)NR^{17B}R^{17C}$, $-OR^{17A}$, $-NR^{17B}SO_2R^{17A}$, $-NR^{17B}C(O)R^{17D}$, $-NR^{17B}C(O)OR^{17D}$, $-NR^{17B}OR^{17D}$, $-OCX^{17.1}_3$, $-OCHX^{17.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{18}$ is hydrogen, halogen, $-CX^{18.1}_3$, $-CHX^{18.1}_2$, $-CH_2X^{18.1}$, $-CN$, $-SO_{n1}R^{18A}$, $-SO_{v1}NR^{18B}R^{18C}$, $-NHNR^{18B}R^{18C}$, $-ONR^{18B}R^{18C}$, $-NHC(O)NHNR^{18B}R^{18C}$, $-NHC(O)NR^{18B}R^{18C}$, $-N(O)_{m1}$, $-NR^{18B}R^{18C}$, $-C(O)R^{18D}$, $-C(O)OR^{18D}$, $-C(O)NR^{18B}R^{18C}$, $-OR^{18A}$, $-NR^{18B}SO_2R^{18A}$, $-NR^{18B}C(O)R^{18D}$, $-NR^{18B}C(O)OR^{18D}$, $-NR^{18B}OR^{18D}$, $-OCX^{18.1}_3$, $-OCHX^{18.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{19}$ is hydrogen, $-COR^{19D}$, $-C(O)NHR^{19B}R^{19C}$, $-C(O)OR^{19D}$, $-SO_2R^{19A}$, $-C(O)NR^{19B}R^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$ and $R^{18D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{11B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17C}$, $R^{18B}$ and $R^{18C}$ substituents bonded to the same nitrogen atom may optionally be joined to form a substituted or unsubstituted heterocycloalkyl or substituted or unsubstituted heteroaryl. $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$, $X^{12.1}$, $X^{13.1}$, $X^{14.1}$, $X^{15.1}$, $X^{16.1}$, $X^{17.1}$ and $X^{18.1}$ are independently $-Cl$, $-Br$, $-I$ or $-F$. The symbol n1 is 0, 1, 2, 3 or 4. The symbols m1 and v1 are independently 1 or 2.

In a further aspect, there is provided a compound of Formula (IIIc):

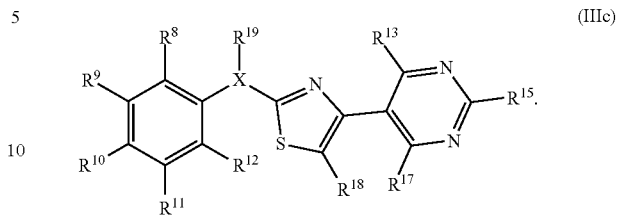

(IIIc)

In the compound of Formula (IIIc), $R^8$ is hydrogen, halogen, $-CX^{8.1}_3$, $-CHX^{8.1}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$ is hydrogen, halogen, $-CX^{9.1}_3$, $-CHX^{9.1}_2$, $-CH_2X^{9.1}$, $-CN$, $-SO_{n1}R^{9A}$, $-SO_{v1}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m1}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ is hydrogen, halogen, $-CX^{10.1}_3$, $-CHX^{10.1}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{11}$ is hydrogen, halogen, $-CX^{11.1}_3$, $-CHX^{11.1}_2$, $-CH_2X^{11.1}$, $-CN$, $-SO_{n1}R^{11A}$, $-SO_{v1}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, $-N(O)_{m1}$, $-NR^{11B}R^{11C}$, $-C(O)R^{11D}$, $-C(O)OR^{11D}$, $-C(O)NR^{11B}R^{11C}$, $-OR^{11A}$, $-NR^{11B}SO_2R^{11A}$, $-NR^{11B}C(O)R^{11D}$, $-NR^{11B}C(O)OR^{11D}$, $-NR^{11B}OR^{11D}$, $-OCX^{11.1}_3$, $-OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{12}$ is hydrogen, halogen, $-CX^{12.1}_3$, $-CHX^{12.1}_2$, $-CH_2X^{12.1}$, $-CN$, $-SO_{n1}R^{12A}$, $-SO_{v1}NR^{12B}R^{12C}$, $-NHNR^{12B}R^{12C}$, $-ONR^{12B}R^{12C}$, $-NHC(O)NHNR^{12B}R^{12C}$, $-NHC(O)NR^{12B}R^{12C}$, $-N(O)_{m1}$, $-NR^{12B}R^{12C}$, $-C(O)R^{12D}$, $-C(O)OR^{12D}$, $-C(O)NR^{12B}R^{12C}$, $-OR^{12A}$, $-NR^{12B}SO_2R^{12A}$, $-NR^{12B}C(O)R^{12D}$, $-NR^{12B}C(O)OR^{12D}$, $-NR^{12B}OR^{12D}$, $-OCX^{12.1}_3$, $-OCHX^{12.1}_2$, substituted or unsubstituted alkyl, substituted or unsubstituted heteroalkyl, substituted or unsubstituted cycloalkyl, substituted or unsubstituted aryl, or substituted or unsubstituted heteroaryl. $R^{13}$ is hydrogen, halogen, $-CX^{13.1}_3$, $-CHX^{13.1}_2$, $-CH_2X^{13.1}$, $-CN$, $-SO_{n1}R^{13A}$, —SO$_{v1}$NR$^{13B}$R$^{13C}$, —NHNR$^{13B}$R$^{13C}$, —ONR$^{13B}$R$^{13C}$, —NHC(O)NHNR$^{13B}$R$^{13C}$, —NHC(O)NR$^{13B}$R$^{13C}$, —N(O)$_{m1}$, —NR$^{13B}$R$^{13C}$, —C(O)R$^{13D}$, —C(O)OR$^{13D}$, —C(O)NR$^{13B}$R$^{13C}$, —OR$^{13A}$, —NR$^{13B}$SO$_2$R$^{13A}$, —NR$^{13B}$C(O)R$^{13D}$, —NR$^{13B}$C(O)OR$^{13D}$, —NR$^{13B}$OR$^{13D}$, —OCX$^{13.1}_3$, —OCHX$^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{15}$ is hydrogen, halogen, —CX$^{15.1}_3$, —CHX$^{15.1}_2$, —CH$_2$X$^{15.1}$, —CN, —SO$_{n1}$R$^{15A}$, —SO$_{v1}$NR$^{15B}$R$^{15C}$, —NHNR$^{15B}$R$^{15C}$, —ONR$^{15B}$R$^{15C}$, —NHC(O)NHNR$^{15B}$R$^{15C}$, —NHC(O)NR$^{15B}$R$^{15C}$, —N(O)$_{m1}$, —NR$^{15B}$R$^{15C}$, —C(O)R$^{15D}$, —C(O)OR$^{15D}$, —C(O)NR$^{15B}$R$^{15C}$, —OR$^{15A}$, —NR$^{15B}$SO$_2$R$^{15A}$, —NR$^{15B}$C(O)R$^{15D}$, —NR$^{15B}$C(O)OR$^{15D}$, —NR$^{15B}$OR$^{15D}$, —OCX$^{15.1}_3$, —OCHX$^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{17}$ is hydrogen, halogen, —CX$^{17.1}_3$, —CHX$^{17.1}_2$, —CH$_2$X$^{17.1}$, —CN, —SO$_{n1}$R$^{17A}$, —SO$_{v1}$NR$^{17B}$R$^{17C}$, —NHNR$^{17B}$R$^{17C}$, —ONR$^{17B}$R$^{17C}$, —NHC(O)NHNR$^{17B}$R$^{17C}$, —NHC(O)NR$^{17B}$R$^{17C}$, —N(O)$_{m1}$, —NR$^{17B}$R$^{17C}$, —C(O)R$^{17D}$, —C(O)OR$^{17D}$, —C(O)NR$^{17B}$R$^{17C}$, —OR$^{17A}$, —NR$^{17B}$SO$_2$R$^{17A}$, —NR$^{17B}$C(O)R$^{17D}$, —NR$^{17B}$C(O)OR$^{17D}$, —NR$^{17B}$OR$^{17D}$, —OCX$^{17.1}_3$, —OCHX$^{17.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{18}$ is hydrogen, halogen, —CX$^{18.1}_3$, —CHX$^{18.1}_2$, —CH$_2$X$^{18.1}$, —CN, —SO$_{n1}$R$^{18A}$, —SO$_{v1}$NR$^{18B}$R$^{18C}$, —NHNR$^{18B}$R$^{18C}$, —ONR$^{18B}$R$^{18C}$, —NHC(O)NHNR$^{18B}$R$^{18C}$, —NHC(O)NR$^{18B}$R$^{18C}$, —N(O)$_{m1}$, —NR$^{18B}$R$^{18C}$, —C(O)R$^{18D}$, —C(O)OR$^{18D}$, —C(O)NR$^{18B}$R$^{18C}$, —OR$^{18A}$, —NR$^{18B}$SO$_2$R$^{18A}$, —NR$^{18B}$C(O)R$^{18D}$, —NR$^{18B}$C(O)OR$^{18D}$, —NR$^{18B}$OR$^{18D}$, —OCX$^{18.1}_3$, —OCHX$^{18.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{19}$ is hydrogen, —COR$^{19D}$, —C(O)NHNR$^{19B}$R$^{19C}$, —C(O)OR$^{19D}$, —SO$_2$R$^{19A}$, C(O)NR$^{19B}$R$^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{11A}$, R$^{11B}$, R$^{11C}$, R$^{11D}$, R$^{12A}$, R$^{12B}$, R$^{12C}$, R$^{12D}$, R$^{13A}$, R$^{13B}$, R$^{13C}$, R$^{13D}$, R$^{14A}$, R$^{14B}$, R$^{14C}$, R$^{14D}$, R$^{15A}$, R$^{15B}$, R$^{15C}$, R$^{15D}$, R$^{16A}$, R$^{16B}$, R$^{16C}$, R$^{16D}$, R$^{17A}$, R$^{17B}$, R$^{17C}$, R$^{17D}$, R$^{18A}$, R$^{18B}$, R$^{18C}$ and R$^{18D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1B}$, R$^{1C}$, R$^{2B}$, R$^{2C}$, R$^{3B}$, R$^{3C}$, R$^{4B}$, R$^{4C}$, R$^{5B}$, R$^{5C}$, R$^{6B}$, R$^{6C}$, R$^{7B}$, R$^{7C}$, R$^{8B}$, R$^{8C}$, R$^{9B}$, R$^{9C}$, R$^{10B}$, R$^{10C}$, R$^{11B}$, R$^{11C}$, R$^{12B}$, R$^{12C}$, R$^{13B}$, R$^{13C}$, R$^{14B}$, R$^{14C}$, R$^{15B}$, R$^{15C}$, R$^{16B}$, R$^{16C}$, R$^{17B}$, R$^{17C}$, R$^{18B}$ and R$^{18C}$ substituents bonded to the same nitrogen atom may optionally be joined to form a substituted or unsubstituted heterocycloalkyl or substituted or unsubstituted heteroaryl. X$^{1.1}$, X$^{2.1}$, X$^{3.1}$, X$^{4.1}$, X$^{5.1}$, X$^{6.1}$, X$^{7.1}$, X$^{8.1}$, X$^{9.1}$, X$^{10.1}$, X$^{11.1}$, X$^{12.1}$, X$^{13.1}$, X$^{14.1}$, X$^{15.1}$, X$^{16.1}$, X$^{17.1}$ and X$^{18.1}$ are independently —Cl, —Br, —I or —F. The symbol n1 is 0, 1, 2, 3 or 4. The symbols m1 and v1 are independently 1 or 2.

Also provided herein are pharmaceutical compositions. In one aspect is a pharmaceutical composition that includes a compound described herein and a pharmaceutically acceptable excipient.

In an aspect, there is provided a method of increasing MYC expression in a cell. The method includes contacting the cell with a binding site 1 gp130 receptor agonist.

In another aspect, there is provided a method of increasing pSTAT3 expression in a cell including contacting the cell with a binding site 1 gp130 receptor agonist.

Provided herein is a method of regulating chondrocyte activation, maturation and/or differentiation, comprising contacting a chondrocyte with a binding site 1 gp130 receptor agonist.

Also provided herein is a method of regenerating or repairing tissue in a subject in need thereof. The method includes administering to the subject a therapeutically effective amount of a binding site 1 gp130 receptor agonist.

Further provided herein is a method of repairing a joint surface injury in a subject, comprising administering to the subject a therapeutically effective amount of a binding site 1 gp130 receptor agonist.

In an aspect, there is provided a method of treating a cartilage degenerative disease in a subject in need thereof, comprising administering to the subject a therapeutically effective amount of a binding site 1 gp130 receptor agonist.

In another aspect, there is provided a method of increasing secretion of cartilaginous matrix in cartilage. The method comprises contacting a gp130 receptor with a binding site 1 gp130 receptor agonist.

In yet another aspect, there is provided a method of modulating the activity of a gp130 receptor in a cell, comprising contacting the cell with a binding site 1 gp130 receptor agonist.

In a further aspect, there is provided a method of transforming a mature adult cell into a progenitor cell, including contacting the cell with a binding site 1 gp130 receptor agonist.

In certain aspects, the binding site 1 gp130 receptor agonist of the methods provided herein is a compound of Formula (III):

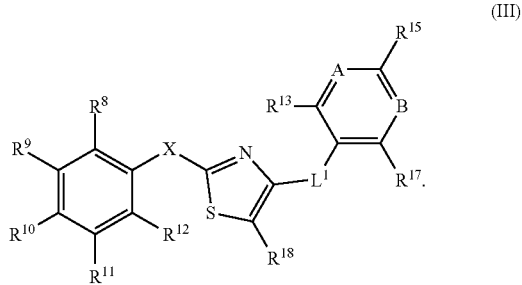

In the binding site 1 gp130 receptor agonist of Formula (III), A is CR$^{14}$ or N. B is CR$^{16}$ or N. X is O, NR$^{19}$ or S. L$^1$ is a bond or substituted or unsubstituted $C_1$-$C_3$ alkylene. $R^8$ is hydrogen, halogen, $-CX^{8.1}_3$, $-CHX^{8.1}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$ is hydrogen, halogen, $-CX^{9.1}_3$, $-CHX^{9.1}_2$, $-CH_2X^{9.1}$, $-CN$, $-SO_{n1}R^{9A}$, $-SO_{v1}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m1}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ is hydrogen, halogen, $-CX^{10.1}_3$, $-CHX^{10.1}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{11}$ is hydrogen, halogen, $-CX^{11.1}_3$, $-CHX^{11.1}_2$, $-CH_2X^{11.1}$, $-CN$, $-SO_{n1}R^{11A}$, $-SO_{v1}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, $-N(O)_{m1}$, $-NR^{11B}R^{11C}$, $-C(O)R^{11D}$, $-C(O)OR^{11D}$, $-C(O)NR^{11B}R^{11C}$, $-OR^{11A}$, $-NR^{11B}SO_2R^{11A}$, $-NR^{11B}C(O)R^{11D}$, $-NR^{11B}C(O)OR^{11D}$, $-NR^{11B}OR^{11D}$, $-OCX^{11.1}_3$, $-OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{12}$ is hydrogen, halogen, $-CX^{12.1}_3$, $-CHX^{12.1}_2$, $-CH_2X^{12.1}$, $-CN$, $-SO_{n1}R^{12A}$, $-SO_{v1}NR^{12B}R^{12C}$, $-NHNR^{12B}R^{12C}$, $-ONR^{12B}R^{12C}$, $-NHC(O)NHNR^{12B}R^{12C}$, $-NHC(O)NR^{12B}R^{12C}$, $-N(O)_{m1}$, $-NR^{12B}R^{12C}$, $-C(O)R^{12D}$, $-C(O)OR^{12D}$, $-C(O)NR^{12B}R^{12C}$, $-OR^{12A}$, $-NR^{12B}SO_2R^{12A}$, $-NR^{12B}C(O)R^{12D}$, $-NR^{12B}C(O)OR^{12D}$, $-NR^{12B}OR^{12D}$, $-OCX^{12.1}_3$, $-OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{13}$ is hydrogen, halogen, $-CX^{13.1}_3$, $-CHX^{13.1}_2$, $-CH_2X^{13.1}$, $-CN$, $-SO_{n1}R^{13A}$, $-SO_{v1}NR^{13B}R^{13C}$, $-NHNR^{13B}R^{13C}$, $-ONR^{13B}R^{13C}$, $-NHC(O)NHNR^{13B}R^{13C}$, $-NHC(O)NR^{13B}R^{13C}$, $-N(O)_{m1}$, $-NR^{13B}R^{13C}$, $-C(O)R^{13D}$, $-C(O)OR^{13D}$, $-C(O)NR^{13B}R^{13C}$, $-OR^{13A}$, $-NR^{13B}SO_2R^{13A}$, $-NR^{13B}C(O)R^{13D}$, $-NR^{13B}C(O)OR^{13D}$, $-NR^{13B}OR^{13D}$, $-OCX^{13.1}_3$, $-OCHX^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{14}$ is hydrogen, halogen, $-CX^{14.1}_3$, $-CHX^{14.1}_2$, $-CH_2X^{14.1}$, $-CN$, $-SO_{n1}R^{14A}$, $-SO_{v1}NR^{14B}R^{14C}$, $-NHNR^{14B}R^{14C}$, $-ONR^{14B}R^{14C}$, $-NHC(O)NHNR^{14B}R^{14C}$, $-NHC(O)NR^{14B}R^{14C}$, $-N(O)_{m1}$, $-NR^{14B}R^{14C}$, $-C(O)R^{14D}$, $-C(O)OR^{14D}$, $-C(O)NR^{14B}R^{14C}$, $-OR^{14A}$, $-NR^{14B}SO_2R^{14A}$, $-NR^{14B}C(O)R^{14D}$, $-NR^{14B}C(O)OR^{14D}$, $-NR^{14B}OR^{14D}$, $-OCX^{14.1}_3$, $-OCHX^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{15}$ is hydrogen, halogen, $-CX^{15.1}_3$, $-CHX^{15.1}_2$, $-CH_2X^{15.1}$, $-CN$, $-SO_{n1}R^{15A}$, $-SO_{v1}NR^{15B}R^{15C}$, $-NHNR^{15B}R^{15C}$, $-ONR^{15B}R^{15C}$, $-NHC(O)NHNR^{15B}R^{15C}$, $-NHC(O)NR^{15B}R^{15C}$, $-N(O)_{m1}$, $-NR^{15B}R^{15C}$, $-C(O)R^{15D}$, $-C(O)OR^{15D}$, $-C(O)NR^{15B}R^{15C}$, $-OR^{15A}$, $-NR^{15B}SO_2R^{15A}$, $-NR^{15B}C(O)R^{15D}$, $-NR^{15B}C(O)OR^{15D}$, $-NR^{15B}OR^{15D}$, $-OCX^{15.1}_3$, $-OCHX^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{16}$ is hydrogen, halogen, $-CX^{16.1}_3$, $-CHX^{16.1}_2$, $-CH_2X^{16.1}$, $-CN$, $-SO_{n1}R^{16A}$, $-SO_{v1}NR^{16B}R^{16C}$, $-NHNR^{16B}R^{16C}$, $-ONR^{16B}R^{16C}$, $-NHC(O)NHNR^{16B}R^{16C}$, $-NHC(O)NR^{16B}R^{16C}$, $-N(O)_{m1}$, $-NR^{16B}R^{16C}$, $-C(O)R^{16D}$, $-C(O)OR^{16D}$, $-C(O)NR^{16B}R^{16C}$, $-OR^{16A}$, $-NR^{16B}SO_2R^{16A}$, $-NR^{16B}C(O)R^{16D}$, $-NR^{16B}C(O)OR^{16D}$, $-NR^{16B}OR^{16D}$, $-OCX^{16.1}_3$, $-OCHX^{16.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{17}$ is hydrogen, halogen, $-CX^{17.1}_3$, $-CHX^{17.1}_2$, $-CH_2X^{17.1}$, $-CN$, $-SO_{n1}R^{17A}$, $-SO_{v1}NR^{17B}R^{17C}$, $-NHNR^{17B}R^{17C}$, $-ONR^{17B}R^{17C}$, $-NHC(O)NHNR^{17B}R^{17C}$, $-NHC(O)NR^{17B}R^{17C}$, $-N(O)_{m1}$, $-NR^{17B}R^{17C}$, $-C(O)R^{17D}$, $-C(O)OR^{17D}$, $-C(O)NR^{17B}R^{17C}$, $-OR^{17A}$, $-NR^{17B}SO_2R^{17A}$, $-NR^{17B}C(O)R^{17D}$, $-NR^{17B}C(O)OR^{17D}$, $-NR^{17B}OR^{17D}$, $-OCX^{17.1}_3$, $-OCHX^{17.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{18}$ is hydrogen, halogen, $-CX^{18.1}_3$, $-CHX^{18.1}_2$, $-CH_2X^{18.1}$, $-CN$, $-SO_{n1}R^{18A}$, $-SO_{v1}NR^{18B}R^{18C}$, $-NHNR^{18B}R^{18C}$, $-ONR^{18B}R^{18C}$, $-NHC(O)NHNR^{18B}R^{18C}$, $-NHC(O)NR^{18B}R^{18C}$, $-N(O)_{m1}$, $-NR^{18B}R^{18C}$, $-C(O)R^{18D}$, $-C(O)OR^{18D}$, $-C(O)NR^{18B}R^{18C}$, $-OR^{18A}$, $-NR^{18B}SO_2R^{18A}$, $-NR^{18B}C(O)R^{18D}$, $-NR^{18B}C(O)OR^{18D}$, $-NR^{18B}OR^{18D}$, $-OCX^{18.1}_3$, $-OCHX^{18.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{19}$ is hydrogen, $-COR^{19D}$, $-C(O)NHNR^{19B}R^{19C}$, $-C(O)OR^{19D}$, $-SO_2R^{19A}$, $C(O)NR^{19B}R^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$ and $R^{18D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{11B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17C}$, $R^{18B}$ and $R^{18C}$ substituents bonded to the same nitrogen atom may optionally be joined to form a substituted or unsubstituted heterocycloalkyl or substituted or unsubstituted heteroaryl. $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$, $X^{12.1}$, $X^{13.1}$, $X^{14.1}$, $X^{15.1}$, $X^{16.1}$, $X^{17.1}$ and $X^{18.1}$ are independently $-Cl$, $-Br$, $-I$ or $-F$. The symbol n1 is 0, 1, 2, 3 or 4. The symbols m1 and v1 are independently 1 or 2.

Provided herein is a composition, comprising a gp130 receptor bound to a binding site 1 gp130 receptor agonist. The binding site 1 gp130 receptor agonist is bound to the binding site 1 of the gp130 receptor.

In aspects, the binding site 1 gp130 receptor agonist of the compositions provided herein is a compound of Formula (III):

(III)

In the binding site 1 gp130 receptor agonist of Formula (III), A is $CR^{14}$ or N. B is $CR^{16}$ or N. X is O, $NR^{19}$ or S. $L^1$ is a bond or substituted or unsubstituted $C_1$-$C_3$ alkylene. $R^8$ is hydrogen, halogen, $-CX^{8.1}_3$, $-CHX^{8.1}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$ is hydrogen, halogen, $-CX^{9.1}_3$, $-CHX^{9.1}_2$, $-CH_2X^{9.1}$, $-CN$, $-SO_{n1}R^{9A}$, $-SO_{v1}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m1}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ is hydrogen, halogen, $-CX^{10.1}_3$, $-CHX^{10.1}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{11}$ is hydrogen, halogen, $-CX^{11.1}_3$, $-CHX^{11.1}_2$, $-CH_2X^{11.1}$, $-CN$, $-SO_{n1}R^{11A}$, $-SO_{v1}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, $-N(O)_{m1}$, $-NR^{11B}R^{11C}$, $-C(O)R^{11D}$, $-C(O)OR^{11D}$, $-C(O)NR^{11B}R^{11C}$, $-OR^{11A}$, $-NR^{11B}SO_2R^{11A}$, $-NR^{11B}C(O)R^{11D}$, $-NR^{11B}C(O)OR^{11D}$, $-NR^{11B}OR^{11D}$, $-OCX^{11.1}_3$, $-OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{12}$ is hydrogen, halogen, $-CX^{12.1}_3$, $-CHX^{12.1}_2$, $-CH_2X^{12.1}$, $-CN$, $-SO_{n1}R^{12A}$, $-SO_{v1}NR^{12B}R^{12C}$, $-NHNR^{12B}R^{12C}$, $-ONR^{12B}R^{12C}$, $-NHC(O)NHNR^{12B}R^{12C}$, $-NHC(O)NR^{12B}R^{12C}$, $-N(O)_{m1}$, $-NR^{12B}R^{12C}$, $-C(O)R^{12D}$, $-C(O)OR^{12D}$, $-C(O)NR^{12B}R^{12C}$, $-OR^{12A}$, $-NR^{12B}SO_2R^{12A}$, $-NR^{12B}C(O)R^{12D}$, $-NR^{12B}C(O)OR^{12D}$, $-NR^{12B}OR^{12D}$, $-OCX^{12.1}_3$, $-OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{13}$ is hydrogen, halogen, $-CX^{13.1}_3$, $-CHX^{13.1}_2$, $-CH_2X^{13.1}$, $-CN$, $-SO_{n1}R^{13A}$, $-SO_{v1}NR^{13B}R^{13C}$, $-NHNR^{13B}R^{13C}$, $-ONR^{13B}R^{13C}$, $-NHC(O)NHNR^{13B}R^{13C}$, $-NHC(O)NR^{13B}R^{13C}$, $-N(O)_{m1}$, $-NR^{13B}R^{13C}$, $-C(O)R^{13D}$, $-C(O)OR^{13D}$, $-C(O)NR^{13B}R^{13C}$, $-OR^{13A}$, $-NR^{13B}SO_2R^{13A}$, $-NR^{13B}C(O)R^{13D}$, $-NR^{13B}C(O)OR^{13D}$, $-NR^{13B}OR^{13D}$, $-OCX^{13.1}_3$, $-OCHX^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{14}$ is hydrogen, halogen, $-CX^{14.1}_3$, $-CHX^{14.1}_2$, $-CH_2X^{14.1}$, $-CN$, $-SO_{n1}R^{14A}$, $-SO_{v1}NR^{14B}R^{14C}$, $-NHNR^{14B}R^{14C}$, $-ONR^{14B}R^{14C}$, $-NHC(O)NHNR^{14B}R^{14C}$, $-NHC(O)NR^{14B}R^{14C}$, $-N(O)_{m1}$, $-NR^{14B}R^{14C}$, $-C(O)R^{14D}$, $-C(O)OR^{14D}$, $-C(O)NR^{14B}R^{14C}$, $-OR^{14A}$, $-NR^{14B}SO_2R^{14A}$, $-NR^{14B}C(O)R^{14D}$, $-NR^{14B}C(O)OR^{14D}$, $-NR^{14B}OR^{14D}$, $-OCX^{14.1}_3$, $-OCHX^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{15}$ is hydrogen, halogen, $-CX^{15.1}_3$, $-CHX^{15.1}_2$, $-CH_2X^{15.1}$, $-CN$, $-SO_{n1}R^{15A}$, $-SO_{v1}NR^{15B}R^{15C}$, $-NHNR^{15B}R^{15C}$, $-ONR^{15B}R^{15C}$, $-NHC(O)NHNR^{15B}R^{15C}$, $-NHC(O)NR^{15B}R^{15C}$, $-N(O)_{m1}$, $-NR^{15B}R^{15C}$, $-C(O)R^{15D}$, $-C(O)OR^{15D}$, $-C(O)NR^{15B}R^{15C}$, $-OR^{15A}$, $-NR^{15B}SO_2R^{15A}$, $-NR^{15B}C(O)R^{15D}$, $-NR^{15B}C(O)OR^{15D}$, $-NR^{15B}OR^{15D}$, $-OCX^{15.1}_3$, $-OCHX^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{16}$ is hydrogen, halogen, $-CX^{16.1}{}_3$, $-CHX^{16.1}{}_2$, $-CH_2X^{16.1}$, $-CN$, $-SO_{n1}R^{16A}$, $-SO_{v1}NR^{16B}R^{16C}$, $-NHNR^{16B}R^{16C}$, $-ONR^{16B}R^{16C}$, $-NHC(O)NHNR^{16B}R^{16C}$, $-NHC(O)NR^{16B}R^{16C}$, $-N(O)_{m1}$, $-NR^{16B}R^{16C}$, $-C(O)R^{16D}$, $-C(O)OR^{16D}$, $-C(O)NR^{16B}R^{16C}$, $-OR^{16A}$, $-NR^{16B}SO_2R^{16A}$, $-NR^{16B}C(O)R^{16D}$, $-NR^{16B}C(O)OR^{16D}$, $-NR^{16B}OR^{16D}$, $-OCX^{16.1}{}_3$, $-OCHX^{16.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{17}$ is hydrogen, halogen, $-CX^{17.1}{}_3$, $-CHX^{17.1}{}_2$, $-CH_2X^{17.1}$, $-CN$, $-SO_{n1}R^{17A}$, $-SO_{v1}NR^{17B}R^{17C}$, $-NHNR^{17B}R^{17C}$, $-ONR^{17B}R^{17C}$, $-NHC(O)NHNR^{17B}R^{17C}$, $-NHC(O)NR^{17B}R^{17C}$, $-N(O)_{m1}$, $-NR^{17B}R^{17C}$, $-C(O)R^{17D}$, $-C(O)OR^{17D}$, $-C(O)NR^{17B}R^{17C}$, $-OR^{17A}$, $-NR^{17B}SO_2R^{17A}$, $-NR^{17B}C(O)R^{17D}$, $-NR^{17B}C(O)OR^{17D}$, $-NR^{17B}OR^{17D}$, $-OCX^{17.1}{}_3$, $-OCHX^{17.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{18}$ is hydrogen, halogen, $-CX^{18.1}{}_3$, $-CHX^{18.1}{}_2$, $-CH_2X^{18.1}$, $-CN$, $-SO_{n1}R^{18A}$, $-SO_{v1}NR^{18B}R^{18C}$, $-NHNR^{18B}R^{18C}$, $-ONR^{18B}R^{18C}$, $-NHC(O)NHNR^{18B}R^{18C}$, $-NHC(O)NR^{18B}R^{18C}$, $-N(O)_{m1}$, $-NR^{18B}R^{18C}$, $-C(O)R^{18D}$, $-C(O)OR^{18D}$, $-C(O)NR^{18B}R^{18C}$, $-OR^{18A}$, $-NR^{18B}SO_2R^{18A}$, $-NR^{18B}C(O)R^{18D}$, $-NR^{18B}C(O)OR^{18D}$, $-NR^{18B}OR^{18D}$, $-OCX^{18.1}{}_3$, $-OCHX^{18.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{19}$ is hydrogen, $-COR^{19D}$, $-C(O)NHNR^{19B}R^{19C}$, $-C(O)OR^{19D}$, $-SO_2R^{19A}$, $C(O)NR^{19B}R^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$ and $R^{18D}$ are independently hydrogen, halogen, $-CF_3$, $-CCl_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{11B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17C}$, $R^{18B}$ and $R^{18C}$ substituents bonded to the same nitrogen atom may optionally be joined to form a substituted or unsubstituted heterocycloalkyl or substituted or unsubstituted heteroaryl. $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$, $X^{12.1}$, $X^{13.1}$, $X^{14.1}$, $X^{15.1}$, $X^{16.1}$, $X^{17.1}$ and $X^{18.1}$ are independently $-Cl$, $-Br$, $-I$ or $-F$. The symbol n1 is 0, 1, 2, 3 or 4. The symbols m1 and v1 are independently 1 or 2.

BRIEF DESCRIPTION OF THE DRAWINGS

FIGS. 1A-1D. Pre-chondrocytes represent a transcriptionally distinct population in developing limbs. (FIG. 1A) Representative image of chondrogenic regions before and after laser capture dissection. Scale bar=100 mm. (FIG. 1B) Unsupervised gene cluster analysis of significantly differentially expressed genes in laser capture microdissected pre-chondrocytes (PC) from a 5-6 week specimen versus total limb cells (TLC) from the same specimen. (FIG. 1C) Cartoon demonstrating principal component analysis. (FIG. 1D) Genes enriched in chondrocyte condensations (pre-chondrocytes) are tabulated.

FIGS. 2A-2D. Definitive resting (immature) chondrocytes at 17 weeks are enriched for components of the LIF signaling pathway. (FIG. 2A) Resting chondrocytes were isolated by dissecting a ~200 mm thick layer of cells from the femoral epiphysis as indicated by the dotted line. (FIG. 2B) Unsupervised clustering of 1222 genes differentially expressed between pre-chondrocytes (PC, 6 independent specimens) and definitive 17 week fetal resting chondrocytes (RC, 3 independent specimens). (FIG. 2C) Principal component analysis performed on all probe sets demonstrated the reproducibility of data between biological replicates. (FIG. 2D) Genes enriched in 17 week fetal resting chondrocytes.

FIGS. 3A-3G. BMPR1B and LIFR delineate resting chondrocytes after de novo chondrogenesis. (FIG. 3A) Developmental dynamics of BMPR1B expression in human chondrocytes. BMPR1B is highly expressed in resting chondrocytes at 8, 12 and 17 weeks of development, but is clearly absent in hypertrophic chondrocytes after 12 weeks. Positive signal is shown in brown color (3, 3'-diaminobenzidine), nuclei counterstained with hematoxylin. (FIG. 3B) LIFR is expressed by resting chondrocytes and not by hypertrophic chondrocytes, while LIF is expressed by both resting chondrocytes and neighboring synovial cells. (FIG. 3C) In postnatal articular cartilage, resting chondrocytes in the superficial zone (negative for Safranin O and Fast Green staining) express both BMPR1B and LIFR, while hypertrophic chondrocytes in the deep zone (positive for Safranin O) are negative for both proteins. (FIG. 3D) Reserve chondrocytes in the growth plate region at the same stage also express BMPR1B and LIFR; hypertrophic chondrocytes are negative. (FIG. 3E) At later adult stages, a subset of BMPR1B+ and LIFR+ cells (arrows) remain in the surface layer of normal articular cartilage from the knee joint, while LIF (FIG. 3F) is minimally secreted by synovial cells. In all panels, positive staining is shown (3, 3'-diaminobenzidine); nuclei counterstained with hematoxylin. Scale bar=50 mM. (FIG. 3G) LIFR+BMPR1B+ cells isolated using FACS from 17 week articular regions evidence enrichment for the chondrocyte progenitor gene SOX9, but express much lower levels of the hypertrophic gene COL10A1 with respect to BMPR1Bneg cells isolated from the same region.

(FIG. 5A) Western blot showing γ-STAT3 and c-MYC levels; Histone 3 is a housekeeping gene. (FIG. 5B) Proliferating, EDU+ cells in cartilage explants. (FIG. 5C) Metabolic profile (Seahorse XF24-3): Oxygen consumption rate (OCR) and extracellular acidification rate (ECAR, reflects the level of lactate production). Oligomycin inhibits mitochondrial oxidative potential. N=3, Mean±SD. (FIG. 5D) Formation of chondrospheres in semisolid cultures; arrows indicate colonies.

FIGS. 8A-8B. FIG. 8A depicts photomicrograph of articular cartilage in 60-year old subject showing BMPR1B+ cells. Boxed section is enlarged in FIG. 8B.

FIGS. 9A-9C. BMPR1B+ cells in fetus are proliferative and produce elevated levels of matrix components compared with adult. FIGS. 9A-9C depict levels of the recited matrix components in fetal (left columns) and adult (right columns) tissue.

(FIG. 10A) Photomicrographs of fetal synovium and cartilage in isotype, LIFR and LIF specimens. (FIG. 10B) Photomicrographs of adult synovium and cartilage in isotype, LIFR and LIF specimens, as indicated. (FIG. 10C) Histogram depicting LIF levels (pg/mL) in fetal (left) and adult (right) tissue. N=3.

(FIG. 12D) Histogram depicting % clonogenic cells (fetal BMPR1B+ chondrocytes) under: control, p-STAT3 and c-MYC inhibitor conditons.

(FIG. 19A) control; (FIG. 19B) LIF (50 ng/mL); (FIG. 19C) CRM-423 (10 uM).

(FIG. 20A) % positive for (left to right): control, BMP4, LIF, CRM-423 1 uM; and CRM-423 10 uM. (FIG. 20B) Clonogenic potential (%) for (left to right): control, LIF, and CRM-A.

(FIG. 21A) cell sorting results for isotype (left), BMPR18$^{neg}$ (middle), and BMPR18+ cells (right). (FIG. 21B) CRM-423 (right panel) stimulates collagen 2 product by adult chondrocytes compared with control (DMSO, left panel).

FIGS. 24A-24D. Compounds disclosed herein were assayed for modulatory effects on p-STAT3 and c-MYC. (FIG. 24A) Stat+/Myc+. (FIG. 24B) Stat−/Myc−. (FIG. 24C) Stat−/Myc+. (FIG. 24D)Stat+/Myc−.

FIGS. 25A-25H. BMPR1B$^+$ articular cartilage cells have distinct molecular and functional signatures at different ontogenetic stages. (FIG. 25A) Sorting strategy to isolate BMPR1B$^+$ cells from human fetal and adult articular cartilage. (FIG. 25B) Hierarchical clustering of RNA-Seq data over all genes; blue indicates stronger positive correlation, while red represents weaker concordance. (FIG. 25C) Selected Gene Ontology (GO) categories derived from differentially expressed genes enriched in fetal cells (p<0.05, >2-fold higher). (FIG. 25D) Heat map depicting average relative gene expression of chondrogenic and mitogenic genes. (FIG. 25E) Selected gene sets enriched in fetal cells as determined by GSEA, with Normalized Enrichment Scores (NES), p values and False Discovery Rates (FDR) shown. (FIG. 25F) Comparison of metabolic activity (Extracellular acidification rate and oxygen consumption rate; ECAR and OCR, respectively) of fetal and adult human articular cartilage cells. ECAR is a measure of glycolytic activity, while OCR is a readout for oxidative phosphorylation. (FIG. 25G) Evaluation of the ability of human fetal and adult articular cartilage cells to transit Millicell membranes. (FIG. 25H) Colony-forming ability of single human fetal and adult articular cartilage cells when plated at low density in Matrigel. Data are represented at mean±SD. See also tables of FIGS. 32A-32B.

(FIG. 26A) Levels of phospho-STAT3 (pSTAT3) and MYC protein were quantitated in human fetal and adult articular chondrocytes relative to histone H3. (FIG. 26B) Effects of soluble LIF receptor (sLIFR) on MYC and pSTAT3 protein levels on fetal articular chondrocytes after 72 hours. (FIG. 26C) Detection of apoptotic cells using TUNEL staining and flow cytometry analysis of fetal articular cartilage explants cultured in the absence (control) or presence of a MYC (10058-F4) or STAT3 (STATTIC) inhibitor for 24 hours. (FIG. 26D) Quantification of proliferating cells via EdU incorporation in fetal articular cartilage explants and also by flow cytometry analysis for BrdU. Scale bars represent 100 μm. (FIG. 26E) Assessment of metabolic activity of human fetal articular chondrocytes cultured in the presence or absence of MYC or STAT3 inhibitors. (FIG. 26F) Migration capacity of fetal articular chondrocytes was assessed using a Transwell® assay in the absence or presence of MYC and STAT3 inhibitors. (FIG. 26G) Protein levels of MYC and pSTAT3 were measured in adult human articular chondrocytes with and without incubation with LIF. Data are shown normalized to histone H3. (FIG. 26H) Migratory capacity of adult human articular chondrocytes in a Transwell® assay measured in the presence or absence of LIF. (FIG. 26I) Single adult human articular chondrocytes were cultured with or without LIF for 5 weeks to allow detection of colony-forming cells. (FIG. 26J) Explants of adult pig articular cartilage were incubated with EdU in the presence or absence of LIF to detect proliferating cells. Scale bars represent 25 µm.

(FIG. 27A) Schematic representation of the high throughput screen performed to identify putative small molecules regulators of chondrocyte differentiation state. Limb mesenchymal cells were isolated from mouse embryos carrying a Col10a1-mCherry transgene. Compounds were considered positive hits if they reduced mCherry signal after induction with pro-differentiation factors. Legend: 2701: Overnight fresh limb digest; 2702: COL10A1:mCherry primary limb mesenchyme; 2703: Culture medium (phenyl red free DMEM/F12, 10% fetal bovine serum, 1% antibiotic, w/BMP-4 at 10 ng/mL); %-positive cell scoring programs computes % viable cells expressing mCherry by DAPI and Cy3 signal overlap; 2704: increase in mCherry signal; 2705: negative control; 2706: decrease in mCherry signal. (FIG. 27B) Quantitation of top 75 positive hits.

FIGS. 28A-28I. Small molecule-mediated activation of a fetal-like molecular and functional phenotype in adult articular cartilage. (FIG. 28A) Adult human articular chondrocytes were incubated with or without RCGD 423 and levels of MYC and pSTAT3 were quantified relative to histone H3. (FIG. 28B) Levels of MYC and pSTAT3 protein were measured in pig adult articular chondrocytes to determine the effects of RCGD 423 in a dose- and time-dependent manner; histone H3 was used as a loading control. (FIG. 28C) Migration of adult human articular chondrocytes in a Transwell® assay was assessed in the presence and absence of RCGD 423. (FIG. 28D) Adult human articular chondrocytes were incubated with or without RCGD 423 in hydrogel for 24 hours and then apoptotic cells were quantitated via flow cytometry for Annexin V. (FIG. 28E) Single human adult articular chondrocytes were cultured for 5 weeks with or without stimulation with RCGD 423. (FIG. 28F) Proliferation in explants of adult pig articular cartilage in the absence or presence of RCGD 423 as shown by EdU incorporation. Explants of adult pig articular cartilage were incubated with EdU in the presence or absence of LIF to detect proliferating cells. Scale bars represent 25 µm. (FIG. 28G) Metabolic activity of human adult articular chondrocytes (ECAR and OCR) was assessed in the presence or absence of RCGD 423; the response in these parameters to stimulation with LIF is shown for comparison. (FIG. 28H) Seven samples of human adult articular chondrocytes were cultured with or without RCGD 423 and then subjected to RNA-Seq. Genes that were significantly enriched in 4/7 drug-treated samples (annotated with "D") when compared to their untreated controls were analyzed using GO. Selected categories and their respective p values are shown. (FIG. 28I) Heat map depicting the 31 genes in the "M phase" GO category. Relative expression for all 14 matched samples are shown.

FIGS. 29A-29C. RCGD 423 acts through a mechanism similar to LIF. (FIG. 29A) Levels of MYC and pSTAT3 protein were measured in adult pig articular chondrocytes in the presence or absence of LIF and JAK or gp130 inhibitors. Histone H3 was used as a loading control. (FIG. 29B) Adult pig articular chondrocytes were cultured in the presence of the indicated combinations of RCGD 423, JAK and/or gp130 inhibitors and the levels of MYC and pSTAT3 proteins were quantitated relative to histone H3. (FIG. 29C) Predicted binding sites 1 and 2 in the extracellular domains 1-3 (C) and 4-6 (D) of gp130. The structure of the indicated gp130 domains is shown in ribbon diagram representation (left) as well as with electrostatic potential mapped on to the molecular surface (right). RCGD 423 and gp130 residues within 4 Å surrounding it are shown in stick representation in the expanded views. The electrostatic potential surfaces are drawn at ±3 kT/e. D1, domain 1; FNIII, fibronectin type-III. Data are represented at mean±SD.

FIGS. 30A-30B. RCGD 423 does not promote catabolism. (FIG. 30A) Adult pig articular chondrocytes were cultured for 24 hours with the indicated cytokines or RCGD 423 and the levels of pSTAT3 and MYC were measured with respect to histone H3. Representative data for other proteins in the MAPK (p38 and MEK1/2), AKT (phospho-AKT; pAKT) or NF-KB (NF-KB p65) are also shown. (FIG. 30B) Levels of transcription of genes indicative of a catabolic response were determined via quantitative PCR in adult pig articular chondrocytes treated with OSM, IL-6, TNF-α, LIF or RCGD 423. Data are represented at mean±SD.

(FIG. 31A) Experiments were conducted to test the tissue reparative function of compounds disclosed herein. FIG. 31A depicts histograms of amounts of glycosaminoglycans (GAGs) and collagen 2 observed under control conditions and after administration of RCGD 423. (FIG. 31B) The duration of the effects elicited by RCGD 423 was determined by applying the drug for 24 hours and then washing it out. Protein levels of pSTAT3 and MYC were determined at the indicated time points after wash out; histone H3 was used as a loading control. (FIG. 31C) Protein levels of MYC and pSTAT3 in adult pig articular chondrocytes were used to determine the time frame in which release of RCGD 423 from PLGA microspheres reaches efficacious levels. Supernatant from drug-loaded PLGA microspheres was harvested at the indicated intervals and applied to pig chondrocytes. Histone H3 was used as a loading control. (FIG. 31D) Repair in a tissue context was assessed by removing small explants from a biopsy punch of adult pig articular cartilage. Matrigel with or without RCGD 423-loaded microspheres was applied to the defects. Safranin O staining was performed on sections of explants following 5 weeks of culture; border of defect and intact tissue is shown.

FIGS. 32A-32B. Adult Human BMPR1B+ Articular Chondrocytes Evidence a Heightened Inflammatory Response Coupled with Reduced Proliferation and Migration. When compared to fetal BMPR1B+ chondrocytes at the transcriptional level, Gene Ontology (GO; FIG. 32A) and Gene Set Enrichment Analysis (GSEA; FIG. 32B) revealed that cells isolated from healthy adult cartilage are enriched for genes that promote cell adhesion and repress proliferation. Additionally, a strong signature of an inflammatory response is present.

(FIG. 34A) Sorting of adult human articular cartilage yields multiple populations, including BMPR1B$^+$LIFR$^+$ chondrocytes that are negative for CD34. (FIG. 34B) Compared to other cartilage populations, these cells express significantly increased levels of the cartilage matrix proteins aggrecan (ACAN) and collagen II (COL2A1).

DETAILED DESCRIPTION OF THE INVENTION

I. Definitions

Figure 1B:
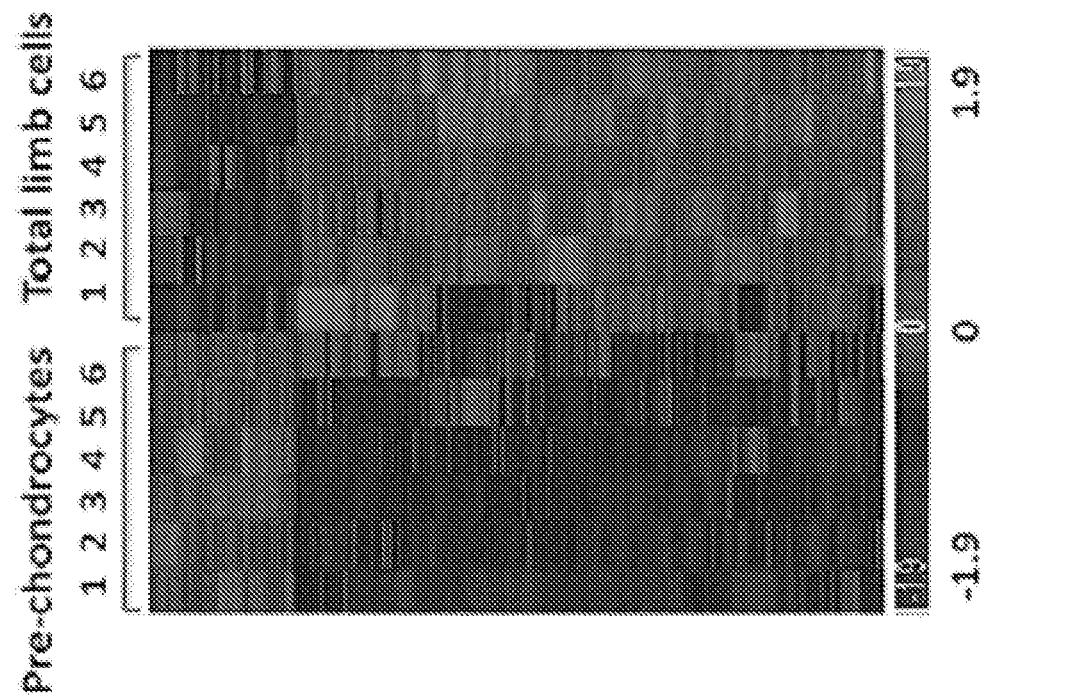

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., C$_1$-C$_{10}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, S, Se and Si, and wherein the nitrogen, selenium, and sulfur atoms may optionally be oxidized, and the nitrogen heteroatom may optionally be quaternized. Heteroalkyl is not cyclized. The heteroatom(s) O, N, P, S, Se, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two heteroatoms may be consecutive, such as, for example, —CH$_2$—NH—OCH$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SeR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (e.g. 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms (e.g. N, O, or S), wherein sulfur heteroatoms are optionally oxidized, and the nitrogen heteroatoms are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

The term "alkylsulfonyl," as used herein, means a moiety having the formula —S($O_2$)—R', where R' is an alkyl group as defined above. R' may have a specified number of carbons (e.g., "$C_1$-$C_4$ alkylsulfonyl").

The term "oxy" as used herein, alone or in combination, refers to —O—.

The term "aryloxy" as used herein, alone or in combination, refers to a substituted or unsubstitued aryl group attached to the parent molecular moiety through an oxy i.e. an ether group. An example of an unsubstituted aryl ether group is phenoxy (i.e. $C_6H_5O$—).

The term "heteroaryloxy" as used herein, alone or in combination, refers to a substituted or unsubstitued heteroaryl group attached to the parent molecular moiety through an oxy i.e. a heteroaryl ether group. An example of an unsubstituted heteroaryl ether group is thiophenyl (i.e. $C_4H_3SO$—).

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"', —NR—C(NR'R")=NR'", —S(O)R', —S(O)$_2$R', —S(O)$_2$NR'R", —NRS$O_2$R', —CN, and —$NO_2$ in a number ranging from zero to (2 m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"', and R" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R"', and R" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"')$_d$—, where s and d are independently integers of from 0 to 3, and X' is —O—, —S—, —S(O)—, —S(O)$_2$—, or —S(O)$_2$NR'—. The substituents R, R', R", and R"' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, and each substituted or unsubstituted heterocycloalkyl is a substituted or unsubstituted 3 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, and/or each substituted or unsubstituted heterocycloalkylene is a substituted or unsubstituted 3 to 7 membered heterocycloalkylene.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)-for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

The term "about" in the context of a numerical value means, unless indicated otherwise, the nominal numerical value ±10% thereof.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "$\sim\!\!\sim$" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished for example as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

A "nitrile" refers to a organic compound having a —CN group.

A "protected secondary amine" refers to the covalent attachment of a monovalent chemical moiety to an amine nitrogen atom that functions to prevent the amine moiety from reacting with reagents used in the chemical synthetic methods described herein (commonly referred to as "protecting" the amine group) and may be removed under conditions that do not substantially degrade the molecule of which the amine moiety forms a part (commonly referred to as "deprotecting" the amine group) thereby yielding a free amine. An amine protecting group can be acid labile, base labile, or labile in the presence of other reagents. Amine protecting groups include but are not limited to: carbamates (such as -carbobenzyloxy (Cbz), -t-butoxycarbonyl (t-Boc), -fluorenylmethyloxycarbonyl (Fmoc), and -allyl carbamates), -benzyl, -4-methoxyphenyl, or -2,4-dimethoxyphenyl.

In some embodiments, the compound is a chemical species set forth in the Examples section or figures.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The terms "contacting" and "reacting" are used synonymously and may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

A "binding site 1 gp130 receptor agonist," as used herein is a compound (e.g. a biomolecule or synthetic chemical molecule (e.g. a small molecule)) capable of binding to the binding site 1 of the gp130 receptor and increasing gp130 activity or function. The binding site 1 gp130 receptor agonist is specifically designed to fit within the binding site 1 of the gp130 receptor and make contact with amino acids residing on the surface of the binding site 1 of the gp130 receptor. In embodiments, the compound is a synthetic chemical molecule designed, according to the disclosure provided herein, to bind to the binding site 1 gp130 receptor. In embodiments, the synthetic chemical molecule is a small molecule (a low molecular weight (<900 daltons) organic compound). In embodiments, the binding site 1 gp130 receptor agonist is a biomolecule. In embodiments, the biomolecule is an antibody or functional fragment thereof designed, according to the disclosure provided herein, to bind to the binding site 1 of the gp130 receptor.

Figure 29A:
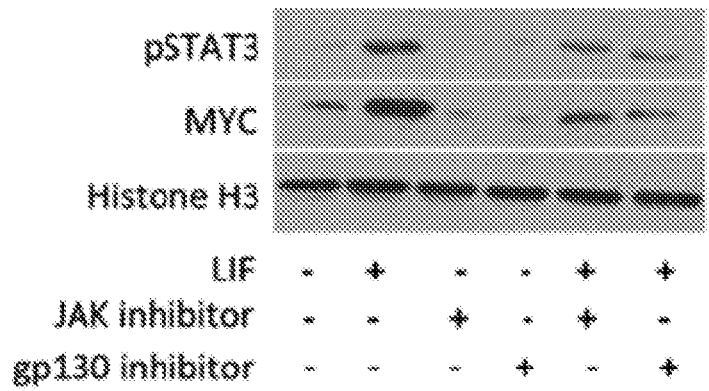

The "binding site 1" of the gp130 receptor, or "binding site 1 gp 130 receptor" is a binding pocket within the gp 130 receptor. The sequence for the gp130 receptor is set forth in SEQ ID NO:1. The sequence for the binding site 1 of the gp130 receptor is set forth in SEQ ID NO:2 and SEQ ID NO:3 and includes amino acids corresponding to positions 173, 174, 175 and 176 in gp130 or amino acid residues KAKR as set forth in SEQ ID NO:4. An amino acid residue in a protein or receptor "corresponds" to a given residue when it occupies the same essential structural position within the protein or receptor as the given residue, for example, in homologous proteins that may have a different numbering convention. The binding site 1 of the gp130 receptor is shown in FIG. 29C. The amino acid residues and fragments of gp130 disclosed herein are referred to as corresponding to the entire (918 amino acid) length of gp130 and/or gp130 without the signaling fragment that is 22 amino acid residues in length (e.g, KAKR as set forth in SEQ ID NO:4 is referred to herein as corresponding to positions 173, 174, 175 and 176 and/or positions 151, 152, 153 and 154 in gp130).

As used herein, "biomolecule" is used in its customary sense and refers to a molecule that is present in living organisms and synthetic derivatives thereof, including macromolecules such as proteins, carbohydrates, lipids, and nucleic acids, as well as small molecules such as primary metabolites, secondary metabolites, and natural products. A biomolecule includes but is not limited to nucleic acids (e.g. DNA and RNA), peptide nucleic acids, sugars, peptides, proteins, antibodies, lipids, small molecule affinity ligands e.g. inhibitors, biotin and haptens.

The terms "gp130 receptor," "gp130," gp130 protein," "IL6ST receptor," "IL6ST" or "IL6ST protein" are here used interchangeably and according to their common, ordinary meaning (e.g., transmembrane protein "glycoprotein 130") and refer to proteins of the same or similar names and functional fragments and homologs thereof. The term includes any recombinant or naturally occurring form of, or variants thereof that maintain gp130 activity (e.g. within at least 30%, 40%, 50%, 60%, 70%, 80%, 90%, 95%, or 100% activity compared to gp130). In embodiments, the gp 130 receptor has at least 80%, 85%, 90%, 95%, 96%, 97%, 98%, 99% or 100% sequence identity to SEQ ID NO:1 or a functional fragment thereof (e.g. 700 contiguous amino acids of SEQ ID NO:1, 750 contiguous amino acids of SEQ ID NO:1, 800 contiguous amino acids of SEQ ID NO:1, 850 contiguous amino acids of SEQ ID NO:1 870 contiguous amino acids of SEQ ID NO:1, 880 contiguous amino acids of SEQ ID NO:1, 890 contiguous amino acids of SEQ ID NO:1, 900 contiguous amino acids of SEQ ID NO:1 or 910 contiguous amino acids of SEQ ID NO:1).

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein include those compounds that readily undergo chemical or enzymatic changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "treating", or "treatment" refer to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; or improving a patient's physical or mental well-being. The treatment or amelioration of symptoms can be based on objective or subjective parameters, including the results of a physical examination, neuropsychiatric exams, and/or a psychiatric evaluation. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In embodiments, a control is the measurement of the activity of a protein in the absence of a compound as described herein (including embodiments and examples).

As defined herein, the term "activation," "activate," "activating" and the like in reference to a protein-activator interaction means positively affecting (e.g. increasing) the activity or function of the protein relative to the activity or function of the protein in the absence of the activator. Activation may refer to reduction of a disease or symptoms of disease. Activation may refer to an increase in the activity of a particular protein or nucleic acid target. The protein may be gp130. Thus, activation includes, at least in part, partially or totally increasing stimulation, increasing, promoting, or expediting activation, or activating, sensitizing, or up-regulating signal transduction or enzymatic activity or the amount of a protein.

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, a modulator of a target protein changes by increasing or decreasing a property or function of the target molecule or the amount of the target molecule. A modulator of a disease decreases a symptom, cause, or characteristic of the targeted disease.

"Selective" or "selectivity" or the like of a compound refers to the compound's ability to discriminate between molecular targets. "Specific", "specifically", "specificity", or the like of a compound refers to the compound's ability to cause a particular action, such as inhibition, to a particular molecular target with minimal or no action to other proteins in the cell.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

The compounds described herein can be used in combination with one another, with other active drugs known to be useful in treating a disease (e.g. joint surface injury, arthritis or cartilage degenerative disease) or with adjunctive agents that may not be effective alone, but may contribute to the efficacy of the active agent. Thus, the compounds described herein may be co-administered with one another or with other active drugs known to be useful in treating a disease.

By "co-administer" it is meant that a compound described herein is administered at the same time, just prior to, or just after the administration of one or more additional therapies, for example, an anti-cartilage degenerative agent as described herein. The compounds described herein can be administered alone or can be co-administered to the patient. Co-administration is meant to include simultaneous or sequential administration of the compound individually or in combination (more than one compound or agent). Thus, the preparations can also be combined, when desired, with other active substances (e.g. anti-cartilage degenerative or anti-arthritic agents).

Co-administration includes administering one active agent (e.g. a complex described herein) within 0.5, 1, 2, 4, 6, 8, 10, 12, 16, 20, or 24 hours of a second active agent (e.g. anti-cartilage degenerative agents). Also contemplated herein, are embodiments, where co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. In other embodiments, the active agents can be formulated separately. The active and/or adjunctive agents may be linked or conjugated to one another. The compounds described herein may be combined with treatments for cartilage degenerative disorders.

The term "associated" or "associated with" in the context of a substance or substance activity or function associated with a disease means that the disease is caused by (in whole or in part), a symptom of the disease is caused by (in whole or in part) the substance or substance activity or function, or a side-effect of the compound (e.g. toxicity) is caused by (in whole or in part) the substance or substance activity or function.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein. Disease as used herein may refer to cartilage degenerative disease, joint surface injury or arthritis.

The term "linker" as described herein is a divalent chemical group that covalently joins one chemical moiety to another. Specific examples of linkers are described herein. Linkers may be polyethylene (PEG) linkers or bioconjugate linkers.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers nucleic acids that have the same basic chemical structure as naturally occurring nucleic acids. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but functions in a manner similar to a naturally occurring nucleic acid. Examples of such analogues include, without limitation, phosphorothioates, phosphoramidates, methyl phosphonates, chiral-methyl phosphonates, 2-O-methyl ribonucleotides, and peptide-nucleic acids (PNAs).

As used herein, the term "proliferative program" and the like refer to the ability of a cell to proliferate. In embodiments, cell proliferation requires production of collagen. The term "activating compound" and the like refer to compounds disclosed herein having the ability to increase expression of p-STAT3 and c-Myc in a competent adult chondrocyte.

I. Compositions

Provided herein are compounds of structural of Formula (I):

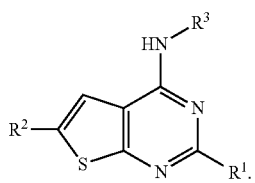

With reference to Formula (I), $R^1$ is substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl; $R^2$ is substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl; and, $R^3$ is substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

In embodiments, the compound of Formula (I) has the structure following:

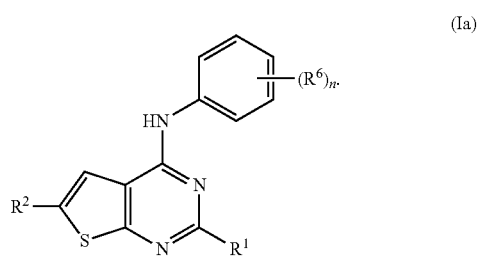

Regarding Formula (Ia), n is an integer in the range 0 to 5, and $R^6$ at each occurrence is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl. In embodiments, $R^6$ is unsubstituted alkyl, unsubstituted cycloalkyl, unsubstituted heteroalkyl, unsubstituted heterocycloalkyl, unsubstituted aryl, or unsubstituted heteroaryl. In embodiments, $R^6$ is substituted alkyl, substituted cycloalkyl, substituted heteroalkyl, substituted heterocycloalkyl, substituted aryl, or substituted heteroaryl. In embodiments, $R^6$ is unsubstituted phenyl. In embodiments, $R^6$ is phenyl substituted with substituted or unsubstituted alkyl, substituted or unsubstituted lower alkyl, —$NH_2$, halogen, —COOH or substituted or unsubstituted heteroaryl.

In embodiments, the activating compound has the structure of Formula (I) following:

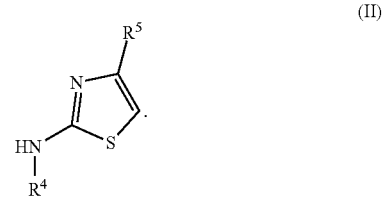

With reference to Formula (II), $R^4$ is substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl; and, $R^5$ is substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

In embodiments, the compound of Formula (II) as the structure following:

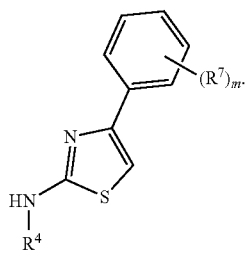

(IIa)

Regarding Formula (IIa), m is an integer in the range 0 to 5, and $R^7$ at each occurrence is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl. In embodiments, $R^7$ is unsubstituted alkyl, unsubstituted cycloalkyl, unsubstituted heteroalkyl, unsubstituted heterocycloalkyl, unsubstituted aryl, or unsubstituted heteroaryl. In embodiments, $R^7$ is substituted alkyl, substituted cycloalkyl, substituted heteroalkyl, substituted heterocycloalkyl, substituted aryl, or substituted heteroaryl.

In another aspect, there is provided a compound of Formula (III):

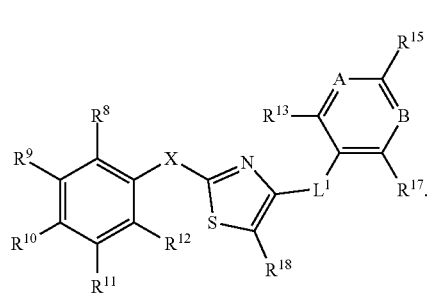

(III)

A is $CR^{14}$ or N. B is $CR^{16}$ or N. X is O, $NR^{19}$ or S. $L^1$ is a bond or substituted or unsubstituted $C_1$-$C_3$ alkylene.

$R^8$ is hydrogen, halogen, —$CX^{8.1}_3$, —$CHX^{8.1}_2$, —$CH_2X^{8.1}$, —CN, —$SO_{n1}R^{8A}$, —$SO_{v1}NR^{8B}R^{8C}$, —$NHNR^{8B}R^{8C}$, —$ONR^{8B}R^{8C}$, —NHC(O)$NHNR^{8B}R^{8C}$, —NHC(O)$NR^{8B}R^{8C}$, —$N(O)_{m1}$, —$NR^{8B}R^{8C}$, —C(O)$R^{8D}$, —C(O)$OR^{8D}$, —C(O)$NR^{8B}R^{8C}$, —$OR^{8A}$, —$NR^{8B}SO_2R^{8A}$, —$NR^{8B}C(O)R^{8D}$, —$NR^{8B}C(O)OR^{8D}$, —$NR^{8B}OR^{8D}$, —$OCX^{8.1}_3$, —$OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^9$ is hydrogen, halogen, —$CX^{9.1}_3$, —$CHX^{9.1}_2$, —$CH_2X^{9.1}$, —CN, —$SO_{n1}R^{9A}$, —$SO_{v1}NR^{9B}R^{9C}$, —$NHNR^{9B}R^{9C}$, —$ONR^{9B}R^{9C}$, —NHC(O)$NHNR^{9B}R^{9C}$, —NHC(O)$NR^{9B}R^{9C}$, —$N(O)_{m1}$, —$NR^{9B}R^{9C}$, —C(O)$R^{9D}$, —C(O)$OR^{9D}$, —C(O)$NR^{9B}R^{9C}$, —$OR^{9A}$, —$NR^{9B}SO_2R^{9A}$, —$NR^{9B}C(O)R^{9D}$, —$NR^{9B}C(O)OR^{9D}$, —$NR^{9B}OR^{9D}$, —$OCX^{9.1}_3$, —$OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{10}$ is hydrogen, halogen, —$CX^{10.1}_3$, —$CHX^{10.1}_2$, —$CH_2X^{10.1}$, —CN, —$SO_{n1}R^{10A}$, —$SO_{v1}NR^{10B}R^{10C}$, —$NHNR^{10B}R^{10C}$, —$ONR^{10B}R^{10C}$, —NHC(O)$NHNR^{10B}R^{10C}$, —NHC(O)$NR^{10B}R^{10C}$, —$N(O)_{m1}$, —$NR^{10B}R^{10C}$, —C(O)$R^{10D}$, —C(O)$OR^{10D}$, —C(O)$NR^{10B}R^{10C}$, —$OR^{10A}$, —$NR^{10B}SO_2R^{10A}$, —$NR^{10B}C(O)R^{10D}$, —$NR^{10B}C(O)OR^{10D}$, —$NR^{10B}OR^{10D}$, —$OCX^{10.1}_3$, —$OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{11}$ is hydrogen, halogen, —$CX^{11.1}_3$, —$CHX^{11.1}_2$, —$CH_2X^{11.1}$, —CN, —$SO_{n1}R^{11A}$, —$SO_{v1}NR^{11B}R^{11C}$, —$NHNR^{11B}R^{11C}$, —$ONR^{11B}R^{11C}$, —NHC(O)$NHNR^{11B}R^{11C}$, —NHC(O)$NR^{11B}R^{11C}$, —$N(O)_{m1}$, —$NR^{11B}R^{11C}$, —C(O)$R^{11D}$, —C(O)$OR^{11D}$, —C(O)$NR^{11B}R^{11C}$, —$OR^{11A}$, —$NR^{11B}SO_2R^{11A}$, —$NR^{11B}C(O)R^{11D}$, —$NR^{11B}C(O)OR^{11D}$, —$NR^{11B}OR^{11D}$, —$OCX^{11.1}_3$, —$OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{12}$ is hydrogen, halogen, —$CX^{12.1}_3$, —$CHX^{12.1}_2$, —$CH_2X^{12.1}$, —CN, —$SO_{n1}R^{12A}$, —$SO_{v1}NR^{12B}R^{12C}$, —$NHNR^{12B}R^{12C}$, —$ONR^{12B}R^{12C}$, —NHC(O)$NHNR^{12B}R^{12C}$, —NHC(O)$NR^{12B}R^{12C}$, —$N(O)_{m1}$, —$NR^{12B}R^{12C}$, —C(O)$R^{12D}$, —C(O)$OR^{12D}$, —C(O)$NR^{12B}R^{12C}$, —$OR^{12A}$, —$NR^{12B}SO_2R^{12A}$, —$NR^{12B}C(O)R^{12D}$, —$NR^{12B}C(O)OR^{12D}$, —$NR^{12B}OR^{12D}$, —$OCX^{12.1}_3$, —$OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{13}$ is hydrogen, halogen, —$CX^{13.1}_3$, —$CHX^{13.1}_2$, —$CH_2X^{13.1}$, —CN, —$SO_{n1}R^{13A}$, —$SO_{v1}NR^{13B}R^{13C}$, —$NHNR^{13B}R^{13C}$, —$ONR^{13B}R^{13C}$, —NHC(O)$NHNR^{13B}R^{13C}$, —NHC(O)$NR^{13B}R^{13C}$, —$N(O)_{m1}$, —$NR^{13B}R^{13C}$, —C(O)$R^{13D}$, —C(O)$OR^{13D}$, —C(O)$NR^{13B}R^{13C}$, —$OR^{13A}$, —$NR^{13B}SO_2R^{13A}$, —$NR^{13B}C(O)R^{13D}$, —$NR^{13B}C(O)OR^{13D}$, —$NR^{13B}OR^{13D}$, —$OCX^{13.1}_3$, —$OCHX^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{14}$ is hydrogen, halogen, —$CX^{14.1}_3$, —$CHX^{14.1}_2$, —$CH_2X^{14.1}$, —CN, —$SO_{n1}R^{14A}$, —$SO_{v1}NR^{14B}R^{14C}$, —$NHNR^{14B}R^{14C}$, —$ONR^{14B}R^{14C}$, —NHC(O)$NHNR^{14B}R^{14C}$, —NHC(O)$NR^{14B}R^{14C}$, —$N(O)_{m1}$, —$NR^{14B}R^{14C}$, —C(O)$R^{14D}$, —C(O)$OR^{14D}$, —C(O)$NR^{14B}R^{14C}$, —$OR^{14A}$, —$NR^{14B}SO_2R^{14A}$, —$NR^{14B}C(O)R^{14D}$, —$NR^{14B}C(O)OR^{14D}$, —$NR^{14B}OR^{14D}$, —$OCX^{14.1}_3$, —$OCHX^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{15}$ is hydrogen, halogen, —$CX^{15.1}_3$, —$CHX^{15.1}_2$, —$CH_2X^{15.1}$, —CN, —$SO_{n1}R^{15A}$, —$SO_{v1}NR^{15B}R^{15C}$, —$NHNR^{15B}R^{15C}$, —$ONR^{15B}R^{15C}$, —NHC(O) $NHNR^{15B}R^{15C}$, —NHC(O)$NR^{15B}R^{15C}$, —$N(O)_{m1}$, —NR$^{15B}$R$^{15C}$, —C(O)R$^{15D}$, —C(O)OR$^{15D}$, —C(O)NR$^{15B}$R$^{15C}$, —OR$^{15A}$, —NR$^{15B}$SO$_2$R$^{15A}$, —NR$^{15B}$C(O)R$^{15D}$, —NR$^{15B}$C(O)OR$^{15D}$, —NR$^{15B}$OR$^{15D}$, —OCX$^{15.1}_3$, —OCHX$^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{16}$ is hydrogen, halogen, —CX$^{16.1}_3$, —CHX$^{16.1}_2$, —CH$_2$X$^{16.1}$, —CN, —SO$_{n1}$R$^{16A}$, —SO$_{v1}$NR$^{16B}$R$^{16C}$, —NHNR$^{16B}$R$^{16C}$, —ONR$^{16B}$R$^{16C}$, —NHC(O)NHNR$^{16B}$R$^{16C}$, —NHC(O)NR$^{16B}$R$^{16C}$, —N(O)$_{m1}$, —NR$^{16B}$R$^{16C}$, —C(O)R$^{16D}$, —C(O)OR$^{16D}$, —C(O)NR$^{16B}$R$^{16C}$, —OR$^{16A}$, —NR$^{16B}$SO$_2$R$^{16A}$, —NR$^{16B}$C(O)R$^{16D}$, —NR$^{16B}$C(O)OR$^{16D}$, —NR$^{16B}$OR$^{16D}$, —OCX$^{16.1}_3$, —OCHX$^{16.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{17}$ is hydrogen, halogen, —CX$^{17.1}_3$, —CHX$^{17.1}_2$, —CH$_2$X$^{17.1}$, —CN, —SO$_{n1}$R$^{17A}$, —SO$_{v1}$NR$^{17B}$R$^{17C}$, —NHNR$^{17B}$R$^{17C}$, —ONR$^{17B}$R$^{17C}$, —NHC(O)NHNR$^{17B}$R$^{17C}$, —NHC(O)NR$^{17B}$R$^{17C}$, —N(O)$_{m1}$, —NR$^{17B}$R$^{17C}$, —C(O)R$^{17D}$, —C(O)OR$^{17D}$, —C(O)NR$^{17B}$R$^{17C}$, —OR$^{17A}$, —NR$^{17B}$SO$_2$R$^{17A}$, —NR$^{17B}$C(O)R$^{17D}$, —NR$^{17B}$C(O)OR$^{17D}$, —NR$^{17B}$OR$^{17D}$, —OCX$^{17.1}_3$, —OCHX$^{17.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{18}$ is hydrogen, halogen, —CX$^{18.1}_3$, —CHX$^{18.1}_2$, —CH$_2$X$^{18.1}$, —CN, —SO$_{n1}$R$^{18A}$, —SO$_{v1}$NR$^{18B}$R$^{18C}$, —NHNR$^{18B}$R$^{18C}$, —ONR$^{18B}$R$^{18C}$, —NHC(O)NHNR$^{18B}$R$^{18C}$, —NHC(O)NR$^{18B}$R$^{18C}$, —N(O)$_{m1}$, —NR$^{18B}$R$^{18C}$, —C(O)R$^{18D}$, —C(O)OR$^{18D}$, —C(O)NR$^{18B}$R$^{18C}$, —OR$^{18A}$, —NR$^{18B}$SO$_2$R$^{18A}$, —NR$^{18B}$C(O)R$^{18D}$, —NR$^{18B}$C(O)OR$^{18D}$, —NR$^{18B}$OR$^{18D}$, —OCX$^{18.1}_3$, —OCHX$^{18.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{19}$ is hydrogen, —COR$^{19D}$, —C(O)NHNR$^{19B}$R$^{19C}$, —C(O)OR$^{19D}$, —SO$_2$R$^{19A}$, C(O)NR$^{19B}$R$^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{11A}$, R$^{11B}$, R$^{11C}$, R$^{11D}$, R$^{12A}$, R$^{12B}$, R$^{12C}$, R$^{12D}$, R$^{13A}$, R$^{13B}$, R$^{13C}$, R$^{13D}$, R$^{14A}$, R$^{14B}$, R$^{14C}$, R$^{14D}$, R$^{15A}$, R$^{15B}$, R$^{15C}$, R$^{15D}$, R$^{16A}$, R$^{16B}$, R$^{16C}$, R$^{16D}$, R$^{17A}$, R$^{17B}$, R$^{17C}$, R$^{17D}$, R$^{18A}$, R$^{18B}$, R$^{15C}$ and R$^{18D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R$^{1B}$, R$^{1C}$, R$^{2B}$, R$^{2C}$, R$^{3B}$, R$^{3C}$, R$^{4B}$, R$^{4C}$, R$^{5B}$, R$^{5C}$, R$^{6B}$, R$^{6C}$, R$^{7B}$, R$^{7C}$, R$^{8B}$, R$^{8C}$, R$^{9B}$, R$^{9C}$, R$^{10B}$, R$^{10C}$, R$^{11B}$, R$^{11C}$, R$^{12B}$, R$^{12C}$, R$^{13B}$, R$^{13C}$, R$^{14B}$, R$^{14C}$, R$^{15B}$, R$^{15C}$, R$^{16B}$, R$^{16C}$, R$^{17B}$, R$^{17C}$, R$^{18B}$ and R$^{18C}$ substituents bonded to the same nitrogen atom may optionally be joined to form a substituted or unsubstituted heterocycloalkyl or substituted or unsubstituted heteroaryl.

X$^{1.1}$, X$^{2.1}$, X$^{3.1}$, X$^{4.1}$, X$^{5.1}$, X$^{6.1}$, X$^{7.1}$, X$^{8.1}$, X$^{9.1}$, X$^{10.1}$, X$^{11.1}$, X$^{12.1}$, X$^{13.1}$, X$^{14.1}$, X$^{15.1}$, X$^{16.1}$, X$^{17.1}$ and X$^{18.1}$ are independently —Cl, —Br, —I or —F. The symbol n1 is 0, 1, 2, 3 or 4. The symbols m1 and v1 are independently 1 or 2.

In embodiments, when A is CR$^{14}$; B is CR$^{16}$; L$^1$ is bond; and R$^8$, R$^9$, R$^{11}$, R$^{12}$, R$^{13}$, R$^{14}$, R$^{15}$, R$^{16}$, R$^{17}$, R$^{18}$ and R$^{19}$ are independently hydrogen, then R$^{10}$ is not bromine. In embodiments, L$^1$ is a bond. In embodiments, X is NH. In embodiments, A is CR$^{14}$. In embodiments, A is N. In embodiments, B is CR$^{16}$. In embodiments, B is N.

In embodiments, the compound has Formula (IIIa):

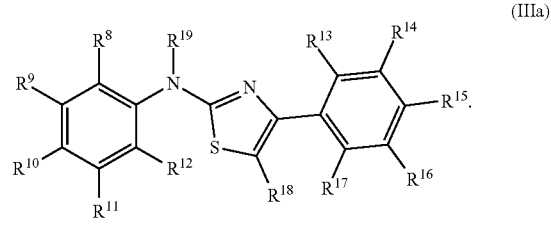

(IIIa)

n1, m1, v1, R$^8$, R$^9$, R$^{10}$, R$^{11}$, R$^{12}$, R$^{13}$, R$^{14}$, R$^{15}$, R$^{16}$, R$^{17}$, R$^{18}$ and R$^{19}$ are as described herein. In embodiments, R$^{14}$ is hydrogen. In embodiments, R$^{16}$ is hydrogen.

In embodiments, the compound has Formula (IIIb):

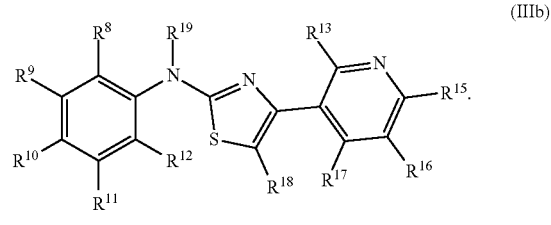

(IIIb)

n1, m1, v1, R$^8$, R$^9$, R$^{10}$, R$^{11}$, R$^{12}$, R$^{13}$, R$^{15}$, R$^{16}$, R$^{17}$, R$^{18}$ and R$^{19}$ are as described herein.

In embodiments, the compound has Formula (IIIc):

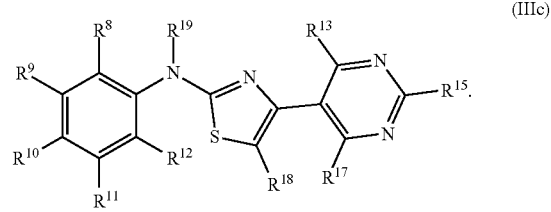

(IIIc)

n1, m1, v1, R$^8$, R$^9$, R$^{10}$, R$^{11}$, R$^{12}$, R$^{13}$, R$^{15}$, R$^{17}$, R$^{18}$ and R$^{19}$ are as described herein.

In embodiments, $R^{13}$, $R^{15}$ and $R^{17}$ are independently hydrogen. In embodiments, $R^8$, $R^9$, $R^{11}$ and $R^{12}$ are independently hydrogen. In embodiments, $R^{18}$ is hydrogen. In embodiments, $R^{19}$ is hydrogen. In embodiments, $R^{10}$ is fluorine, chlorine or iodine, $-CX^{10.1}{}_3$, $-CHX^{10.1}{}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}{}_3$, $-OCHX^{10.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{10}$ is fluorine, chlorine, bromine or iodine. In embodiments, $R^{10}$ is fluorine, chlorine or iodine. In embodiments, $R^{10}$ is fluorine. In embodiments, $R^8$, $R^9$, $R^{11}$, $R^{12}$, $R^{13}$, $R^{15}$, $R^{17}$, $R^{18}$ and $R^{19}$ are independently hydrogen.

In embodiments, $R^8$ is independently hydrogen, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $R^{8E}$-substituted or unsubstituted alkyl, $R^{8E}$-substituted or unsubstituted heteroalkyl, $R^{8E}$-substituted or unsubstituted cycloalkyl, $R^{8E}$-substituted or unsubstituted heterocycloalkyl, $R^{8E}$-substituted or unsubstituted aryl, or $R^{8E}$-substituted or unsubstituted heteroaryl. In embodiments, $R^8$ is independently hydrogen, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $R^{8E}$-substituted or unsubstituted $C_1$-$C_6$ alkyl, $R^{8E}$-substituted or unsubstituted 2 to 6 membered heteroalkyl, $R^{8E}$-substituted or unsubstituted $C_3$-$C_6$ cycloalkyl, $R^{8E}$-substituted or unsubstituted 3 to 6 membered heterocycloalkyl, $R^{8E}$-substituted or unsubstituted phenyl, or $R^{8E}$-substituted or unsubstituted 5 to 6 membered heteroaryl.

$R^{8E}$ is independently oxo, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $R^{8F}$-substituted or unsubstituted alkyl, $R^{8F}$-substituted or unsubstituted heteroalkyl, $R^{8F}$-substituted or unsubstituted cycloalkyl, $R^{8F}$-substituted or unsubstituted heterocycloalkyl, $R^{8F}$-substituted or unsubstituted aryl, or $R^{8F}$-substituted or unsubstituted heteroaryl. In embodiments, $R^{8E}$ is independently oxo, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $R^{8F}$-substituted or unsubstituted $C_1$-$C_6$ alkyl, $R^{8F}$-substituted or unsubstituted 2 to 6 membered heteroalkyl, $R^{8F}$-substituted or unsubstituted $C_3$-$C_6$ cycloalkyl, $R^{8F}$-substituted or unsubstituted 3 to 6 membered heterocycloalkyl, $R^{8F}$-substituted or unsubstituted phenyl, or $R^{8F}$-substituted or unsubstituted 5 to 6 membered heteroaryl.

In embodiments, $R^9$ is independently hydrogen, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $R^{9E}$-substituted or unsubstituted alkyl, $R^{9E}$-substituted or unsubstituted heteroalkyl, $R^{9E}$-substituted or unsubstituted cycloalkyl, $R^{9E}$-substituted or unsubstituted heterocycloalkyl, $R^{9E}$-substituted or unsubstituted aryl, or $R^{9E}$-substituted or unsubstituted heteroaryl. In embodiments, $R^9$ is independently hydrogen, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $R^{9E}$-substituted or unsubstituted $C_1$-$C_6$ alkyl, $R^{9E}$-substituted or unsubstituted 2 to 6 membered heteroalkyl, $R^{9E}$-substituted or unsubstituted $C_3$-$C_6$ cycloalkyl, $R^{9E}$-substituted or unsubstituted 3 to 6 membered heterocycloalkyl, $R^{9E}$-substituted or unsubstituted phenyl, or $R^{9E}$-substituted or unsubstituted 5 to 6 membered heteroaryl.

$R^{9E}$ is independently oxo, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $R^{9F}$-substituted or unsubstituted alkyl, $R^{9F}$-substituted or unsubstituted heteroalkyl, $R^{9F}$-substituted or unsubstituted cycloalkyl, $R^{9F}$-substituted or unsubstituted heterocycloalkyl, $R^{9F}$-substituted or unsubstituted aryl, or $R^{9F}$-substituted or unsubstituted heteroaryl. In embodiments, $R^{9E}$ is independently oxo, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $R^{9F}$-substituted or unsubstituted $C_1$-$C_6$ alkyl, $R^{9F}$-substituted or unsubstituted 2 to 6 membered heteroalkyl, $R^{9F}$-substituted or unsubstituted $C_3$-$C_6$ cycloalkyl, $R^{9F}$-substituted or unsubstituted 3 to 6 membered heterocycloalkyl, $R^{9F}$-substituted or unsubstituted phenyl, or $R^{9F}$-substituted or unsubstituted 5 to 6 membered heteroaryl.

In embodiments, $R^{10}$ is independently hydrogen, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $R^{10E}$-substituted or unsubstituted alkyl, $R^{10E}$-substituted or unsubstituted heteroalkyl, $R^{10E}$-substituted or unsubstituted cycloalkyl, $R^{10E}$-substituted or unsubstituted heterocycloalkyl, $R^{10E}$-substituted or unsubstituted aryl, or $R^{10E}$-substituted or unsubstituted heteroaryl. In embodiments, $R^{10}$ is independently hydrogen, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, —OCBr$_3$, —OCI$_3$, —OCHF$_2$, —OCHCl$_2$, —OCHBr$_2$, —OCHI$_2$, R$^{10E}$-substituted or unsubstituted C$_1$-C$_6$ alkyl, R$^{10E}$-substituted or unsubstituted 2 to 6 membered heteroalkyl, R$^{10E}$-substituted or unsubstituted C$_3$-C$_6$ cycloalkyl, R$^{10E}$-substituted or unsubstituted 3 to 6 membered heterocycloalkyl, R$^{10E}$-substituted or unsubstituted phenyl, or R$^{10E}$-substituted or unsubstituted 5 to 6 membered heteroaryl. In embodiments, R$^{10}$ is fluorine, chlorine or iodine.

R$^{10E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{10F}$-substituted or unsubstituted alkyl, R$^{10F}$-substituted or unsubstituted heteroalkyl, R$^{10F}$-substituted or unsubstituted cycloalkyl, R$^{10F}$-substituted or unsubstituted heterocycloalkyl, R$^{10F}$-substituted or unsubstituted aryl, or R$^{10F}$-substituted or unsubstituted heteroaryl. In embodiments, R$^{10E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{10F}$-substituted or unsubstituted C$_1$-C$_6$ alkyl, R$^{10F}$-substituted or unsubstituted 2 to 6 membered heteroalkyl, R$^{10F}$-substituted or unsubstituted C$_3$-C$_6$ cycloalkyl, R$^{10F}$-substituted or unsubstituted 3 to 6 membered heterocycloalkyl, R$^{10F}$-substituted or unsubstituted phenyl, or R$^{10F}$-substituted or unsubstituted 5 to 6 membered heteroaryl.

In embodiments, R$^{11}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{11E}$-substituted or unsubstituted alkyl, R$^{11E}$-substituted or unsubstituted heteroalkyl, R$^{11E}$-substituted or unsubstituted cycloalkyl, R$^{11E}$-substituted or unsubstituted heterocycloalkyl, R$^{11E}$-substituted or unsubstituted aryl, or R$^{11E}$-substituted or unsubstituted heteroaryl. In embodiments, R$^{11}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{11E}$-substituted or unsubstituted C$_1$-C$_6$ alkyl, R$^{11E}$-substituted or unsubstituted 2 to 6 membered heteroalkyl, R$^{11E}$-substituted or unsubstituted C$_3$-C$_6$ cycloalkyl, R$^{11E}$-substituted or unsubstituted 3 to 6 membered heterocycloalkyl, R$^{11E}$-substituted or unsubstituted phenyl, or R$^{11E}$-substituted or unsubstituted 5 to 6 membered heteroaryl.

R$^{11E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{11F}$-substituted or unsubstituted alkyl, R$^{11F}$-substituted or unsubstituted heteroalkyl, R$^{11F}$-substituted or unsubstituted cycloalkyl, R$^{11F}$-substituted or unsubstituted heterocycloalkyl, R$^{11F}$-substituted or unsubstituted aryl, or R$^{11F}$-substituted or unsubstituted heteroaryl. In embodiments, R$^{11E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{11F}$-substituted or unsubstituted C$_1$-C$_6$ alkyl, R$^{11F}$-substituted or unsubstituted 2 to 6 membered heteroalkyl, R$^{11F}$-substituted or unsubstituted C$_3$-C$_6$ cycloalkyl, R$^{11F}$-substituted or unsubstituted 3 to 6 membered heterocycloalkyl, R$^{11F}$-substituted or unsubstituted phenyl, or R$^{11F}$-substituted or unsubstituted 5 to 6 membered heteroaryl.

In embodiments, R$^{12}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{12E}$-substituted or unsubstituted alkyl, R$^{12E}$-substituted or unsubstituted heteroalkyl, R$^{12E}$-substituted or unsubstituted cycloalkyl, R$^{12E}$-substituted or unsubstituted heterocycloalkyl, R$^{12E}$-substituted or unsubstituted aryl, or R$^{12E}$-substituted or unsubstituted heteroaryl. In embodiments, R$^{12}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{12E}$-substituted or unsubstituted C$_1$-C$_6$ alkyl, R$^{12E}$-substituted or unsubstituted 2 to 6 membered heteroalkyl, R$^{12E}$-substituted or unsubstituted C$_3$-C$_6$ cycloalkyl, R$^{12E}$-substituted or unsubstituted 3 to 6 membered heterocycloalkyl, R$^{12E}$-substituted or unsubstituted phenyl, or R$^{12E}$-substituted or unsubstituted 5 to 6 membered heteroaryl.

R$^{12E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{12F}$-substituted or unsubstituted alkyl, R$^{12F}$-substituted or unsubstituted heteroalkyl, R$^{12F}$-substituted or unsubstituted cycloalkyl, R$^{12F}$-substituted or unsubstituted heterocycloalkyl, R$^{12F}$-substituted or unsubstituted aryl, or R$^{12F}$-substituted or unsubstituted heteroaryl. In embodiments, R$^{12E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{12F}$-substituted or unsubstituted C$_1$-C$_6$ alkyl, R$^{12F}$-substituted or unsubstituted 2 to 6 membered heteroalkyl, R$^{12F}$-substituted or unsubstituted C$_3$-C$_6$ cycloalkyl, R$^{12F}$-substituted or unsubstituted 3 to 6 membered heterocycloalkyl, R$^{12F}$-substituted or unsubstituted phenyl, or R$^{12F}$-substituted or unsubstituted 5 to 6 membered heteroaryl.

In embodiments, $R^{13}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{13E}$-substituted or unsubstituted alkyl, $R^{13E}$-substituted or unsubstituted heteroalkyl, $R^{13E}$-substituted or unsubstituted cycloalkyl, $R^{13E}$-substituted or unsubstituted heterocycloalkyl, $R^{13E}$-substituted or unsubstituted aryl, or $R^{13E}$-substituted or unsubstituted heteroaryl. In embodiments, $R^{13}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{13E}$-substituted or unsubstituted $C_1$-$C_6$ alkyl, $R^{13E}$-substituted or unsubstituted 2 to 6 membered heteroalkyl, $R^{13E}$-substituted or unsubstituted $C_3$-$C_6$ cycloalkyl, $R^{13E}$-substituted or unsubstituted 3 to 6 membered heterocycloalkyl, $R^{13E}$-substituted or unsubstituted phenyl, or $R^{13E}$-substituted or unsubstituted 5 to 6 membered heteroaryl.

$R^{13E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{13F}$-substituted or unsubstituted alkyl, $R^{13F}$-substituted or unsubstituted heteroalkyl, $R^{13F}$-substituted or unsubstituted cycloalkyl, $R^{13F}$-substituted or unsubstituted heterocycloalkyl, $R^{13F}$-substituted or unsubstituted aryl, or $R^{13F}$-substituted or unsubstituted heteroaryl. In embodiments, $R^{13E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{13F}$-substituted or unsubstituted $C_1$-$C_6$ alkyl, $R^{13F}$-substituted or unsubstituted 2 to 6 membered heteroalkyl, $R^{13F}$-substituted or unsubstituted $C_3$-$C_6$ cycloalkyl, $R^{13F}$-substituted or unsubstituted 3 to 6 membered heterocycloalkyl, $R^{13F}$-substituted or unsubstituted phenyl, or $R^{13F}$-substituted or unsubstituted 5 to 6 membered heteroaryl.

In embodiments, $R^{14}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{14E}$-substituted or unsubstituted alkyl, $R^{14E}$-substituted or unsubstituted heteroalkyl, $R^{14E}$-substituted or unsubstituted cycloalkyl, $R^{14E}$-substituted or unsubstituted heterocycloalkyl, $R^{14E}$-substituted or unsubstituted aryl, or $R^{14E}$-substituted or unsubstituted heteroaryl. In embodiments, $R^{14}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{14E}$-substituted or unsubstituted $C_1$-$C_6$ alkyl, $R^{14E}$-substituted or unsubstituted 2 to 6 membered heteroalkyl, $R^{14E}$-substituted or unsubstituted $C_3$-$C_6$ cycloalkyl, $R^{14E}$-substituted or unsubstituted 3 to 6 membered heterocycloalkyl, $R^{14E}$-substituted or unsubstituted phenyl, or $R^{14E}$-substituted or unsubstituted 5 to 6 membered heteroaryl.

$R^{14E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{14F}$-substituted or unsubstituted alkyl, $R^{14F}$-substituted or unsubstituted heteroalkyl, $R^{14F}$-substituted or unsubstituted cycloalkyl, $R^{14F}$-substituted or unsubstituted heterocycloalkyl, $R^{14F}$-substituted or unsubstituted aryl, or $R^{14F}$-substituted or unsubstituted heteroaryl. In embodiments, $R^{14E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{14F}$-substituted or unsubstituted $C_1$-$C_6$ alkyl, $R^{14F}$-substituted or unsubstituted 2 to 6 membered heteroalkyl, $R^{14F}$-substituted or unsubstituted $C_3$-$C_6$ cycloalkyl, $R^{14F}$-substituted or unsubstituted 3 to 6 membered heterocycloalkyl, $R^{14F}$-substituted or unsubstituted phenyl, or $R^{14F}$-substituted or unsubstituted 5 to 6 membered heteroaryl.

In embodiments, $R^{15}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{15E}$-substituted or unsubstituted alkyl, $R^{15E}$-substituted or unsubstituted heteroalkyl, $R^{15E}$-substituted or unsubstituted cycloalkyl, $R^{15E}$-substituted or unsubstituted heterocycloalkyl, $R^{15E}$-substituted or unsubstituted aryl, or $R^{15E}$-substituted or unsubstituted heteroaryl. In embodiments, $R^{15}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{15E}$-substituted or unsubstituted $C_1$-$C_6$ alkyl, $R^{15E}$-substituted or unsubstituted 2 to 6 membered heteroalkyl, $R^{15E}$-substituted or unsubstituted $C_3$-$C_6$ cycloalkyl, $R^{15E}$-substituted or unsubstituted 3 to 6 membered heterocycloalkyl, $R^{15E}$-substituted or unsubstituted phenyl, or $R^{15E}$-substituted or unsubstituted 5 to 6 membered heteroaryl.

$R^{15E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{15F}$-substituted or unsubstituted alkyl, $R^{15F}$-substituted or unsubstituted heteroalkyl, $R^{15F}$-substituted or unsubstituted cycloalkyl, $R^{15F}$- substituted or unsubstituted heterocycloalkyl, $R^{15F}$-substituted or unsubstituted aryl, or $R^{15F}$-substituted or unsubstituted heteroaryl. In embodiments, $R^{15E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{15F}$-substituted or unsubstituted $C_1$-$C_6$ alkyl, $R^{15F}$-substituted or unsubstituted 2 to 6 membered heteroalkyl, $R^{15F}$-substituted or unsubstituted $C_3$-$C_6$ cycloalkyl, $R^{15F}$-substituted or unsubstituted 3 to 6 membered heterocycloalkyl, $R^{15F}$-substituted or unsubstituted phenyl, or $R^{15F}$-substituted or unsubstituted 5 to 6 membered heteroaryl.

In embodiments, $R^{16}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{16E}$-substituted or unsubstituted alkyl, $R^{16E}$-substituted or unsubstituted heteroalkyl, $R^{16E}$-substituted or unsubstituted cycloalkyl, $R^{16E}$-substituted or unsubstituted heterocycloalkyl, $R^{16E}$-substituted or unsubstituted aryl, or $R^{16E}$-substituted or unsubstituted heteroaryl. In embodiments, $R^{16}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{16E}$-substituted or unsubstituted $C_1$-$C_6$ alkyl, $R^{16E}$-substituted or unsubstituted 2 to 6 membered heteroalkyl, $R^{16E}$-substituted or unsubstituted $C_3$-$C_6$ cycloalkyl, $R^{16E}$-substituted or unsubstituted 3 to 6 membered heterocycloalkyl, $R^{16E}$-substituted or unsubstituted phenyl, or $R^{16E}$-substituted or unsubstituted 5 to 6 membered heteroaryl.

$R^{16E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{16F}$-substituted or unsubstituted alkyl, $R^{16F}$-substituted or unsubstituted heteroalkyl, $R^{16F}$-substituted or unsubstituted cycloalkyl, $R^{16F}$-substituted or unsubstituted heterocycloalkyl, $R^{16F}$-substituted or unsubstituted aryl, or $R^{16F}$-substituted or unsubstituted heteroaryl. In embodiments, $R^{16E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{16F}$-substituted or unsubstituted $C_1$-$C_6$ alkyl, $R^{16F}$-substituted or unsubstituted 2 to 6 membered heteroalkyl, $R^{16F}$-substituted or unsubstituted $C_3$-$C_6$ cycloalkyl, $R^{16F}$-substituted or unsubstituted 3 to 6 membered heterocycloalkyl, $R^{16F}$-substituted or unsubstituted phenyl, or $R^{16F}$-substituted or unsubstituted 5 to 6 membered heteroaryl.

In embodiments, $R^{17}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{17E}$-substituted or unsubstituted alkyl, $R^{17E}$-substituted or unsubstituted heteroalkyl, $R^{17E}$-substituted or unsubstituted cycloalkyl, $R^{17E}$-substituted or unsubstituted heterocycloalkyl, $R^{17E}$-substituted or unsubstituted aryl, or $R^{17E}$-substituted or unsubstituted heteroaryl. In embodiments, $R^{17}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{17E}$-substituted or unsubstituted $C_1$-$C_6$ alkyl, $R^{17E}$-substituted or unsubstituted 2 to 6 membered heteroalkyl, $R^{17E}$-substituted or unsubstituted $C_3$-$C_6$ cycloalkyl, $R^{17E}$-substituted or unsubstituted 3 to 6 membered heterocycloalkyl, $R^{17E}$-substituted or unsubstituted phenyl, or $R^{17E}$-substituted or unsubstituted 5 to 6 membered heteroaryl.

$R^{17E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{17F}$-substituted or unsubstituted alkyl, $R^{17F}$-substituted or unsubstituted heteroalkyl, $R^{17F}$-substituted or unsubstituted cycloalkyl, $R^{17F}$-substituted or unsubstituted heterocycloalkyl, $R^{17F}$-substituted or unsubstituted aryl, or $R^{17F}$-substituted or unsubstituted heteroaryl. In embodiments, $R^{17E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{17F}$-substituted or unsubstituted $C_1$-$C_6$ alkyl, $R^{17F}$-substituted or unsubstituted 2 to 6 membered heteroalkyl, $R^{17F}$-substituted or unsubstituted $C_3$-$C_6$ cycloalkyl, $R^{17F}$-substituted or unsubstituted 3 to 6 membered heterocycloalkyl, $R^{17F}$-substituted or unsubstituted phenyl, or $R^{17F}$-substituted or unsubstituted 5 to 6 membered heteroaryl.

In embodiments, $R^{18}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{18E}$-substituted or unsubstituted alkyl, $R^{18E}$-substituted or unsubstituted heteroalkyl, $R^{18E}$-substituted or unsubstituted cycloalkyl, $R^{18E}$-substituted or unsubstituted heterocycloalkyl, $R^{18E}$-substituted or unsubstituted aryl, or $R^{18E}$-substituted or unsubstituted heteroaryl. In embodiments, $R^{18}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —OCBr$_3$, —OCI$_3$, —OCHF$_2$, —OCHCl$_2$, —OCHBr$_2$, —OCHI$_2$, R$^{18E}$-substituted or unsubstituted C$_1$-C$_6$ alkyl, R$^{18E}$-substituted or unsubstituted 2 to 6 membered heteroalkyl, R$^{18E}$-substituted or unsubstituted C$_3$-C$_6$ cycloalkyl, R$^{18E}$-substituted or unsubstituted 3 to 6 membered heterocycloalkyl, R$^{18E}$-substituted or unsubstituted phenyl, or R$^{18E}$-substituted or unsubstituted 5 to 6 membered heteroaryl.

R$^{18E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{18F}$-substituted or unsubstituted alkyl, R$^{18F}$-substituted or unsubstituted heteroalkyl, R$^{18F}$-substituted or unsubstituted cycloalkyl, R$^{18F}$-substituted or unsubstituted heterocycloalkyl, R$^{18F}$-substituted or unsubstituted aryl, or R$^{18F}$-substituted or unsubstituted heteroaryl. In embodiments, R$^{18E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{18F}$-substituted or unsubstituted C$_1$-C$_6$ alkyl, R$^{18F}$-substituted or unsubstituted 2 to 6 membered heteroalkyl, R$^{18F}$-substituted or unsubstituted C$_3$-C$_6$ cycloalkyl, R$^{18F}$-substituted or unsubstituted 3 to 6 membered heterocycloalkyl, R$^{18F}$-substituted or unsubstituted phenyl, or R$^{18F}$-substituted or unsubstituted 5 to 6 membered heteroaryl.

In embodiments, R$^{19}$ is independently hydrogen, —COH, —C(O)NHNH$_2$, —C(O)OH, —SO$_2$H, —C(O)NH$_2$, R$^{19E}$-substituted or unsubstituted alkyl, R$^{19E}$-substituted or unsubstituted heteroalkyl, R$^{19E}$-substituted or unsubstituted cycloalkyl, R$^{19E}$-substituted or unsubstituted heterocycloalkyl, R$^{19E}$-substituted or unsubstituted aryl, or R$^{19E}$-substituted or unsubstituted heteroaryl.

R$^{19E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{19F}$-substituted or unsubstituted alkyl, R$^{19F}$-substituted or unsubstituted heteroalkyl, R$^{19F}$-substituted or unsubstituted cycloalkyl, R$^{19F}$-substituted or unsubstituted heterocycloalkyl, R$^{19F}$-substituted or unsubstituted aryl, or R$^{19F}$-substituted or unsubstituted heteroaryl. In embodiments, R$^{19E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{19F}$-substituted or unsubstituted C$_1$-C$_6$ alkyl, R$^{19F}$-substituted or unsubstituted 2 to 6 membered heteroalkyl, R$^{19F}$-substituted or unsubstituted C$_3$-C$_6$ cycloalkyl, R$^{19F}$-substituted or unsubstituted 3 to 6 membered heterocycloalkyl, R$^{19F}$-substituted or unsubstituted phenyl, or R$^{19F}$-substituted or unsubstituted 5 to 6 membered heteroaryl.

In embodiments, R$^{8A}$ is independently hydrogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{8AF}$-substituted or unsubstituted alkyl, R$^{8AF}$-substituted or unsubstituted heteroalkyl, R$^{8AF}$-substituted or unsubstituted cycloalkyl, R$^{8AF}$-substituted or unsubstituted heterocycloalkyl, R$^{8AF}$-substituted or unsubstituted aryl, or R$^{8AF}$-substituted or unsubstituted heteroaryl. In embodiments, R$^{8A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{8AF}$-substituted or unsubstituted C$_1$-C$_6$ alkyl, R$^{8AF}$-substituted or unsubstituted 2 to 6 membered heteroalkyl, R$^{8AF}$-substituted or unsubstituted C$_3$-C$_6$ cycloalkyl, R$^{8AF}$-substituted or unsubstituted 3 to 6 membered heterocycloalkyl, R$^{8AF}$-substituted or unsubstituted phenyl, or R$^{8AF}$-substituted or unsubstituted 5 to 6 membered heteroaryl.

In embodiments, R$^{8B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{8BF}$-substituted or unsubstituted alkyl, R$^{8BF}$-substituted or unsubstituted heteroalkyl, R$^{8BF}$-substituted or unsubstituted cycloalkyl, R$^{8BF}$-substituted or unsubstituted heterocycloalkyl, R$^{8BF}$-substituted or unsubstituted aryl, or R$^{8BF}$-substituted or unsubstituted heteroaryl. In embodiments, R$^{8B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{8BF}$-substituted or unsubstituted C$_1$-C$_6$ alkyl, R$^{8BF}$-substituted or unsubstituted 2 to 6 membered heteroalkyl, R$^{8BF}$-substituted or unsubstituted C$_3$-C$_6$ cycloalkyl, R$^{8BF}$-substituted or unsubstituted 3 to 6 membered heterocycloalkyl, R$^{8BF}$-substituted or unsubstituted phenyl, or R$^{8BF}$-substituted or unsubstituted 5 to 6 membered heteroaryl.

In embodiments, R$^{8C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{8CF}$-substituted or unsubstituted alkyl, R$^{8CF}$-substituted or unsubstituted heteroalkyl, R$^{8CF}$-substituted or unsubstituted cycloalkyl, R$^{8CF}$-substituted or unsubstituted heterocycloalkyl, R$^{8CF}$-substituted or unsubstituted aryl, or R$^{8CF}$-substituted or unsubstituted heteroaryl. In embodiments, R$^{BC}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{8CF}$-substituted or unsubstituted C$_1$-C$_6$ alkyl, $R^{8CF}$-substituted or unsubstituted 2 to 6 membered heteroalkyl, $R^{8CF}$-substituted or unsubstituted $C_3$-$C_6$ cycloalkyl, $R^{8CF}$-substituted or unsubstituted 3 to 6 membered heterocycloalkyl, $R^{8CF}$-substituted or unsubstituted phenyl, or $R^{8CF}$-substituted or unsubstituted 5 to 6 membered heteroaryl. $R^{BB}$ and $R^{BC}$ bonded to the same nitrogen atom may optionally be joined to form a $R^{8CF}$-substituted or unsubstituted 3 to 6 membered heterocycloalkyl or $R^{8CF}$-substituted or unsubstituted 5 to 6 membered heteroaryl.

In embodiments, $R^{8D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{8DF}$-substituted or unsubstituted alkyl, $R^{8DF}$-substituted or unsubstituted heteroalkyl, $R^{8DF}$-substituted or unsubstituted cycloalkyl, $R^{8DF}$-substituted or unsubstituted heterocycloalkyl, $R^{8DF}$-substituted or unsubstituted aryl, or $R^{8DF}$-substituted or unsubstituted heteroaryl. In embodiments, $R^{8D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{8DF}$-substituted or unsubstituted $C_1$-$C_6$ alkyl, $R^{8DF}$-substituted or unsubstituted 2 to 6 membered heteroalkyl, $R^{8DF}$-substituted or unsubstituted $C_3$-$C_6$ cycloalkyl, $R^{8DF}$-substituted or unsubstituted 3 to 6 membered heterocycloalkyl, $R^{8DF}$-substituted or unsubstituted phenyl, or $R^{8DF}$-substituted or unsubstituted 5 to 6 membered heteroaryl.

In embodiments, $R^{9A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{9AF}$-substituted or unsubstituted alkyl, $R^{9AF}$-substituted or unsubstituted heteroalkyl, $R^{9AF}$-substituted or unsubstituted cycloalkyl, $R^{9AF}$-substituted or unsubstituted heterocycloalkyl, $R^{9AF}$-substituted or unsubstituted aryl, or $R^{9AF}$-substituted or unsubstituted heteroaryl. In embodiments, $R^{9A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{9AF}$-substituted or unsubstituted $C_1$-$C_6$ alkyl, $R^{9AF}$-substituted or unsubstituted 2 to 6 membered heteroalkyl, $R^{9AF}$-substituted or unsubstituted $C_3$-$C_6$ cycloalkyl, $R^{9AF}$-substituted or unsubstituted 3 to 6 membered heterocycloalkyl, $R^{9AF}$-substituted or unsubstituted phenyl, or $R^{9AF}$-substituted or unsubstituted 5 to 6 membered heteroaryl.

In embodiments, $R^{9B}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{9BF}$-substituted or unsubstituted alkyl, $R^{9BF}$-substituted or unsubstituted heteroalkyl, $R^{9BF}$-substituted or unsubstituted cycloalkyl, $R^{9BF}$-substituted or unsubstituted heterocycloalkyl, $R^{9BF}$-substituted or unsubstituted aryl, or $R^{9BF}$-substituted or unsubstituted heteroaryl. In embodiments, $R^{9B}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{9BF}$-substituted or unsubstituted $C_1$-$C_6$ alkyl, $R^{9BF}$-substituted or unsubstituted 2 to 6 membered heteroalkyl, $R^{9BF}$-substituted or unsubstituted $C_3$-$C_6$ cycloalkyl, $R^{9BF}$-substituted or unsubstituted 3 to 6 membered heterocycloalkyl, $R^{9BF}$-substituted or unsubstituted phenyl, or $R^{9BF}$-substituted or unsubstituted 5 to 6 membered heteroaryl.

In embodiments, $R^{9C}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{9CF}$-substituted or unsubstituted alkyl, $R^{9CF}$-substituted or unsubstituted heteroalkyl, $R^{9CF}$-substituted or unsubstituted cycloalkyl, $R^{9CF}$-substituted or unsubstituted heterocycloalkyl, $R^{9CF}$-substituted or unsubstituted aryl, or $R^{9CF}$-substituted or unsubstituted heteroaryl. In embodiments, $R^{9C}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{9CF}$-substituted or unsubstituted $C_1$-$C_6$ alkyl, $R^{9CF}$-substituted or unsubstituted 2 to 6 membered heteroalkyl, $R^{9CF}$-substituted or unsubstituted $C_3$-$C_6$ cycloalkyl, $R^{9CF}$-substituted or unsubstituted 3 to 6 membered heterocycloalkyl, $R^{9CF}$-substituted or unsubstituted phenyl, or $R^{9CF}$-substituted or unsubstituted 5 to 6 membered heteroaryl. $R^{9B}$ and $R^{9C}$ bonded to the same nitrogen atom may optionally be joined to form a $R^{9CF}$-substituted or unsubstituted 3 to 6 membered heterocycloalkyl or $R^{9CF}$-substituted or unsubstituted 5 to 6 membered heteroaryl.

In embodiments, $R^{9D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{9DF}$-substituted or unsubstituted alkyl, $R^{9DF}$-substituted or unsubstituted heteroalkyl, $R^{9DF}$-substituted or unsubstituted cycloalkyl, $R^{9DF}$-substituted or unsubstituted heterocycloalkyl, $R^{9DF}$-substituted or unsubstituted aryl, or $R^{9DF}$-substituted or unsubstituted heteroaryl. In embodiments, $R^{9D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{9DF}$-substituted or unsubstituted $C_1$-$C_6$ alkyl, $R^{9DF}$-substituted or unsubstituted 2 to 6 membered heteroalkyl, $R^{9DF}$-substituted or unsubstituted $C_3$-$C_6$ cycloalkyl, $R^{9DF}$-substituted or unsubstituted 3 to 6 membered heterocycloalkyl, $R^{9DF}$-substituted or unsubstituted phenyl, or $R^{9DF}$-substituted or unsubstituted 5 to 6 membered heteroaryl.

In embodiments, $R^{10A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{10AF}$-substituted or unsubstituted alkyl, $R^{10AF}$-substituted or unsubstituted heteroalkyl, $R^{10AF}$-substituted or unsubstituted cycloalkyl, $R^{10F}$-substituted or unsubstituted heterocycloalkyl, $R^{10AF}$-substituted or unsubstituted aryl, or $R^{10AF}$-substituted or unsubstituted heteroaryl. In embodiments, $R^{10A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{10AF}$-substituted or unsubstituted $C_1$-$C_6$ alkyl, $R^{10AF}$-substituted or unsubstituted 2 to 6 membered heteroalkyl, $R^{10AF}$-substituted or unsubstituted $C_3$-$C_6$ cycloalkyl, $R^{10AF}$-substituted or unsubstituted 3 to 6 membered heterocycloalkyl, $R^{10AF}$-substituted or unsubstituted phenyl, or $R^{10AF}$-substituted or unsubstituted 5 to 6 membered heteroaryl.

In embodiments, $R^{10B}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{10BF}$-substituted or unsubstituted alkyl, $R^{10BF}$-substituted or unsubstituted heteroalkyl, $R^{10BF}$-substituted or unsubstituted cycloalkyl, $R^{10BF}$-substituted or unsubstituted heterocycloalkyl, $R^{10BF}$-substituted or unsubstituted aryl, or $R^{10BF}$-substituted or unsubstituted heteroaryl. In embodiments, $R^{10B}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{10BF}$-substituted or unsubstituted $C_1$-$C_6$ alkyl, $R^{10BF}$-substituted or unsubstituted 2 to 6 membered heteroalkyl, $R^{10BF}$-substituted or unsubstituted $C_3$-$C_6$ cycloalkyl, $R^{10BF}$-substituted or unsubstituted 3 to 6 membered heterocycloalkyl, $R^{10BF}$-substituted or unsubstituted phenyl, or $R^{10BF}$-substituted or unsubstituted 5 to 6 membered heteroaryl.

In embodiments, $R^{10C}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{10CF}$-substituted or unsubstituted alkyl, $R^{10CF}$-substituted or unsubstituted heteroalkyl, $R^{10CF}$-substituted or unsubstituted cycloalkyl, $R^{10CF}$-substituted or unsubstituted heterocycloalkyl, $R^{10CF}$-substituted or unsubstituted aryl, or $R^{10CF}$-substituted or unsubstituted heteroaryl. In embodiments, $R^{10C}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{10CF}$-substituted or unsubstituted $C_1$-$C_6$ alkyl, $R^{10CF}$-substituted or unsubstituted 2 to 6 membered heteroalkyl, $R^{10CF}$-substituted or unsubstituted $C_3$-$C_6$ cycloalkyl, $R^{10CF}$-substituted or unsubstituted 3 to 6 membered heterocycloalkyl, $R^{10CF}$-substituted or unsubstituted phenyl, or $R^{10CF}$-substituted or unsubstituted 5 to 6 membered heteroaryl. $R^{10B}$ and $R^{10C}$ bonded to the same nitrogen atom may optionally be joined to form a $R^{10CF}$-substituted or unsubstituted 3 to 6 membered heterocycloalkyl or $R^{10CF}$-substituted or unsubstituted 5 to 6 membered heteroaryl.

In embodiments, $R^{10D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{10DF}$-substituted or unsubstituted alkyl, $R^{10DF}$-substituted or unsubstituted heteroalkyl, $R^{10DF}$-substituted or unsubstituted cycloalkyl, $R^{10DF}$-substituted or unsubstituted heterocycloalkyl, $R^{10DF}$-substituted or unsubstituted aryl, or $R^{10DF}$-substituted or unsubstituted heteroaryl. In embodiments, $R^{10D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{10DF}$-substituted or unsubstituted $C_1$-$C_6$ alkyl, $R^{10DF}$-substituted or unsubstituted 2 to 6 membered heteroalkyl, $R^{10DF}$-substituted or unsubstituted $C_3$-$C_6$ cycloalkyl, $R^{10DF}$-substituted or unsubstituted 3 to 6 membered heterocycloalkyl, $R^{10DF}$-substituted or unsubstituted phenyl, or $R^{10DF}$-substituted or unsubstituted 5 to 6 membered heteroaryl.

In embodiments, $R^{11A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{11AF}$-substituted or unsubstituted alkyl, $R^{11AF}$-substituted or unsubstituted heteroalkyl, $R^{11AF}$-substituted or unsubstituted cycloalkyl, $R^{11AF}$-substituted or unsubstituted heterocycloalkyl, $R^{11AF}$-substituted or unsubstituted aryl, or $R^{11AF}$-substituted or unsubstituted heteroaryl. In embodiments, $R^{11A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{11AF}$-substituted or unsubstituted $C_1$-$C_6$ alkyl, $R^{11AF}$-substituted or unsubstituted 2 to 6 membered heteroalkyl, $R^{11AF}$-substituted or unsubstituted $C_3$-$C_6$ cycloalkyl, $R^{11AF}$-substituted or unsubstituted 3 to 6 membered heterocycloalkyl, $R^{11AF}$-substituted or unsubstituted phenyl, or $R^{11AF}$-substituted or unsubstituted 5 to 6 membered heteroaryl.

In embodiments, $R^{11B}$ is independently hydrogen, halogen, —$CF_3$, —$CCl_3$, —$CBr_3$, —$CI_3$, —CN, —OH, —$NH_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{11BF}$-substituted or unsubstituted alkyl, R$^{11BF}$-substituted or unsubstituted heteroalkyl, R$^{11BF}$-substituted or unsubstituted cycloalkyl, R$^{11BF}$-substituted or unsubstituted heterocycloalkyl, R$^{11BF}$-substituted or unsubstituted aryl, or R$^{11BF}$-substituted or unsubstituted heteroaryl. In embodiments, R$^{11B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{11BF}$-substituted or unsubstituted C$_1$-C$_6$ alkyl, R$^{11BF}$-substituted or unsubstituted 2 to 6 membered heteroalkyl, R$^{11BF}$-substituted or unsubstituted C$_3$-C$_6$ cycloalkyl, R$^{11BF}$-substituted or unsubstituted 3 to 6 membered heterocycloalkyl, R$^{11BF}$-substituted or unsubstituted phenyl, or R$^{11BF}$-substituted or unsubstituted 5 to 6 membered heteroaryl.

In embodiments, R$^{11C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{11CF}$-substituted or unsubstituted alkyl, R$^{11CF}$-substituted or unsubstituted heteroalkyl, R$^{11CF}$-substituted or unsubstituted cycloalkyl, R$^{11CF}$-substituted or unsubstituted heterocycloalkyl, R$^{11CF}$-substituted or unsubstituted aryl, or R$^{11CF}$-substituted or unsubstituted heteroaryl. In embodiments, R$^{11C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{11CF}$-substituted or unsubstituted C$_1$-C$_6$ alkyl, R$^{11CF}$-substituted or unsubstituted 2 to 6 membered heteroalkyl, R$^{11CF}$-substituted or unsubstituted C$_3$-C$_6$ cycloalkyl, R$^{11CF}$-substituted or unsubstituted 3 to 6 membered heterocycloalkyl, R$^{11CF}$-substituted or unsubstituted phenyl, or R$^{11CF}$-substituted or unsubstituted 5 to 6 membered heteroaryl. R$^{11B}$ and R$^{11C}$ bonded to the same nitrogen atom may optionally be joined to form a R$^{11CF}$-substituted or unsubstituted 3 to 6 membered heterocycloalkyl or R$^{11CF}$-substituted or unsubstituted 5 to 6 membered heteroaryl.

In embodiments, R$^{11D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{11DF}$-substituted or unsubstituted alkyl, R$^{11DF}$-substituted or unsubstituted heteroalkyl, R$^{11DF}$-substituted or unsubstituted cycloalkyl, R$^{11DF}$-substituted or unsubstituted heterocycloalkyl, R$^{11DF}$-substituted or unsubstituted aryl, or R$^{11DF}$-substituted or unsubstituted heteroaryl. In embodiments, R$^{11D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{11DF}$-substituted or unsubstituted C$_1$-C$_6$ alkyl, R$^{11DF}$-substituted or unsubstituted 2 to 6 membered heteroalkyl, R$^{11DF}$-substituted or unsubstituted C$_3$-C$_6$ cycloalkyl, R$^{11DF}$-substituted or unsubstituted 3 to 6 membered heterocycloalkyl, R$^{11DF}$-substituted or unsubstituted phenyl, or R$^{11DF}$-substituted or unsubstituted 5 to 6 membered heteroaryl.

In embodiments, R$^{12A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{12AF}$-substituted or unsubstituted alkyl, R$^{12AF}$-substituted or unsubstituted heteroalkyl, R$^{12AF}$-substituted or unsubstituted cycloalkyl, R$^{12AF}$-substituted or unsubstituted heterocycloalkyl, R$^{12AF}$-substituted or unsubstituted aryl, or R$^{12AF}$-substituted or unsubstituted heteroaryl. In embodiments, R$^{12A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{12AF}$-substituted or unsubstituted C$_1$-C$_6$ alkyl, R$^{12AF}$-substituted or unsubstituted 2 to 6 membered heteroalkyl, R$^{12AF}$-substituted or unsubstituted C$_3$-C$_6$ cycloalkyl, R$^{12AF}$-substituted or unsubstituted 3 to 6 membered heterocycloalkyl, R$^{12AF}$-substituted or unsubstituted phenyl, or R$^{12AF}$-substituted or unsubstituted 5 to 6 membered heteroaryl.

In embodiments, R$^{12B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{12BF}$-substituted or unsubstituted alkyl, R$^{12BF}$-substituted or unsubstituted heteroalkyl, R$^{12BF}$-substituted or unsubstituted cycloalkyl, R$^{12BF}$-substituted or unsubstituted heterocycloalkyl, R$^{12BF}$-substituted or unsubstituted aryl, or R$^{12BF}$-substituted or unsubstituted heteroaryl. In embodiments, R$^{12B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{12BF}$-substituted or unsubstituted C$_1$-C$_6$ alkyl, R$^{12BF}$-substituted or unsubstituted 2 to 6 membered heteroalkyl, R$^{12BF}$-substituted or unsubstituted C$_3$-C$_6$ cycloalkyl, R$^{12BF}$-substituted or unsubstituted 3 to 6 membered heterocycloalkyl, R$^{12BF}$-substituted or unsubstituted phenyl, or R$^{12BF}$-substituted or unsubstituted 5 to 6 membered heteroaryl.

In embodiments, R$^{12C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{12CF}$-substituted or unsubstituted alkyl, $R^{12CF}$-substituted or unsubstituted heteroalkyl, $R^{12CF}$-substituted or unsubstituted cycloalkyl, $R^{12CF}$-substituted or unsubstituted heterocycloalkyl, $R^{12CF}$-substituted or unsubstituted aryl, or $R^{12CF}$-substituted or unsubstituted heteroaryl. In embodiments, $R^{12C}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{12CF}$-substituted or unsubstituted $C_1$-$C_6$ alkyl, $R^{12CF}$-substituted or unsubstituted 2 to 6 membered heteroalkyl, $R^{12CF}$-substituted or unsubstituted $C_3$-$C_6$ cycloalkyl, $R^{12CF}$-substituted or unsubstituted 3 to 6 membered heterocycloalkyl, $R^{12CF}$-substituted or unsubstituted phenyl, or $R^{12CF}$-substituted or unsubstituted 5 to 6 membered heteroaryl. $R^{12B}$ and $R^{12C}$ bonded to the same nitrogen atom may optionally be joined to form a $R^{12CF}$-substituted or unsubstituted 3 to 6 membered heterocycloalkyl or $R^{12CF}$-substituted or unsubstituted 5 to 6 membered heteroaryl.

In embodiments, $R^{12D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{12DF}$-substituted or unsubstituted alkyl, $R^{12DF}$-substituted or unsubstituted heteroalkyl, $R^{12DF}$-substituted or unsubstituted cycloalkyl, $R^{12DF}$-substituted or unsubstituted heterocycloalkyl, $R^{12DF}$-substituted or unsubstituted aryl, or $R^{12DF}$-substituted or unsubstituted heteroaryl. In embodiments, $R^{12D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{12DF}$-substituted or unsubstituted $C_1$-$C_6$ alkyl, $R^{12DF}$-substituted or unsubstituted 2 to 6 membered heteroalkyl, $R^{12DF}$-substituted or unsubstituted $C_3$-$C_6$ cycloalkyl, $R^{12DF}$-substituted or unsubstituted 3 to 6 membered heterocycloalkyl, $R^{12DF}$-substituted or unsubstituted phenyl, or $R^{12DF}$-substituted or unsubstituted 5 to 6 membered heteroaryl.

In embodiments, $R^{13A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{13AF}$-substituted or unsubstituted alkyl, $R^{13AF}$-substituted or unsubstituted heteroalkyl, $R^{13AF}$-substituted or unsubstituted cycloalkyl, $R^{13AF}$-substituted or unsubstituted heterocycloalkyl, $R^{13AF}$-substituted or unsubstituted aryl, or $R^{13AF}$-substituted or unsubstituted heteroaryl. In embodiments, $R^{13A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{13AF}$-substituted or unsubstituted $C_1$-$C_6$ alkyl, $R^{13AF}$-substituted or unsubstituted 2 to 6 membered heteroalkyl, $R^{13AF}$-substituted or unsubstituted $C_3$-$C_6$ cycloalkyl, $R^{13AF}$-substituted or unsubstituted 3 to 6 membered heterocycloalkyl, $R^{13AF}$-substituted or unsubstituted phenyl, or $R^{13AF}$-substituted or unsubstituted 5 to 6 membered heteroaryl.

In embodiments, $R^{13B}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{13BF}$-substituted or unsubstituted alkyl, $R^{13BF}$-substituted or unsubstituted heteroalkyl, $R^{13BF}$-substituted or unsubstituted cycloalkyl, $R^{13BF}$-substituted or unsubstituted heterocycloalkyl, $R^{13BF}$-substituted or unsubstituted aryl, or $R^{13BF}$-substituted or unsubstituted heteroaryl. In embodiments, $R^{13B}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{13BF}$-substituted or unsubstituted $C_1$-$C_6$ alkyl, $R^{13BF}$-substituted or unsubstituted 2 to 6 membered heteroalkyl, $R^{13BF}$-substituted or unsubstituted $C_3$-$C_6$ cycloalkyl, $R^{13BF}$-substituted or unsubstituted 3 to 6 membered heterocycloalkyl, $R^{13BF}$-substituted or unsubstituted phenyl, or $R^{13BF}$-substituted or unsubstituted 5 to 6 membered heteroaryl.

In embodiments, $R^{13C}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{13CF}$-substituted or unsubstituted alkyl, $R^{13CF}$-substituted or unsubstituted heteroalkyl, $R^{13CF}$-substituted or unsubstituted cycloalkyl, $R^{13CF}$-substituted or unsubstituted heterocycloalkyl, $R^{13CF}$-substituted or unsubstituted aryl, or $R^{13CF}$-substituted or unsubstituted heteroaryl. In embodiments, $R^{13C}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{13CF}$-substituted or unsubstituted $C_1$-$C_6$ alkyl, $R^{13CF}$-substituted or unsubstituted 2 to 6 membered heteroalkyl, $R^{13CF}$-substituted or unsubstituted $C_3$-$C_6$ cycloalkyl, $R^{13CF}$-substituted or unsubstituted 3 to 6 membered heterocycloalkyl, $R^{13CF}$-substituted or unsubstituted phenyl, or $R^{13CF}$-substituted or unsubstituted 5 to 6 membered heteroaryl. $R^{13B}$ and $R^{13C}$ bonded to the same nitrogen atom may optionally be joined to form a $R^{13CF}$-substituted or unsubstituted 3 to 6 membered heterocycloalkyl or $R^{13CF}$-substituted or unsubstituted 5 to 6 membered heteroaryl.

In embodiments, $R^{13D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{13DF}$-substituted or unsubstituted alkyl, $R^{13DF}$-substituted or unsubstituted heteroalkyl, $R^{13DF}$-substituted or unsubstituted cycloalkyl, $R^{13DF}$-substituted or unsubstituted heterocycloalkyl, $R^{13DF}$-substituted or unsubstituted aryl, or $R^{13DF}$-substituted or unsubstituted heteroaryl. In embodiments, $R^{13D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{13DF}$-substituted or unsubstituted C$_1$-C$_6$ alkyl, $R^{13DF}$-substituted or unsubstituted 2 to 6 membered heteroalkyl, $R^{13DF}$-substituted or unsubstituted C$_3$-C$_6$ cycloalkyl, $R^{13DF}$-substituted or unsubstituted 3 to 6 membered heterocycloalkyl, $R^{13DF}$-substituted or unsubstituted phenyl, or $R^{13DF}$-substituted or unsubstituted 5 to 6 membered heteroaryl.

In embodiments, $R^{14A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{13AF}$-substituted or unsubstituted alkyl, $R^{13AF}$-substituted or unsubstituted heteroalkyl, $R^{13AF}$-substituted or unsubstituted cycloalkyl, $R^{13AF}$-substituted or unsubstituted heterocycloalkyl, $R^{13AF}$-substituted or unsubstituted aryl, or $R^{13AF}$-substituted or unsubstituted heteroaryl. In embodiments, $R^{14A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{14AF}$-substituted or unsubstituted C$_1$-C$_6$ alkyl, $R^{14AF}$-substituted or unsubstituted 2 to 6 membered heteroalkyl, $R^{14AF}$-substituted or unsubstituted C$_3$-C$_6$ cycloalkyl, $R^{14AF}$-substituted or unsubstituted 3 to 6 membered heterocycloalkyl, $R^{14AF}$-substituted or unsubstituted phenyl, or $R^{14AF}$-substituted or unsubstituted 5 to 6 membered heteroaryl.

In embodiments, $R^{14B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{14BF}$-substituted or unsubstituted alkyl, $R^{14BF}$-substituted or unsubstituted heteroalkyl, $R^{14BF}$-substituted or unsubstituted cycloalkyl, $R^{14BF}$-substituted or unsubstituted heterocycloalkyl, $R^{14BF}$-substituted or unsubstituted aryl, or $R^{14BF}$-substituted or unsubstituted heteroaryl. In embodiments, $R^{14B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{14BF}$-substituted or unsubstituted C$_1$-C$_6$ alkyl, $R^{14BF}$-substituted or unsubstituted 2 to 6 membered heteroalkyl, $R^{14BF}$-substituted or unsubstituted C$_3$-C$_6$ cycloalkyl, $R^{14BF}$-substituted or unsubstituted 3 to 6 membered heterocycloalkyl, $R^{14BF}$-substituted or unsubstituted phenyl, or $R^{14BF}$-substituted or unsubstituted 5 to 6 membered heteroaryl.

In embodiments, $R^{14C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{14CF}$-substituted or unsubstituted alkyl, $R^{14CF}$-substituted or unsubstituted heteroalkyl, $R^{14CF}$-substituted or unsubstituted cycloalkyl, $R^{14CF}$-substituted or unsubstituted heterocycloalkyl, $R^{14CF}$-substituted or unsubstituted aryl, or $R^{14CF}$-substituted or unsubstituted heteroaryl. In embodiments, $R^{14C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{14CF}$-substituted or unsubstituted C$_1$-C$_6$ alkyl, $R^{14CF}$-substituted or unsubstituted 2 to 6 membered heteroalkyl, $R^{14CF}$-substituted or unsubstituted C$_3$-C$_6$ cycloalkyl, $R^{14CF}$-substituted or unsubstituted 3 to 6 membered heterocycloalkyl, $R^{14CF}$-substituted or unsubstituted phenyl, or $R^{14CF}$-substituted or unsubstituted 5 to 6 membered heteroaryl. $R^{14B}$ and $R^{14C}$ bonded to the same nitrogen atom may optionally be joined to form a $R^{14CF}$-substituted or unsubstituted 3 to 6 membered heterocycloalkyl or $R^{14CF}$-substituted or unsubstituted 5 to 6 membered heteroaryl.

In embodiments, $R^{14D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{14DF}$-substituted or unsubstituted alkyl, $R^{14DF}$-substituted or unsubstituted heteroalkyl, $R^{14DF}$-substituted or unsubstituted cycloalkyl, $R^{14DF}$-substituted or unsubstituted heterocycloalkyl, $R^{14DF}$-substituted or unsubstituted aryl, or $R^{14DF}$-substituted or unsubstituted heteroaryl. In embodiments, $R^{14D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{14DF}$-substituted or unsubstituted C$_1$-C$_6$ alkyl, $R^{14DF}$-substituted or unsubstituted 2 to 6 membered heteroalkyl, $R^{14DF}$-substituted or unsubstituted C$_3$-C$_6$ cycloalkyl, $R^{14DF}$-substituted or unsubstituted 3 to 6 membered heterocycloalkyl, $R^{14DF}$-substituted or unsubstituted phenyl, or $R^{14DF}$-substituted or unsubstituted 5 to 6 membered heteroaryl.

In embodiments, $R^{15A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{15AF}$-substituted or unsubstituted alkyl, $R^{15AF}$-substituted or unsubstituted heteroalkyl, $R^{15AF}$-substituted or unsubstituted cycloalkyl, $R^{15AF}$-substituted or unsubstituted heterocycloalkyl, $R^{15AF}$-substituted or unsubstituted aryl, or $R^{15AF}$-substituted or unsubstituted heteroaryl. In embodiments, $R^{15A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{15AF}$-substituted or unsubstituted C$_1$-C$_6$ alkyl, R$^{15AF}$-substituted or unsubstituted 2 to 6 membered heteroalkyl, R$^{15AF}$-substituted or unsubstituted C$_3$-C$_6$ cycloalkyl, R$^{15AF}$-substituted or unsubstituted 3 to 6 membered heterocycloalkyl, R$^{15AF}$-substituted or unsubstituted phenyl, or R$^{15AF}$-substituted or unsubstituted 5 to 6 membered heteroaryl.

In embodiments, R$^{15B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{15BF}$-substituted or unsubstituted alkyl, R$^{15BF}$-substituted or unsubstituted heteroalkyl, R$^{15BF}$-substituted or unsubstituted cycloalkyl, R$^{15BF}$-substituted or unsubstituted heterocycloalkyl, R$^{15BF}$-substituted or unsubstituted aryl, or R$^{15BF}$-substituted or unsubstituted heteroaryl. In embodiments, R$^{15B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{15BF}$-substituted or unsubstituted C$_1$-C$_6$ alkyl, R$^{15BF}$-substituted or unsubstituted 2 to 6 membered heteroalkyl, R$^{15BF}$-substituted or unsubstituted C$_3$-C$_6$ cycloalkyl, R$^{15BF}$-substituted or unsubstituted 3 to 6 membered heterocycloalkyl, R$^{15BF}$-substituted or unsubstituted phenyl, or R$^{15BF}$-substituted or unsubstituted 5 to 6 membered heteroaryl.

In embodiments, R$^{15C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{15CF}$-substituted or unsubstituted alkyl, R$^{15CF}$-substituted or unsubstituted heteroalkyl, R$^{15CF}$-substituted or unsubstituted cycloalkyl, R$^{15CF}$-substituted or unsubstituted heterocycloalkyl, R$^{15CF}$-substituted or unsubstituted aryl, or R$^{15CF}$-substituted or unsubstituted heteroaryl. In embodiments, R$^{15C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{15CF}$-substituted or unsubstituted C$_1$-C$_6$ alkyl, R$^{15CF}$-substituted or unsubstituted 2 to 6 membered heteroalkyl, R$^{15CF}$-substituted or unsubstituted C$_3$-C$_6$ cycloalkyl, R$^{15CF}$-substituted or unsubstituted 3 to 6 membered heterocycloalkyl, R$^{15CF}$-substituted or unsubstituted phenyl, or R$^{15CF}$-substituted or unsubstituted 5 to 6 membered heteroaryl. R$^{15B}$ and R$^{15C}$ bonded to the same nitrogen atom may optionally be joined to form a R$^{15CF}$-substituted or unsubstituted 3 to 6 membered heterocycloalkyl or R$^{15CF}$-substituted or unsubstituted 5 to 6 membered heteroaryl.

In embodiments, R$^{15D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{15DF}$-substituted or unsubstituted alkyl, R$^{15DF}$-substituted or unsubstituted heteroalkyl, R$^{15DF}$-substituted or unsubstituted cycloalkyl, R$^{15DF}$-substituted or unsubstituted heterocycloalkyl, R$^{15DF}$-substituted or unsubstituted aryl, or R$^{15DF}$-substituted or unsubstituted heteroaryl. In embodiments, R$^{15D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{15DF}$-substituted or unsubstituted C$_1$-C$_6$ alkyl, R$^{15DF}$-substituted or unsubstituted 2 to 6 membered heteroalkyl, R$^{15DF}$-substituted or unsubstituted C$_3$-C$_6$ cycloalkyl, R$^{15DF}$-substituted or unsubstituted 3 to 6 membered heterocycloalkyl, R$^{15DF}$-substituted or unsubstituted phenyl, or R$^{15DF}$-substituted or unsubstituted 5 to 6 membered heteroaryl.

In embodiments, R$^{16A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{16AF}$-substituted or unsubstituted alkyl, R$^{16AF}$-substituted or unsubstituted heteroalkyl, R$^{16AF}$-substituted or unsubstituted cycloalkyl, R$^{16AF}$-substituted or unsubstituted heterocycloalkyl, R$^{16AF}$-substituted or unsubstituted aryl, or R$^{16AF}$-substituted or unsubstituted heteroaryl. In embodiments, R$^{16A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{16AF}$-substituted or unsubstituted C$_1$-C$_6$ alkyl, R$^{16AF}$-substituted or unsubstituted 2 to 6 membered heteroalkyl, R$^{16AF}$-substituted or unsubstituted C$_3$-C$_6$ cycloalkyl, R$^{10F}$-substituted or unsubstituted 3 to 6 membered heterocycloalkyl, R$^{10F}$-substituted or unsubstituted phenyl, or R$^{16AF}$-substituted or unsubstituted 5 to 6 membered heteroaryl.

In embodiments, R$^{16B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{16BF}$-substituted or unsubstituted alkyl, R$^{16BF}$-substituted or unsubstituted heteroalkyl, R$^{16BF}$-substituted or unsubstituted cycloalkyl, R$^{16BF}$-substituted or unsubstituted heterocycloalkyl, R$^{16BF}$-substituted or unsubstituted aryl, or R$^{16BF}$-substituted or unsubstituted heteroaryl. In embodiments, R$^{16B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, $R^{16BF}$-substituted or unsubstituted $C_1$-$C_6$ alkyl, $R^{16BF}$-substituted or unsubstituted 2 to 6 membered heteroalkyl, $R^{16BF}$-substituted or unsubstituted $C_3$-$C_6$ cycloalkyl, $R^{16BF}$-substituted or unsubstituted 3 to 6 membered heterocycloalkyl, $R^{16BF}$-substituted or unsubstituted phenyl, or $R^{16BF}$-substituted or unsubstituted 5 to 6 membered heteroaryl.

In embodiments, $R^{16C}$ is independently hydrogen, halogen, —CF₃, —CCl₃, —CBr₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, $R^{16CF}$-substituted or unsubstituted alkyl, $R^{16CF}$-substituted or unsubstituted heteroalkyl, $R^{16CF}$-substituted or unsubstituted cycloalkyl, $R^{16CF}$-substituted or unsubstituted heterocycloalkyl, $R^{16CF}$-substituted or unsubstituted aryl, or $R^{16CF}$-substituted or unsubstituted heteroaryl. In embodiments, $R^{16C}$ is independently hydrogen, halogen, —CF₃, —CCl₃, —CBr₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, $R^{16CF}$-substituted or unsubstituted $C_1$-$C_6$ alkyl, $R^{16CF}$-substituted or unsubstituted 2 to 6 membered heteroalkyl, $R^{16CF}$-substituted or unsubstituted $C_3$-$C_6$ cycloalkyl, $R^{16CF}$-substituted or unsubstituted 3 to 6 membered heterocycloalkyl, $R^{16CF}$-substituted or unsubstituted phenyl, or $R^{16CF}$-substituted or unsubstituted 5 to 6 membered heteroaryl. $R^{16B}$ and $R^{16C}$ bonded to the same nitrogen atom may optionally be joined to form a $R^{16CF}$-substituted or unsubstituted 3 to 6 membered heterocycloalkyl or $R^{16CF}$-substituted or unsubstituted 5 to 6 membered heteroaryl.

In embodiments, $R^{16D}$ is independently hydrogen, halogen, —CF₃, —CCl₃, —CBr₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, $R^{16DF}$-substituted or unsubstituted alkyl, $R^{16DF}$-substituted or unsubstituted heteroalkyl, $R^{16DF}$-substituted or unsubstituted cycloalkyl, $R^{16DF}$-substituted or unsubstituted heterocycloalkyl, $R^{16DF}$-substituted or unsubstituted aryl, or $R^{16DF}$-substituted or unsubstituted heteroaryl. In embodiments, $R^{16D}$ is independently hydrogen, halogen, —CF₃, —CCl₃, —CBr₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, $R^{16DF}$-substituted or unsubstituted $C_1$-$C_6$ alkyl, $R^{16DF}$-substituted or unsubstituted 2 to 6 membered heteroalkyl, $R^{16DF}$-substituted or unsubstituted $C_3$-$C_6$ cycloalkyl, $R^{16DF}$-substituted or unsubstituted 3 to 6 membered heterocycloalkyl, $R^{16DF}$-substituted or unsubstituted phenyl, or $R^{16DF}$-substituted or unsubstituted 5 to 6 membered heteroaryl.

In embodiments, $R^{17A}$ is independently hydrogen, halogen, —CF₃, —CCl₃, —CBr₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, $R^{17AF}$-substituted or unsubstituted alkyl, $R^{17AF}$-substituted or unsubstituted heteroalkyl, $R^{17AF}$-substituted or unsubstituted cycloalkyl, $R^{17AF}$-substituted or unsubstituted heterocycloalkyl, $R^{17AF}$-substituted or unsubstituted aryl, or $R^{17AF}$-substituted or unsubstituted heteroaryl. In embodiments, $R^{17A}$ is independently hydrogen, halogen, —CF₃, —CCl₃, —CBr₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, $R^{17AF}$-substituted or unsubstituted $C_1$-$C_6$ alkyl, $R^{17AF}$-substituted or unsubstituted 2 to 6 membered heteroalkyl, $R^{17AF}$-substituted or unsubstituted $C_3$-$C_6$ cycloalkyl, $R^{17AF}$-substituted or unsubstituted 3 to 6 membered heterocycloalkyl, $R^{17AF}$-substituted or unsubstituted phenyl, or $R^{17AF}$-substituted or unsubstituted 5 to 6 membered heteroaryl.

In embodiments, $R^{17B}$ is independently hydrogen, halogen, —CF₃, —CCl₃, —CBr₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, $R^{17BF}$-substituted or unsubstituted alkyl, $R^{17BF}$-substituted or unsubstituted heteroalkyl, $R^{17BF}$-substituted or unsubstituted cycloalkyl, $R^{17BF}$-substituted or unsubstituted heterocycloalkyl, $R^{17BF}$-substituted or unsubstituted aryl, or $R^{17BF}$-substituted or unsubstituted heteroaryl. In embodiments, $R^{17B}$ is independently hydrogen, halogen, —CF₃, —CCl₃, —CBr₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, $R^{17BF}$-substituted or unsubstituted $C_1$-$C_6$ alkyl, $R^{17BF}$-substituted or unsubstituted 2 to 6 membered heteroalkyl, $R^{17BF}$-substituted or unsubstituted $C_3$-$C_6$ cycloalkyl, $R^{17BF}$-substituted or unsubstituted 3 to 6 membered heterocycloalkyl, $R^{17BF}$-substituted or unsubstituted phenyl, or $R^{17BF}$-substituted or unsubstituted 5 to 6 membered heteroaryl.

In embodiments, $R^{17C}$ is independently hydrogen, halogen, —CF₃, —CCl₃, —CBr₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, $R^{17CF}$-substituted or unsubstituted alkyl, $R^{17CF}$-substituted or unsubstituted heteroalkyl, $R^{17CF}$-substituted or unsubstituted cycloalkyl, $R^{17CF}$-substituted or unsubstituted heterocycloalkyl, $R^{17CF}$-substituted or unsubstituted aryl, or $R^{17CF}$-substituted or unsubstituted heteroaryl. In embodiments, $R^{17C}$ is independently hydrogen, halogen, —CF₃, —CCl₃, —CBr₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, $R^{17CF}$-substituted or unsubstituted $C_1$-$C_6$ alkyl, $R^{17CF}$-substituted or unsubstituted 2 to 6 membered heteroalkyl, $R^{17CF}$-substituted or unsubstituted $C_3$-$C_6$ cycloalkyl, $R^{17CF}$-substituted or unsubstituted 3 to 6 membered heterocycloalkyl, $R^{17CF}$-substituted or unsubstituted phenyl, or $R^{17CF}$-substituted or unsubstituted 5 to 6 membered heteroaryl. $R^{17B}$ and $R^{17C}$ bonded to the same nitrogen atom may optionally be joined to form a $R^{17CF}$-substituted or unsubstituted 3 to 6 membered heterocycloalkyl or $R^{17CF}$-substituted or unsubstituted 5 to 6 membered heteroaryl.

In embodiments, $R^{17D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{17DF}$-substituted or unsubstituted alkyl, $R^{17DF}$-substituted or unsubstituted heteroalkyl, $R^{17DF}$-substituted or unsubstituted cycloalkyl, $R^{17DF}$-substituted or unsubstituted heterocycloalkyl, $R^{17DF}$-substituted or unsubstituted aryl, or $R^{17DF}$-substituted or unsubstituted heteroaryl. In embodiments, $R^{17D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{17DF}$-substituted or unsubstituted $C_1$-$C_6$ alkyl, $R^{17DF}$-substituted or unsubstituted 2 to 6 membered heteroalkyl, $R^{17DF}$-substituted or unsubstituted $C_3$-$C_6$ cycloalkyl, $R^{17DF}$-substituted or unsubstituted 3 to 6 membered heterocycloalkyl, $R^{17DF}$-substituted or unsubstituted phenyl, or $R^{17DF}$-substituted or unsubstituted 5 to 6 membered heteroaryl.

In embodiments, $R^{18A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{18AF}$-substituted or unsubstituted alkyl, $R^{18AF}$-substituted or unsubstituted heteroalkyl, $R^{18AF}$-substituted or unsubstituted cycloalkyl, $R^{18AF}$-substituted or unsubstituted heterocycloalkyl, $R^{18AF}$-substituted or unsubstituted aryl, or $R^{18AF}$-substituted or unsubstituted heteroaryl. In embodiments, $R^{18A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{18AF}$-substituted or unsubstituted $C_1$-$C_6$ alkyl, $R^{18AF}$-substituted or unsubstituted 2 to 6 membered heteroalkyl, $R^{18AF}$-substituted or unsubstituted $C_3$-$C_6$ cycloalkyl, $R^{18AF}$-substituted or unsubstituted 3 to 6 membered heterocycloalkyl, $R^{18AF}$-substituted or unsubstituted phenyl, or $R^{18AF}$-substituted or unsubstituted 5 to 6 membered heteroaryl.

In embodiments, $R^{18B}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{18BF}$-substituted or unsubstituted alkyl, $R^{18BF}$-substituted or unsubstituted heteroalkyl, $R^{18BF}$-substituted or unsubstituted cycloalkyl, $R^{18BF}$-substituted or unsubstituted heterocycloalkyl, $R^{18BF}$-substituted or unsubstituted aryl, or $R^{18BF}$-substituted or unsubstituted heteroaryl. In embodiments, $R^{18B}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{18BF}$-substituted or unsubstituted $C_1$-$C_6$ alkyl, $R^{18BF}$-substituted or unsubstituted 2 to 6 membered heteroalkyl, $R^{18BF}$-substituted or unsubstituted $C_3$-$C_6$ cycloalkyl, $R^{18BF}$-substituted or unsubstituted 3 to 6 membered heterocycloalkyl, $R^{18BF}$-substituted or unsubstituted phenyl, or $R^{18BF}$-substituted or unsubstituted 5 to 6 membered heteroaryl.

In embodiments, $R^{18C}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{18CF}$-substituted or unsubstituted alkyl, $R^{18CF}$-substituted or unsubstituted heteroalkyl, $R^{18CF}$-substituted or unsubstituted cycloalkyl, $R^{18CF}$-substituted or unsubstituted heterocycloalkyl, $R^{18CF}$-substituted or unsubstituted aryl, or $R^{18CF}$-substituted or unsubstituted heteroaryl. In embodiments, $R^{18C}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{18CF}$-substituted or unsubstituted $C_1$-$C_6$ alkyl, $R^{18CF}$-substituted or unsubstituted 2 to 6 membered heteroalkyl, $R^{18CF}$-substituted or unsubstituted $C_3$-$C_6$ cycloalkyl, $R^{18CF}$-substituted or unsubstituted 3 to 6 membered heterocycloalkyl, $R^{18CF}$-substituted or unsubstituted phenyl, or $R^{18CF}$-substituted or unsubstituted 5 to 6 membered heteroaryl. $R^{18B}$ and $R^{18C}$ bonded to the same nitrogen atom may optionally be joined to form a $R^{18CF}$-substituted or unsubstituted 3 to 6 membered heterocycloalkyl or $R^{18CF}$-substituted or unsubstituted 5 to 6 membered heteroaryl.

In embodiments, $R^{18D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{18DF}$-substituted or unsubstituted alkyl, $R^{18DF}$-substituted or unsubstituted heteroalkyl, $R^{18DF}$-substituted or unsubstituted cycloalkyl, $R^{18DF}$-substituted or unsubstituted aryl, or $R^{18DF}$-substituted or unsubstituted heteroaryl. In embodiments, $R^{18D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{18DF}$-substituted or unsubstituted $C_1$-$C_6$ alkyl, $R^{18DF}$-substituted or unsubstituted 2 to 6 membered heteroalkyl, $R^{18DF}$-substituted or unsubstituted $C_3$-$C_6$ cycloalkyl, $R^{18DF}$-substituted or unsubstituted 3 to 6 membered heterocycloalkyl, $R^{18DF}$-substituted or unsubstituted phenyl, or $R^{18DF}$-substituted or unsubstituted 5 to 6 membered heteroaryl.

In embodiments, $R^{19A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{19AF}$-substituted or unsubstituted alkyl, $R^{19AF}$-substituted or unsubstituted heteroalkyl, $R^{19AF}$-substituted or unsubstituted cycloalkyl, $R^{19AF}$-substituted or unsubstituted heterocycloalkyl, $R^{19AF}$-substituted or unsubstituted aryl, or $R^{19AF}$-substituted or unsubstituted heteroaryl. In embodiments, $R^{19A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{19AF}$-substituted or unsubstituted $C_1$-$C_6$ alkyl, $R^{19AF}$-substituted or unsubstituted 2 to 6 membered heteroalkyl, $R^{19AF}$-substituted or unsubstituted $C_3$-$C_6$ cycloalkyl, $R^{19AF}$-substituted or unsubstituted 3 to 6 membered heterocycloalkyl, $R^{19AF}$-substituted or unsubstituted phenyl, or $R^{19AF}$-substituted or unsubstituted 5 to 6 membered heteroaryl.

In embodiments, $R^{19B}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{19BF}$-substituted or unsubstituted alkyl, $R^{19BF}$-substituted or unsubstituted heteroalkyl, $R^{19BF}$-substituted or unsubstituted cycloalkyl, $R^{19BF}$-substituted or unsubstituted heterocycloalkyl, $R^{19BF}$-substituted or unsubstituted aryl, or $R^{19BF}$-substituted or unsubstituted heteroaryl. In embodiments, $R^{19B}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{19BF}$-substituted or unsubstituted $C_1$-$C_6$ alkyl, $R^{19BF}$-substituted or unsubstituted 2 to 6 membered heteroalkyl, $R^{19BF}$-substituted or unsubstituted $C_3$-$C_6$ cycloalkyl, $R^{19BF}$-substituted or unsubstituted 3 to 6 membered heterocycloalkyl, $R^{19BF}$-substituted or unsubstituted phenyl, or $R^{19BF}$-substituted or unsubstituted 5 to 6 membered heteroaryl.

In embodiments, $R^{19C}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{19CF}$-substituted or unsubstituted alkyl, $R^{19CF}$-substituted or unsubstituted heteroalkyl, $R^{19CF}$-substituted or unsubstituted cycloalkyl, $R^{19CF}$-substituted or unsubstituted heterocycloalkyl, $R^{19CF}$-substituted or unsubstituted aryl, or $R^{19CF}$-substituted or unsubstituted heteroaryl. In embodiments, $R^{19C}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{19CF}$-substituted or unsubstituted $C_1$-$C_6$ alkyl, $R^{19CF}$-substituted or unsubstituted 2 to 6 membered heteroalkyl, $R^{19CF}$-substituted or unsubstituted $C_3$-$C_6$ cycloalkyl, $R^{19CF}$-substituted or unsubstituted 3 to 6 membered heterocycloalkyl, $R^{19CF}$-substituted or unsubstituted phenyl, or $R^{19CF}$-substituted or unsubstituted 5 to 6 membered heteroaryl. $R^{19B}$ and $R^{19C}$ bonded to the same nitrogen atom may optionally be joined to form a $R^{19CF}$-substituted or unsubstituted 3 to 6 membered heterocycloalkyl or $R^{19CF}$-substituted or unsubstituted 5 to 6 membered heteroaryl.

In embodiments, $R^{19D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{19DF}$-substituted or unsubstituted alkyl, $R^{19DF}$-substituted or unsubstituted heteroalkyl, $R^{19DF}$-substituted or unsubstituted cycloalkyl, $R^{19DF}$-substituted or unsubstituted heterocycloalkyl, $R^{19DF}$-substituted or unsubstituted aryl, or $R^{19DF}$-substituted or unsubstituted heteroaryl. In embodiments, $R^{19D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{19DF}$-substituted or unsubstituted $C_1$-$C_6$ alkyl, $R^{19DF}$-substituted or unsubstituted 2 to 6 membered heteroalkyl, $R^{19DF}$-substituted or unsubstituted $C_3$-$C_6$ cycloalkyl, $R^{19DF}$-substituted or unsubstituted 3 to 6 membered heterocycloalkyl, $R^{19DF}$-substituted or unsubstituted phenyl, or $R^{19DF}$-substituted or unsubstituted 5 to 6 membered heteroaryl.

In embodiments, $L^1$ is independently a bond, O, N($R^{20}$), S or $R^{20E}$-substituted or unsubstituted $C_1$-$C_3$ alkylene.

$R^{20}$ is independently hydrogen, —COH, —C(O)$NHNH_2$, —C(O)OH, —$SO_2H$, —C(O)$NH_2$, $R^{20E}$-substituted or unsubstituted alkyl, $R^{20E}$-substituted or unsubstituted heteroalkyl, $R^{20E}$-substituted or unsubstituted cycloalkyl, $R^{20E}$-substituted or unsubstituted heterocycloalkyl, $R^{20E}$-substituted or unsubstituted aryl, or $R^{20E}$-substituted or unsubstituted heteroaryl.

$R^{20E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{20E}$-substituted or unsubstituted alkyl, $R^{20E}$-substituted or unsubstituted heteroalkyl, $R^{20E}$-substituted or unsubstituted cycloalkyl, $R^{20E}$-substituted or unsubstituted heterocycloalkyl, $R^{20E}$-substituted or unsubstituted aryl, or $R^{20E}$-substituted or unsubstituted heteroaryl. In embodiments, $R^{20E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{20E}$-substituted or unsubstituted $C_1$-$C_6$ alkyl, $R^{20E}$-substituted or unsubstituted 2 to 6 membered heteroalkyl, $R^{20E}$-substituted or unsubstituted $C_3$-$C_6$ cycloalkyl, $R^{20E}$-substituted or unsubstituted 3 to 6 membered heterocycloalkyl, $R^{20E}$-substituted or unsubstituted phenyl, or $R^{20E}$-substituted or unsubstituted 5 to 6 membered heteroaryl.

$R^{8F}$, $R^{9F}$, $R^{10F}$, $R^{11F}$, $R^{12F}$, $R^{13F}$, $R^{14F}$, $R^{15F}$, $R^{16F}$, $R^{17F}$, $R^{18F}$, $R^{19F}$, $R^{20F}$, $R^{8AF}$, $R^{8BF}$, $R^{8CF}$, $R^{8DF}$, $R^{9AF}$, $R^{9BF}$, $R^{9CF}$, $R^{9DF}$, $R^{10AF}$, $R^{10BF}$, $R^{10CF}$, $R^{10DF}$, $R^{11AF}$, $R^{11BF}$, $R^{11CF}$, $R^{11DF}$, $R^{12AF}$, $R^{12BF}$, $R^{12CF}$, $R^{12DF}$, $R^{13AF}$, $R^{13BF}$, $R^{13CF}$, $R^{13DF}$, $R^{14AF}$, $R^{14BF}$, $R^{14CF}$, $R^{14DF}$, $R^{15AF}$, $R^{15BF}$, $R^{15CF}$, $R^{15DF}$, $R^{16AF}$, $R^{16BF}$, $R^{16CF}$, $R^{16DF}$, $R^{17AF}$, $R^{17BF}$, $R^{17CF}$, $R^{17DF}$, $R^{18AF}$, $R^{18BF}$, $R^{18CF}$, $R^{18DF}$, $R^{19AF}$, $R^{19BF}$, $R^{19CF}$ and $R^{19DF}$ are independently oxo, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{8F}$, $R^{9F}$, $R^{10F}$, $R^{11F}$, $R^{12F}$, $R^{13F}$, $R^{14F}$, $R^{15F}$, $R^{16F}$, $R^{17F}$, $R^{18F}$, $R^{19F}$, $R^{20F}$, $R^{8AF}$, $R^{8BF}$, $R^{8CF}$, $R^{8DF}$, $R^{9AF}$, $R^{9BF}$, $R^{9CF}$, $R^{9DF}$, $R^{10AF}$, $R^{10BF}$, $R^{10CF}$, $R^{10DF}$, $R^{11AF}$, $R^{11BF}$, $R^{11CF}$, $R^{11DF}$, $R^{12AF}$, $R^{12BF}$, $R^{12CF}$, $R^{12DF}$, $R^{13AF}$, $R^{13BF}$, $R^{13CF}$, $R^{13DF}$, $R^{14AF}$, $R^{14BF}$, $R^{14CF}$, $R^{14DF}$, $R^{15AF}$, $R^{15BF}$, $R^{15CF}$, $R^{15DF}$, $R^{16AF}$, $R^{16BF}$, $R^{16CF}$, $R^{16DF}$, $R^{17AF}$, $R^{17BF}$, $R^{17CF}$, $R^{17DF}$, $R^{18AF}$, $R^{18BF}$, $R^{18CF}$, $R^{18DF}$, $R^{19AF}$, $R^{19BF}$, $R^{19CF}$ and $R^{19DF}$ are independently oxo, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In some embodiments, a compound as described herein may include multiple instances of $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{20E}$, m1, n1, v1, and/or other variables. In such embodiments, each variable may optional be different and be appropriately labeled to distinguish each group for greater clarity. For example, where each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{20E}$, m1, n1, v1, is different, they may be referred to, for example, as $R^{8.1}$, $R^{8.2}$, $R^{8.3}$, $R^{8.4}$, $R^{8.5}$, $R^{8.6}$, $R^{9.1}$, $R^{9.2}$, $R^{9.3}$, $R^{9.4}$, $R^{9.5}$, $R^{9.6}$, $R^{10.1}$, $R^{10.2}$, $R^{10.3}$, $R^{10.4}$, $R^{10.5}$, $R^{10.6}$, $R^{11.1}$, $R^{11.2}$, $R^{11.3}$, $R^{11.4}$, $R^{11.5}$, $R^{11.6}$, $R^{12.1}$, $R^{12.2}$, $R^{12.3}$, $R^{12.4}$, $R^{12.5}$, $R^{12.6}$, $R^{13.1}$, $R^{13.2}$, $R^{13.3}$, $R^{13.4}$, $R^{13.5}$, $R^{13.6}$, $R^{14.1}$, $R^{14.2}$, $R^{14.3}$, $R^{14.4}$, $R^{14.5}$, $R^{14.6}$, $R^{15.1}$, $R^{15.2}$, $R^{15.3}$, $R^{15.4}$, $R^{15.5}$, $R^{15.6}$, $R^{16.1}$, $R^{16.2}$, $R^{16.3}$, $R^{16.4}$, $R^{16.5}$, $R^{16.6}$, $R^{17.1}$, $R^{17.2}$, $R^{17.3}$, $R^{17.4}$, $R^{17.5}$, $R^{17.6}$, $R^{18.1}$, $R^{18.2}$, $R^{18.3}$, $R^{18.4}$, $R^{18.5}$, $R^{18.6}$, $R^{19.1}$, $R^{19.2}$, $R^{19.3}$, $R^{19.4}$, $R^{19.5}$, $R^{19.6}$, $R^{20.1}$, $R^{20.2}$, $R^{20.3}$, $R^{20.4}$, $R^{20.5}$, $R^{20.6}$, $R^{20E.1}$, $R^{20E.2}$, $R^{20E.3}$, $R^{20E.4}$, $R^{20E.5}$, $R^{20E.6}$, m1$^1$, m1$^2$, m1$^3$, m1$^4$ m1$^5$, m1$^6$, n1$^1$, n1$^2$, n1$^3$, n1$^4$, n1$^5$, n1$^6$, v1$^1$, v1$^2$, v1$^3$, v1$^4$, v1$^5$, v1$^6$, respectively, wherein the definition of $R^8$ is assumed by $R^{8.1}$, $R^{8.2}$, $R^{8.3}$, $R^{8.4}$, $R^{8.5}$, $R^{8.6}$, the definition of $R^9$ is assumed by $R^{9.1}$, $R^{9.2}$, $R^{9.3}$, $R^{9.4}$, $R^{9.5}$, $R^{9.6}$, the definition of $R^{10}$ is assumed by $R^{10.1}$, $R^{10.2}$, $R^{10.3}$, $R^{10.4}$, $R^{10.5}$, $R^{10.6}$ the definition of $R^{11}$ is assumed by $R^{11.1}$, $R^{11.2}$, $R^{11.3}$, $R^{11.4}$, $R^{11.5}$, $R^{11.6}$, $R^{11.7}$, the definition of $R^{12}$ is assumed by $R^{12.1}$, $R^{12.2}$, $R^{12.3}$, $R^{12.4}$, $R^{12.5}$, $R^{12.6}$, $R^{12.7}$, the definition of $R^{13}$ is assumed by $R^{13.1}$, $R^{13.2}$, $R^{13.3}$, $R^{13.4}$, $R^{13.5}$, $R^{13.6}$, the definition of $R^{14}$ is assumed by $R^{14.1}$, $R^{14.2}$, $R^{14.3}$, $R^{14.4}$, $R^{14.5}$, $R^{14.6}$, the definition of $R^{15}$ is assumed by $R^{15.1}$, $R^{15.2}$, $R^{15.3}$, $R^{15.4}$, $R^{15.5}$, $R^{15.6}$, the definition of $R^{16}$ is assumed by $R^{16.1}$, $R^{16.2}$, $R^{16.3}$, $R^{16.4}$, $R^{16.5}$, $R^{16.6}$, the definition of $R^{17}$ is assumed by $R^{17.1}$, $R^{17.2}$, $R^{17.3}$, $R^{17.4}$, $R^{17.5}$, $R^{17.6}$, the definition of $R^{18}$ is assumed by $R^{18.1}$, $R^{18.2}$, $R^{18.3}$, $R^{18.4}$, $R^{18.5}$, $R^{18.6}$, the definition of $R^{19}$ is assumed by $R^{19.1}$, $R^{19.2}$, $R^{19.3}$, $R^{19.4}$, $R^{19.5}$, $R^{19.6}$, the definition of $R^{20}$ is assumed by $R^{20.1}$, $R^{20.2}$, $R^{20.3}$, $R^{20.4}$, $R^{20.5}$, $R^{20.6}$, the definition of $R^{20E}$ is assumed by $R^{20E.1}$, $R^{20E.2}$, $R^{20E.3}$, $R^{20E.4}$, $R^{20E.5}$, $R^{20E.6}$, the definition of m1 is assumed by m1$^1$, m1$^2$, m1$^3$, m1$^4$, m1$^5$, m1$^6$, the definition of n1 is assumed by n1$^1$, n1$^2$, n1$^3$, n1$^4$, n1$^5$, n1$^6$, and the definition of v1 is assumed by v1$^1$, v1$^2$, v1$^3$, v1$^4$, v1$^5$, v1$^6$.

The variables used within a definition of $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{20E}$, m1, n1, v1, and/or other variables that appear at multiple instances and are different may similarly be appropriately labeled to distinguish each group for greater clarity.

In embodiments, the compound is

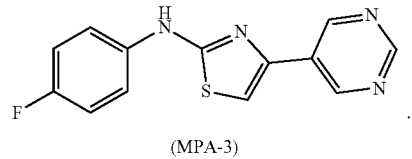 [SMILES: Fc1ccc(Nc2nc(-c3cncnc3)cs2)cc1 ; "."]

(MPA-3)

In embodiments, the compound is

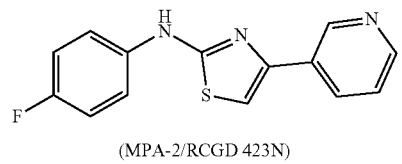

(MPA-2/RCGD 423N)

In embodiments, the compound is

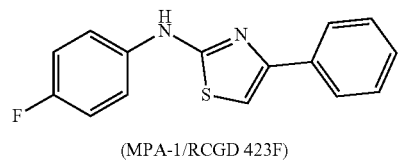

(MPA-1/RCGD 423F)

In embodiments, the compound is a compound described herein (e.g., in an aspect, embodiment, example, table, figure, scheme, appendix, or claim).

II. Compositions

Provided herein are compositions comprising a gp130 receptor bound to a binding site 1 gp130 receptor agonist. In an aspect, the binding site 1 gp130 receptor agonist is bound to the binding site one of the gp130 receptor.

In embodiments, the binding site 1 gp130 receptor agonist is non-covalently bound to gp130 receptor. In embodiments, binding site 1 comprises amino acid residues lysine, alanine, arginine and lysine corresponding to positions 173, 174, 175 and 176 (SEQ ID NO:3) within the binding site 1 of the gp130 receptor as set forth in SEQ ID NO:2. In embodiments, the binding site 1 gp130 receptor agonist is a small molecule, an antibody or a polypeptide. In one aspect is a pharmaceutical composition that includes a compound described herein and a pharmaceutically acceptable excipient. In embodiments, the binding site 1 gp130 receptor agonist is a compound described herein.

III. Pharmaceutical Compositions

Also provided herein are pharmaceutical formulations. In one aspect is a pharmaceutical composition that includes a compound described herein and a pharmaceutically acceptable excipient.

In embodiments of the pharmaceutical compositions, the compound, or pharmaceutically acceptable salt thereof, is included in a therapeutically effective amount.

1. Formulations

The pharmaceutical composition may be prepared and administered in a wide variety of dosage formulations. Compounds described may be administered orally, rectally, or by injection (e.g. intravenously, intramuscularly, intracutaneously, subcutaneously, intraduodenally, or intraperitoneally).

For preparing pharmaceutical compositions from compounds described herein, pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

2. Effective Dosages

The pharmaceutical composition may include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

Therapeutically effective amounts for use in humans may be determined from animal models. For example, a dose for humans can be formulated to achieve a concentration that has been found to be effective in animals. The dosage in humans can be adjusted by monitoring response of the constipation or dry eye to the treatment and adjusting the dosage upwards or downwards, as described above.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

3. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

When parenteral application is needed or desired, particularly suitable admixtures for the compounds included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. Pharmaceutical admixtures suitable for use in the pharmaceutical compositions presented herein may include those described, for example, in Pharmaceutical Sciences (17th Ed., Mack Pub. Co., Easton, Pa.) and WO 96/05309, the teachings of both of which are hereby incorporated by reference.

IV. Methods

Further provided herein are methods of increasing MYC expression in a cell. In one aspect, the method includes contacting the cell with a binding site 1 gp130 receptor agonist or with an effective amount of a compound described herein thereby increasing MYC expression.

Also provided herein is a method of increasing pSTAT3 expression in a cell including contacting the cell with a binding site 1 gp130 receptor agonist or with an effective amount of a compound described herein thereby increasing pSTAT3 expression.

The contacting may be performed in vitro. The contacting may be performed in vivo.

Provided herein is a method of regulating chondrocyte activation, maturation and/or differentiation. In certain aspects, the method includes contacting a chondrocyte with a binding site 1 gp130 receptor agonist or with an effective amount of a compound described herein.

In embodiments, the chondrocyte activation includes an increase in proliferation, migration, metabolism or any combination thereof.

Provided herein are methods of regenerating or repairing tissue in a subject in need thereof, including administering to the subject a therapeutically effective amount of a binding site 1 gp130 receptor agonist or with an effective amount of a compound described herein.

In embodiments, the tissue is cartilage.

Provided herein is a method of repairing a joint surface injury in a subject, comprising administering to the subject a therapeutically effective amount of a binding site 1 gp130 receptor agonist or with an effective amount of a compound described herein.

Also provided herein is a method of treating a cartilage degenerative disease in a subject in need thereof. The method includes administering to the subject a therapeutically effective amount of a binding site 1 gp130 receptor agonist or with an effective amount of a compound described herein. In embodiments, the disorder is arthritis. In embodiments, the disorder is osteoarthritis. In embodiments, the disorder is rheumatoid arthritis.

Further provided herein are methods of increasing secretion of cartilaginous matrix in cartilage, including contacting a gp130 receptor with a binding site 1 gp130 receptor agonist or with an effective amount of a compound described herein.

In embodiments, the cartilaginous matrix is in articular cartilage. In embodiments, the cartilaginous matrix includes collagens and proteoglycans.

Provided herein is a method of modulating the activity of a gp130 receptor in a cell. The method includes contacting the cell with a binding site 1 gp130 receptor agonist or with an effective amount of a compound described herein.

In embodiments, the activity of the gp130 receptor is increased. In embodiments, the activity of the gp130 receptor is decreased or inhibited. In embodiments, the activity is heterodimerization.

Also provided herein is a method of transforming a mature adult cell to a progenitor cell, comprising contacting the cell with a binding site 1 gp130 receptor agonist or with an effective amount of a compound described herein.

In embodiments, the cell is a human cell. In embodiments, the cell is a chondrocyte. In embodiments, the chondrocyte is an adult chondrocyte. In embodiments, the binding site 1 gp130 receptor agonist is a compound described herein (e.g., a compound of Formula (III) as described herein, Formula (IIIa) as described herein, Formula (IIIb) as described herein, Formula (IIIc) as described herein, in an aspect, embodiment, example, table, figure, scheme, appendix or claim).

In embodiments, the compound is

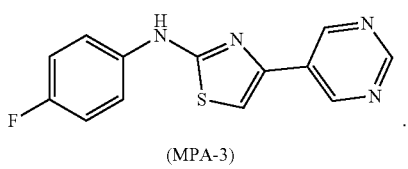 [SMILES: Fc1ccc(Nc2nc(-c3cncnc3)cs2)cc1 ; "."]

(MPA-3)

In embodiments, the compound is

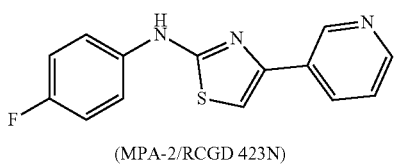

(MPA-2/RCGD 423N)

In embodiments, the compound is

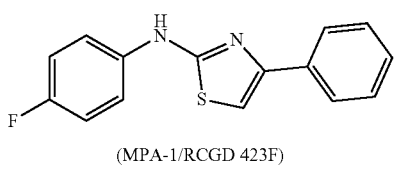

(MPA-1/RCGD 423F)

In embodiments, the compound is

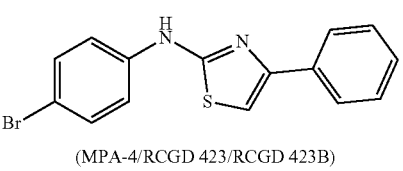

(MPA-4/RCGD 423/RCGD 423B)

V. Other Aspects

In a first aspect, there is provided a method for activating a proliferative program in competent adult chondrocytes. The method includes contacting a competent adult chondrocyte with an activating compound. The activating compound is capable of increasing expression of p-STAT3 and c-Myc in the competent adult chondrocyte.

Embodiments disclosed herein include embodiments P1 to P5 following.

Embodiment P1

A method for activating a proliferative program in competent adult chondrocytes, said method comprising contacting a competent adult chondrocyte with an activating compound, said activating compound capable of increasing expression of p-STAT3 and c-Myc in said competent adult chondrocyte.

Embodiment P2

The method according to embodiment P1, wherein said activating compound has the structure of Formulae (PI):

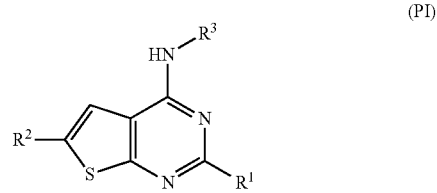

(PI)

wherein $R^1$ is substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl; $R^2$ is substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl; and $R^3$ is substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl; or Formula (PII):

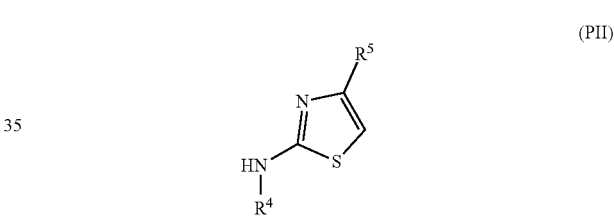

(PII)

wherein $R^4$ is substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl; and $R^5$ is substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

Embodiment P3

The method according to embodiment P2, wherein said activating compound has the structure of Formula (PIa):

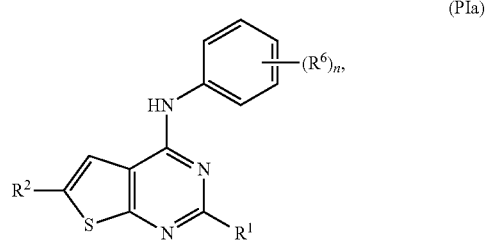

(PIa)

wherein n is an integer from 0 to 5; and $R^6$ at each occurrence is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

Embodiment P4

The method according to embodiment P3, wherein $R^6$ is phenyl substituted with substituted or unsubstituted alkyl, substituted or unsubstituted lower alkyl, —$NH_2$, halogen, —COOH, or substituted or unsubstituted heteroaryl.

Embodiment P5

The method according to embodiment P2, wherein said activating compound has the structure of Formula (PIIa):

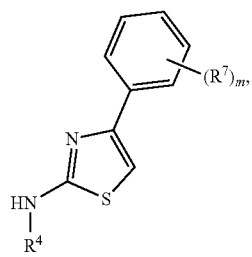

(PIIa)

wherein m is an integer from 0 to 5; and $R^7$ at each occurrence is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

Further embodiments include embodiments 1 to 52 following.

Embodiment 1

A compound of structural Formula (III):

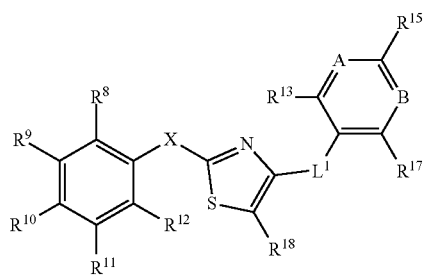

(III)

or a pharmaceutically acceptable salt thereof, wherein: A is $CR^{14}$ or N; B is $CR^{16}$ or N; X is O, $NR^{19}$ or S; $L^1$ is a bond or substituted or unsubstituted $C_1$-$C_3$ alkylene; n1 is an integer from 0 to 4; m1 and v1 are independently 1 or 2; $R^8$ is hydrogen, halogen, —$CX^{8.1}_3$, —$CHX^{8.1}_2$, —$CH_2X^{8.1}$, —CN, —$SO_{n1}R^{8A}$, —$SO_{v1}NR^{8B}R^{8C}$, —$NHNR^{8B}R^{8C}$, —$ONR^{8B}R^{8C}$, —NHC(O)$NHNR^{8B}R^{8C}$, —NHC(O)$NR^{8B}R^{8C}$, —$N(O)_{m1}$, —$NR^{8B}R^{8C}$, —C(O)$R^{8D}$, —C(O)$OR^{8D}$, —C(O)$NR^{8B}R^{8C}$, —$OR^{8A}$, —$NR^{8B}SO_2R^{8A}$, —$NR^{8B}C(O)R^{8D}$, —$NR^{8B}C(O)OR^{8D}$, —$NR^{8B}OR^{8D}$, —$OCX^{8.1}_3$, —$OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, —$CX^{9.1}_3$, —$CHX^{9.1}_2$, —$CH_2X^{9.1}$, —CN, —$SO_{n1}R^{9A}$, —$SO_{v1}NR^{9B}R^{9C}$, —$NHNR^{9B}R^{9C}$, —$ONR^{9B}R^{9C}$, —NHC(O)$NHNR^{9B}R^{9C}$, —NHC(O)$NR^{9B}R^{9C}$, —$N(O)_{m1}$, —$NR^{9B}R^{9C}$, —C(O)$R^{9D}$, —C(O)$OR^{9D}$, —C(O)$NR^{9B}R^{9C}$, —$OR^{9A}$, —$NR^{9B}SO_2R^{9A}$, —$NR^{9B}C(O)R^{9D}$, —$NR^{9B}C(O)OR^{9D}$, —$NR^{9B}OR^{9D}$, —$OCX^{9.1}_3$, —$OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ is hydrogen, halogen, —$CX^{10.1}_3$, —$CHX^{10.1}_2$, —$CH_2X^{10.1}$, —CN, —$SO_{n1}R^{10A}$, —$SO_{v1}NR^{10B}R^{10C}$, —$NHNR^{10B}R^{10C}$, —$ONR^{10B}R^{10C}$, —NHC(O)$NHNR^{10B}R^{10C}$, —NHC(O)$NR^{10B}R^{10C}$, —$N(O)_{m1}$, —$NR^{10B}R^{10C}$, —C(O)$R^{10D}$, —C(O)$OR^{10D}$, —C(O)$NR^{10B}R^{10C}$, —$OR^{10A}$, —$NR^{10B}SO_2R^{10A}$, —$NR^{10B}C(O)R^{10D}$, —$NR^{10B}C(O)OR^{10D}$, —$NR^{10B}OR^{10D}$, —$OCX^{10.1}_3$, —$OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ is hydrogen, halogen, —$CX^{11.1}_3$, —$CHX^{11.1}_2$, —$CH_2X^{11.1}$, —CN, —$SO_{n1}R^{11A}$, —$SO_{v1}NR^{11B}R^{11C}$, —$NHNR^{11B}R^{11C}$, —$ONR^{11B}R^{11C}$, —NHC(O)$NHNR^{11B}R^{11C}$, —NHC(O)$NR^{11B}R^{11C}$, —$N(O)_{m1}$, —$NR^{11B}R^{11C}$, —C(O)$R^{11D}$, —C(O)$OR^{11D}$, —C(O)$NR^{11B}R^{11C}$, —$OR^{11A}$, —$NR^{11B}SO_2R^{11A}$, —$NR^{11B}C(O)R^{11D}$, —$NR^{11B}C(O)OR^{11D}$, —$NR^{11B}OR^{11D}$, —$OCX^{11.1}_3$, —$OCHX^{11.1}_2$, substituted or unsubstituted alkyl, substituted or unsubstituted cycloalkyl, substituted or unsubstituted heterocycloalkyl, substituted or unsubstituted aryl, or substituted or unsubstituted heteroaryl; $R^{12}$ is hydrogen, halogen, —$CX^{12.1}_3$, —$CHX^{12.1}_2$, —$CH_2X^{12.1}$, —CN, —$SO_{n1}R^{12A}$, —$SO_{v1}NR^{12B}R^{12C}$, —$NHNR^{12B}R^{12C}$, —$ONR^{12B}R^{12C}$, —NHC(O)$NHNR^{12B}R^{12C}$, —NHC(O)$NR^{12B}R^{12C}$, —$N(O)_{m1}$, —$NR^{12B}R^{12C}$, —C(O)$R^{12D}$, —C(O)$OR^{12D}$, —C(O)$NR^{12B}R^{12C}$, —$OR^{12A}$, —$NR^{12B}SO_2R^{12A}$, —$NR^{12B}C(O)R^{12D}$, —$NR^{12B}C(O)OR^{12D}$, —$NR^{12B}OR^{12D}$, —$OCX^{12.1}_3$, —$OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{13}$ is hydrogen, halogen, —$CX^{13.1}_3$, —$CHX^{13.1}_2$, —$CH_2X^{13.1}$, —CN, —$SO_{n1}R^{13A}$, —$SO_{v1}NR^{13B}R^{13C}$, —$NHNR^{13B}R^{13C}$, —$ONR^{13B}R^{13C}$, —NHC(O)$NHNR^{13B}R^{13C}$, —NHC(O)$NR^{13B}R^{13C}$, —$N(O)_{m1}$, —$NR^{13B}R^{13C}$, —C(O)$R^{13D}$, —C(O)$OR^{13D}$, —C(O)$NR^{13B}R^{13C}$, —$OR^{13A}$, —$NR^{13B}SO_2R^{13A}$, —$NR^{13B}C(O)R^{13D}$, —$NR^{13B}C(O)OR^{13D}$, —$NR^{13B}OR^{13D}$, —$OCX^{13.1}_3$, —$OCHX^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{14}$ is hydrogen, halogen, $-CX^{14.1}_3$, $-CHX^{14.1}_2$, $-CH_2X^{14.1}$, $-CN$, $-SO_{n1}R^{14A}$, $-SO_{v1}NR^{14B}R^{14C}$, $-NHNR^{14B}R^{14C}$, $-ONR^{14B}R^{14C}$, $-NHC(O)NHNR^{14B}R^{14C}$, $-NHC(O)NR^{14B}R^{14C}$, $-N(O)_{m1}$, $-NR^{14B}R^{14C}$, $-C(O)R^{14D}$, $-C(O)OR^{14D}$, $-C(O)NR^{14B}R^{14C}$, $-OR^{14A}$, $-NR^{14B}SO_2R^{14A}$, $-NR^{14B}C(O)R^{14D}$, $-NR^{14B}C(O)OR^{14D}$, $-NR^{14B}OR^{14D}$, $-OCX^{14.1}_3$, $-OCHX^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15}$ is hydrogen, halogen, $-CX^{15.1}_3$, $-CHX^{15.1}_2$, $-CH_2X^{15.1}$, $-CN$, $-SO_{n1}R^{15A}$, $-SO_{v1}NR^{15B}R^{15C}$, $-NHNR^{15B}R^{15C}$, $-ONR^{15B}R^{15C}$, $-NHC(O)NHNR^{15B}R^{15C}$, $-NHC(O)NR^{15B}R^{15C}$, $-N(O)_{m1}$, $-NR^{15B}R^{15C}$, $-C(O)R^{15D}$, $-C(O)OR^{15D}$, $-C(O)NR^{15B}R^{15C}$, $-OR^{15A}$, $-NR^{15B}SO_2R^{15A}$, $-NR^{15B}C(O)R^{15D}$, $-NR^{15B}C(O)OR^{15D}$, $-NR^{15B}OR^{15D}$, $-OCX^{15.1}_3$, $-OCHX^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$ is hydrogen, halogen, $-CX^{16.1}_3$, $-CHX^{16.1}_2$, $-CH_2X^{16.1}$, $-CN$, $-SO_{n1}R^{16A}$, $-SO_{v1}NR^{16B}R^{16C}$, $-NHNR^{16B}R^{16C}$, $-ONR^{16B}R^{16C}$, $-NHC(O)NHNR^{16B}R^{16C}$, $-NHC(O)NR^{16B}R^{16C}$, $-N(O)_{m1}$, $-NR^{16B}R^{16C}$, $-C(O)R^{16D}$, $-C(O)OR^{16D}$, $-C(O)NR^{16B}R^{16C}$, $-OR^{16A}$, $-NR^{16B}SO_2R^{16A}$, $-NR^{16B}C(O)R^{16D}$, $-NR^{16B}C(O)OR^{16D}$, $-NR^{16B}OR^{16D}$, $-OCX^{16.1}_3$, $-OCHX^{16.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{17}$ is hydrogen, halogen, $-CX^{17.1}_3$, $-CHX^{17.1}_2$, $-CH_2X^{17.1}$, $-CN$, $-SO_{n1}R^{17A}$, $-SO_{v1}NR^{17B}R^{17C}$, $-NHNR^{17B}R^{17C}$, $-ONR^{17B}R^{17C}$, $-NHC(O)NHNR^{17B}R^{17C}$, $-NHC(O)NR^{17B}R^{17C}$, $-N(O)_{m1}$, $-NR^{17B}R^{17C}$, $-C(O)R^{17D}$, $-C(O)OR^{17D}$, $-C(O)NR^{17B}R^{17C}$, $-OR^{17A}$, $-NR^{17B}SO_2R^{17A}$, $-NR^{17B}C(O)R^{17D}$, $-NR^{17B}C(O)OR^{17D}$, $-NR^{17B}OR^{17D}$, $-OCX^{17.1}_3$, $-OCHX^{17.1}_2$, substituted or unsubstituted alkyl, substituted or unsubstituted heteroalkyl, substituted or unsubstituted cycloalkyl, substituted or unsubstituted aryl, or substituted or unsubstituted heteroaryl; $R^{18}$ is hydrogen, halogen, $-CX^{18.1}_3$, $-CHX^{18.1}_2$, $-CH_2X^{18.1}$, $-CN$, $-SO_{n1}R^{18A}$, $-SO_{v1}NR^{18B}R^{18C}$, $-NHNR^{18B}R^{18C}$, $-ONR^{18B}R^{18C}$, $-NHC(O)NHNR^{18B}R^{18C}$, $-NHC(O)NR^{18B}R^{18C}$, $-N(O)_{m1}$, $-NR^{18B}R^{18C}$, $-C(O)R^{18D}$, $-C(O)OR^{18D}$, $-C(O)NR^{18B}R^{18C}$, $-OR^{18A}$, $-NR^{18B}SO_2R^{18A}$, $-NR^{18B}C(O)R^{18D}$, $-NR^{18B}C(O)OR^{18D}$, $-NR^{18B}OR^{18D}$, $-OCX^{18.1}_3$, $-OCHX^{18.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{19}$ is hydrogen, $-COR^{19D}$, $-C(O)NHR^{19B}R^{19C}$, $-C(O)OR^{19D}$, $-SO_2R^{19A}$, $C(O)NR^{19B}R^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$ and $R^{18D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{11B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17C}$, $R^{18B}$ and $R^{18C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$, $X^{12.1}$, $X^{13.1}$, $X^{14.1}$, $X^{15.1}$, $X^{16.1}$, $X^{17.1}$ and $X^{18.1}$ are independently $-Cl$, $-Br$, $-I$ or $-F$, with the proviso that when A is $CR^{14}$; B is $CR^{16}$; $L^1$ is bond; and $R^8$, $R^9$, $R^{11}$, $R^{12}$, $R^{13}$, $R^{14}$, $R^{15}$, $R^{16}$, $R^{17}$, $R^{18}$ and $R^{19}$ are independently hydrogen, then $R^{10}$ is not bromine.

Embodiment 2

The compound of embodiment 1, wherein $L^1$ is a bond and X is NH.

Embodiment 3

The compound of embodiment 2, wherein $R^{13}$, $R^{15}$, $R^{17}$ and $R^{18}$ are independently hydrogen.

Embodiment 4

The compound of embodiment 3, wherein $R^8$, $R^9$, $R^{11}$ and $R^{12}$ are independently hydrogen.

Embodiment 5

The compound of embodiment 4, wherein: A is $CR^{14}$; and B is $CR^{16}$.

Embodiment 6

The compound of embodiment 5, wherein: $R^{10}$ is hydrogen, fluorine, chlorine, iodine, $-CX^{10.1}_3$, $-CHX^{10.1}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{14}$ and $R^{16}$ are independently hydrogen.

Embodiment 7

The compound of embodiment 6, wherein $R^{10}$ is fluorine, chlorine or iodine.

Embodiment 8

The compound of embodiment 2, wherein $R^8$, $R^9$, $R^{11}$, $R^{12}$, $R^{13}$, $R^{15}$, $R^{17}$ and $R^{18}$ are independently hydrogen.

Embodiment 9

The compound of embodiment 8, wherein: A is N; B is $CR^{16}$; and $R^{16}$ is hydrogen.

Embodiment 10

The compound of embodiment 9, wherein $R^{10}$ is fluorine, chlorine, bromine or iodine.

Embodiment 11

The compound of embodiment 8, wherein A and B are independently N; and $R^{10}$ is fluorine, chlorine, bromine or iodine.

Embodiment 12

A compound of structural Formula (IIIa):

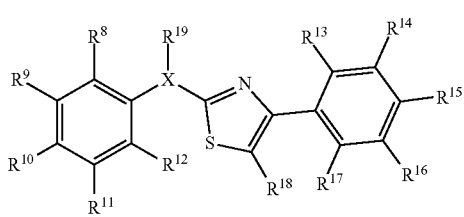

(IIIa)

or a pharmaceutically acceptable salt thereof, wherein: n1 is an integer from 0 to 4; m1 and v1 are independently 1 or 2; $R^8$ is hydrogen, halogen, $-CX^{8.1}_3$, $-CHX^{8.1}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, $-CX^{9.1}_3$, $-CHX^{9.1}_2$, $-CH_2X^{9.1}$, $-CN$, $-SO_{n1}R^{9A}$, $-SO_{v1}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m1}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ is hydrogen, fluorine, chlorine or iodine, $-CX^{10.1}_3$, $-CHX^{10.1}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)$ NHNR$^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ is hydrogen, halogen, $-CX^{11.1}_3$, $-CHX^{11.1}_2$, $-CH_2X^{11.1}$, $-CN$, $-SO_{n1}R^{11A}$, $-SO_{v1}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, $-N(O)_{m1}$, $-NR^{11B}R^{11C}$, $-C(O)R^{11D}$, $-C(O)OR^{11D}$, $-C(O)NR^{11B}R^{11C}$, $-OR^{11A}$, $-NR^{11B}SO_2R^{11A}$, $-NR^{11B}C(O)R^{11D}$, $-NR^{11B}C(O)OR^{11D}$, $-NR^{11B}OR^{11D}$, $-OCX^{11.1}_3$, $-OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{12}$ is hydrogen, halogen, $-CX^{12.1}_3$, $-CHX^{12.1}_2$, $-CH_2X^{12.1}$, $-CN$, $-SO_{n1}R^{12A}$, $-SO_{v1}NR^{12B}R^{12C}$, $-NHNR^{12B}R^{12C}$, $-ONR^{12B}R^{12C}$, $-NHC(O)NHNR^{12B}R^{12C}$, $-NHC(O)NR^{12B}R^{12C}$, $-N(O)_{m1}$, $-NR^{12B}R^{12C}$, $-C(O)R^{12D}$, $-C(O)OR^{12D}$, $-C(O)NR^{12B}R^{12C}$, $-OR^{12A}$, $-NR^{12B}SO_2R^{12A}$, $-NR^{12B}C(O)R^{12D}$, $-NR^{12B}C(O)OR^{12D}$, $-NR^{12B}OR^{12D}$, $-OCX^{12.1}_3$, $-OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{13}$ is hydrogen, halogen, $-CX^{13.1}_3$, $-CHX^{13.1}_2$, $-CH_2X^{13.1}$, $-CN$, $-SO_{n1}R^{13A}$, $-SO_{v1}NR^{13B}R^{13C}$, $-NHNR^{13B}R^{13C}$, $-ONR^{13B}R^{13C}$, $-NHC(O)NHNR^{13B}R^{13C}$, $-NHC(O)NR^{13B}R^{13C}$, $-N(O)_{m1}$, $-NR^{13B}R^{13C}$, $-C(O)R^{13D}$, $-C(O)OR^{13D}$, $-C(O)NR^{13B}R^{13C}$, $-OR^{13A}$, $-NR^{13B}SO_2R^{13A}$, $-NR^{13B}C(O)R^{13D}$, $-NR^{13B}C(O)OR^{13D}$, $-NR^{13B}OR^{13D}$, $-OCX^{13.1}_3$, $-OCHX^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{14}$ is hydrogen, halogen, $-CX^{14.1}_3$, $-CHX^{14.1}_2$, $-CH_2X^{14.1}$, $-CN$, $-SO_{n1}R^{14A}$, $-SO_{v1}NR^{14B}R^{14C}$, $-NHNR^{14B}R^{14C}$, $-ONR^{14B}R^{14C}$, $-NHC(O)NHNR^{14B}R^{14C}$, $-NHC(O)NR^{14B}R^{14C}$, $-N(O)_{m1}$, $-NR^{14B}R^{14C}$, $-C(O)R^{14D}$, $-C(O)OR^{14D}$, $-C(O)NR^{14B}R^{14C}$, $-OR^{14A}$, $-NR^{14B}SO_2R^{14A}$, $-NR^{14B}C(O)R^{14D}$, $-NR^{14B}C(O)OR^{14D}$, $-NR^{14B}OR^{14D}$, $-OCX^{14.1}_3$, $-OCHX^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15}$ is hydrogen, halogen, $-CX^{15.1}_3$, $-CHX^{15.1}_2$, $-CH_2X^{15.1}$, $-CN$, $-SO_{n1}R^{15A}$, $-SO_{v1}NR^{15B}R^{15C}$, $-NHNR^{15B}R^{15C}$, $-ONR^{15B}R^{15C}$, $-NHC(O)NHNR^{15B}R^{15C}$, $-NHC(O)NR^{15B}R^{15C}$, $-N(O)_{m1}$, $-NR^{15B}R^{15C}$, $-C(O)R^{15D}$, $-C(O)OR^{15D}$, $-C(O)NR^{15B}R^{15C}$, $-OR^{15A}$, $-NR^{15B}SO_2R^{15A}$, $-NR^{15B}C(O)R^{15D}$, $-NR^{15B}C(O)OR^{15D}$, $-NR^{15B}OR^{15D}$, $-OCX^{15.1}_3$, $-OCHX^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$ is hydrogen, halogen, $-CX^{16.1}_3$, $-CHX^{16.1}_2$, $-CH_2X^{16.1}$, $-CN$, $-SO_{n1}R^{16A}$, $-SO_{v1}NR^{16B}R^{16C}$, $-NHNR^{16B}R^{16C}$, $-ONR^{16B}R^{16C}$, $-NHC(O)NHNR^{16B}R^{16C}$, $-NHC(O)NR^{16B}R^{16C}$, —N(O)$_{m1}$, —NR$^{16B}$R$^{16C}$, —C(O)R$^{16D}$, —C(O)OR$^{16D}$, —C(O)NR$^{16B}$R$^{16C}$, —OR$^{16A}$, —NR$^{16B}$SO$_2$R$^{16A}$, —NR$^{16B}$C(O)R$^{16D}$, —NR$^{16B}$C(O)OR$^{16D}$, —NR$^{16B}$OR$^{16D}$, —OCX$^{16.1}_3$, —OCHX$^{16.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{17}$ is hydrogen, halogen, —CX$^{17.1}_3$, —CHX$^{17.1}_2$, —CH$_2$X$^{17.1}$, —CN, —SO$_{n1}$R$^{17A}$, —SO$_{v1}$NR$^{17B}$R$^{17C}$, —NHNR$^{17B}$R$^{17C}$, —ONR$^{17B}$R$^{17C}$, —NHC(O)NHNR$^{17B}$R$^{17C}$, —NHC(O)NR$^{17B}$R$^{17C}$, —N(O)$_{m1}$, —NR$^{17B}$R$^{17C}$, —C(O)R$^{17D}$, —C(O)OR$^{17D}$, —C(O)NR$^{17B}$R$^{17C}$, —OR$^{17A}$, —NR$^{17B}$SO$_2$R$^{17A}$, —NR$^{17B}$C(O)R$^{17D}$, —NR$^{17B}$C(O)OR$^{17D}$, —NR$^{17B}$OR$^{17D}$, —OCX$^{17.1}_3$, —OCHX$^{17.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{18}$ is hydrogen, halogen, —CX$^{18.1}_3$, —CHX$^{18.1}_2$, —CH$_2$X$^{18.1}$, —CN, —SO$_{n1}$R$^{18A}$, —SO$_{v1}$NR$^{18B}$R$^{18C}$, —NHNR$^{18B}$R$^{18C}$, —ONR$^{18B}$R$^{18C}$, —NHC(O)NHNR$^{18B}$R$^{18C}$, —NHC(O)NR$^{18B}$R$^{18C}$, —N(O)$_{m1}$, —NR$^{18B}$R$^{18C}$, —C(O)R$^{18D}$, —C(O)OR$^{18D}$, —C(O)NR$^{18B}$R$^{18C}$, —OR$^{18A}$, —NR$^{18B}$SO$_2$R$^{18A}$, —NR$^{18B}$C(O)R$^{18D}$, —NR$^{18B}$C(O)OR$^{18D}$, —NR$^{18B}$OR$^{18D}$, —OCX$^{18.1}_3$, —OCHX$^{18.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; R$^{19}$ is hydrogen, —COR$^{19D}$, —C(O)NHNR$^{19B}$R$^{19C}$, —C(O)OR$^{19D}$, —SO$_2$R$^{19A}$, C(O)NR$^{19B}$R$^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{11A}$, R$^{11B}$, R$^{11C}$, R$^{11D}$, R$^{12A}$, R$^{12B}$, R$^{12C}$, R$^{12D}$, R$^{13A}$, R$^{13B}$, R$^{13C}$, R$^{13D}$, R$^{14A}$, R$^{14B}$, R$^{14C}$, R$^{14D}$, R$^{15A}$, R$^{15B}$, R$^{15C}$, R$^{15D}$, R$^{16A}$, R$^{16B}$, R$^{16C}$, R$^{16D}$, R$^{17A}$, R$^{17B}$, R$^{17C}$, R$^{17D}$, R$^{18A}$, R$^{18B}$, R$^{18C}$ and R$^{18D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1B}$, R$^{1C}$, R$^{2B}$, R$^{2C}$, R$^{3B}$, R$^{3C}$, R$^{4B}$, R$^{4C}$, R$^{5B}$, R$^{5C}$, R$^{6B}$, R$^{6C}$, R$^{7B}$, R$^{7C}$, R$^{8B}$, R$^{8C}$, R$^{9B}$, R$^{9C}$, R$^{10B}$, R$^{10C}$, R$^{11B}$, R$^{11C}$, R$^{12B}$, R$^{12C}$, R$^{13B}$, R$^{13C}$, R$^{14B}$, R$^{14C}$, R$^{15B}$, R$^{15C}$, R$^{16B}$, R$^{16C}$, R$^{17B}$, R$^{17C}$, R$^{18B}$ and R$^{18C}$ substituents bonded to the same nitrogen atom may optionally be joined to form a substituted or unsubstituted heterocycloalkyl or substituted or unsubstituted heteroaryl; and X$^{1.1}$, X$^{2.1}$, X$^{3.1}$, X$^{4.1}$, X$^{5.1}$, X$^{6.1}$, X$^{7.1}$, X$^{8.1}$, X$^{9.1}$, X$^{10.1}$, X$^{11.1}$, X$^{12.1}$, X$^{13.1}$, X$^{14.1}$, X$^{15.1}$, X$^{16.1}$, X$^{17.1}$ and X$^{18.1}$ are independently —Cl, —Br, —I or —F.

Embodiment 13

A compound of structural Formula (Mb):

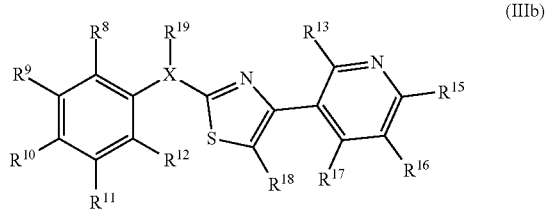

(IIIb)

or a pharmaceutically acceptable salt thereof, wherein: n1 is an integer from 0 to 4; m1 and v1 are independently 1 or 2; R$^8$ is hydrogen, halogen, —CX$^{8.1}_3$, —CHX$^{8.1}_2$, —CH$_2$X$^{8.1}$, —CN, —SO$_{n1}$R$^{8A}$, —SO$_{v1}$NR$^{8B}$R$^{8C}$, —NHNR$^{8B}$R$^{8C}$, —ONR$^{8B}$R$^{8C}$, —NHC(O)NHNR$^{8B}$R$^{8C}$, —NHC(O)NR$^{8B}$R$^{8C}$, —N(O)$_{m1}$, —NR$^{8B}$R$^{8C}$, —C(O)R$^{8D}$, —C(O)OR$^{8D}$, —C(O)NR$^{8B}$R$^{8C}$, —OR$^{8A}$, —NR$^{8B}$SO$_2$R$^{8A}$, —NR$^{8B}$C(O)R$^{8D}$, —NR$^{8B}$C(O)OR$^{8D}$, —NR$^{8B}$OR$^{8D}$, —OCX$^{8.1}_3$, —OCHX$^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^9$ is hydrogen, halogen, —CX$^{9.1}_3$, —CHX$^{9.1}_2$, —CH$_2$X$^{9.1}$, —CN, —SO$_{n1}$R$^{9A}$, —SO$_{v1}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m1}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}_3$, —OCHX$^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{10}$ is hydrogen, halogen, —CX$^{10.1}_3$, —CHX$^{10.1}_2$, —CH$_2$X$^{10.1}$, —CN, —SO$_{n1}$R$^{10A}$, —SO$_{v1}$NR$^{10B}$R$^{10C}$, —NHNR$^{10B}$R$^{10C}$, —ONR$^{10B}$R$^{10C}$, —NHC(O)NHNR$^{10B}$R$^{10C}$, —NHC(O)NR$^{10B}$R$^{10C}$, —N(O)$_{m1}$, —NR$^{10B}$R$^{10C}$, —C(O)R$^{10D}$, —C(O)OR$^{10D}$, —C(O)NR$^{10B}$R$^{10C}$, —OR$^{10A}$, —NR$^{10B}$SO$_2$R$^{10A}$, —NR$^{10B}$C(O)R$^{10D}$, —NR$^{10B}$C(O)OR$^{10D}$, —NR$^{10B}$OR$^{10D}$, —OCX$^{10.1}_3$, —OCHX$^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{11}$ is hydrogen, halogen, —CX$^{11.1}_3$, —CHX$^{11.1}_2$, —CH$_2$X$^{11.1}$, —CN, —SO$_{n1}$R$^{11A}$, —SO$_{v1}$NR$^{11B}$R$^{11C}$, —NHNR$^{11B}$R$^{11C}$, —ONR$^{11B}$R$^{11C}$, —NHC(O)NHNR$^{11B}$R$^{11C}$, —NHC(O)NR$^{11B}$R$^{11C}$, —N(O)$_{m1}$, —NR$^{11B}$R$^{11C}$, —C(O)R$^{11D}$, —C(O)OR$^{11D}$, —C(O)NR$^{11B}$R$^{11C}$, —OR$^{11A}$, —NR$^{11B}$SO$_2$R$^{11A}$, —NR$^{11B}$C(O)R$^{11D}$, —NR$^{11B}$C(O)OR$^{11D}$, —NR$^{11B}$OR$^{11D}$, —OCX$^{11.1}_3$, —OCHX$^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{12}$ is hydrogen, halogen, —CX$^{12.1}_3$, —CHX$^{12.1}_2$, —CH$_2$X$^{12.1}$, —CN, —SO$_{n1}$R$^{12A}$, —SO$_{v1}$NR$^{12B}$R$^{12C}$, —NHNR$^{12B}$R$^{12C}$, —ONR$^{12B}$R$^{12C}$, —NHC(O)NHNR$^{12B}$R$^{12C}$, —NHC(O)NR$^{12B}$R$^{12C}$, —N(O)$_{m1}$, —NR$^{12B}$R$^{12C}$, —C(O)R$^{12D}$, —C(O)OR$^{12D}$, —C(O)NR$^{12B}$R$^{12C}$, —OR$^{12A}$, —NR$^{12B}$SO$_2$R$^{12A}$, —NR$^{12B}$C(O)R$^{12D}$, —NR$^{12B}$C(O)OR$^{12D}$, —NR$^{12B}$OR$^{12D}$, —OCX$^{12.1}_3$, —OCHX$^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{13}$ is hydrogen, halogen, —CX$^{13.1}_3$, —CHX$^{13.1}_2$, —CH$_2$X$^{13.1}$, —CN, —SO$_{n1}$R$^{13A}$, —SO$_{v1}$NR$^{13B}$R$^{13C}$, —NHNR$^{13B}$R$^{13C}$, —ONR$^{13B}$R$^{13C}$, —NHC(O)NHNR$^{13B}$R$^{13C}$, —NHC(O)NR$^{13B}$R$^{13C}$, —N(O)$_{m1}$, —NR$^{13B}$R$^{13C}$, —C(O)R$^{13D}$, —C(O)OR$^{13D}$, —C(O)NR$^{13B}$R$^{13C}$, —OR$^{13A}$, —NR$^{13B}$SO$_2$R$^{13A}$, —NR$^{13B}$C(O)R$^{13D}$, —NR$^{13B}$C(O)OR$^{13D}$, —NR$^{13B}$OR$^{13D}$, —OCX$^{13.1}_3$, —OCHX$^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15}$ is hydrogen, halogen, —CX$^{15.1}_3$, —CHX$^{15.1}_2$, —CH$_2$X$^{15.1}$, —CN, —SO$_{n1}$R$^{15A}$, —SO$_{v1}$NR$^{15B}$R$^{15C}$, —NHNR$^{15B}$R$^{15C}$, —ONR$^{15B}$R$^{15C}$, —NHC(O)NHNR$^{15B}$R$^{15C}$, —NHC(O)NR$^{15B}$R$^{15C}$, —N(O)$_{m1}$, —NR$^{15B}$R$^{15C}$, —C(O)R$^{15D}$, —C(O)OR$^{15D}$, —C(O)NR$^{15B}$R$^{15C}$, —OR$^{15A}$, —NR$^{15B}$SO$_2$R$^{15A}$, —NR$^{15B}$C(O)R$^{15D}$, —NR$^{15B}$C(O)OR$^{15D}$, —NR$^{15B}$OR$^{15D}$, —OCX$^{15.1}_3$, —OCHX$^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$ is hydrogen, halogen, —CX$^{16.1}_3$, —CHX$^{16.1}_2$, —CH$_2$X$^{16.1}$, —CN, —SO$_{n1}$R$^{16A}$, —SO$_{v1}$NR$^{16B}$R$^{16C}$, —NHNR$^{16B}$R$^{16C}$, —ONR$^{16B}$R$^{16C}$, —NHC(O)NHNR$^{16B}$R$^{16C}$, —NHC(O)NR$^{16B}$R$^{16C}$, —N(O)$_{m1}$, —NR$^{16B}$R$^{16C}$, —C(O)R$^{16D}$, —C(O)OR$^{16D}$, —C(O)NR$^{16B}$R$^{16C}$, —OR$^{16A}$, —NR$^{16B}$SO$_2$R$^{16A}$, —NR$^{16B}$C(O)R$^{16D}$, —NR$^{16B}$C(O)OR$^{16D}$, —NR$^{16B}$OR$^{16D}$, —OCX$^{16.1}_3$, —OCHX$^{16.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{17}$ is hydrogen, halogen, —CX$^{17.1}_3$, —CHX$^{17.1}_2$, —CH$_2$X$^{17.1}$, —CN, —SO$_{n1}$R$^{17A}$, —SO$_{v1}$NR$^{17B}$R$^{17C}$, —NHNR$^{17B}$R$^{17C}$, —ONR$^{17B}$R$^{17C}$, —NHC(O)NHNR$^{17B}$R$^{17C}$, —NHC(O)NR$^{17B}$R$^{17C}$, —N(O)$_{m1}$, —NR$^{17B}$R$^{17C}$, —C(O)R$^{17D}$, —C(O)OR$^{17D}$, —C(O)NR$^{17B}$R$^{17C}$, —OR$^{17A}$, —NR$^{17B}$SO$_2$R$^{17A}$, —NR$^{17B}$C(O)R$^{17D}$, —NR$^{17B}$C(O)OR$^{17D}$, —NR$^{17B}$OR$^{17D}$, —OCX$^{17.1}_3$, —OCHX$^{17.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{18}$ is hydrogen, halogen, —CX$^{18.1}_3$, —CHX$^{18.1}_2$, —CH$_2$X$^{18.1}$, —CN, —SO$_{n1}$R$^{18A}$, —SO$_{v1}$NR$^{18B}$R$^{18C}$, —NHNR$^{18B}$R$^{18C}$, —ONR$^{18B}$R$^{18C}$, —NHC(O)NHNR$^{18B}$R$^{18C}$, —NHC(O)NR$^{18B}$R$^{18C}$, —N(O)$_{m1}$, —NR$^{18B}$R$^{18C}$, —C(O)R$^{18D}$, —C(O)OR$^{18D}$, —C(O)NR$^{18B}$R$^{18C}$, —OR$^{18A}$, —NR$^{18B}$SO$_2$R$^{18A}$, —NR$^{18B}$C(O)R$^{18D}$, —NR$^{18B}$C(O)OR$^{18D}$, —NR$^{18B}$OR$^{18D}$, —OCX$^{18.1}_3$, —OCHX$^{18.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{19}$ is hydrogen, —COR$^{19D}$, —C(O)NHNR$^{19B}$R$^{19C}$, —C(O)OR$^{19D}$, —SO$_2$R$^{19A}$, C(O)NR$^{19B}$R$^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$ and $R^{18D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{11B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17C}$, $R^{18B}$ and $R^{18C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$, $X^{12.1}$, $X^{13.1}$, $X^{14.1}$, $X^{15.1}$, $X^{16.1}$, $X^{17.1}$ and $X^{18.1}$ are independently —Cl, —Br, —I or —F.

Embodiment 14

A compound of structural Formula (IIIc):

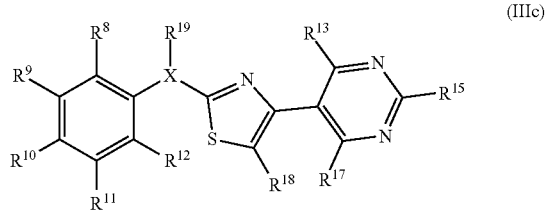

(IIIc)

or a pharmaceutically acceptable salt thereof, wherein: n1 is an integer from 0 to 4; m1 and v1 are independently 1 or 2; $R^8$ is hydrogen, halogen, —CX$^{8.1}_3$, —CHX$^{8.1}_2$, —CH$_2$X$^{8.1}$, —CN, —SO$_{n1}$R$^{8A}$, —SO$_{v1}$NR$^{8B}$R$^{8C}$, —NHNR$^{8B}$R$^{8C}$, —ONR$^{8B}$R$^{8C}$, —NHC(O)NHNR$^{8B}$R$^{8C}$, —NHC(O)NR$^{8B}$R$^{8C}$, —N(O)$_{m1}$, —NR$^{8B}$R$^{8C}$, —C(O)R$^{8D}$, —C(O)OR$^{8D}$, —C(O)NR$^{8B}$R$^{8C}$, —OR$^{8A}$, —NR$^{8B}$SO$_2$R$^{8A}$, —NR$^{8B}$C(O)R$^{8D}$, —NR$^{8B}$C(O)OR$^{8D}$, —NR$^{8B}$OR$^{8D}$, —OCX$^{8.1}_3$, —OCHX$^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, —CX$^{9.1}_3$, —CHX$^{9.1}_2$, —CH$_2$X$^{9.1}$, —CN, —SO$_{n1}$R$^{9A}$, —SO$_{v1}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m1}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}_3$, —OCHX$^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ is hydrogen, halogen, —CX$^{10.1}_3$, —CHX$^{10.1}_2$, —CH$_2$X$^{10.1}$, —CN, —SO$_{n1}$R$^{10A}$, —SO$_{v1}$NR$^{10B}$R$^{10C}$, —NHNR$^{10B}$R$^{10C}$, —ONR$^{10B}$R$^{10C}$, —NHC(O)NHNR$^{10B}$R$^{10C}$, —NHC(O)

$NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ is hydrogen, halogen, $-CX^{11.1}_3$, $-CHX^{11.1}_2$, $-CH_2X^{11.1}$, $-CN$, $-SO_{n1}R^{11A}$, $-SO_{v1}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, $-N(O)_{m1}$, $-NR^{11B}R^{11C}$, $-C(O)R^{11D}$, $-C(O)OR^{11D}$, $-C(O)NR^{11B}R^{11C}$, $-OR^{11A}$, $-NR^{11B}SO_2R^{11A}$, $-NR^{11B}C(O)R^{11D}$, $-NR^{11B}C(O)OR^{11D}$, $-NR^{11B}OR^{11D}$, $-OCX^{11.1}_3$, $-OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{12}$ is hydrogen, halogen, $-CX^{12.1}_3$, $-CHX^{12.1}_2$, $-CH_2X^{12.1}$, $-CN$, $-SO_{n1}R^{12A}$, $-SO_{v1}NR^{12B}R^{12C}$, $-NHNR^{12B}R^{12C}$, $-ONR^{12B}R^{12C}$, $-NHC(O)NHNR^{12B}R^{12C}$, $-NHC(O)NR^{12B}R^{12C}$, $-N(O)_{m1}$, $-NR^{12B}R^{12C}$, $-C(O)R^{12D}$, $-C(O)OR^{12D}$, $-C(O)NR^{12B}R^{12C}$, $-OR^{12A}$, $-NR^{12B}SO_2R^{12A}$, $-NR^{12B}C(O)R^{12D}$, $-NR^{12B}C(O)OR^{12D}$, $-NR^{12B}OR^{12D}$, $-OCX^{12.1}_3$, $-OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{13}$ is hydrogen, halogen, $-CX^{13.1}_3$, $-CHX^{13.1}_2$, $-CH_2X^{13.1}$, $-CN$, $-SO_{n1}R^{13A}$, $-SO_{v1}NR^{13B}R^{13C}$, $-NHNR^{13B}R^{13C}$, $-ONR^{13B}R^{13C}$, $-NHC(O)NHNR^{13B}R^{13C}$, $-NHC(O)NR^{13B}R^{13C}$, $-N(O)_{m1}$, $-NR^{13B}R^{13C}$, $-C(O)R^{13D}$, $-C(O)OR^{13D}$, $-C(O)NR^{13B}R^{13C}$, $-OR^{13A}$, $-NR^{13B}SO_2R^{13A}$, $-NR^{13B}C(O)R^{13D}$, $-NR^{13B}C(O)OR^{13D}$, $-NR^{13B}OR^{13D}$, $-OCX^{13.1}_3$, $-OCHX^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15}$ is hydrogen, halogen, $-CX^{15.1}_3$, $-CHX^{15.1}_2$, $-CH_2X^{15.1}$, $-CN$, $-SO_{n1}R^{15A}$, $-SO_{v1}NR^{15B}R^{15C}$, $-NHNR^{15B}R^{15C}$, $-ONR^{15B}R^{15C}$, $-NHC(O)NHNR^{15B}R^{15C}$, $-NHC(O)NR^{15B}R^{15C}$, $-N(O)_{m1}$, $-NR^{15B}R^{15C}$, $-C(O)R^{15D}$, $-C(O)OR^{15D}$, $-C(O)NR^{15B}R^{15C}$, $-OR^{15A}$, $-NR^{15B}SO_2R^{15A}$, $-NR^{15B}C(O)R^{15D}$, $-NR^{15B}C(O)OR^{15D}$, $-NR^{15B}OR^{15D}$, $-OCX^{15.1}_3$, $-OCHX^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{17}$ is hydrogen, halogen, $-CX^{17.1}_3$, $-CHX^{17.1}_2$, $-CH_2X^{17.1}$, $-CN$, $-SO_{n1}R^{17A}$, $-SO_{v1}NR^{17B}R^{17C}$, $-NHNR^{17B}R^{17C}$, $-ONR^{17B}R^{17C}$, $-NHC(O)NHNR^{17B}R^{17C}$, $-NHC(O)NR^{17B}R^{17C}$, $-N(O)_{m1}$, $-NR^{17B}R^{17C}$, $-C(O)R^{17D}$, $-C(O)OR^{17D}$, $-C(O)NR^{17B}R^{17C}$, $-OR^{17A}$, $-NR^{17B}SO_2R^{17A}$, $-NR^{17B}C(O)R^{17D}$, $-NR^{17B}C(O)OR^{17D}$, $-NR^{17B}OR^{17D}$, $-OCX^{17.1}_3$, $-OCHX^{17.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{18}$ is hydrogen, halogen, $-CX^{18.1}_3$, $-CHX^{18.1}_2$, $-CH_2X^{18.1}$, $-CN$, $-SO_{n1}R^{18A}$, $-SO_{v1}NR^{18B}R^{18C}$, $-NHNR^{18B}R^{18C}$, $-ONR^{18B}R^{18C}$, $-NHC(O)NHNR^{18B}R^{18C}$, $-NHC(O)NR^{18B}R^{18C}$, $-N(O)_{m1}$, $-NR^{18B}R^{18C}$, $-C(O)R^{18D}$, $-C(O)OR^{18D}$, $-C(O)NR^{18B}R^{18C}$, $-OR^{18A}$, $-NR^{18B}SO_2R^{18A}$, $-NR^{18B}C(O)R^{18D}$, $-NR^{18B}C(O)OR^{18D}$, $-NR^{18B}OR^{18D}$, $-OCX^{18.1}_3$, $-OCHX^{18.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{19}$ is hydrogen, $-COR^{19D}$, $-C(O)NHNR^{19B}R^{19C}$, $-C(O)OR^{19D}$, $-SO_2R^{19A}$, $C(O)NR^{19B}R^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$ and $R^{18D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{11B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17C}$, $R^{18B}$ and $R^{18C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$, $X^{12.1}$, $X^{13.1}$, $X^{14.1}$, $X^{15.1}$, $X^{16.1}$, $X^{17.1}$ and $X^{18.1}$ are independently $-Cl$, $-Br$, $-I$ or $-F$.

Embodiment 15

A method of increasing MYC expression in a cell, comprising contacting the cell with a binding site 1 gp130 receptor agonist.

Embodiment 16

The method of embodiment 15, wherein the cell is a chondrocyte.

Embodiment 17

A method of increasing pSTAT3 expression in a cell, comprising contacting the cell with a binding site 1 gp130 receptor agonist.

Embodiment 18

The method of embodiment 17, wherein the cell is a chondrocyte.

Embodiment 19

A method of regulating chondrocyte activation, maturation and/or differentiation, comprising contacting a chondrocyte with a binding site 1 gp130 receptor agonist.

Embodiment 20

The method of embodiment 19, wherein the chondrocyte activation comprises an increase in proliferation, migration, metabolism or any combination thereof.

Embodiment 21

The method of embodiment 19, wherein the chondrocyte is an adult chondrocyte.

Embodiment 22

A method of regenerating or repairing tissue in a subject in need thereof, comprising administering to the subject a therapeutically effective amount of a binding site 1 gp130 receptor agonist.

Embodiment 23

The method of embodiment 22, wherein the tissue is cartilage.

Embodiment 24

A method of repairing a joint surface injury in a subject, comprising administering to the subject a therapeutically effective amount of a binding site 1 gp130 receptor agonist.

Embodiment 25

A method of treating a cartilage degenerative disease in a subject in need thereof, comprising administering to the subject a therapeutically effective amount of a binding site 1 gp130 receptor agonist.

Embodiment 26

A method of increasing secretion of cartilaginous matrix in cartilage, comprising contacting a gp130 receptor with a binding site 1 gp130 receptor agonist.

Embodiment 27

The method of embodiment 26, wherein the cartilaginous matrix is in articular cartilage.

Embodiment 28

The method of embodiment 26, wherein the cartilaginous matrix comprises collagens and proteoglycans.

Embodiment 29

A method of modulating the activity of a gp130 receptor in a cell, comprising contacting the cell with a binding site 1 gp130 receptor agonist.

Embodiment 30

The method of embodiment 29, wherein the activity of the gp130 receptor is increased.

Embodiment 31

The method of embodiment 29, wherein the activity of the gp130 receptor is decreased or inhibited.

Embodiment 32

The method of embodiment 30, wherein the activity is homodimerization.

Embodiment 33

The method of embodiment 29, wherein the cell is a chondrocyte.

Embodiment 34

A method of transforming a mature adult cell to a progenitor cell, comprising contacting the cell with a binding site 1 gp130 receptor agonist.

Embodiment 35

The method of embodiment 34, wherein the cell is a human cell.

Embodiment 36

The method of embodiment 34, wherein the cell is a chondrocyte.

Embodiment 37

The method of any one of embodiments 15 to 36, wherein the binding site 1 gp130 receptor agonist is a compound of Formula (III):

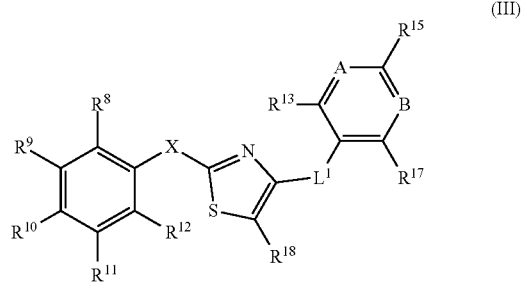

(III)

or a pharmaceutically acceptable salt thereof, wherein: A is $CR^{14}$ or N; B is $CR^{16}$ or N; X is O, $NR^{19}$ or S; $L^1$ is a bond or substituted or unsubstituted $C_1$-$C_3$ alkylene; n1 is an integer from 0 to 4; m1 and v1 are independently 1 or 2; $R^8$ is hydrogen, halogen, —$CX^{8.1}_3$, —$CHX^{8.1}_2$, —$CH_2X^{8.1}$, —CN, —$SO_{n1}R^{8A}$, —$SO_{v1}NR^{8B}R^{8C}$, —$NHNR^{8B}R^{8C}$, —$ONR^{8B}R^{8C}$, —$NHC(O)NHNR^{8B}R^{8C}$, —$NHC(O)NR^{8B}R^{8C}$, —$N(O)_{m1}$, —$NR^{8B}R^{8C}$, —$C(O)R^{8D}$, —$C(O)OR^{8D}$, —$C(O)NR^{8B}R^{8C}$, —$OR^{8A}$, —$NR^{8B}SO_2R^{8A}$, —$NR^{8B}C(O)R^{8D}$, —$NR^{8B}C(O)OR^{8D}$, —$NR^{8B}OR^{8D}$, —$OCX^{8.1}_3$, —$OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, —$CX^{9.1}_3$, —$CHX^{9.1}_2$, —$CH_2X^{9.1}$, —CN, —$SO_{n1}R^{9A}$, —$SO_{v1}NR^{9B}R^{9C}$, —$NHNR^{9B}R^{9C}$, —$ONR^{9B}R^{9C}$, —NHC(O)NHNR$^{9B}$R$^{9C}$, —NHC(O)NR$^{9B}$R$^{9C}$, —$N(O)_{m1}$, —$NR^{9B}R^{9C}$, —$C(O)R^{9D}$, —$C(O)OR^{9D}$, —$C(O)NR^{9B}R^{9C}$, —$OR^{9A}$, —$NR^{9B}SO_2R^{9A}$, —$NR^{9B}C(O)R^{9D}$, —$NR^{9B}C(O)OR^{9D}$, —$NR^{9B}OR^{9D}$, —$OCX^{9.1}_3$, —$OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ is hydrogen, halogen, $-CX^{10.1}{}_3$, $-CHX^{10.1}{}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}{}_3$, $-OCHX^{10.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ is hydrogen, halogen, $-CX^{11.1}{}_3$, $-CHX^{11.1}{}_2$, $-CH_2X^{11.1}$, $-CN$, $-SO_{n1}R^{11A}$, $-SO_{v1}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, $-N(O)_{m1}$, $-NR^{11B}R^{11C}$, $-C(O)R^{11D}$, $-C(O)OR^{11D}$, $-C(O)NR^{11B}R^{11C}$, $-OR^{11A}$, $-NR^{11B}SO_2R^{11A}$, $-NR^{11B}C(O)R^{11D}$, $-NR^{11B}C(O)OR^{11D}$, $-NR^{11B}OR^{11D}$, $-OCX^{11.1}{}_3$, $-OCHX^{11.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{12}$ is hydrogen, halogen, $-CX^{12.1}{}_3$, $-CHX^{12.1}{}_2$, $-CH_2X^{12.1}$, $-CN$, $-SO_{n1}R^{12A}$, $-SO_{v1}NR^{12B}R^{12C}$, $-NHNR^{12B}R^{12C}$, $-ONR^{12B}R^{12C}$, $-NHC(O)NHNR^{12B}R^{12C}$, $-NHC(O)NR^{12B}R^{12C}$, $-N(O)_{m1}$, $-NR^{12B}R^{12C}$, $-C(O)R^{12D}$, $-C(O)OR^{12D}$, $-C(O)NR^{12B}R^{12C}$, $-OR^{12A}$, $-NR^{12B}SO_2R^{12A}$, $-NR^{12B}C(O)R^{12D}$, $-NR^{12B}C(O)OR^{12D}$, $-NR^{12B}OR^{12D}$, $-OCX^{12.1}{}_3$, $-OCHX^{12.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{13}$ is hydrogen, halogen, $-CX^{13.1}{}_3$, $-CHX^{13.1}{}_2$, $-CH_2X^{13.1}$, $-CN$, $-SO_{n1}R^{13A}$, $-SO_{v1}NR^{13B}R^{13C}$, $-NHNR^{13B}R^{13C}$, $-ONR^{13B}R^{13C}$, $-NHC(O)NHNR^{13B}R^{13C}$, $-NHC(O)NR^{13B}R^{13C}$, $-N(O)_{m1}$, $-NR^{13B}R^{13C}$, $-C(O)R^{13D}$, $-C(O)OR^{13D}$, $-C(O)NR^{13B}R^{13C}$, $-OR^{13A}$, $-NR^{13B}SO_2R^{13A}$, $-NR^{13B}C(O)R^{13D}$, $-NR^{13B}C(O)OR^{13D}$, $-NR^{13B}OR^{13D}$, $-OCX^{13.1}{}_3$, $-OCHX^{13.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{14}$ is hydrogen, halogen, $-CX^{14.1}{}_3$, $-CHX^{14.1}{}_2$, $-CH_2X^{14.1}$, $-CN$, $-SO_{n1}R^{14A}$, $-SO_{v1}NR^{14B}R^{14C}$, $-NHNR^{14B}R^{14C}$, $-ONR^{14B}R^{14C}$, $-NHC(O)NHNR^{14B}R^{14C}$, $-NHC(O)NR^{14B}R^{14C}$, $-N(O)_{m1}$, $-NR^{14B}R^{14C}$, $-C(O)R^{14D}$, $-C(O)OR^{14D}$, $-C(O)NR^{14B}R^{14C}$, $-OR^{14A}$, $-NR^{14B}SO_2R^{14A}$, $-NR^{14B}C(O)R^{14D}$, $-NR^{14B}C(O)OR^{14D}$, $-NR^{14B}OR^{14D}$, $-OCX^{14.1}{}_3$, $-OCHX^{14.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15}$ is hydrogen, halogen, $-CX^{15.1}{}_3$, $-CHX^{15.1}{}_2$, $-CH_2X^{15.1}$, $-CN$, $-SO_{n1}R^{15A}$, $-SO_{v1}NR^{15B}R^{15C}$, $-NHNR^{15B}R^{15C}$, $-ONR^{15B}R^{15C}$, $-NHC(O)NHNR^{15B}R^{15C}$, $-NHC(O)NR^{15B}R^{15C}$, $-N(O)_{m1}$, $-NR^{15B}R^{15C}$, $-C(O)R^{15D}$, $-C(O)OR^{15D}$, $-C(O)NR^{15B}R^{15C}$, $-OR^{15A}$, $-NR^{15B}SO_2R^{15A}$, $-NR^{15B}C(O)R^{15D}$, $-NR^{15B}C(O)OR^{15D}$, $-NR^{15B}OR^{15D}$, $-OCX^{15.1}{}_3$, $-OCHX^{15.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$ is hydrogen, halogen, $-CX^{16.1}{}_3$, $-CHX^{16.1}{}_2$, $-CH_2X^{16.1}$, $-CN$, $-SO_{n1}R^{16A}$, $-SO_{v1}NR^{16B}R^{16C}$, $-NHNR^{16B}R^{16C}$, $-ONR^{16B}R^{16C}$, $-NHC(O)NHNR^{16B}R^{16C}$, $-NHC(O)NR^{16B}R^{16C}$, $-N(O)_{m1}$, $-NR^{16B}R^{16C}$, $-C(O)R^{16D}$, $-C(O)OR^{16D}$, $-C(O)NR^{16B}R^{16C}$, $-OR^{16A}$, $-NR^{16B}SO_2R^{16A}$, $-NR^{16B}C(O)R^{16D}$, $-NR^{16B}C(O)OR^{16D}$, $-NR^{16B}OR^{16D}$, $-OCX^{16.1}{}_3$, $-OCHX^{16.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{17}$ is hydrogen, halogen, $-CX^{17.1}{}_3$, $-CHX^{17.1}{}_2$, $-CH_2X^{17.1}$, $-CN$, $-SO_{n1}R^{17A}$, $-SO_{v1}NR^{17B}R^{17C}$, $-NHNR^{17B}R^{17C}$, $-ONR^{17B}R^{17C}$, $-NHC(O)NHNR^{17B}R^{17C}$, $-NHC(O)NR^{17B}R^{17C}$, $-N(O)_{m1}$, $-NR^{17B}R^{17C}$, $-C(O)R^{17D}$, $-C(O)OR^{17D}$, $-C(O)NR^{17B}R^{17C}$, $-OR^{17A}$, $-NR^{17B}SO_2R^{17A}$, $-NR^{17B}C(O)R^{17D}$, $-NR^{17B}C(O)OR^{17D}$, $-NR^{17B}OR^{17D}$, $-OCX^{17.1}{}_3$, $-OCHX^{17.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{18}$ is hydrogen, halogen, $-CX^{18.1}{}_3$, $-CHX^{18.1}{}_2$, $-CH_2X^{18.1}$, $-CN$, $-SO_{n1}R^{18A}$, $-SO_{v1}NR^{18B}R^{18C}$, $-NHNR^{18B}R^{18C}$, $-ONR^{18B}R^{18C}$, $-NHC(O)NHNR^{18B}R^{18C}$, $-NHC(O)NR^{18B}R^{18C}$, $-N(O)_{m1}$, $-NR^{18B}R^{18C}$, $-C(O)R^{18D}$, $-C(O)OR^{18D}$, $-C(O)NR^{18B}R^{18C}$, $-OR^{18A}$, $-NR^{18B}SO_2R^{18A}$, $-NR^{18B}C(O)R^{18D}$, $-NR^{18B}C(O)OR^{18D}$, $-NR^{18B}OR^{18D}$, $-OCX^{18.1}{}_3$, $-OCHX^{18.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{19}$ is hydrogen, $-COR^{19D}$, $-C(O)NHNR^{19B}R^{19C}$, $-C(O)OR^{19D}$, $-SO_2R^{19A}$, $C(O)NR^{19B}R^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$ and $R^{18D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{11B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17C}$, $R^{18B}$ and $R^{18C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$, $X^{12.1}$, $X^{13.1}$, $X^{14.1}$, $X^{15.1}$, $X^{16.1}$, $X^{17.1}$ and $X^{18.1}$ are independently —Cl, —Br, —I or —F.

Embodiment 38

The method of embodiment 37, wherein $L^1$ is a bond and X is NH.

Embodiment 39

The method of embodiment 38, wherein $R^{13}$, $R^{15}$, $R^{17}$ and $R^{18}$ are independently hydrogen.

Embodiment 40

The method of embodiment 39, wherein $R^8$, $R^9$, $R^{11}$ and $R^{12}$ are independently hydrogen.

Embodiment 41

The method of embodiment 40, wherein: A is $CR^{14}$; and B is $CR^{16}$.

Embodiment 42

The method of embodiment 41, wherein: $R^{10}$ is fluorine, bromine, chlorine, or iodine; and $R^{14}$ and $R^{16}$ are independently hydrogen.

Embodiment 43

The method of embodiment 38, wherein $R^8$, $R^9$, $R^{11}$, $R^{12}$, $R^{13}$, $R^{15}$, $R^{17}$ and $R^{18}$ are independently hydrogen.

Embodiment 44

The method of embodiment 43, wherein: A is N; B is $CR^{16}$; and $R^{16}$ is hydrogen.

Embodiment 45

The method of embodiment 44, wherein $R^{10}$ is fluorine, chlorine, bromine or iodine.

Embodiment 46

The method of embodiment 43, wherein: A and B are independently N; and $R^{10}$ is fluorine, chlorine, bromine or iodine.

Embodiment 47

A composition comprising a gp130 receptor bound to a binding site 1 gp130 receptor agonist, wherein the binding site 1 gp130 receptor agonist is bound to the binding site one of the gp130 receptor.

Embodiment 48

The composition of embodiment 47, wherein the binding site 1 gp130 receptor agonist is non-covalently bound to gp130 receptor.

Embodiment 49

The composition of embodiment 47, wherein binding site 1 comprises amino acid residues lysine, alanine, arginine and lysine corresponding to positions 173, 174, 175 and 176 of the gp130 receptor.

Embodiment 50

The composition of embodiment 47, wherein the binding site 1 gp130 receptor agonist is a small molecule, an antibody, protein or a polypeptide.

Embodiment 51

The composition of embodiment any one of embodiments 47 to 50, wherein the binding site 1 gp130 receptor agonist is a compound of structural Formula (III):

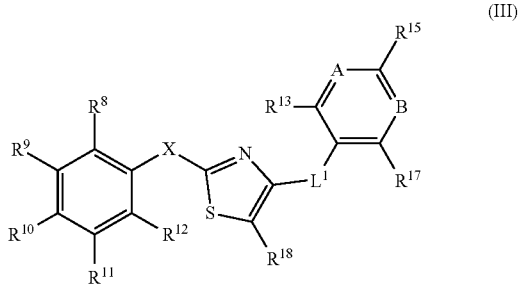

(III)

or a pharmaceutically acceptable salt thereof, wherein: A is $CR^{14}$ or N; B is $CR^{16}$ or N; X is O, $NR^{19}$ or S; $L^1$ is a bond or substituted or unsubstituted $C_1$-$C_3$ alkylene; n1 is an integer from 0 to 4; m1 and v1 are independently 1 or 2; $R^8$ is hydrogen, halogen, —$CX^{8.1}_3$, —$CHX^{8.1}_2$, —$CH_2X^{8.1}$, —CN, —$SO_{n1}R^{8A}$, —$SO_{v1}NR^{8B}R^{8C}$, —$NHNR^{8B}R^{8C}$, —$ONR^{8B}R^{8C}$, —$NHC(O)NHNR^{8B}R^{8C}$, —$NHC(O)NR^{8B}R^{8C}$, —$N(O)_{m1}$, —$NR^{8B}R^{8C}$, —$C(O)R^{8D}$, —$C(O)OR^{8D}$, —$C(O)NR^{8B}R^{8C}$, —$OR^{8A}$, —$NR^{8B}SO_2R^{8A}$, —$NR^{8B}C(O)R^{8D}$, —$NR^{8B}C(O)OR^{8D}$, —$NR^{8B}OR^{8D}$, —$OCX^{8.1}_3$, —$OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, —$CX^{9.1}_3$, —$CHX^{9.1}_2$, —$CH_2X^{9.1}$, —CN, —$SO_{n1}R^{9A}$, —$SO_{v1}NR^{9B}R^{9C}$, —$NHNR^{9B}R^{9C}$, —$ONR^{9B}R^{9C}$, —$NHC(O)NHNR^{9B}R^{9C}$, —$NHC(O)NR^{9B}R^{9C}$, —$N(O)_{m1}$, —$NR^{9B}R^{9C}$, —$C(O)R^{9D}$, —$C(O)OR^{9D}$, —$C(O)NR^{9B}R^{9C}$, —$OR^{9A}$, —$NR^{9B}SO_2R^{9A}$, —$NR^{9B}C(O)R^{9D}$, —$NR^{9B}C(O)OR^{9D}$, —$NR^{9B}OR^{9D}$, —$OCX^{9.1}_3$, —$OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ is hydrogen, halogen, —$CX^{10.1}_3$, —$CHX^{10.1}_2$, —$CH_2X^{10.1}$, —CN, —$SO_{n1}R^{10A}$, —$SO_{v1}NR^{10B}R^{10C}$, —$NHNR^{10B}R^{10C}$, —$ONR^{10B}R^{10C}$, —$NHC(O)NHNR^{10B}R^{10C}$, —$NHC(O)NR^{10B}R^{10C}$, —$N(O)_{m1}$, —$NR^{10B}R^{10C}$, —$C(O)R^{10D}$, —$C(O)OR^{10D}$, —$C(O)NR^{10B}R^{10C}$, —$OR^{10A}$, —$NR^{10B}SO_2R^{10A}$, —$NR^{10B}C(O)R^{10D}$, —$NR^{10B}C(O)OR^{10D}$, —$NR^{10B}OR^{10D}$, —$OCX^{10.1}_3$, —$OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ is hydrogen, halogen, $-CX^{11.1}{}_3$, $-CHX^{11.1}{}_2$, $-CH_2X^{11.1}$, $-CN$, $-SO_{n1}R^{11A}$, $-SO_{v1}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, $-N(O)_{m1}$, $-NR^{11B}R^{11C}$, $-C(O)R^{11D}$, $-C(O)OR^{11D}$, $-C(O)NR^{11B}R^{11C}$, $-OR^{11A}$, $-NR^{11B}SO_2R^{11A}$, $-NR^{11B}C(O)R^{11D}$, $-NR^{11B}C(O)OR^{11D}$, $-NR^{11B}OR^{11D}$, $-OCX^{11.1}{}_3$, $-OCHX^{11.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{12}$ is hydrogen, halogen, $-CX^{12.1}{}_3$, $-CHX^{12.1}{}_2$, $-CH_2X^{12.1}$, $-CN$, $-SO_{n1}R^{12A}$, $-SO_{v1}NR^{12B}R^{12C}$, $-NHNR^{12B}R^{12C}$, $-ONR^{12B}R^{12C}$, $-NHC(O)NHNR^{12B}R^{12C}$, $-NHC(O)NR^{12B}R^{12C}$, $-N(O)_{m1}$, $-NR^{12B}R^{12C}$, $-C(O)R^{12D}$, $-C(O)OR^{12D}$, $-C(O)NR^{12B}R^{12C}$, $-OR^{12A}$, $-NR^{12B}SO_2R^{12A}$, $-NR^{12B}C(O)R^{12D}$, $-NR^{12B}C(O)OR^{12D}$, $-NR^{12B}OR^{12D}$, $-OCX^{12.1}{}_3$, $-OCHX^{12.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{13}$ is hydrogen, halogen, $-CX^{13.1}{}_3$, $-CHX^{13.1}{}_2$, $-CH_2X^{13.1}$, $-CN$, $-SO_{n1}R^{13A}$, $-SO_{v1}NR^{13B}R^{13C}$, $-NHNR^{13B}R^{13C}$, $-ONR^{13B}R^{13C}$, $-NHC(O)NHNR^{13B}R^{13C}$, $-NHC(O)NR^{13B}R^{13C}$, $-N(O)_{m1}$, $-NR^{13B}R^{13C}$, $-C(O)R^{13D}$, $-C(O)OR^{13D}$, $-C(O)NR^{13B}R^{13C}$, $-OR^{13A}$, $-NR^{13B}SO_2R^{13A}$, $-NR^{13B}C(O)R^{13D}$, $-NR^{13B}C(O)OR^{13D}$, $-NR^{13B}OR^{13D}$, $-OCX^{13.1}{}_3$, $-OCHX^{13.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{14}$ is hydrogen, halogen, $-CX^{14.1}{}_3$, $-CHX^{14.1}{}_2$, $-CH_2X^{14.1}$, $-CN$, $-SO_{n1}R^{14A}$, $-SO_{v1}NR^{14B}R^{14C}$, $-NHNR^{14B}R^{14C}$, $-ONR^{14B}R^{14C}$, $-NHC(O)NHNR^{14B}R^{14C}$, $-NHC(O)NR^{14B}R^{14C}$, $-N(O)_{m1}$, $-NR^{14B}R^{14C}$, $-C(O)R^{14D}$, $-C(O)OR^{14D}$, $-C(O)NR^{14B}R^{14C}$, $-OR^{14A}$, $-NR^{14B}SO_2R^{14A}$, $-NR^{14B}C(O)R^{14D}$, $-NR^{14B}C(O)OR^{14D}$, $-NR^{14B}OR^{14D}$, $-OCX^{14.1}{}_3$, $-OCHX^{14.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15}$ is hydrogen, halogen, $-CX^{15.1}{}_3$, $-CHX^{15.1}{}_2$, $-CH_2X^{15.1}$, $-CN$, $-SO_{n1}R^{15A}$, $-SO_{v1}NR^{15B}R^{15C}$, $-NHNR^{15B}R^{15C}$, $-ONR^{15B}R^{15C}$, $-NHC(O)NHNR^{15B}R^{15C}$, $-NHC(O)NR^{15B}R^{15C}$, $-N(O)_{m1}$, $-NR^{15B}R^{15C}$, $-C(O)R^{15D}$, $-C(O)OR^{15D}$, $-C(O)NR^{15B}R^{15C}$, $-OR^{15A}$, $-NR^{15B}SO_2R^{15A}$, $-NR^{15B}C(O)R^{15D}$, $-NR^{15B}C(O)OR^{15D}$, $-NR^{15B}OR^{15D}$, $-OCX^{15.1}{}_3$, $-OCHX^{15.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$ is hydrogen, halogen, $-CX^{16.1}{}_3$, $-CHX^{16.1}{}_2$, $-CH_2X^{16.1}$, $-CN$, $-SO_{n1}R^{16A}$, $-SO_{v1}NR^{16B}R^{16C}$, $-NHNR^{16B}R^{16C}$, $-ONR^{16B}R^{16C}$, $-NHC(O)NHNR^{16B}R^{16C}$, $-NHC(O)NR^{16B}R^{16C}$, $-N(O)_{m1}$, $-NR^{16B}R^{16C}$, $-C(O)R^{16D}$, $-C(O)OR^{16D}$, $-C(O)NR^{16B}R^{16C}$, $-OR^{16A}$, $-NR^{16B}SO_2R^{16A}$, $-NR^{16B}C(O)R^{16D}$, $-NR^{16B}C(O)OR^{16D}$, $-NR^{16B}OR^{16D}$, $-OCX^{16.1}{}_3$, $-OCHX^{16.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{17}$ is hydrogen, halogen $-CX^{17.1}{}_3$, $-CHX^{17.1}{}_2$, $-CH_2X^{17.1}$, $-CN$, $-SO_{n1}R^{17A}$, $-SO_{v1}NR^{17B}R^{17C}$, $-NHNR^{17B}R^{17C}$, $-ONR^{17B}R^{17C}$, $-NHC(O)NHNR^{17B}R^{17C}$, $-NHC(O)NR^{17B}R^{17C}$, $-N(O)_{m1}$, $-NR^{17B}R^{17C}$, $-C(O)R^{17D}$, $-C(O)OR^{17D}$, $-C(O)NR^{17B}R^{17C}$, $-OR^{17A}$, $-NR^{17B}SO_2R^{17A}$, $-NR^{17B}C(O)R^{17D}$, $-NR^{17B}C(O)OR^{17D}$, $-NR^{17B}OR^{17D}$, $-OCX^{17.1}{}_3$, $-OCHX^{17.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{18}$ is hydrogen, halogen, $-CX^{18.1}{}_3$, $-CHX^{18.1}{}_2$, $-CH_2X^{18.1}$, $-CN$, $-SO_{n1}R^{18A}$, $-SO_{v1}NR^{18B}R^{18C}$, $-NHNR^{18B}R^{18C}$, $-ONR^{18B}R^{18C}$, $-NHC(O)NHNR^{18B}R^{18C}$, $-NHC(O)NR^{18B}R^{18C}$, $-N(O)_{m1}$, $-NR^{18B}R^{18C}$, $-C(O)R^{18D}$, $-C(O)OR^{18D}$, $-C(O)NR^{18B}R^{18C}$, $-OR^{18A}$, $-NR^{18B}SO_2R^{18A}$, $-NR^{18B}C(O)R^{18D}$, $-NR^{18B}C(O)OR^{18D}$, $-NR^{18B}OR^{18D}$, $-OCX^{18.1}{}_3$, $-OCHX^{18.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{19}$ is hydrogen, $-COR^{19D}$, $-C(O)NHNR^{19B}R^{19C}$, $-C(O)OR^{19D}$, $-SO_2R^{19A}$, $C(O)NR^{19B}R^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$ and $R^{18D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{11B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17C}$, $R^{18B}$ and $R^{18C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$, $X^{12.1}$, $X^{13.1}$, $X^{14.1}$, $X^{15.1}$, $X^{16.1}$, $X^{17.1}$ and $X^{18.1}$ are independently $-Cl$, $-Br$, $-I$ or $-F$.

Embodiment 52

A pharmaceutical composition, comprising a compound of Formula (III) and a pharmaceutically acceptable excipient:

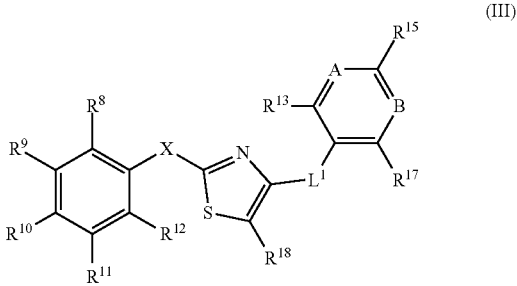

(III)

or a pharmaceutically acceptable salt thereof, wherein: A is $CR^{14}$ or N; B is $CR^{16}$ or N; X is O, $NR^{19}$ or S; $L^1$ is a bond or substituted or unsubstituted $C_1$-$C_3$ alkylene; n1 is an integer from 0 to 4; m1 and v1 are independently 1 or 2; $R^8$ is hydrogen, halogen, $-CX^{8.1}_3$, $-CHX^{8.1}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, $-CX^{9.1}_3$, $-CHX^{9.1}_2$, $-CH_2X^{9.1}$, $-CN$, $-SO_{n1}R^{9A}$, $-SO_{v1}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m1}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ is hydrogen, halogen, $-CX^{10.1}_3$, $-CHX^{10.1}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ is hydrogen, halogen, $-CX^{11.1}_3$, $-CHX^{11.1}_2$, $-CH_2X^{11.1}$, $-CN$, $-SO_{n1}R^{11A}$, $-SO_{v1}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, $-N(O)_{m1}$, $-NR^{11B}R^{11C}$, $-C(O)R^{11D}$, $-C(O)OR^{11D}$, $-C(O)NR^{11B}R^{11C}$, $-OR^{11A}$, $-NR^{11B}SO_2R^{11A}$, $-NR^{11B}C(O)R^{11D}$, $-NR^{11B}C(O)OR^{11D}$, $-NR^{11B}OR^{11D}$, $-OCX^{11.1}_3$, $-OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{12}$ is hydrogen, halogen, $-CX^{12.1}_3$, $-CHX^{12.1}_2$, $-CH_2X^{12.1}$, $-CN$, $-SO_{n1}R^{12A}$, $-SO_{v1}NR^{12B}R^{12C}$, $-NHNR^{12B}R^{12C}$, $-ONR^{12B}R^{12C}$, $-NHC(O)NHNR^{12B}R^{12C}$, $-NHC(O)NR^{12B}R^{12C}$, $-N(O)_{m1}$, $-NR^{12B}R^{12C}$, $-C(O)R^{12D}$, $-C(O)OR^{12D}$, $-C(O)NR^{12B}R^{12C}$, $-OR^{12A}$, $-NR^{12B}SO_2R^{12A}$, $-NR^{12B}C(O)R^{12D}$, $-NR^{12B}C(O)OR^{12D}$, $-NR^{12B}OR^{12D}$, $-OCX^{12.1}_3$, $-OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{13}$ is hydrogen, halogen, $-CX^{13.1}_3$, $-CHX^{13.1}_2$, $-CH_2X^{13.1}$, $-CN$, $-SO_{n1}R^{13A}$, $-SO_{v1}NR^{13B}R^{13C}$, $-NHNR^{13B}R^{13C}$, $-ONR^{13B}R^{13C}$, $-NHC(O)NHNR^{13B}R^{13C}$, $-NHC(O)NR^{13B}R^{13C}$, $-N(O)_{m1}$, $-NR^{13B}R^{13C}$, $-C(O)R^{13D}$, $-C(O)OR^{13D}$, $-C(O)NR^{13B}R^{13C}$, $-OR^{13A}$, $-NR^{13B}SO_2R^{13A}$, $-NR^{13B}C(O)R^{13D}$, $-NR^{13B}C(O)OR^{13D}$, $-NR^{13B}OR^{13D}$, $-OCX^{13.1}_3$, $-OCHX^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{14}$ is hydrogen, halogen, $-CX^{14.1}_3$, $-CHX^{14.1}_2$, $-CH_2X^{14.1}$, $-CN$, $-SO_{n1}R^{14A}$, $-SO_{v1}NR^{14B}R^{14C}$, $-NHNR^{14B}R^{14C}$, $-ONR^{14B}R^{14C}$, $-NHC(O)NHNR^{14B}R^{14C}$, $-NHC(O)NR^{14B}R^{14C}$, $-N(O)_{m1}$, $-NR^{14B}R^{14C}$, $-C(O)R^{14D}$, $-C(O)OR^{14D}$, $-C(O)NR^{14B}R^{14C}$, $-OR^{14A}$, $-NR^{14B}SO_2R^{14A}$, $-NR^{14B}C(O)R^{14D}$, $-NR^{14B}C(O)OR^{14D}$, $-NR^{14B}OR^{14D}$, $-OCX^{14.1}_3$, $-OCHX^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15}$ is hydrogen, halogen, $-CX^{15.1}_3$, $-CHX^{15.1}_2$, $-CH_2X^{15.1}$, $-CN$, $-SO_{n1}R^{15A}$, $-SO_{v1}NR^{15B}R^{15C}$, $-NHNR^{15B}R^{15C}$, $-ONR^{15B}R^{15C}$, $-NHC(O)NHNR^{15B}R^{15C}$, $-NHC(O)NR^{15B}R^{15C}$, $-N(O)_{m1}$, $-NR^{15B}R^{15C}$, $-C(O)R^{15D}$, $-C(O)OR^{15D}$, $-C(O)NR^{15B}R^{15C}$, $-OR^{15A}$, $-NR^{15B}SO_2R^{15A}$, $-NR^{15B}C(O)R^{15D}$, $-NR^{15B}C(O)OR^{15D}$, $-NR^{15B}OR^{15D}$, $-OCX^{15.1}_3$, $-OCHX^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$ is hydrogen, halogen, $-CX^{16.1}_3$, $-CHX^{16.1}_2$, $-CH_2X^{16.1}$, $-CN$, $-SO_{n1}R^{16A}$, $-SO_{v1}NR^{16B}R^{16C}$, $-NHNR^{16B}R^{16C}$, $-ONR^{16B}R^{16C}$, $-NHC(O)NHNR^{16B}R^{16C}$, $-NHC(O)NR^{16B}R^{16C}$, $-N(O)_{m1}$, $-NR^{16B}R^{16C}$, $-C(O)R^{16D}$, $-C(O)OR^{16D}$, $-C(O)NR^{16B}R^{16C}$, $-OR^{16A}$, $-NR^{16B}SO_2R^{16A}$, $-NR^{16B}C(O)R^{16D}$, $-NR^{16B}C(O)OR^{16D}$, $-NR^{16B}OR^{16D}$, $-OCX^{16.1}_3$, $-OCHX^{16.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{17}$ is hydrogen, halogen, $-CX^{17.1}_3$, $-CHX^{17.1}_2$, $-CH_2X^{17.1}$, $-CN$, $-SO_{n1}R^{17A}$, $-SO_{v1}NR^{17B}R^{17C}$, $-NHNR^{17B}R^{17C}$, $-ONR^{17B}R^{17C}$, $-NHC(O)NHNR^{17B}R^{17C}$, $-NHC(O)NR^{17B}R^{17C}$, $-N(O)_{m1}$, $-NR^{17B}R^{17C}$, $-C(O)R^{17D}$, $-C(O)OR^{17D}$, $-C(O)NR^{17B}R^{17C}$, $-OR^{17A}$, $-NR^{17B}SO_2R^{17A}$, $-NR^{17B}C(O)R^{17D}$, $-NR^{17B}C(O)OR^{17D}$, $-NR^{17B}OR^{17D}$, $-OCX^{17.1}_3$, $-OCHX^{17.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{18}$ is hydrogen, halogen, $-CX^{18.1}_3$, $-CHX^{18.1}_2$, $-CH_2X^{18.1}$, $-CN$, $-SO_{n1}R^{18A}$, $-SO_{v1}NR^{18B}R^{18C}$, $-NHNR^{18B}R^{18C}$, $-ONR^{18B}R^{18C}$, $-NHC(O)NHNR^{18B}R^{18C}$, $-NHC(O)NR^{18B}R^{18C}$, $-N(O)_{m1}$, $-NR^{18B}R^{18C}$, $-C(O)R^{18D}$, $-C(O)OR^{18D}$, $-C(O)NR^{18B}R^{18C}$, $-OR^{18A}$, $-NR^{18B}SO_2R^{18A}$, $-NR^{18B}C(O)R^{18D}$, $-NR^{18B}C(O)OR^{18D}$, $-NR^{18B}OR^{18D}$, —OCX$^{18.1}_3$, —OCHX$^{18.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{19}$ is hydrogen, —COR$^{19D}$, —C(O)NHNR$^{19B}$R$^{19C}$, —C(O)OR$^{19D}$, —SO$_2$R$^{19A}$, C(O)NR$^{19B}$R$^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$ and $R^{18D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, -OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{11B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17C}$, $R^{18B}$ and $R^{18C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$, $X^{12.1}$, $X^{13.1}$, $X^{14.1}$, $X^{15.1}$, $X^{16.1}$, $X^{17.1}$ and $X^{18.1}$ are independently —Cl, —Br, —I or —F.

The current disclosure bridges the fields of orthopedic surgery, stem cell research and developmental biology to develop a novel, clinically-relevant approach for cartilage regeneration. Specifically, our preliminary data have unveiled LIF signaling as a novel potential regulator of chondrocyte status that is highly present in developing human joints but minimally expressed in adult. To uncover this potential mechanism, we have generated, for the first time, molecular maps of human chondrogenesis using RNA-seq at different stages of human development. This highly sensitive bioinformatics-based approach can define the effects of LIF signaling modulation on chondrocytes during rejuvenation and monitor the transition of adult chondrocytes to a highly proliferative fetal-like phenotype. These data can be corroborated with detailed molecular and functional assessments of LIF signaling on competent adult LIFR$^+$ chondrocytes. To further study cartilage dynamics during homeostasis and repair, and the role of LIF signaling in these processes, we can utilize lineage tracing and LIFR-$^{flox/flox}$ mice. To our knowledge, these experiments can for the first time define normal cartilage turnover rates, define the cell of origin responsible for cartilage repair and delineate the requirement for LIF signaling to achieve these processes. In order to manipulate the maturational and proliferative state of chondrocytes in a clinically-relevant manner, we designed and conducted a screen to identify novel small molecules we have designated Cartilage Regulatory Molecules (CRMs). After secondary screening, we have discovered two candidate CRMs that mimic the effects of LIF on STAT3 and c-MYC activation and induce in situ proliferation of LIFR$^+$ chondrocytes. These molecules, and their effects on competent chondrocytes, can be studied in detail both in vitro and in vivo. Based on our preliminary results, we can pursue an innovative therapeutic approach that combines mini-implants derived from the superficial layer of healthy regions of articular cartilage co-implanted in cartilage defects in the presence of nanoparticles loaded with CRMs in a large animal model. Together, these approaches can advance our understanding of cartilage development and regeneration and can indicate treatment modalities.

VI. Examples

Figure 1A:
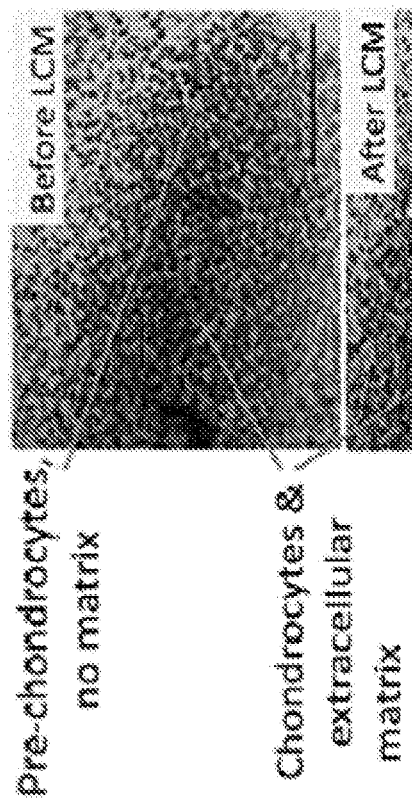

Example 1. Identification of the Molecular Phenotype for Cartilage Committed-Cells During Human Embryogenesis Our recent study identified molecular phenotypes of the most primitive cartilage-committed cells present in the joints throughout human ontogeny. Chondrogenic development in the proximal regions of the limbs occurs earlier than the distal ones and at 5-6 weeks of human embryogenesis, after the anatomically defined cartilaginous anlagen of long bones such as the humerus has already formed, groups of undifferentiated pre-chondrocytes remain in distinct sites of the limbs. Cartilage-committed mesenchymal cells (pre-chondrocytes) could be identified as nodules with a morphologically "dense" appearance in chondrogenic condensations at weeks 5-6 and minimally stained with cresyl violet, suggesting that they produced little cartilaginous matrix (FIG. 1A).

Figure 1C:
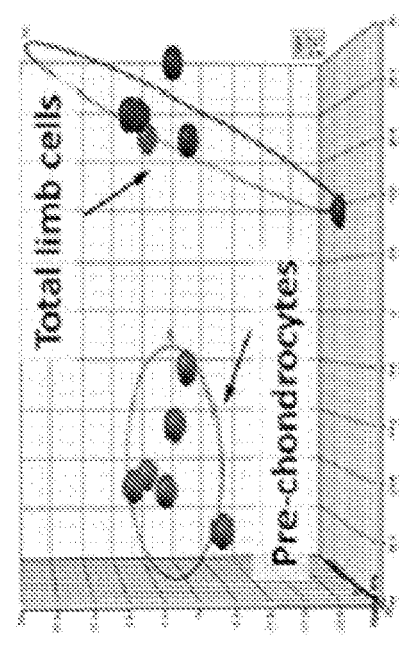

Pre-chondrocytes from 5-6 week old human limbs were isolated using laser capture microdissection (LCM; FIG. 1A, N=6) and subjected to genome-wide expression analysis. To nominate candidate genes that distinguish pre-chondrocytes from other cell types in the limb at this embryonic stage, RNA was isolated from the same specimens following LCM of pre-chondrocytes and used for microarray analysis. Ingenuity Pathway Analysis (IPA) revealed 585 genes significantly differentially expressed in pre-chondrocytes versus total limb cells, which at this stage includes myoblasts, blood, endothelial cells, keratinocytes, mature chondrocytes, nerves, dermal fibroblasts and other cell types (FIGS. 1B-1C). Many of the genes enriched in human pre-chondrocytes were previously found at the initial stages of chondrogenesis in the chick or mouse embryo, indicating the purity of LCM isolated pre-chondrocytes. These genes included SOX5, SOX6, SOX9, NKX 3.2, FOXP4, PTCH1, PCDH 8 and 10, BMPR1B and GDF5, the primary ligand for bone morphogenetic protein receptor 1B (BMPR1B) and an established marker for mouse articular cartilage precursors (FIG. 1D). In agreement with this data, principal component analysis carried out on total expression data (FIG. 1C) demonstrated that all 6 replicates of pre-chondrocyte data clustered together and distinctly from total limb cells.

Example 2. Defining Molecular Landmarks of Pre-Chondrocyte Differentiation and Maturation We have identified surface markers that would demarcate definitive resting (immature) articular chondrocytes from hypertrophic chondrocytes during their maturation from pre-chondrocytes. To define molecular markers during the process of pre-chondrocyte maturation, resting articular chondrocytes (RC) were dissected from femoral bone epiphysis of 17 week specimens (FIG. 2A) and compared them with pre-chondrocytes dissected with LCM from 5-6 week old specimens (FIGS. 2B-2C).

Figure 3A:
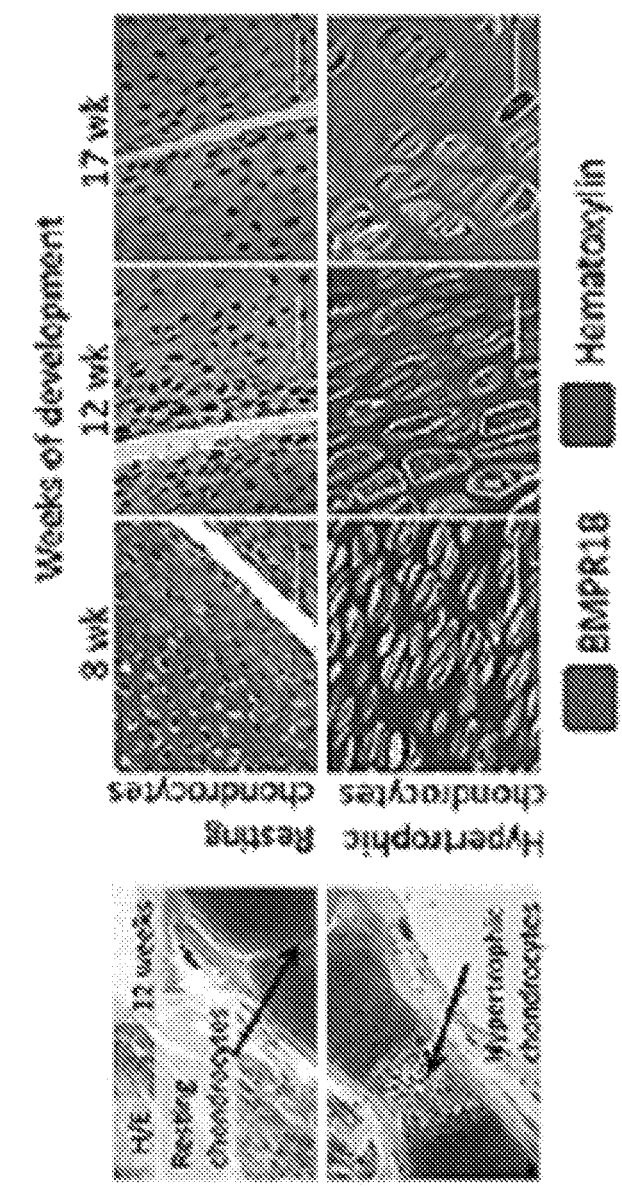
Figure 3B:
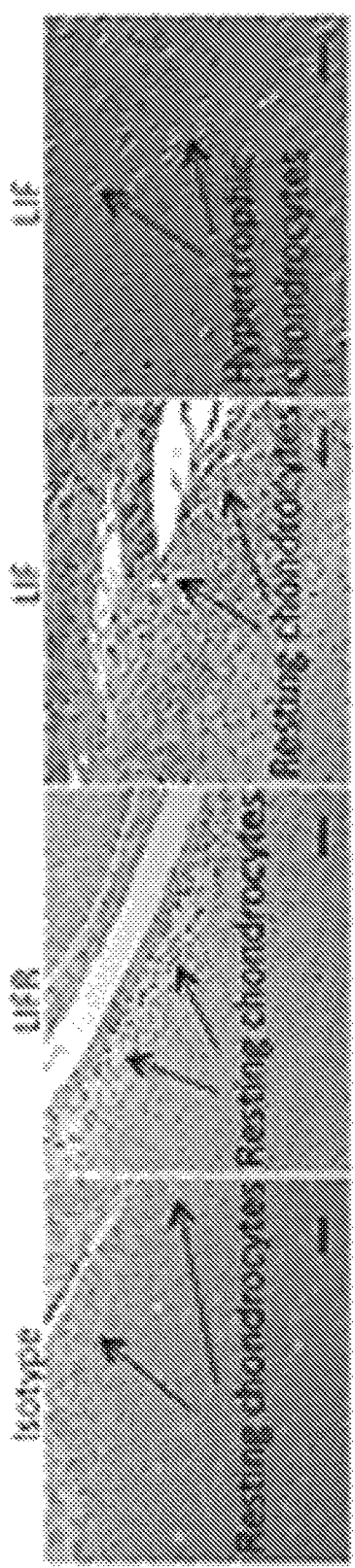

Comparison of the articular chondrocytes dissected from 17 week old joints with LCM-isolated cells at 5-6 weeks cells unexpectedly showed that leukemia inhibitory factor (LIF) and LIF receptor (LIFR) are among the most enriched transcripts in fetal human articular chondrocytes at 17 weeks of development (FIG. 2D). Subsequent immunohistochemistry showed that starting in 8 week limbs and progressing through gestation, LIFR and BMPR1B are expressed primarily on immature resting chondrocytes in the surface layers of articular cartilage; more differentiated and hypertrophic chondrocytes located in deeper zones did not express LIFR or BMPR1B (FIGS. 3A-3C). Both resting articular chondrocytes and adjacent synovial cells highly expressed LIF (FIG. 3B). In postnatal articular cartilage (FIG. 3C), BMPR1B+ and LIFR+ cells were also clearly detectable in the superficial zone coinciding with the known location of the most primitive cartilage progenitor pool, but not in the more differentiated deep zone. Of note, not all BMPR1B+ cells expressed LIFR. In post-natal growth plates, where chondrogenesis is still active, immature chondrogenic cells were also BMPR1B+ and LIFR+, while hypertrophic chondrocytes were negative for both (FIG. 3D). Finally, BMPR1B and LIFR are preferentially expressed on cells located in the superficial zone vs. chondrocytes present in the deep zone in articular cartilage from a knee joint even at 60 years of age (FIG. 3E). Synovial cells in older adult joints minimally express LIF (FIG. 3F). To further confirm that BMPR1B and LIFR are enriched on less differentiated chondrocytes after de novo chondrogenesis is completed (after 12 weeks of development), we isolated LIFR+ BMPR1B+ and LIFRnegBMPR1Bneg chondrocytes from 17 week articular regions by flow cytometry and compared the expression levels of the immature chondrocyte gene SOX9 and highly specific hypertrophic marker COL10A1 in both sorted populations (FIG. 3G). BMPR1B+LIFR+ chondrocytes expressed higher levels of SOX9 but had much lower levels of COL10A1 [13].

Thus, our data suggest that LIFR and BMPR1B distinguish immature or "competent" cells from more differentiated chondrocytes at all stages of human development. Together, these data implicate BMPR1B and LIFR as potential surface markers for immature/competent chondrocytes after the culmination of de novo chondrogenesis and throughout the human lifespan.

Leukemia inhibitory factor, or LIF, is an interleukin 6 (IL-6)-class cytokine that effects cell growth by inhibiting differentiation. When LIF binds to the LIF receptor (LIFR), it induces its heterodimerization with gp130 and activates Janus kinase (JAK); this causes recruitment, dimerization and phosphorylation of signal transducer and activator of transcription 3 (STAT3). Phosphorylation activates the STAT3 signaling cascade, which is essential for gp130-mediated cell survival. LIF is sufficient for the maintenance of pluripotency in mouse embryonic stem cells. LIF has been also shown to prevent differentiation of hematopoietic and neural progenitor cells. The mechanisms through which LIF maintains stem/progenitor cells are complex. In part, this is achieved through activation of STAT3 phosphorylation and subsequent activation of downstream targets including c-MYC and NANOG. Forced delivery of c-MYC, in combination with other pluripotency factors such as OCT4 (POU5F1), KLF4 and SOX2, causes direct reprogramming of somatic cells into induced pluripotent stem cells. Although it remains unclear to which extent cell reprogramming may occur in normal cells in response to stressors, the upregulation of STAT3 and c-MYC in response to inflammation or other stressors is well documented. Interestingly, regeneration of the liver after partial hepatectomy is triggered through the IL-6-mediated activation of STAT3, leading to de-differentiation and in situ expansion of fully differentiated hepatocytes. These studies further highlight the role of STAT3 signaling in controlling cell fate decisions and the ability to divide and differentiate under normal and pathological conditions.

Figure 4:
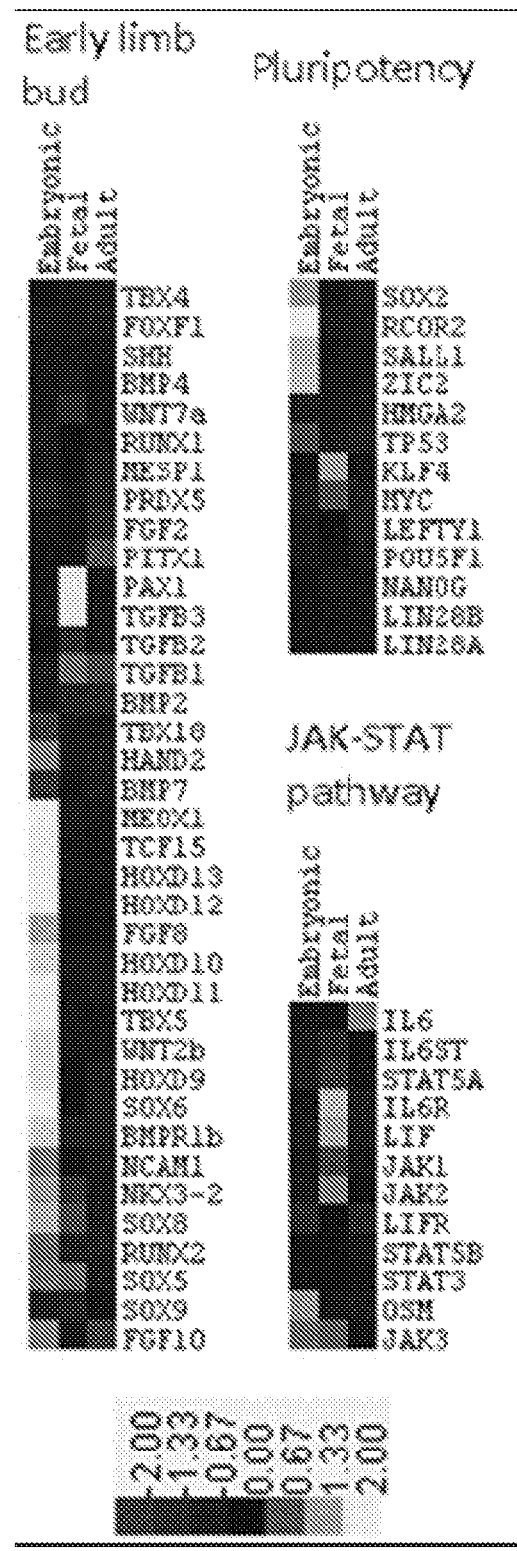
FIG. 4. RNA-seq analysis of early limb bud, pluripotency and JAK-STAT pathway genes in human embryonic (5-6 weeks), fetal (17 weeks) and adult articular chondrocytes. Average expression from 3 independent donors for each group is shown.

We next used RNA-seq to define the expression patterns of major pluripotency genes, chondrogenic developmental genes and components of the LIF/JAK/STAT3 pathway at different stages of human chondrogenesis (FIG. 4) in sorted LIFR+ BMPR1B+ cells. At 5-6 weeks, embryonic pre-chondrocytes (chondrocyte specification stage) were clearly enriched for genes known to specify chondrocytes from mesoderm, while fetal chondrocytes (proliferative, fully-specified chondrocytes) showed high levels of c-MYC and KLF4; adult cells have minimal expression of these genes, consistent with a homeostatic state and low turnover rate of adult chondrocytes. Other stem cell/pluripotency genes including SOX2, LIN28 and OCT4 (POU5F1) were minimally expressed in all tested cells, indicating that inactivation of these genes occurs earlier than 5 weeks of development. Interestingly, fetal chondrocytes were enriched in components of the JAK/STAT3 pathway. Together, these data suggest that following chondrogenic specification, c-MYC expression and LIF/STAT3 signaling may sustain fetal chondrocytes in a highly proliferative state.

It has been previously shown that stress signals such as inflammation or injury may trigger regenerative responses in organs that lack a stem/progenitor pool. This activation is tightly controlled and requires an "initiation" signal to trigger de-differentiation and proliferation and also a "termination" signal to terminate cell proliferation and trigger re-differentiation. If the stimulatory signal is present for too long, chronic inflammation may cause significant damage to the organ and also induce fibrosis. Is high activity of LIF/STAT3 in fetal joints part of the mechanism that provides maintenance of the chondrogenic blastema during early development and can this mechanism be utilized to induce proliferation and regeneration in adult.

It is plausible to predict that LIF may cause activation or de-differentiation of competent chondrocytes in situ; some pro-inflammatory cytokines, including IL-6 and to some extent LIF, are known to cause degradation of cartilage matrix and this effect has been considered for many years as an indicator of degeneration leading to osteoarthritis. However, many activated progenitors in blood, the neural system as well as the most primitive metastatic tumor cells demonstrate a high degree of matrix degradation and motility required for cell spreading. We next directly compared fetal and adult (both pig and human) articular chondrocytes using Western blot analysis to measure levels of p-STAT3 and c-MYC. As expected, p-STAT3 and c-MYC were significantly higher during early development and correlated well with high proliferation rates (FIGS. 5A-5B).

Figure 5A:
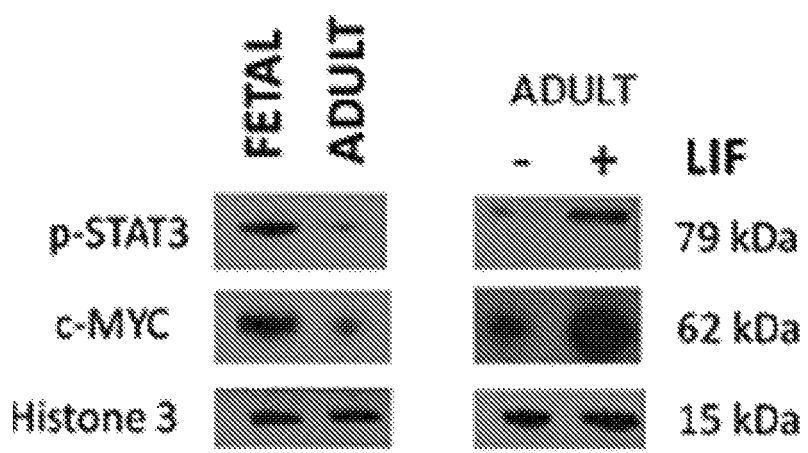
FIGS. 5A-5D. Molecular and functional comparison of adult and fetal human articular cartilage.
Figure 5B:
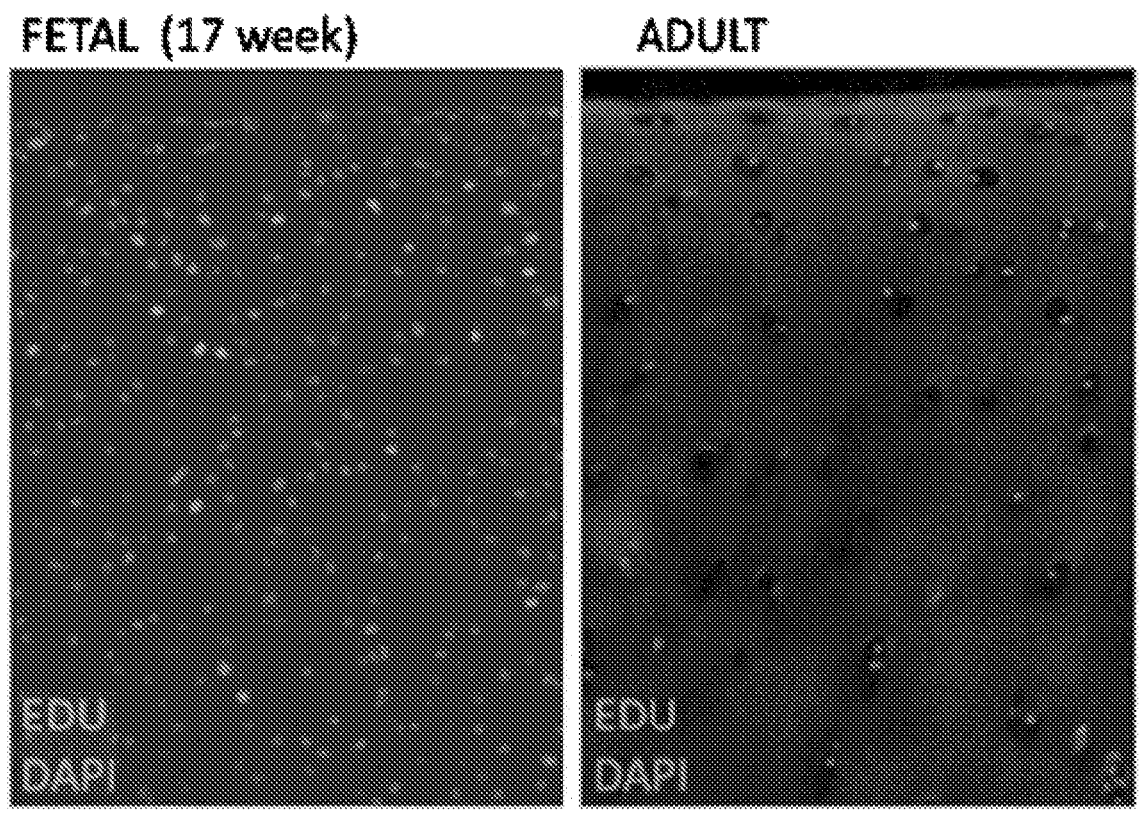
Figure 5C:
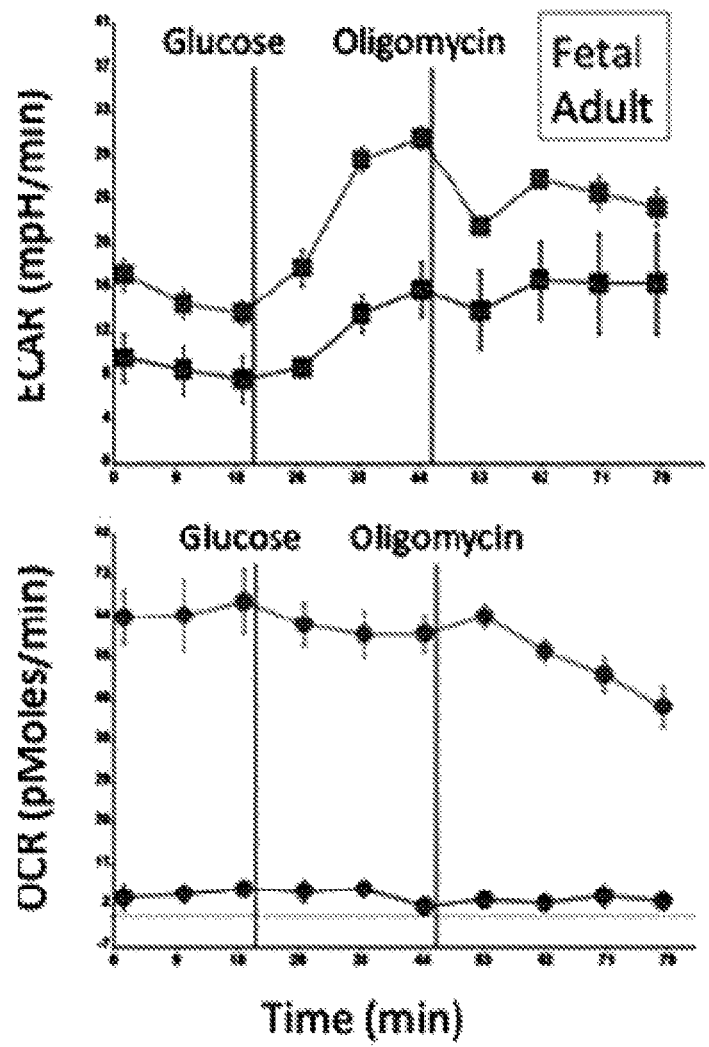
Figure 5D:
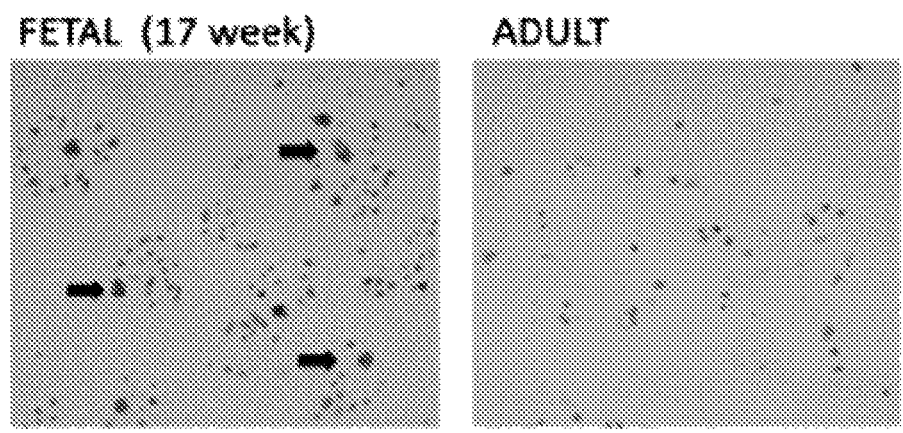
Figure 6:
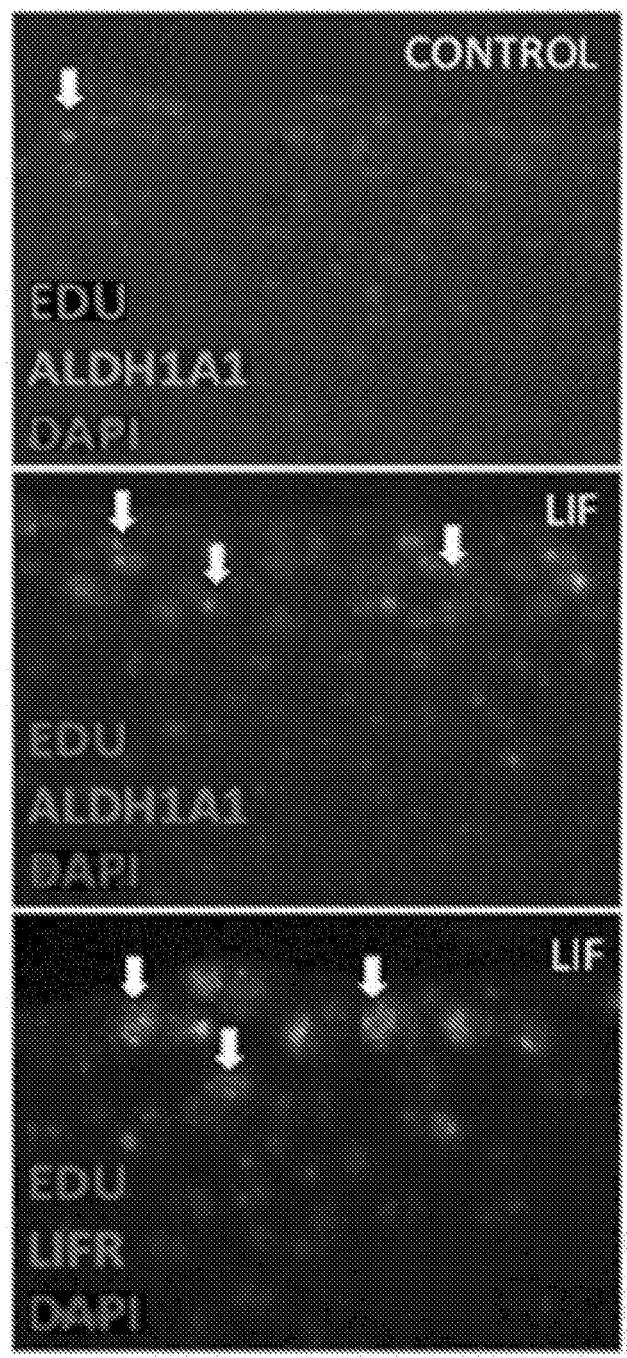
FIG. 6. Proliferation of chondrocytes (arrows) and expression of the stem cell marker ALDH 1A1 and LIFR in adult articular cartilage explants treated with LIF (50 ng/mL for 3 days).

To test the ability of LIF to stimulate LIFR+ cells and cause their activation in situ, we exposed human adult articular cartilage cells to high doses of LIF for 72 hours (FIG. 5A). This treatment evoked large increases both in p-STAT3 and c-MYC in cells from 3 donors tested independently. Adult pig chondrocytes showed a similar pattern of p-STAT3 and c-MYC activation in response to LIF. Analysis of cell metabolism using Seahorse Analyzer showed much higher levels of oxygen consumption and extracellular acidification by fetal cells, indicating much higher metabolic activity, which is consistent with a high proliferative capacity (FIG. 5C). We next tested the clonogenic potential of fetal and adult human chondrocytes and found that while only 1-3% of adult cells formed chondrospheres/clones in methylcellulose semisolid culture, fetal cells evidenced up to 20% clonogenicity (FIG. 5D). A STAT3 inhibitor stattic dramatically reduced clonogenic potential of fetal chondrocytes (data not shown). Finally, exposure of adult pig cartilage explants to LIF resulted in increased expression of the stem/progenitor cell marker ALDH 1A1 in the surface layer, and also significantly increased numbers of LIFR$^+$ EDU$^+$ cells, indicating increased cell proliferation (FIG. 6).

In a clinical setting, treatment with exogenous growth factors would present a difficult and expensive strategy. To address this, our group designed a high throughput screen to identify small molecule modulators of chondrogenic differentiation based on the prevention of the hypertrophy-associated marker collagen X (COLX). Out of 170,000 molecules screened, 75 of these compounds markedly inhibited mouse embryonic limb-derived mesenchymal cell terminal differentiation to COLX-expressing chondrocytes (COLX-mCherry mice, Jackson Labs). Further secondary screening showed that 4 of the 75 compounds had potent effects on p-STAT3/c-MYC protein levels. Two of these compounds, Cartilage Regulatory Molecule (CRM)-398 or CRM-423 have the most prominent effects. Treatment of human and pig adult articular chondrocytes with 1 µM CRM-398 or CRM-423 resulted in elevated levels of p-STAT3 and c-MYC, and also showed significant inhibition of terminal differentiation (COLX expression) of human fetal chondrocytes. Both compounds showed no toxicity in chondrocyte cultures and demonstrated highly specific and selective effect for p-STAT3 and c-MYC. Importantly, the stimulatory effect of CRMs on p-STAT3 and c-MYC was reversible; protein levels of both p-STAT-3 and c-MYC decreased 48 hours after CRM-398 or -423 withdrawal (data not shown). Identification of such compounds can not only allow us to control differentiation of chondrocytes, but also manipulate the expression of STAT3 and c-MYC to achieve rejuvenation of adult chondrocytes. CRM-398 and -423 can be tested in parallel with LIF and their effects on adult articular chondrocyte activation can be assessed as described herein.

In summary, our preliminary studies have mapped human chondrogenesis from 5 weeks of development up to 60 years of age and suggest a novel, previously unrecognized role of LIF/STAT3 signaling in human articular cartilage. Molecular analysis has shown that the most primitive cartilage-committed cells present in developing joints highly express LIFR. Developing joint tissues including synovium and cartilage highly express LIF at both mRNA and protein level and are actively proliferating, while adult synovium and chondrocytes minimally express LIF and are mostly quiescent Immature fetal chondrocytes, defined by LIFR and BMPR1B, possess high levels of p-STAT3 and c-MYC, transcriptional regulators activated downstream of LIFR. Although a subset of adult articular cartilage cells express LIFR, p-STAT3 and c-MYC are minimally expressed in normal adult cartilage, suggesting the pathway is inactive. Activation of these transcription factors has been previously shown to drive cell proliferation and confer a stem/progenitor phenotype. Stimulation of adult cartilage with LIF activates p-STAT3 and c-MYC and induces in situ proliferation and expansion of cells. Furthermore, we have identified a series of small molecules that result in similar responses in chondrocytes. Based on our preliminary data and published literature, we hypothesize that the LIF/LIFR/STAT3 axis plays an important role in the maintenance and/or re-activation of competent cartilage cells. We also hypothesize that dysfunction of this pathway is implicated in the pathogenesis of OA and that targeting this pathway with small molecule modulators of LIF signaling may reactivate competent LIFR$^+$ cells and improve cartilage regeneration in a large animal model of cartilage injury.

Figure 7:
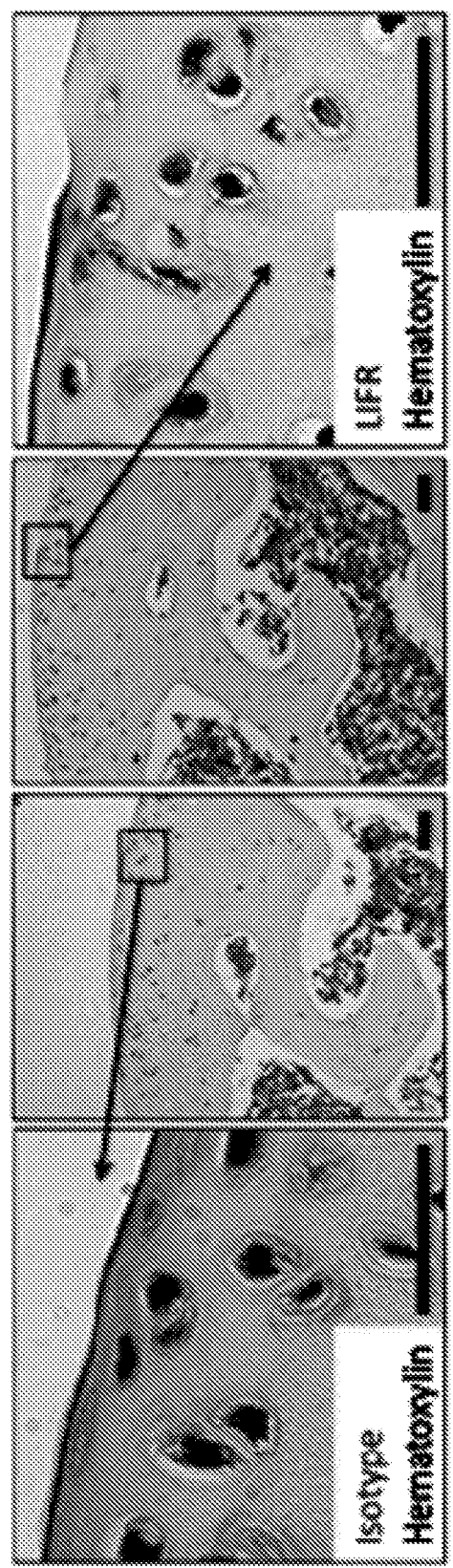
FIG. 7. LIF receptor (LIFR) is expressed in the superficial layer of murine articular cartilage. Scale bar=20 μm. Positive staining is shown. Nuclei counterstained with hematoxylin.

Example 3. Defining the Cellular Hierarchy and Molecular Mechanisms that Sustain Articular Cartilage During Homeostasis and Injury Rationale:

Articular cartilage is generally characterized as a static tissue with little intrinsic regenerative capacity, and this effect is amplified with age. As a result, defects in the surface of cartilage typically continue to degenerate over time, resulting in pain and joint dysfunction. Two main types of cells have been used to regenerate articular cartilage clinically: mesenchymal stem cells via microfracture surgery and autologous chondrocytes expanded ex vivo and then re-implanted (ACI). Although both cell types can lead to short-term pain relief and improvement in joint function, their ability to prevent continued degradation of articular cartilage over time is debatable. We hypothesize that stimulation of endogenous competent chondrocytes in situ may provide an alternative treatment modality for acute cartilage injuries and osteoarthritis. To date, the identity of cells responsible for maintaining homeostasis and enacting repair in articular cartilage has remained elusive. Studies in bovine, mouse and human cartilage have suggested that cells with progenitor characteristics, including matrix synthesis and label-retaining abilities, reside in the superficial zone (30). Our recent and preliminary data reveal that cells in this region express LIFR in human, pig and mouse cartilage (FIG. 7), and indicate that stimulation of these cells with LIF induces proliferation in situ in pig cartilage explants. Based on these results, we hypothesize that competent chondrocytes capable of neocartilage formation are localized in the superficial zone and can be identified as LIFR+ cells. We propose that these cells support the homeostatic maintenance of articular cartilage, are responsible for cartilage regeneration following injury in mice and are regulated by a LIF/STATS dependent mechanism.

Example 3.1. Identifying Specific Cell Populations Capable of Generating all Cell Types within Articular Cartilage During Homeostasis and Injury Approach:

In order to evaluate lineage potential of specific cell types, we can employ transgenic mice carrying an inducible Cre allele and the Rosa26-stop-tdtomato (R26-tom) reporter allele. Prg4 (lubricin) is gene expressed by chondrocytes specifically localized in the superficial zone; mice homozygous mutant for a null allele evidence a loss of chondrocytes at the surface of articular cartilage (30). To assess the potential of cells deeper in cartilage, we can rely upon expression of the Acan (aggrecan) gene, which is localized uniformly in articular cartilage with the clear exception of the superficial zone. Tamoxifen-inducible versions of both Prg4-Cre and Acan-Cre are commercially available from Jackson Laboratories. We can first validate the published expression profiles of both Cre lines by crossing them to R26-tom mice and administering tamoxifen; three days later, knee joints can be harvested and evaluated by immunofluorescence (IF) for tdtomato, lubricin and collagen II (pancartilage). We can also verify in these preliminary experiments that cells demarcated by Prg4-Cre express LIFR via IF. We can then assess which of these two distinct cell populations is responsible for tissue homeostasis in articular cartilage using a pulse-chase experiment. Tamoxifen can be administered to three cohorts of mice at different time points (E15.5, P14 and 6 months), and labeling in knee joints in each of the cohorts can be assessed 6 months later. Finally, we can also perform these lineage-tracing experiments in the context of joint injury. Tamoxifen can be administered three days before surgery, and then full-thickness cartilage defects can be created in the articular cartilage of the knee joint. Eight weeks after injury, joints can be harvested and the origin of neocartilage assessed using IF for tdtomato and collagen II.

Data Analysis:

For each genotype, cohorts can consist of at least four animals to establish lineage contribution values. Five sections from each animal can be stained for collagen II, and the ratio of tdtomato$^+$ area vs. collagen IL area can be averaged across all five sections; results from all animals can then be combined and the two genotypes compared. In mice with joint injury, the quantitation can be performed on the injury site and the remaining cartilage separately, thus providing an internal measure of cell sources for turnover vs. healing.

Example 3.2. Determine the Function of LIF Signaling in the Maintenance and Repair of Articular Cartilage Approach:

Our preliminary data indicate that chondrocytes in the superficial layer in human and pig articular cartilage are LIFR+ and are competent to proliferate in response to LIF. We hypothesize that signaling through the LIFR/STAT3 pathway is responsible for enabling competent chondrocytes to maintain cartilage homeostasis and enable repair. To test this, we can cross LIFR$^{fl/fl}$ mice (commercially available from EMSA) to both Prd4-Cre R26-tom and Acan-Cre R26-tom mice to generate Prd4-Cre LIFR$^{fl/fl}$ R26-tom and Acan-Cre LIFR$^{fl/fl}$ R26-tom strains. In these animals, activation of Cre protein via tamoxifen injection can delete the fourth exon of the LIFR gene, resulting in a non-functional protein; additionally, all descendants of these LIFR deleted cells will also express the tdtomato protein. We can first validate the efficiency of LIFR deletion following tamoxifen injection using IF and PCR on cartilage extracts. To address the function of LIFR during homeostasis, we can then repeat the experiments described in Subaim 1.1, administering tamoxifen at E15.5, P14 and 6 months to induce simultaneous LIFR deletion and lineage tracing; animals heterozygous for the LIFR$^{fl}$ allele can serve as controls. To determine the function of LIFR in cartilage regeneration, tamoxifen can be injected three days before generation of full-thickness cartilage injury; healing can then be assessed eight weeks later.

Data Analysis:

For both Prd4-Cre and Acan-Cre, four animals that are LIFR$^{fl/fl}$ can be compared to four animals that are LIFR$^{fl/+}$ at each time point. Contribution to homeostatic cartilage turnover can be defined by assessing the tdtomato/collagen II ratio as above. To quantitate healing, four LIFR deleted and four LIFR heterozygous animals can be compared. In addition, as the loss of the superficial cell layer has been shown to lead to cartilage degeneration and an osteoarthritis-like condition, knee joints of injured animals can be quantified for an OA score using standard techniques; the function of LIFR in preventing OA following injury can be defined by comparing the LIFR deleted and LIFR heterozygous animals.

Potential Problems and Alternative Strategies:

It is possible that neither Prg4-Cre nor Acan-Cre can provide the desired pattern of expression. Accordingly, we can generate a tamoxifen-inducible BMPR1B-Cre allele using standard gene targeting techniques and use this strain to manipulate gene expression in cells of the superficial layer. To provide additional mechanistic insight into signaling downstream of LIFR and its role in homeostasis and repair, we can also employ a conditional STAT3 allele; this strain would allow the deletion of STAT3 in defined cell types and can validate our data that the effects of LIFR stimulation are largely mediated by STAT3.

Example 4. Determining the Mechanism of LIF-Dependent Re-Activation/Rejuvenation of Adult Articular Chondrocytes We hypothesize that transient exposure of competent LIFR$^+$ cells to LIF, or small molecule modulators of STAT3 and/or c-MYC signaling, reactivates these cells through chromatin modification events leading to de-differentiation and ability to expand in situ.

Rationale.

Several transcription factors including OCT4, KLF2, SOX2 and c-MYC, have been shown to cause fundamental epigenetic changes in somatic cells leading to cellular reprogramming to pluripotency. Multiple studies clearly indicate that under cellular stress, some cell types including terminally differentiated hepatocytes or memory immune cells, undergo de-differentiation and behave as undifferentiated progenitors within the same cell lineage. After transient de-differentiation and proliferation, expanded cells undergo re-differentiation and become fully functional and highly specialized cells; this is in clear contrast to cancerous transformation, when proliferation and differentiation are not controlled, or generation of stable pluripotent cells. Although inductive signals that lead to cell de-differentiation are partially known in some systems, the exact molecular mechanism driving the acquisition of a progenitor phenotype remains elusive. Activation of STAT3 and c-MYC has been previously shown to drive de-differentiation of competent cells to progenitors. As was mentioned in the SIGNIFICANCE section, c-MYC is one of the direct targets for p-STAT3; c-MYC regulates cell proliferation and stem cell self-renewal. In a recently published study, c-MYC was identified as a central mechanism causing lymphocyte de-differentiation via metabolic re-programming. Our recent studies described for the first time high levels of LIF in developing joints, and also show that the most primitive chondrocytes express LIFR. Our current pilot data show that fetal chondrocytes have high levels of p-STAT3 and c-MYC, while non-proliferative adult chondrocytes have little or no expression. However, a subset of adult chondrocytes that express LIFR can markedly activate p-STAT3 and c-MYC in response to LIF treatment and adopt a proliferative phenotype in situ. We hypothesize that LIF plays a crucial role in rejuvenating competent adult chondrocytes to a more "primitive" or fetal-like proliferative state via a STAT3 signaling cascade involving c-MYC activation.

Approach.

A definite mechanism of how LIF might re-activate adult chondrocytes in cartilage through STAT3 signaling is still elusive. This specific aim is designed to test the hypothesis that a signaling cascade initiated by LIF plays an essential role in regulating differentiation state of adult chondrocytes via p-STAT3 and c-MYC signaling. Our initial experiments can involve 6, 12, 24, 48 and 72-hour LIF treatment of adult human LIFR$^+$ articular chondrocytes sorted by FACS in various conditions at concentrations ranging from 1 to 10 ng/mL. Our pilot data showed significant p-STAT3 and c-MYC upregulation within the 6 h-72 h window. Following the initial treatment, cells can be tested using metabolic, chondrosphere, migration, telomerase and chromatin accessibility assays. Addition of inhibitors of JAK, p-STAT3 and c-MYC signaling during LIF stimulation, such as INCB-018424, STATTIC and 10058-F4, respectively, can allow for the dissection of the precise role of these factors in the re-activation of adult chondrocytes and acquisition of a fetal-like phenotype. Human fetal chondrocytes can be used in parallel experiments as controls.

Our data have established several parameters that are clearly different between fetal and adult chondrocytes, including gene expression (FIG. 4), proliferation/clonogenicity (FIG. 5B) and metabolism (FIG. 5C). We can use these assays as indicators of induction of a fetal-like state in adult cells following experimental treatments. For the chondrosphere assay, cells are cultured in Matrigel (Corning) or 1% methylcellulose (R&D Systems) in a 24-well plate with 5,000 cells/well for 3 days. Their ability to form multiple "spheres" in 3D after treatment with LIF in the presence or absence of small molecule signaling modulators can serve as an indicator of LIF, STAT3 and c-MYC involvement in rejuvenation of adult chondrocytes. Analysis of metabolism can be carried out using Seahorse Bioscience XF24-3 analyzer using control and treated cells seeded at high density in low-melting agarose. OCR and ECAR can be determined with and without glucose and in the presence of oligomycin (mitochondrial electron transport chain inhibitor). Telomerase activity also serves as a marker of proliferative and differentiation potential of cells. By using the TRAPeze Telomerase Detection Kit from Millipore, we can detect in vitro telomerase activity, which is a main mechanism supporting maintenance of telomere length. Measuring the number of cells traversing a porous membrane and monitoring cell movement through extracellular matrices in a migration assay can further serve to confirm chondrocyte capability to grow aggressively following the treatments described above. Accessibility of DNA is related to nucleosome positioning along the genome, with actively transcribed genes mostly devoid of nucleosomes; comparison of nucleosome localization in adult chondrocytes treated with LIF and other small molecules to fetal chondrocytes (EpiQuik chromatin accessibility assay from Epigentek) can serve as another measure of rejuvenation.

The most efficient treatments in producing prominent increases in chondrosphere generation, metabolism change and changes in chromatin condensation can be subjected to more detailed molecular analysis including RNA-seq and ChIP-seq. Gene expression is modulated by accessibility of promoters and enhancers, and chromatin state can be largely determined by defining the methylation and acetylation of histone 3 on several lysine residues: H3K4me3 (active genes), H3K4me1 (primed enhancers), H3K27me3 (repressed genes/enhancers) and H3K27ac (active enhancers). Without wishing to be bound by theory, we expect that by modifying the epigenetic landscape we can re-activate adult chondrocytes through gene activation or repression. In previous studies we have generated transcriptome (RNA-seq) and epigenetic (H3K4me3, H3K4me1, H3K27me3 and H3K27ac) profiles for human cartilage cells from 5-6 weeks, 17 weeks and LIFR$^+$ adult articular cartilage cells. These profiles can be used as a backdrop on which to assess the extent of reactivation of cartilage progenitor gene networks present during human cartilage development following treatment. Ultimately, the methods disclosed herein can focus on LIF's ability to de-differentiate adult chondrocytes to primitive cells to encourage proliferation of articular cartilage via p-STAT3 and c-MYC manipulation in situ. These novel findings can further allow us to utilize this information for translational research.

Alternative Strategies:

We predict that assessment of cell transcriptome, epigenetic status, protein expression and proliferation are the best ways to confirm the primitiveness of chondrocytes and the significance of LIF, c-MYC and STAT3 in facilitating the induction of this property. Although LIF remains a promising factor, we cannot exclude the possibility that it is not the only cytokine responsible for activation of primitiveness within the STAT3 signaling cascade. Therefore, in another approach we can study rejuvenation via another two activators of STAT3 IL-6 and oncostatin. As shown by our RNA-seq studies (FIG. 4), both of these factors are expressed during normal human development. IL-6 competes with LIF in binding to the receptor gp130, and is known to also activate the STAT3 signaling cascade. It has been previously reported that IL-6 upregulation controls the regeneration process after liver injury. Exploring IL-6 as a potential reprogramming factor serves as an alternative strategy for adult chondrocytes to acquire the phenotype of fetal development.

Example 5. Determining Whether Cartilage Mini-Implants Co-Transplanted with Small Molecule Modulators of LIF/p-STAT3/c-MYC Signaling Enhance Healing in Pig Model of Joint Injury We hypothesize that transplantation of autologous mini-implants combined with small molecule analogs of LIF/p-STAT3/c-MYC signaling can cause rapid expansion and dissemination of LIFR$^+$ cells into the defect, and thus regenerate damaged articular cartilage. Without wishing to be bound by theory, we predict that biomechanics of injured joints after this treatment can be significantly improved.

Rationale.

Our pilot studies showed that LIFR$^+$ cells are cable of expanding into non-critical size defects in rat and partially regenerating articular cartilage. Our pilot work with adult pig explants treated with high doses of LIF showed proliferation LIFR$^+$ cells in situ and significant expansion of autologous cartilage tissue. Other factors including BMP4, TGF-beta 1 and the BMPR1B ligand GDF5 have little or no effect. The same stimulatory effect was achieved after treatment of explants with CRMs identified in our small molecule screen. Indeed, the expansion of autologous tissue and cell migration outside of the explant was much more prominent when CRM-398 was used. This can test if activation of p-STAT3 and c-MYC by selected small molecules CRM-398 and -423 can result in in situ expansion of articular cartilage tissue.

Approach:

We have chosen a porcine cartilage repair model because of its size and our expertise in generating focal articular cartilage defects in the porcine knee. A novel cartilage mini-implant approach can be used; 1 mm explants can be harvested from the same knee using a disposable biopsy punch. A 6 mm circular, full-thickness cartilage defect will be generated in the medial and lateral femoral condyle of the same knee joint. Mini-explants will be than inserted into a collagen I sponge to preserve their original apical-basal orientation. Next, we will apply fibrin gel to the defect area and deliver the sponge into the defect embedded into a photo-crosslinkable hydrogel containing PLGA nanoparticles loaded with CRMs. We will use either CRM-398 or -423 depending on the molecular validation studies described in Aim 2. Our team (Min Lee, collaborator) has previously successfully used this hydrogel for cartilage tissue engineering. The drug-loaded nanoparticle preparation protocol has been also previously validated by our group. See Table 1 for a breakdown of experimental groups. To test our hypothesis, we will examine the efficacy of mini-implants loaded in photo-crosslinkable hydrogel in the presence of small molecules in a clinically relevant porcine articular cartilage defect model. Comparisons will be to the current standard of care (microfracture) as well as to each treatment alone (mini-implants or CRM alone). Donor sites will be filled with hydrogel with nanoparticles loaded with CRM to stimulate the healing process. The size of the defect was chosen because it is a critical-sized defect that resembles what is seen in humans.

Assessment of Structural and Functional Repair.

(i) Biomechanical assessment. A six degree-of-freedom (DOF) robotic test system can be used to measure porcine knee joint stiffness and range of motion (ROM) as employed by our group previously. Biomechanical and other tests can be carried out at 3 months after the surgery. Pilot studies using five matched right-left pairs of porcine normal (non-operated) knees (n=10 knees total) showed no right-left differences in joint stiffness, with maximum joint stiffness occurring at 0° flexion. Maximum anterior/posterior (AP) stiffness was 18.5±4.3 N/mm for right knees and 18.9±4.8 N/mm for left knees, medio-lateral (ML) stiffness was 17.8±5.4 N/mm for right knees and 19.0±5.0 N/mm for left knees and internal-external (IE) rotational stiffness was 4.3±0.6 Nm/rad for right knees and 4.4±0.7 Nm/rad for left knees. In addition, during passive flexion the flexion-extension (FE) stiffness was 2.5±0.5 Nm/rad for right knees and 2.3±0.1 Nm/rad for left knees. There were also no right-left differences in total ROM, with maximum ROM occurring at 30° flexion. Maximum AP ROM was 7.6±1.3 mm for right knees and 8.1±1.6 mm for left knees, ML ROM was 9.2±2.6 mm for right knees and 9.4±2.8 mm for left knees and IE ROM was 93.3±11.5° for right knees and 94.8±10.4° for left knees. Pilot studies also included 3 animals with open knee surgery and 6 mm circular cartilage defects. In these animals, a consistent 30-40% increase in joint stiffness was observed at 6 weeks after the surgery compared to non-operated contralateral joint. To test whether mini-implant/CRM therapy improves biomechanics following injury, injured knees or control knees can be mounted to a force-moment sensor (the tibial fixture) at the end of the robotic manipulator and the femoral fixture can be mounted to a base plate. A three-dimensional digitizer can be used to reference a tibial-based x, y, z joint coordinate system to align the anatomic axes of the tibia with the sensor axes. Joint stiffness and ROM can be measured at 0°, 10°, 20° and 30° of flexion. For this series of testing, at each fixed flexion angle the robot can apply a target force and measure the corresponding displacement. First, ±50 N can be applied along the AP direction, then ±50 N can be applied along the ML direction and lastly ±2 N can be applied about the IE axis. After this series of tests, the robot then can simulate passive FE by moving the knee through a continuous 0° to 30° flexion motion path while seeking zero forces and torques in the remaining DOFs. The flexion torque required to do so can be recorded and used to analyze FE stiffness. (ii) Mechanical assessment. Indentation tests can be performed on the central defect and on the adjacent healthy cartilage as a control. The Arthro-BST (Biomomentum, Laval, Canada) can be used, which is an electromechanical indentation probe that measures the force with which cartilage resists a constant deformation. The other half of the harvested tissue can be used for biochemical analysis. (iii) Histological and biochemical assessment. These assays will be performed using the ICRS macroscopic scoring system. This can be performed post-mortem at the 3 month time point. Tissue at the injury site can be dissected, and one half can be processed for histological analysis. To quantify the regenerated cartilage tissue, samples can be stained with H&E and Safranin O and scored using the modified O'Driscoll scoring system. Randomized images can be scored by two independent investigators to obtain an average score. In addition, careful examination and characterization of mineralization/osteophytes (size, degree and number), fibrosis (degree and thickness) and inflammation (infiltrate quantity and composition) can be performed. Dried tissue can be digested with proteinase K and the total glycosaminoglycan content and collagen I and II content can be quantified with DMMB assay and ELISA, respectively, as described previously (41).

Alternative Strategies:

Cartilage defects can be generated in the load-bearing areas, and it cannot be completely excluded that implants will not be retained in the defect after fixation with the photo-crosslinkable hydrogel. We can start our experiments with 3 animals in which we can deliver collagen sponge and hydrogel without implanting cartilage tissue. If the implanted scaffold is not retained, we can suture the scaffold to the surrounding cartilage using the same technique as applied for autologous cartilage implantation surgery. Our preliminary studies showed stable slow release of loaded drugs from nanoparticles for up to 10 days. This time is expected to be sufficient to induce reactivation. However, if the experiments do not result in sufficient expansion in vivo, an intra-articular injection of the nanoparticles may be considered at day 7 or 10 after surgery.

Statistics and power calculations: Statistical significance can be computed using the ANOVA and Tukey-Fisher LSD criterion based on post hoc t statistics. Unpaired Student's t-test can be used to analyze experiments of two groups. Individual comparisons between two groups can be determined using the Mann-Whitney test for non-parametric data. Statistically significant differences can be considered at P≤0.05. In addition, we may also conduct non-parametric analysis using the Kruskal-Wallis one-way analysis with Dunn's method in pairwise comparison.

Example 6. BMPR1B+ Cells are Present in Postnatal Articular Cartilage

As depicted in photomicrograph of FIG. 8A, and enlarged section depicted in FIG. 8B, BMPR1B+ cells are present in postnatal articular cartilage. The subject was 60-years old.

Example 7. Comparison of Fetal and Adult BMPR1B+ Chondrocytes

BMPR1B+ cells in fetus are proliferative and produce much higher levels of matrix components than in adult; see FIGS. 9A-9C.

Example 8. Fetal and Adult Synovium and Cartilage

Figure 10A:
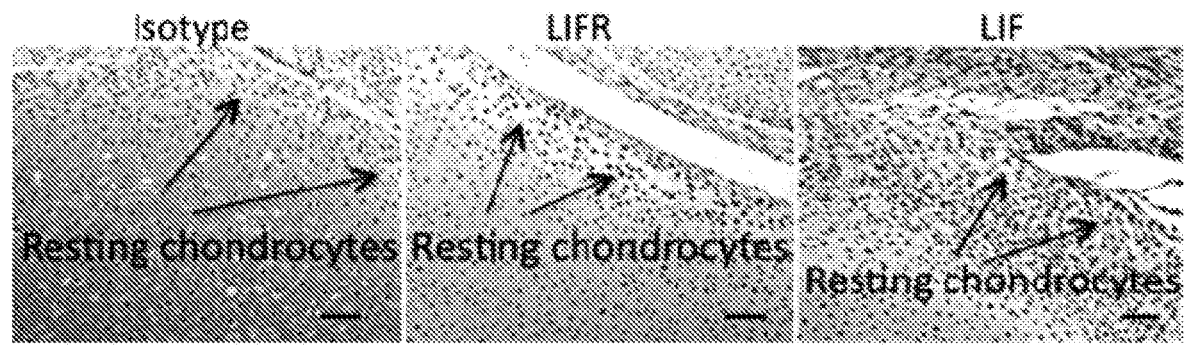
FIGS. 10A-10C.
Figure 10B:
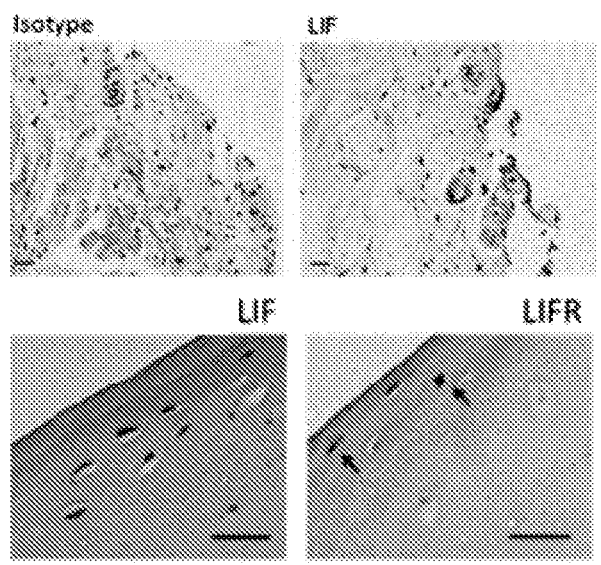

As depicted in FIG. 10A, fetal synovium and cartilage demonstrate resting chondrocytes. For comparison, adult synovium and cartilage photomicrographs are presented in FIG. 10B. The histogram (FIG. 10C) demonstrates that LIF protein levels are significantly elevated in fetal tissue.

Example 9. Effect of Soluble LIFR on pSTAT3 and c-Myc Levels

Figure 11:
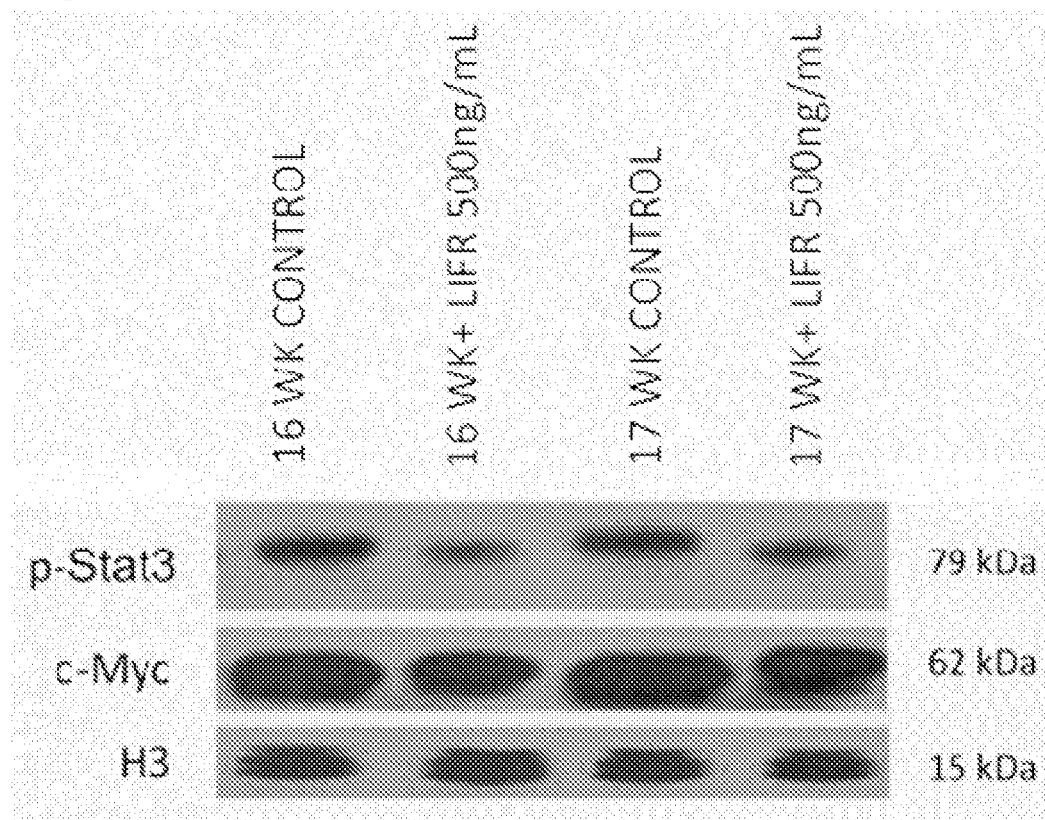
FIG. 11. Analysis of effect of soluble LIFR on levels of pSTAT3, γ-Myc and H3. Reagent conditions are as indicated in the figure. It is observed that soluble LIF receptor reduces levels of γ-STAT3 and c-MYC in fetal chondrocytes.

As depicted in FIG. 11, LIFR reduces levels of p-STAT3 and c-Myc in fetal chondrocytes.

Example 10. Effects of p-STAT3 and c-Myc on Fetal Chondrocyte Survival

Figures 12A, 12B, 12C:
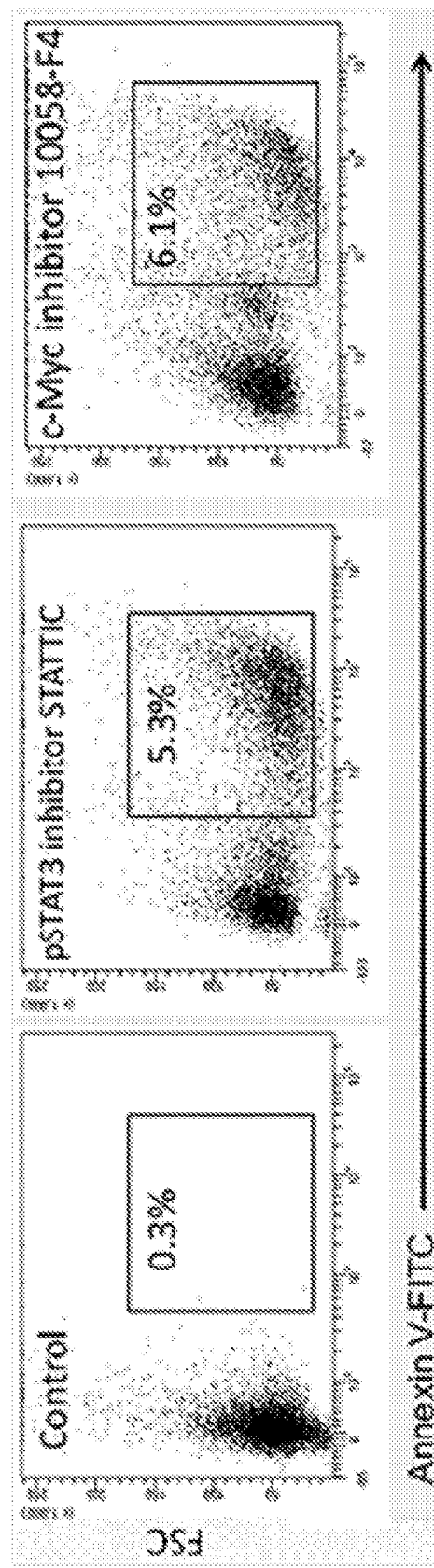
FIGS. 12A-12D. Inhibition of p-STAT and c-Myc markedly reduced fetal chondrocyte survival and clonal potential. Cell sorting results for control (FIG. 12A), p-STAT3 inhibitor (FIG. 12B) and c-MYC inhibitor (FIG. 12C). y-axis: FSC (forward scatter). x-axis: increasing concentration of Annexin V-FITC.
Figure 12D:
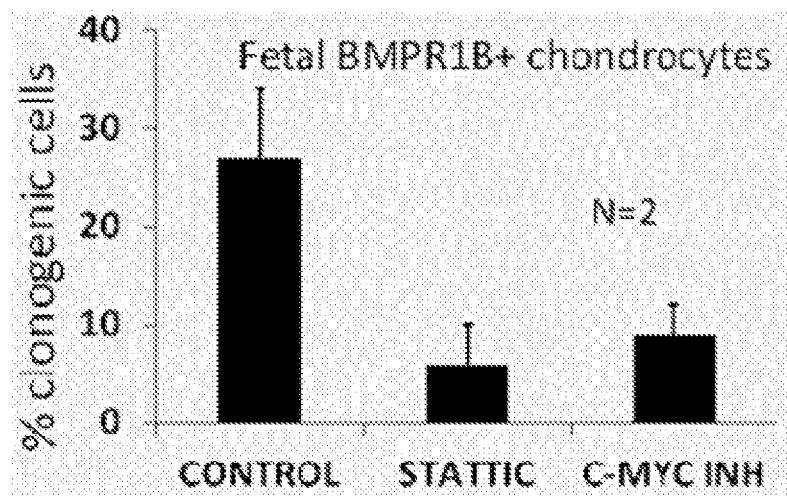

As depicted in FIGS. 12A-12D, inhibition of p-STAT3 and Myc markedly reduces fetal chondrocyte survival (FIGS. 12A-12C) and clonal potential (FIG. 12D).

Example 11. Effects of LIF on Levels of p-STAT3 and c-Myc

Figure 13A:
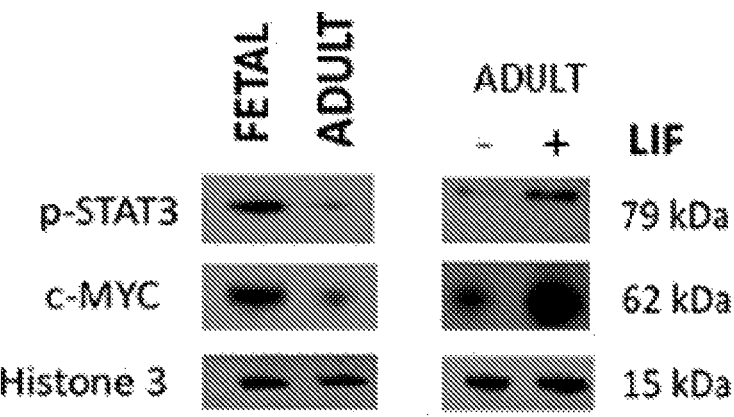
FIG. 13. LIF increases levels of pSTAT and c-Myc and stimulated proliferation of BMPR1B+ chondrocytes in adult cartilage explants. Figure depict photomicrographs of control (left) and LIF (right) for BMPR1B, EDU and Dapi.
Figure 13B:
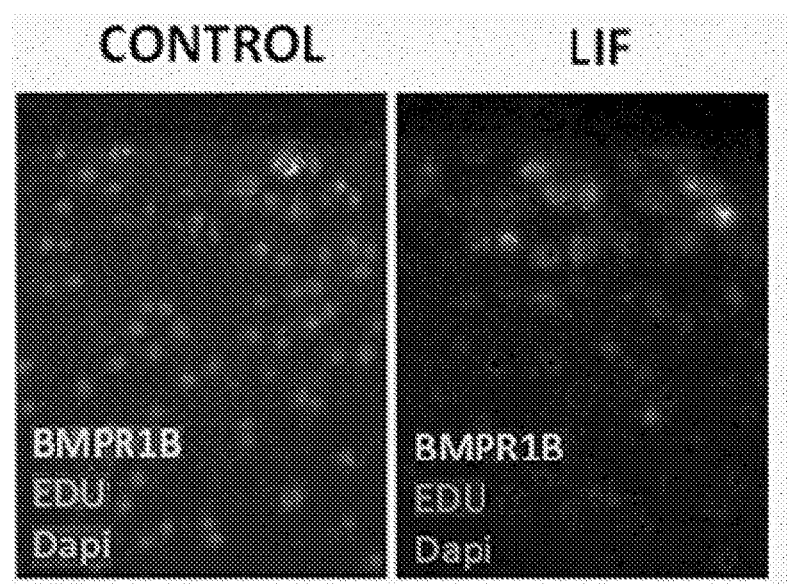

As depicted in FIGS. 13A-13B, LIF increases levels of p-STAT and c-Myc (FIG. 13A) and stimulated proliferation of BMPR1B+ chondrocytes in adult cartilage explants (FIG. 13B).

Example 12. Screening Strategies and Results

Figure 14:
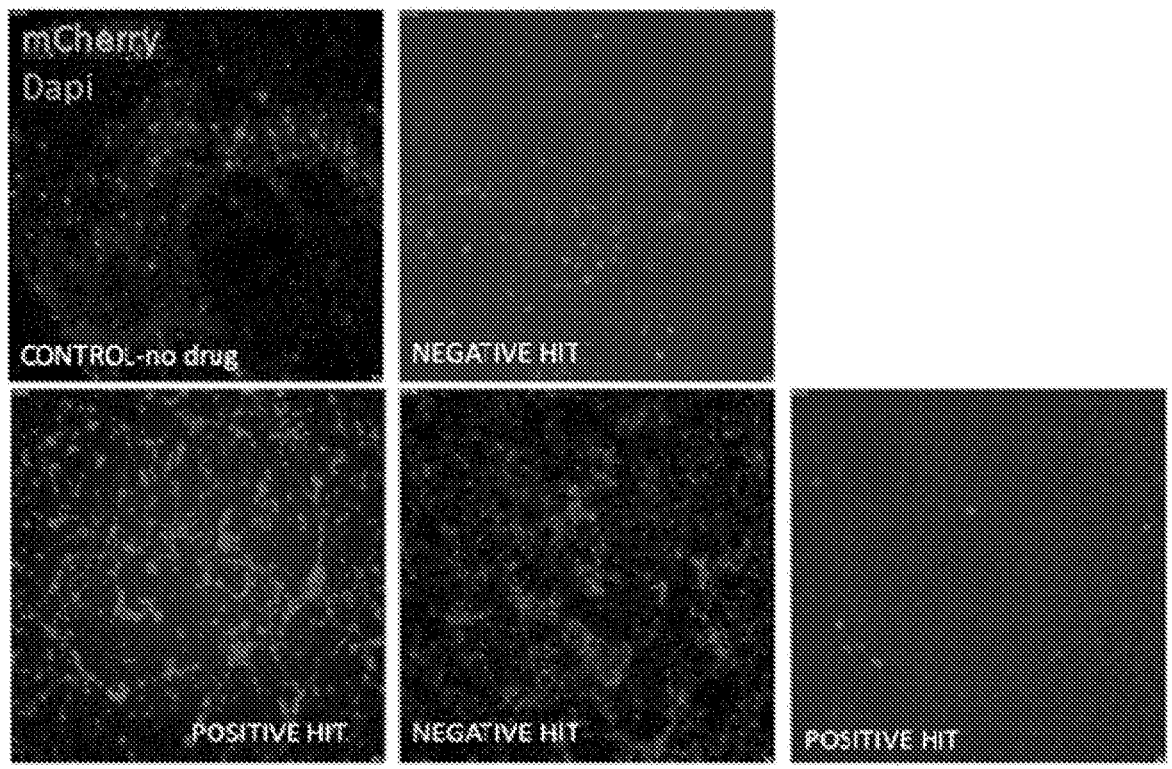
FIG. 14. Figures depict results spectrum of screening from 170,000 compounds to identify 469 compounds.
Figure 15:
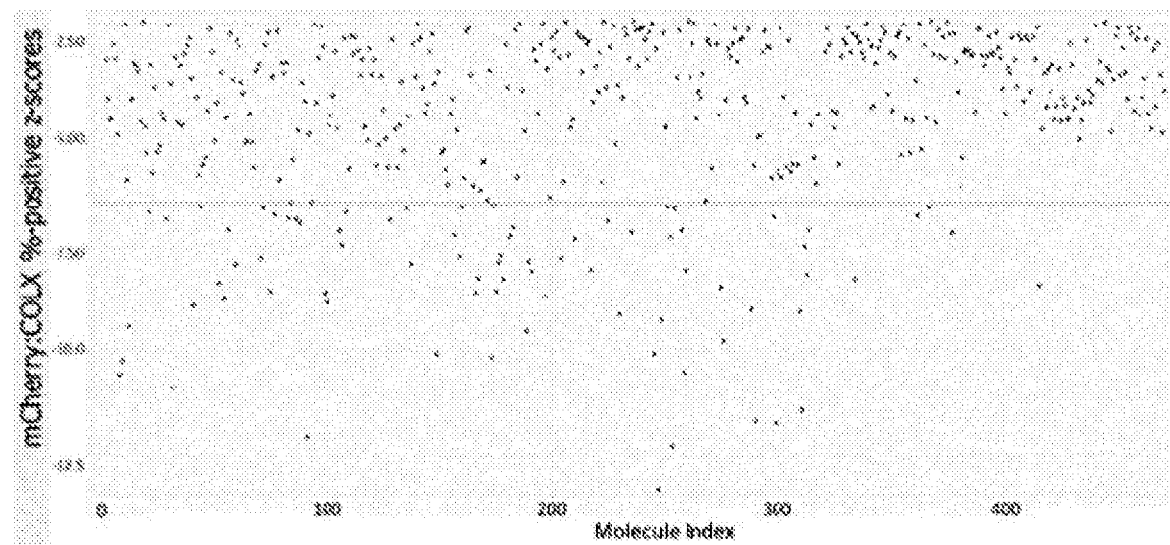
FIG. 15. Figure depicts % positive z-scores for 469 compounds selected for least mCherry expression. % positive as defined as the percentage of live nuclei that overlapped with mCherry signal, which is a multi-wavelength cell scoring function used to select for greatest loss of mCherry signal.
Figure 16:
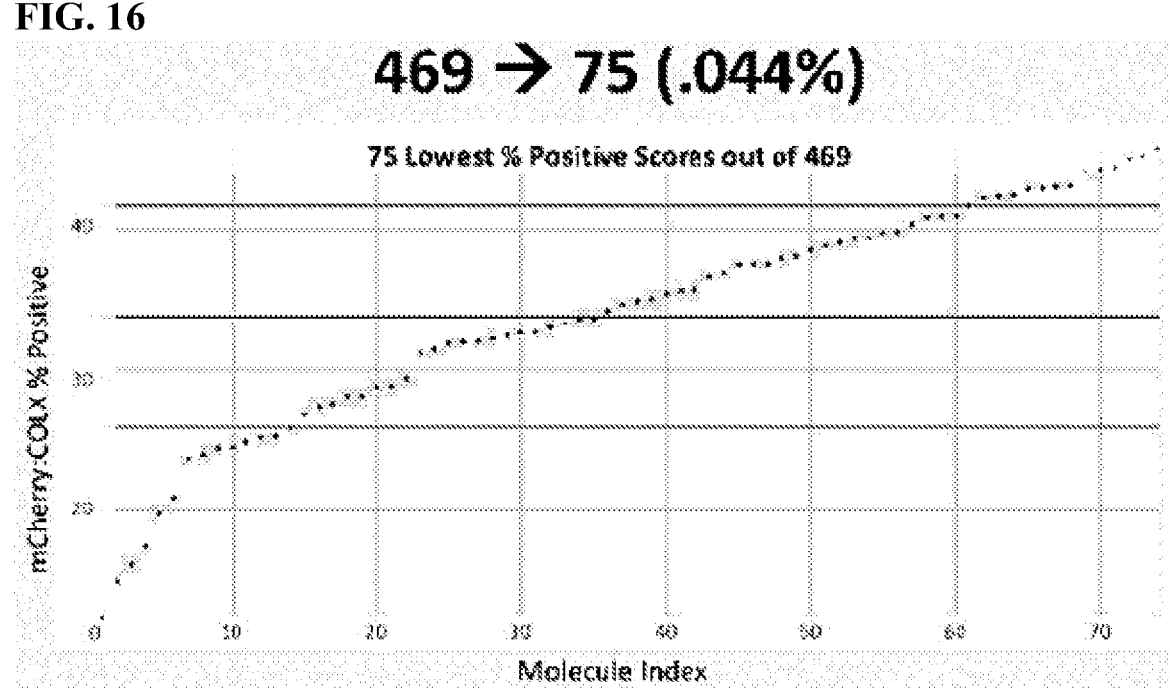
FIG. 16. Figure depicts results of further screening of 75 compounds having lowest positive scores in mCherry procedure. 469 compounds were re-tested to confirm first round results. Compounds with the 75 lowest % positive scores were selected for further studies, all of which showed at least 50% decrease compared to mean negative control scores. Mean (75) 33.78%; Min: 12.32%; Max: 45.69%. Mean (469) 79.89%. (−) Control mean: 96.83%.
Figure 17:
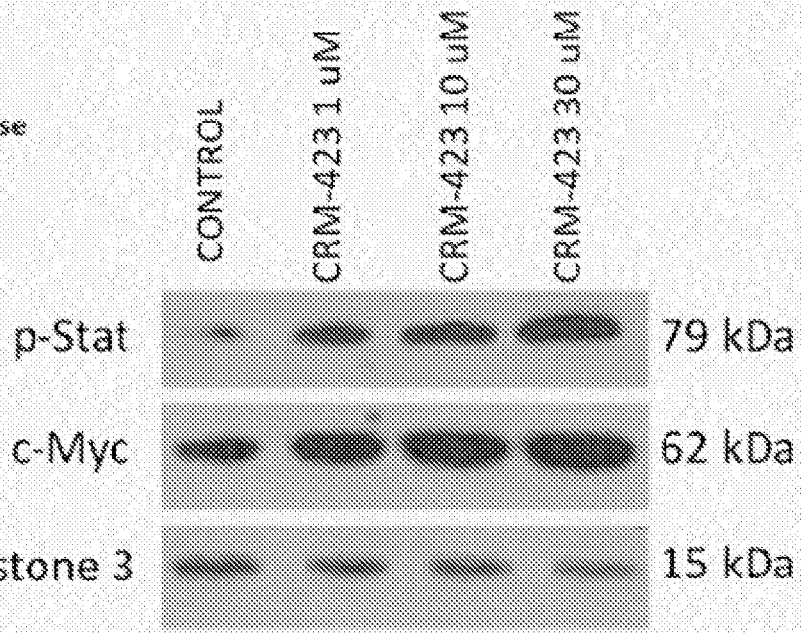
FIG. 17. Figure depicts results of further screening to arrive at seven compounds. Assayed protein and reagent conditions are set forth in the figure.
Figure 18:
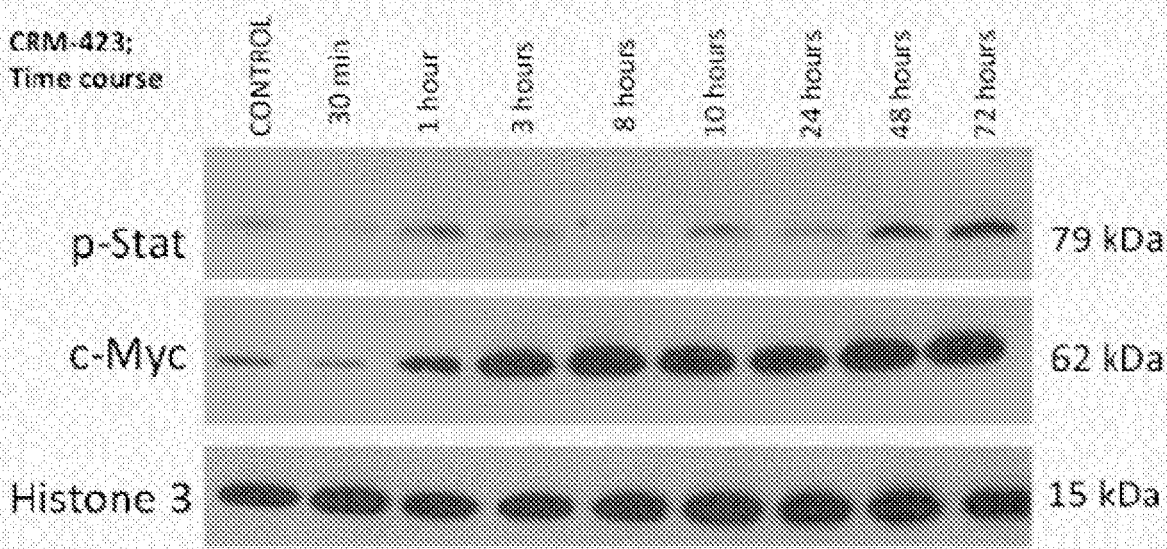
FIG. 18. Figure depicts expression of p-STAT, c-Myc and Histone (H3) for compound CRM-423 (Cmpd 423).

A strategy for screening for molecules with anti-differentiation effects includes observation of primary limb mesenchyme from mCherry-COL10A1 mice. The screening strategy identifies molecules with STAT3 and c-Myc modulatory activity. FIG. 14 depicts exemplary results for a screening conducted on 170,000 compounds, resulting in 469 hits. FIG. 15 depicts percentage positive z-scores for the 469 compounds identified. FIG. 16 depicts a further screening analysis of the previously identified 469 hit compounds, resulting in 75 refined hits. FIG. 17 depicts expression assay for seven compounds identified from the previously identified 75 compounds, with respect to p-Stat3, c-Myc and Histone 3 (H3) levels. FIG. 18 provides further expression data for the seven hit compounds.

Figure 19A:
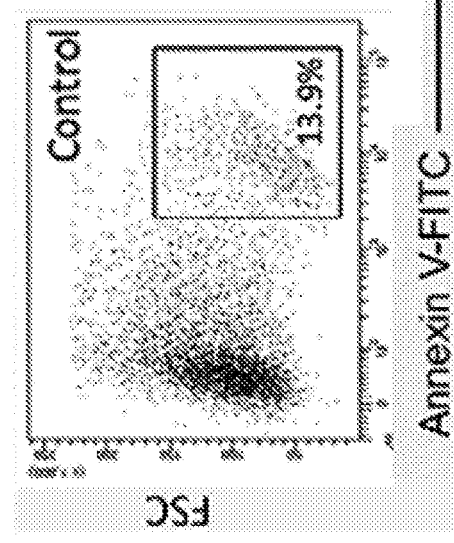
FIGS. 19A-19C. Figures depict result of cell sorting experiment showing that LIF and Cmpd 423 increase chondrocytes survival in adult explants.
Figure 19B:
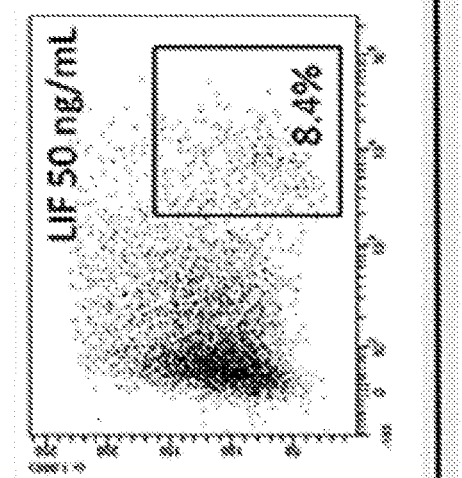
Figure 19C:
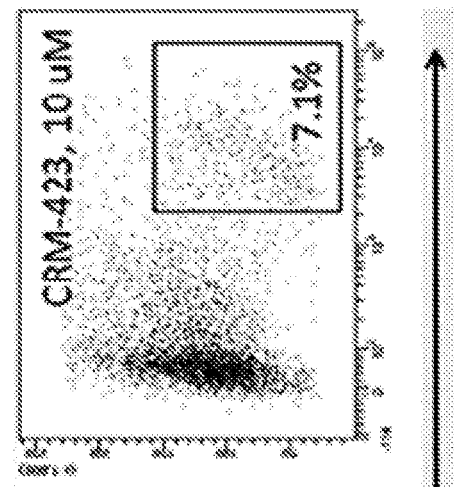

Example 13. Effects of LIF and Cmpd 423 on Chondrocytes Survival in Adult Explants FIG. 19 depicts cell survival in adult explants treated with LIF and Cmpd 423.

Figure 20A:
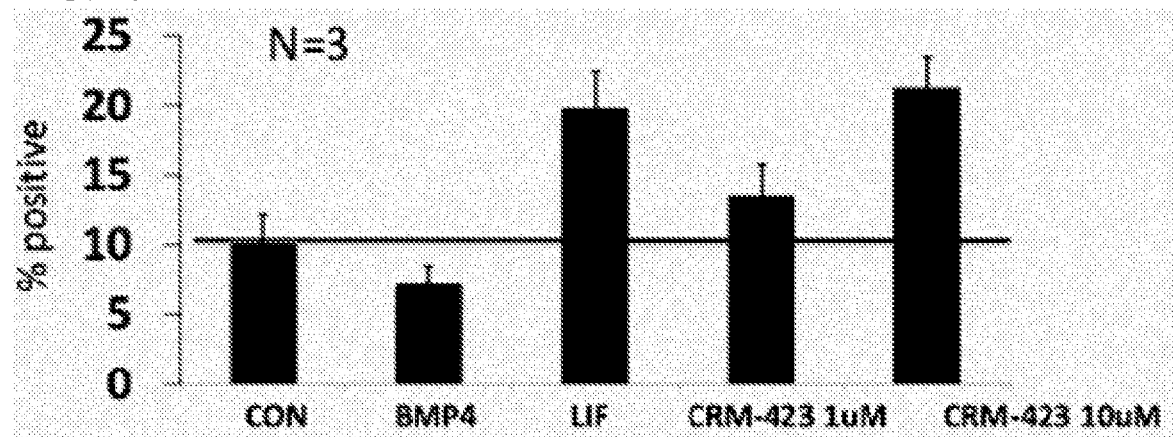
FIG. 20A-20B. Figures depict histogram results showing that LIF and compounds disclosed herein increase percentage of BMPR1B+ immature chondrocytes in culture.
Figure 20B:
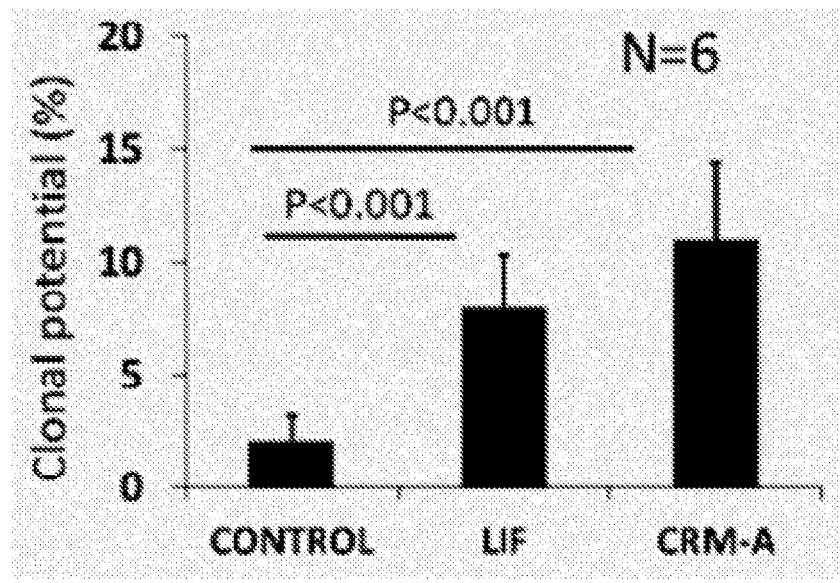

Example 14. Effects of LIF and Identified Compounds on BMPR1B+ Immature Chondrocytes in Culture FIGS. 20A-20B depict histograms showing the effects of LIF and Cmpd 423 on percentage levels of BMPR1B+ immature chondrocytes in culture (FIG. 20A) and on clonogenic potential (FIG. 20B).

Example 15. Collagen Product Potential of BMPR1B+ and BMPR1B− Cells

Figure 21A:
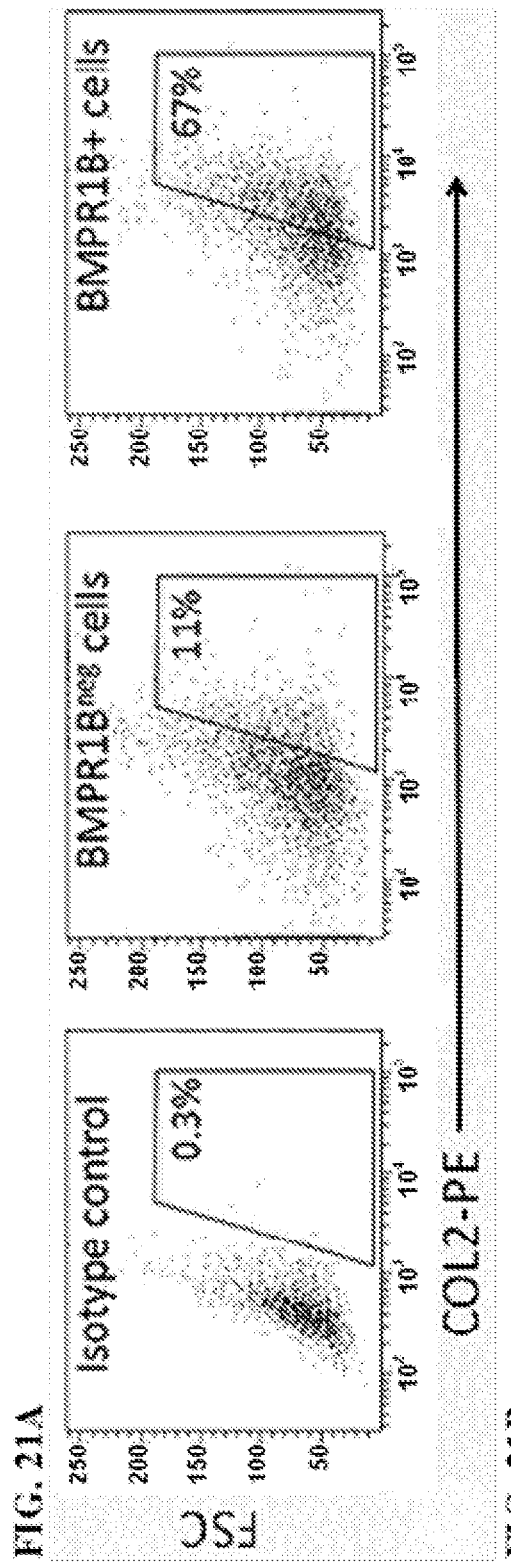
FIGS. 21A-21B. Figures depict that BMPR1B+ adult chondrocytes demonstrate significantly higher collagen production potential BMPR1B+ cells.
Figure 21B:
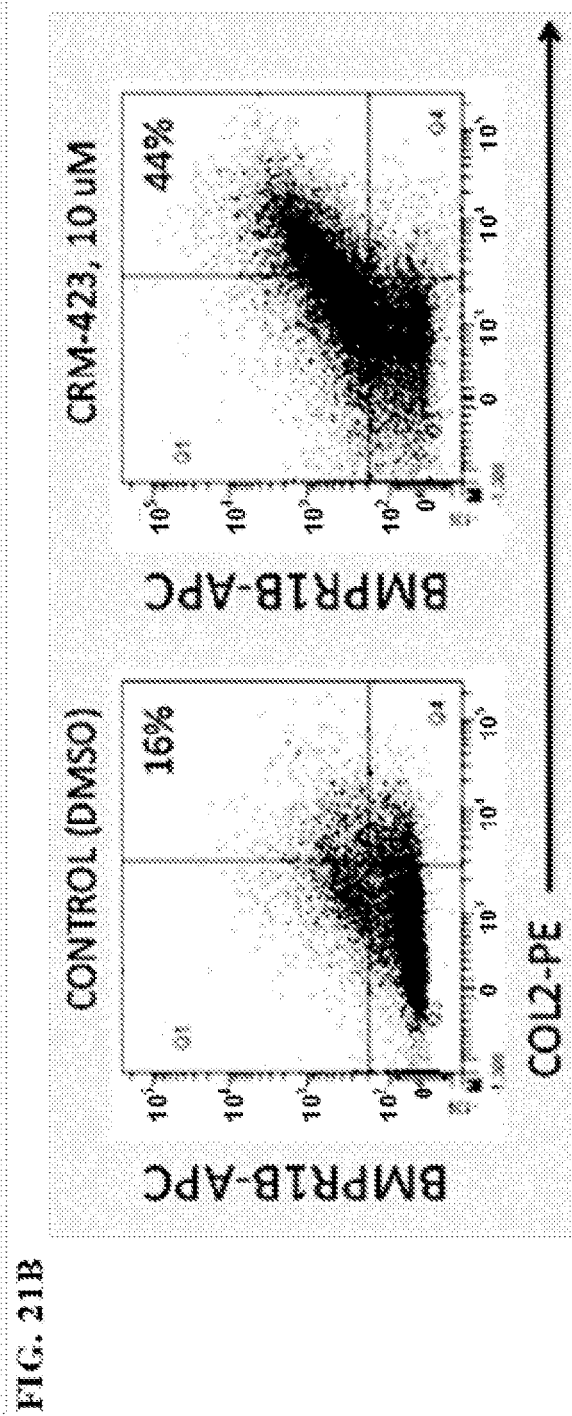

As depicted in FIG. 21A, BMPR1B+ adult chondrocytes demonstrate significantly higher collagen production potential than BMPR1B− cells. Cmpd 423 stimulates collagen 2 product by adult chondrocytes (FIG. 21B).

Example 16. Chondrocyte Expansion in Cultured Cartilage Explants

Figure 22:
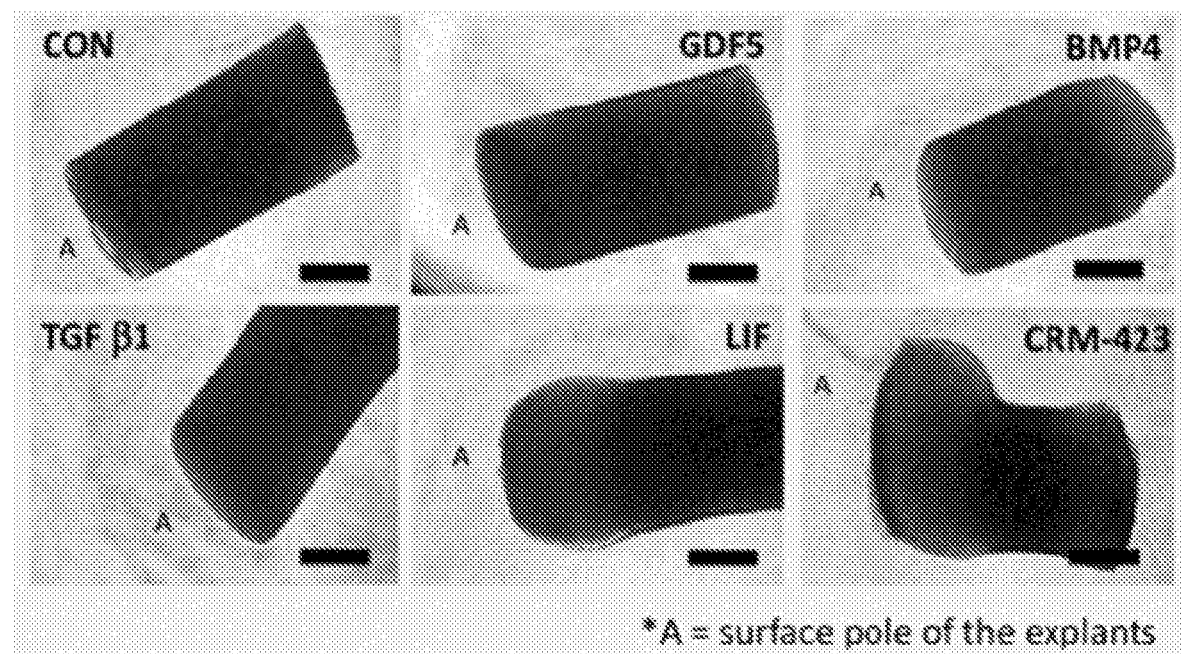
FIG. 22. Figure provides photomicrographs showing expansion of chondrocytes in the apical region of cultured cartilage explants, increasing autologous cartilage tissue.

As depicted in FIG. 22, expansion of chondrocytes is observed in the apical region of cultures cartilage explants.

Example 17. Structure Activity Relationships of Compounds Disclosed Herein

Figure 23:
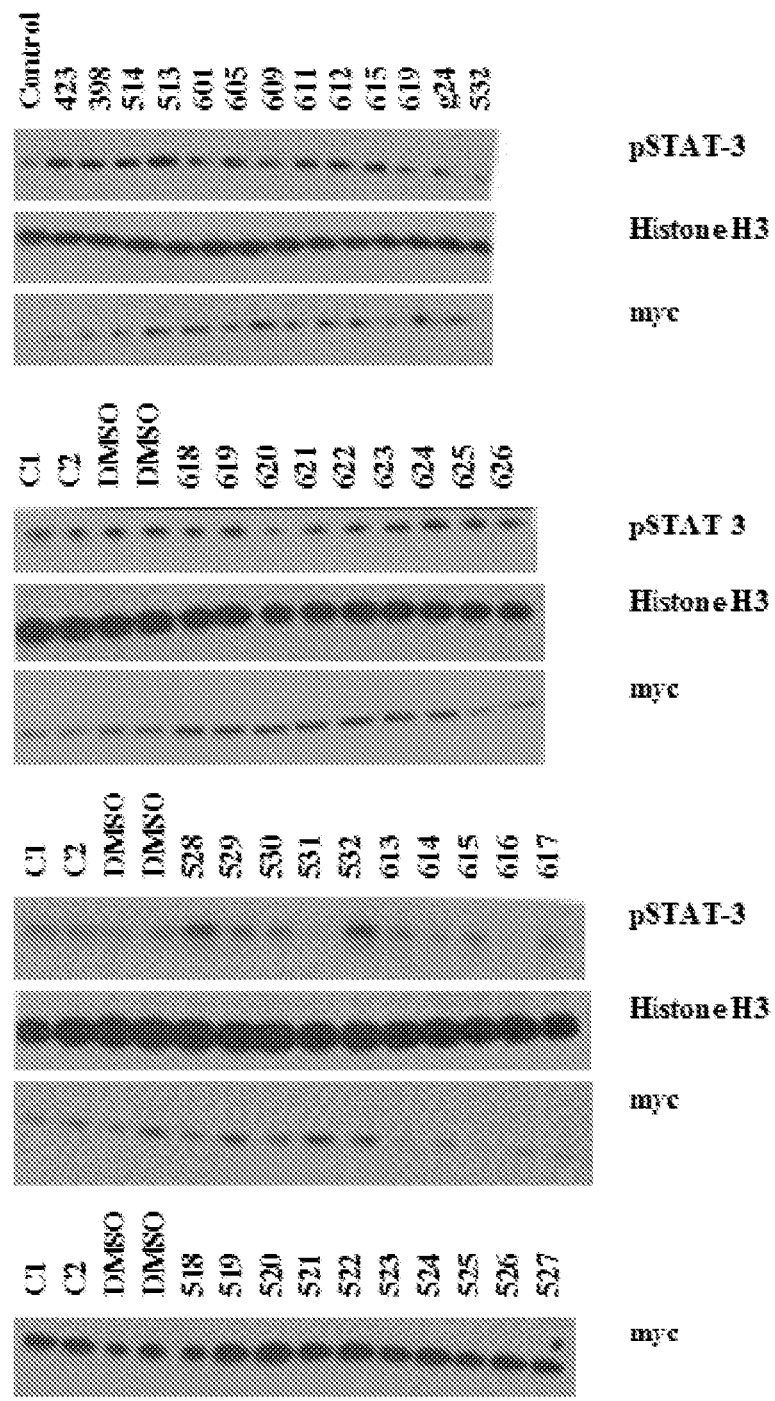
FIG. 23. Figure provides expression levels for compounds disclosed herein and indicated in the figure.

Compounds of Formula (I) and Formula (II) were assayed for modulatory effects on p-STAT3 and c-Myc. Tables 18.1 to 18.4 following disclose compounds that are Stat+/Myc+, Stat−/Myc−, Stat−/Myc+, and Stat+/Myc−, respectively. Supporting Western plot data are provided in FIG. 23 for compounds disclosed in the tables of FIGS. 24A-24D.

Example 18. Drug-Induced STAT3/MYC Activation Confers Fetal-Like Functionality on Adult Articular Chondrocytes Abstract.

Human adult articular cartilage is one of several static tissues that have little capacity for repair; joint surface injuries create irreversible damage and often result in arthritis. It is demonstrated herein that LIF signaling regulates articular chondrocyte activation and that a small molecule partial agonist of this pathway. RNA-sequencing and functional assays demonstrated that fetal chondrocytes are significantly more proliferative, migratory and metabolically active than adult cells and that this difference is largely controlled by a LIF-STAT3-MYC circuit. Adult chondrocytes can respond to LIF and activate a functional program similar to fetal chondrocytes. High throughput screening identified a partial agonist of LIF signaling that elicited robust but transient increases in MYC and active STAT3 in adult chondrocytes, driving increased proliferation, migration and metabolism. These results identify a potential method of promoting regeneration in not only cartilage but possibly in other senescent tissues that respond to STAT3/MYC activation, such as the heart.

Introduction.

In several organ systems generally considered to have low capacity for repair and regeneration, including the kidney, heart and brain, activation of STAT3 has been shown to result in a proliferative response. Moreover, $STAT_3$ activation by IL-6 signaling is a cornerstone of the major regeneration that the liver is capable of undergoing. In all of these cases, heterodimerization of gp130 (IL6ST) with a cognate receptor, e.g. IL-6R or LIFR, upon ligand binding results in phosphorylation of STAT3 and activation of a downstream proliferative program facilitated by MYC. The function of IL-6 family members in cartilage have long been debated, although they have generally been considered as pro-inflammatory and promoting cartilage degeneration.

Here, by examining differences in fetal and adult articular chondrocytes, we show that the IL-6 family member LIF drives several key functional properties in cartilage: proliferation, survival, migration and metabolic activity. These properties are mediated by increases in phosphorylated STAT3 (pSTAT3) and MYC protein levels. Treatment of adult chondrocytes with LIF, which typically evidence low basal levels of LIF activity, increases pSTAT3/MYC levels and reasserts a fetal-like functional program.

We designed a high throughput screen to uncover potential small molecule mediators of cartilage activation state and discovered Regulator of Cartilage Growth and Differentiation (RCGD) 423, a potent partial agonist of the LIF signaling pathway. Treatment of adult articular chondrocytes with RCGD 423 results in strong but transient increases in pSTAT3 and MYC protein levels. In concordance with our other data, this results in adoption of a fetal-like functional state including significant increases in proliferation, survival, migration and metabolism. Importantly, in the context of injured articular cartilage tissue, RCGD 423 stimulates the repair of defects and deposition of new matrix.

Based on the functional properties elicited by RCGD 423, we propose that it (or compounds functionally similar to it) may represent core components of treatment regimens for articular cartilage injury. Moreover, our unpublished preliminary data indicate that RCGD 423 promotes increases in pSTAT3 and MYC proteins and documented downstream responses in other cells/tissues, including embryonic stem cells and the heart. To our knowledge, RCGD 423 represents one of the first described agonists of the gp130/STAT3/MYC pathway, and our data suggests that it or similar compounds could have broad applications in both basic biology as well as regenerative medicine.

Articular cartilage is an avascular, highly specialized tissue found in diarthroidal joints and acts as a substrate to enable fluid motion of opposing joint surfaces. Adult articular cartilage is comprised mostly of extracellular matrix and water, with chondrocytes (the cellular component) constituting only 2-5% of total tissue volume (Sophia Fox et al., 2009). The cartilaginous matrix is secreted by highly specialized cells—chondrocytes, and is composed mostly of collagens, with collagen II (COL2) being the most abundant, and proteoglycans including aggrecan. The regenerative potential of mature articular cartilage is minimal. Recently, chondrocytes closest to the joint surface in the superficial zone have been shown to have some proliferative capacity (Dowthwaite et al., 2004; Yasuhara et al., 2011), but the frequency of cells that can divide and deposit large amounts of matrix is low and is clearly insufficient to enact cartilage repair. Moreover, the limited intrinsic regenerative capacity of articular cartilage decreases further with age (Tran-Khanh et al., 2010).

Regeneration of tissues occurs through two main mechanisms: constant output from tissue resident stem cells or reactivation and proliferation of committed cells within a tissue (Forbes and Rosenthal, 2014). The hematopoietic system represents the prototypical example of stem cell-based regeneration, in which hematopoietic stem cells generate lineage-committed progenitors which then produce terminally differentiated blood cells (Orkin and Zon, 2008). In contrast, liver regeneration is driven by fully differentiated hepatocytes that balance hypertrophy and proliferation based on the extent of the damage (Miayaoka et al. 2012). One of the critical signals that promotes regeneration is the pro-inflammatory cytokine IL-6 (Cressman et al., 1996). The IL-6 family of cytokines is defined by structurally similar proteins that all share a common co-receptor, IL-6RST (gp130), and includes IL-6, IL-11, leukemia inhibitory factor (LIF), cardiotrophin-1, oncostatin M (OSM), ciliary neurotrophic factor and cardiotrophin-like cytokine (Scheller et al., 2011). Signaling downstream of these cytokines involves phosphorylation and activation MAPKs as well as JAK and STAT proteins. Activity of Stat3 is essential for mouse liver regeneration, functioning to promote hepatocyte proliferation and survival (Li et al., 2002). Notably, livers in aged mice, rats and humans show diminished capacity to regenerate, though the mechanisms underlying this remain unclear (Pibiri et al., 2015; Timchenko, 2009).

Here we focused on understanding the differences in molecular and functional properties of human cartilage cells, and thus the potential for regeneration, at different stages of development. By comparing rapidly growing fetal and functionally inert adult articular chondrocytes, we identified the LIF/STAT3/MYC signaling axis as a critical regulator of chondrocyte metabolism, survival, proliferation and migration. High throughput screening enabled the discovery of a novel partial agonist of LIF signaling, which we have termed Regulator of Cartilage Growth and Differentiation (RCGD) 423. This small molecule elicits a robust proliferative response in adult articular chondrocytes in their native 3-dimensional microenvironment and promotes the healing of cartilage defects within the context of a tissue without inducing significant catabolic events or loss of chondrogenic commitment. These results describe a potential therapeutic intervention for degenerative diseases of cartilage that may also have applications in other tissues and organ systems.

Results

Primitive Chondrocytes Vary in their Molecular and Functional Characteristics Based on Developmental Stage.

We recently defined a population of BMPR1B$^+$ chondrocytes present in the superficial layer of articular cartilage throughout ontogeny (Wu et al., 2013). When compared to BMPR1B− chondrocytes, these cells expressed higher levels of the chondrogenic transcription factor SOX9 and lower levels of matrix protein COL10A1, indicating that these cells represent a more primitive subset of articular cartilage cells. In order to understand how this population changes over developmental time, we sorted BMPR1B$^+$ cells from the knee joints of human fetal specimens, when cartilage is rapidly growing, and from quiescent adult human cartilage tissue and performed RNA-Sequencing (FIG. 25A). Hierarchical clustering performed at the whole transcriptome level (FIG. 25B) indicated strong differences between fetal and adult samples; as expected, there was also variability amongst the adult samples. Differential expression analysis identified 1,025 transcripts ($p<0.05$, $\geq$2-fold) enriched in fetal cells.

Figures 25E, 25F:
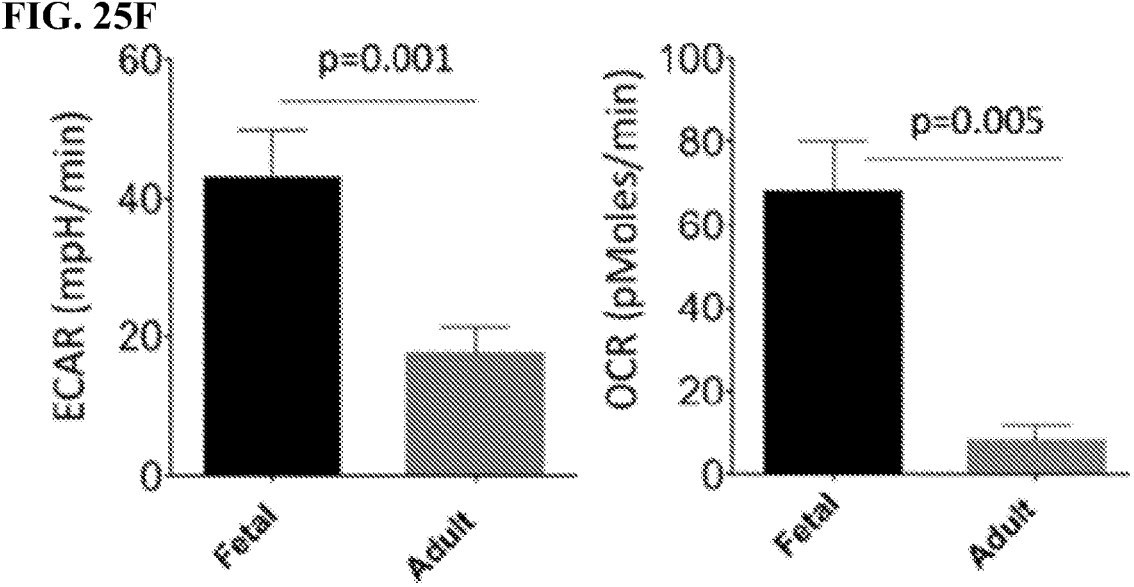

Expression levels of several genes known to be required in primitive chondrocytes, including SOX9, SOX6 and NKX3-2, were more highly expressed in fetal cells, while genes associated with hypertrophy and matrix degradation (COL10A1, ADAMTS4 and ADAMTS5) were enriched in adult chondrocytes (FIG. 25C). Unbiased analysis of genes significantly enriched in fetal cells using Gene Ontology (GO) (Huang da et al., 2009a, b) revealed enrichment of categories related to skeletal system and cartilage development, cellular metabolism, proliferation, motility and extracellular matrix organization (ECM; FIG. 25D). To further understand the potential mechanisms driving fetal gene expression, we performed Gene Set Enrichment Analysis (GSEA; (Mootha et al., 2003; Subramanian et al., 2005). These results (FIG. 25E) further confirmed that fetal cells are more proliferative and have higher expression of ECM genes; additionally, a strong signature linked to transcriptional regulation by MYC was evident. In contrast, adult cells were enriched for genes related to inflammation and cell death. See e.g., tables set forth in FIGS. 32A-32B.

Figure 25G:
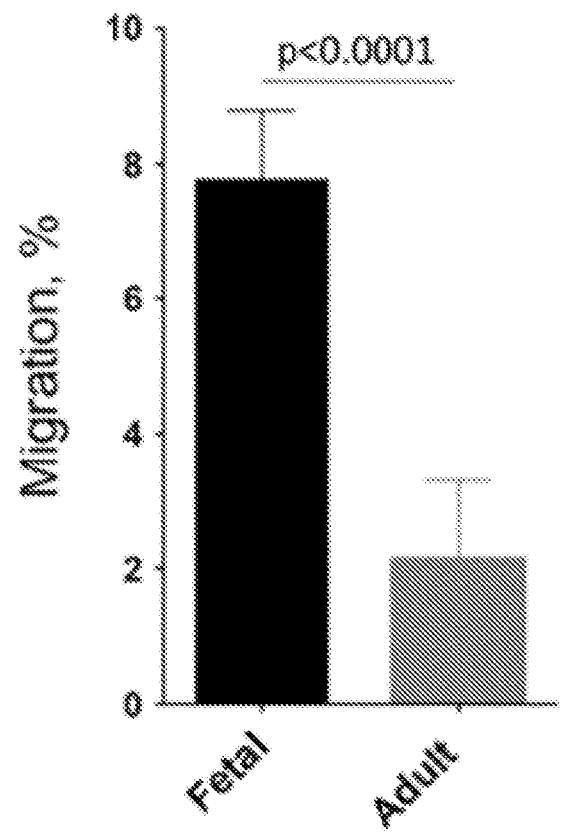
Figure 25H:
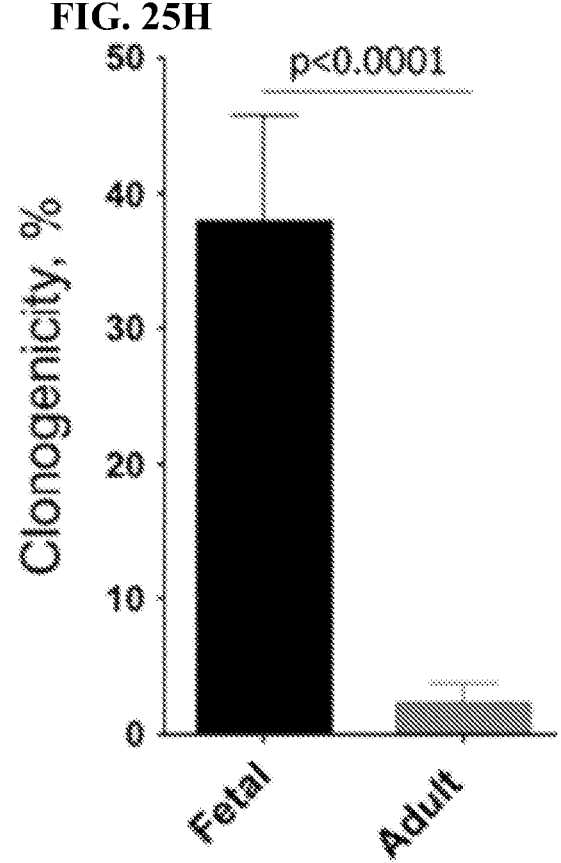

To functionally confirm the RNA-Seq data, we incubated explants of human fetal and adult cartilage with EdU to assess proliferative capacity in situ. As expected, fetal cells evidenced dramatically enhanced uptake of EdU (FIG. 5B) in the superficial zone. Fetal articular chondrocytes were also substantially more metabolically active than adult cells, demonstrating both increased glycolysis and cellular respiration in Seahorse assays (FIG. 25F). Finally, at the single cell level, fetal articular chondrocytes were more migratory (FIG. 25G) and clonogenic (FIG. 25H), further supporting the gene expression data. Overall, these results show that fetal articular chondrocytes have augmented capabilities in several cellular functions, including proliferation, migration and metabolism, which would likely support a regenerative response.

The LIF Signaling Axis Drives the Proliferative Phenotype in Fetal Chondrocytes.

Figure 10C:
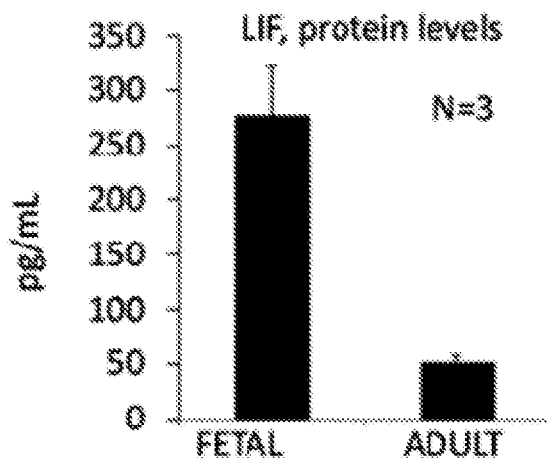
Figure 26A:
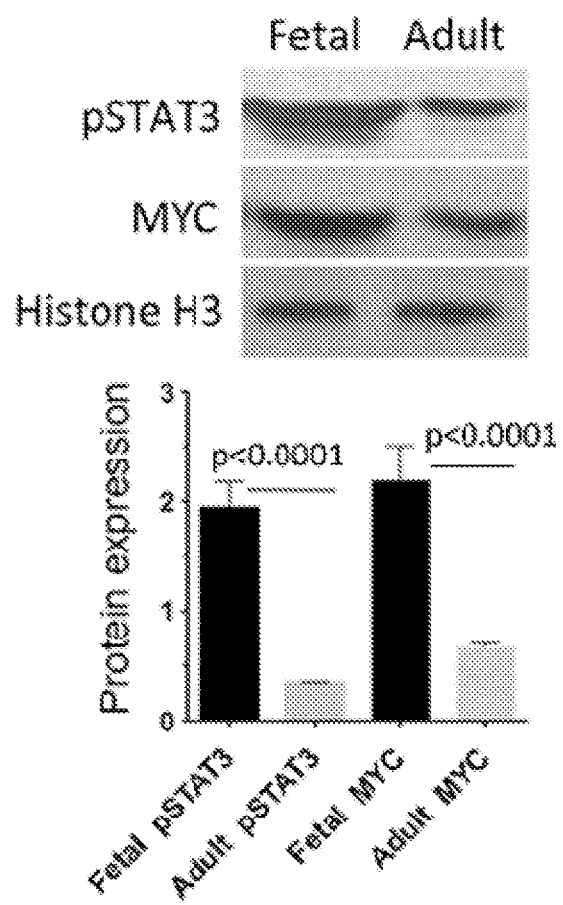
FIGS. 26A-26J. LIF/STAT3/MYC signaling is prominent in fetal articular chondrocytes and can activate a fetal-like phenotype in adult cells.
Figure 26B:
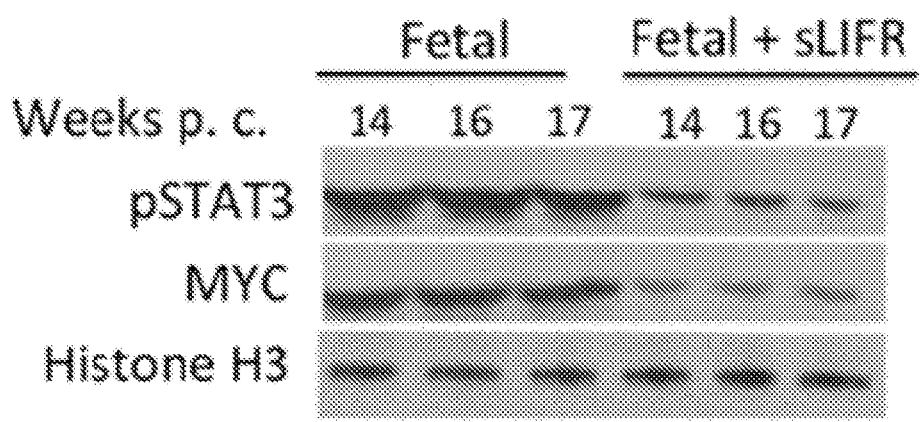
Figure 33:
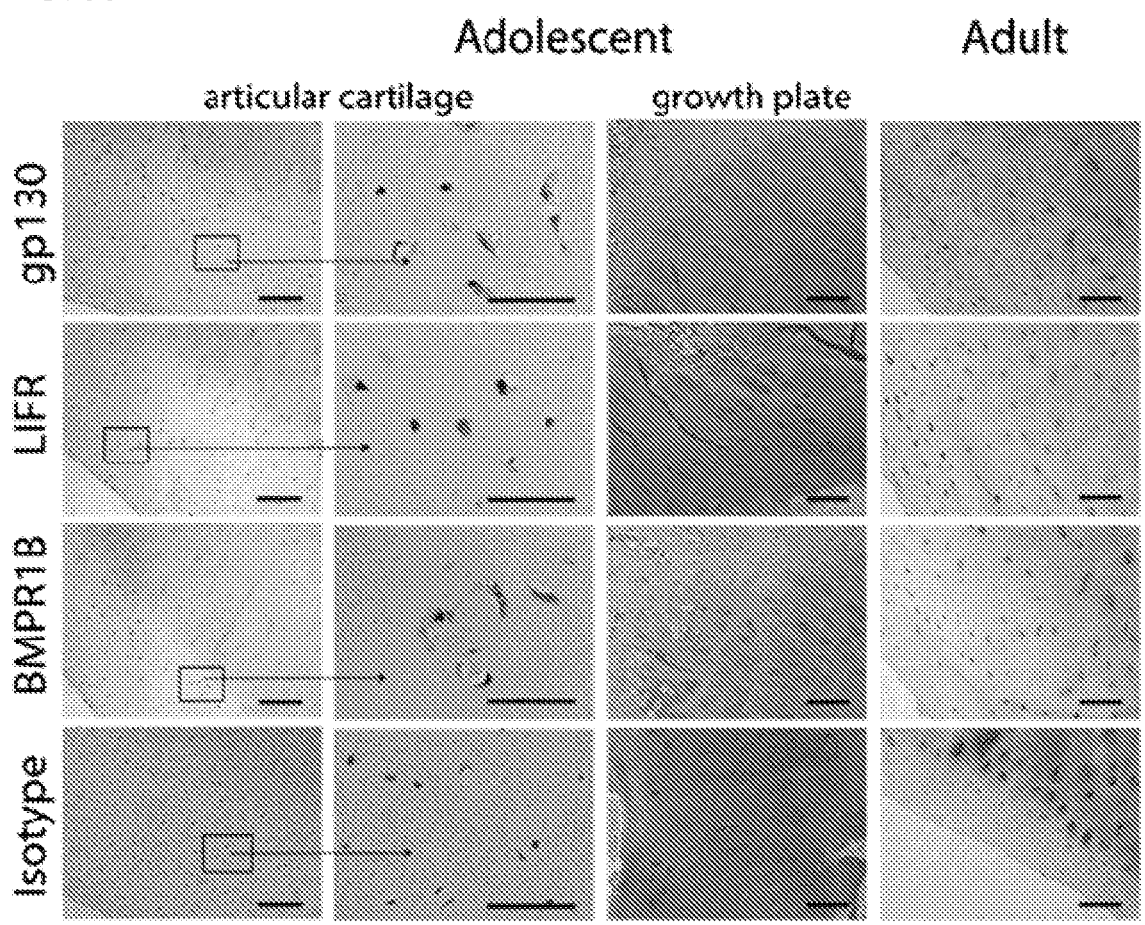
FIG. 33. BMPR1B, LIFR and gp130 Identify Largely Overlapping Populations of Articular Chondrocytes Throughout Development Immunohistochemistry for LIFR and its co-receptor gp130 demonstrated that their expression mostly overlaps in both adolescent (left three columns) and adult (rightmost panel) articular chondrocytes in the superficial zone; a similar population of chondrocytes expressed BMPR1B. All three proteins were absent from chondrocytes present in the adolescent growth plate. Positive signal is indicatged. Scale bars represent 25 µm.
Figure 34A:
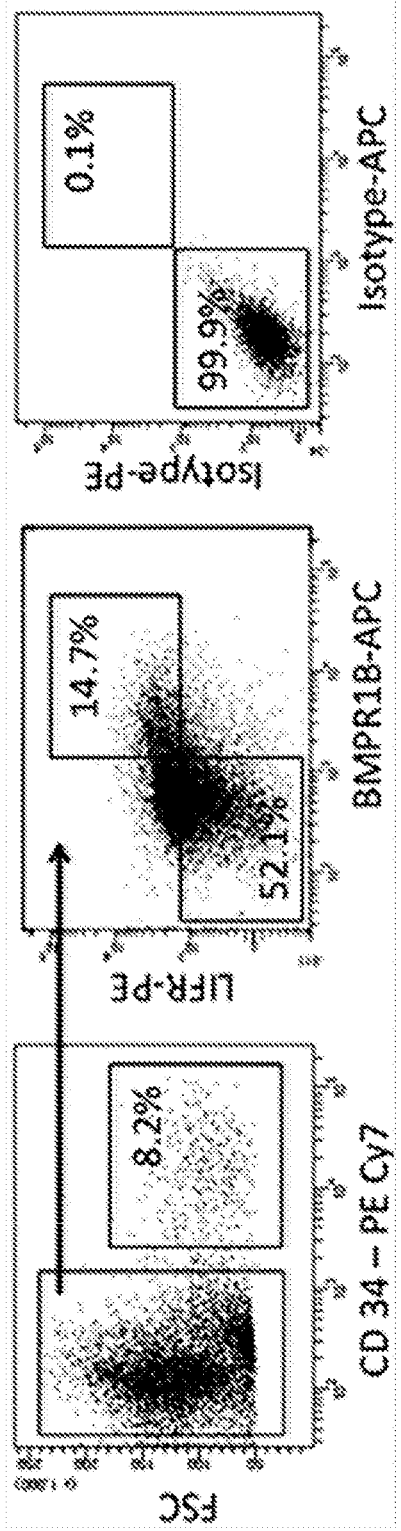
FIGS. 34A-34B. BMPR1B$^+$LIFR$^+$ Cells are Enriched for Anabolic Gene Expression.
Figure 34B:
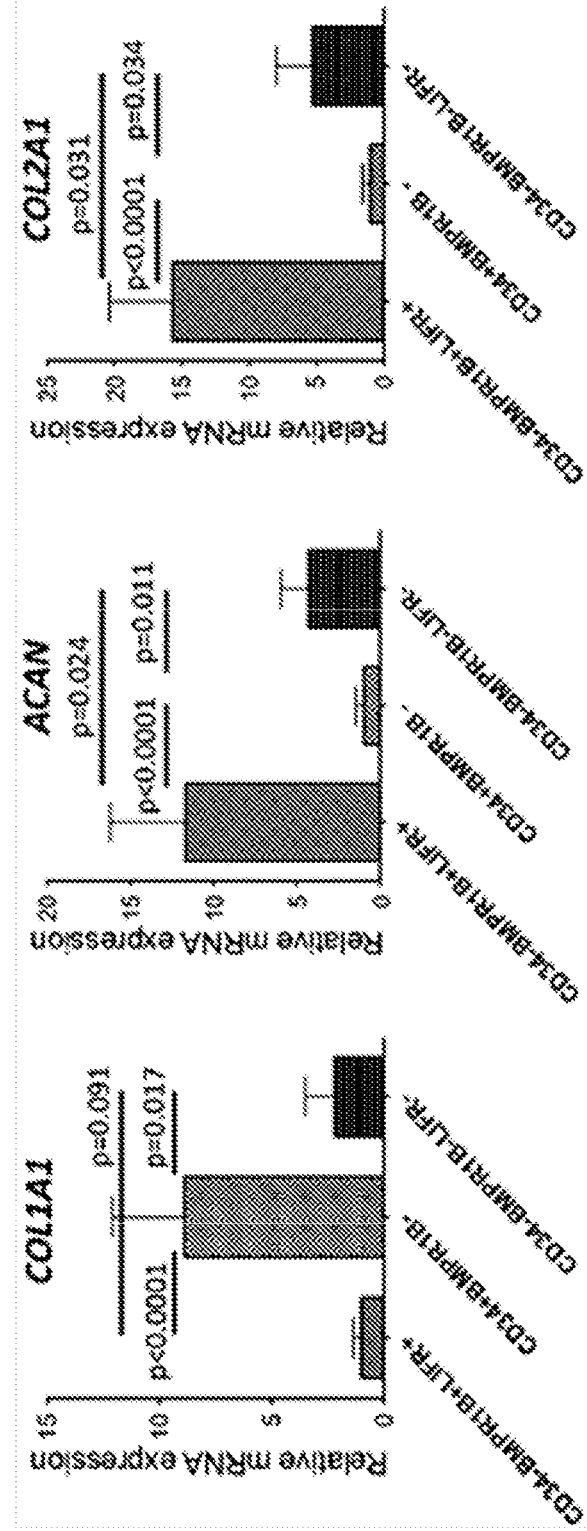

In our previous work (Wu et al., 2013), we showed that LIF could prevent chondrocyte maturation and hypertrophy in primary cells and promote the specification and survival of chondrocytes from pluripotent stem cells. Moreover, LIFR expression is localized to chondrocytes in the superficial zone of articular cartilage throughout ontogeny. In contrast, LIF expression is strongest during fetal development and then diminishes over time (Table S1). Based on these data, we hypothesized that LIF signaling regulates the proliferation and survival of fetal chondrocytes. LIF signals through a heterodimeric receptor comprised of LIFR and gp130 (IL6RST); upon binding extracellular ligand, both receptors are phosphorylated and recruit members of the JAK family which in turn phosphorylate STAT3 (pSTAT3). pSTAT3 then enters the nucleus to act as a transcriptional regulator. In mouse pluripotent stem cells, LIF/STAT3 signaling has also been shown to regulate levels of both Myc transcript and protein (Cartwright et al., 2005). We first performed ELISA on human fetal and adult synovial fluid to determine if LIF protein levels change over time. These results revealed that LIF levels were 5-fold higher in fetal vs. adult samples (FIG. 10C). Western blot analysis of the downstream effectors of LIF signaling, pSTAT3 and MYC, further supported reduced levels of LIF signaling in adult articular cartilage (FIG. 26A). We then confirmed that adolescent and adult articular chondrocytes in the superficial zone express both receptors required for LIF signaling (FIG. 33) and that these cells are the most anabolic of adult chondrocytes (FIGS. 34A-34B). Because STAT3 and MYC can respond to a variety of stimuli, we next wanted to determine if the increased levels of pSTAT3 and MYC in fetal cells were a direct result of increased LIF/LIFR signaling. Incubation of fetal articular chondrocytes with soluble LIFR (sLIFR), which binds and sequesters LIF, resulted in substantially reduced levels of both pSTAT3 and MYC (FIG. 26B). These data indicate that LIF signaling, which is highly active in fetal chondrocytes, is primarily responsible for activation of STAT3 and increased levels of MYC protein.

Figure 26C:
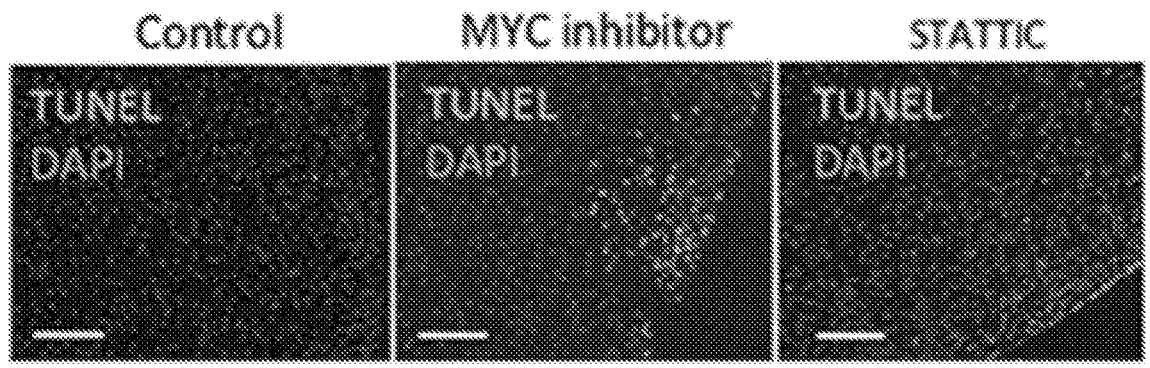
Figure 26D:
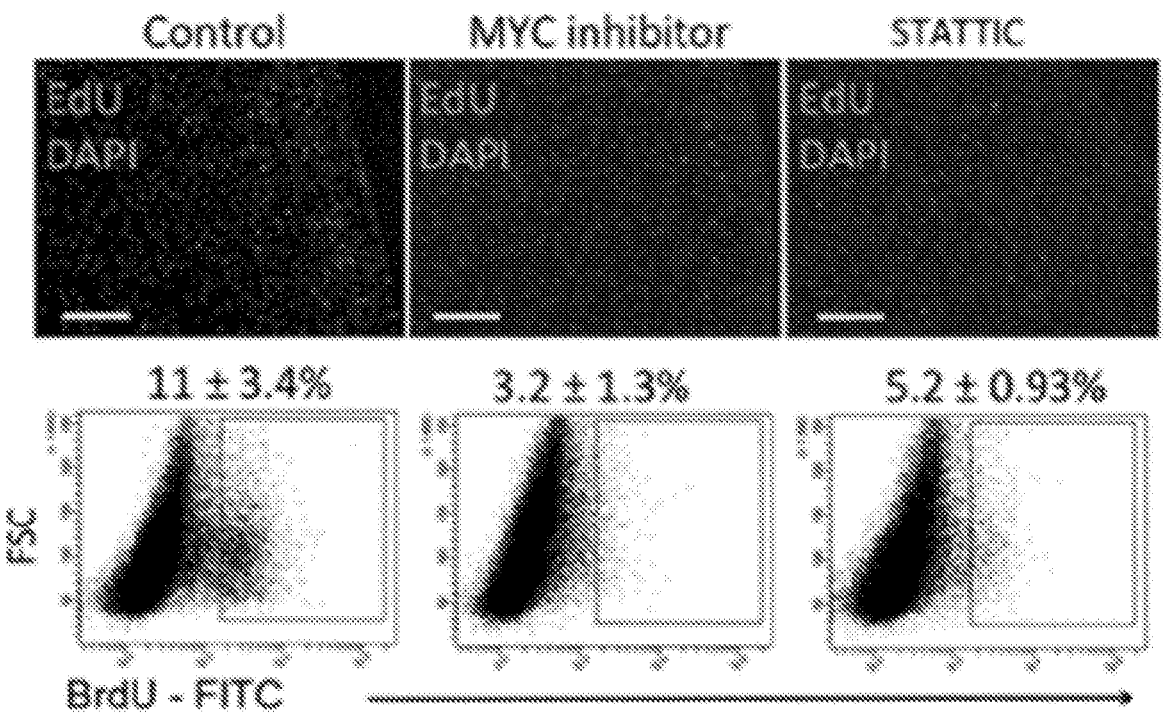
Figure 26E:
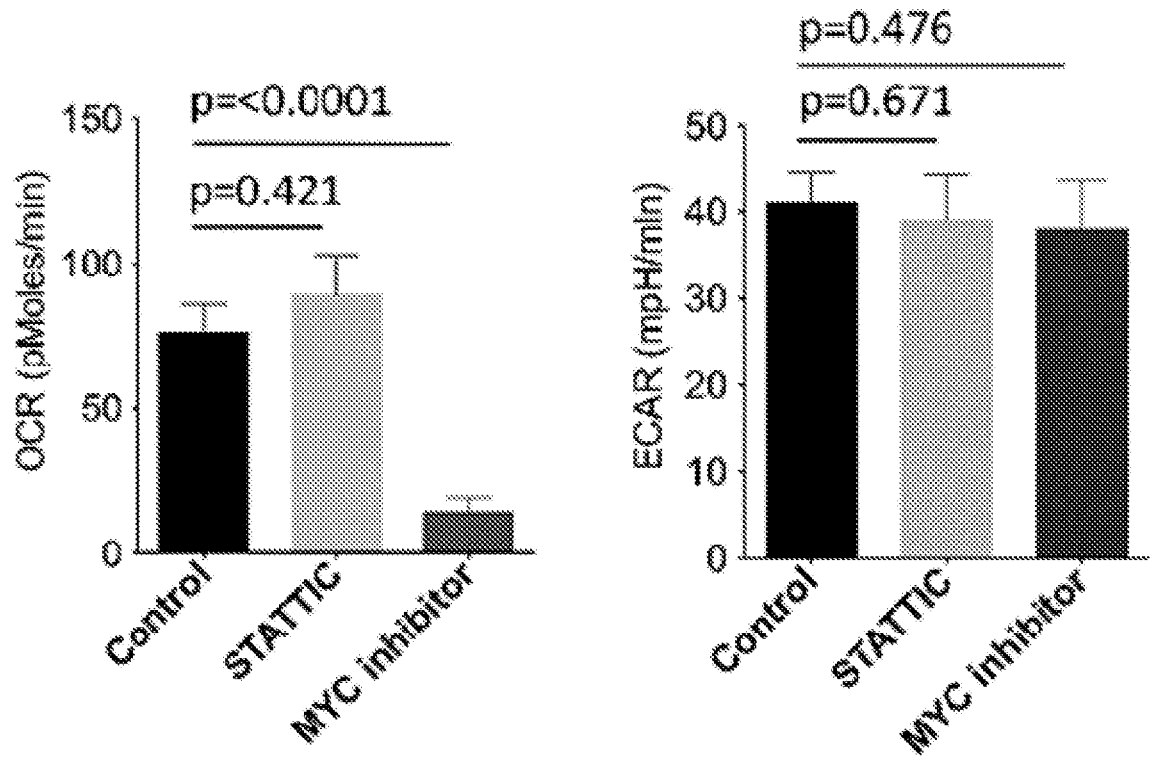
Figure 26F:
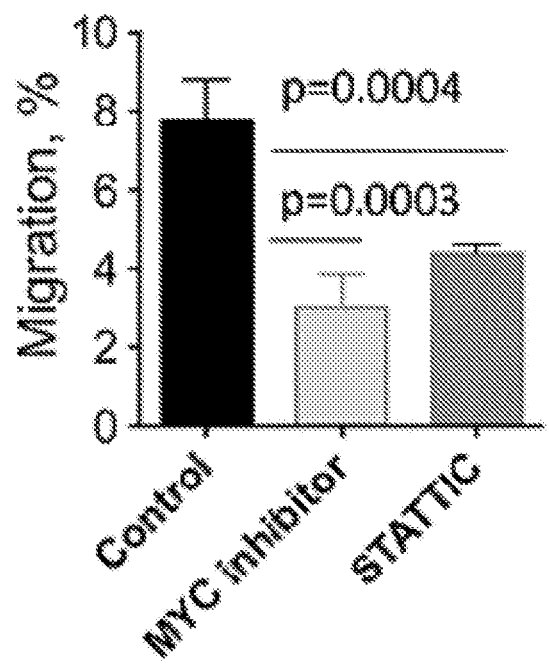

To assess the functional consequences of LIF signaling, explants of fetal cartilage were cultured with inhibitors of MYC or STAT3 (Schust et al., 2006) and then TUNEL stained; flow cytometry was used to quantitate the results of parallel experiments. Incubation of explants with either inhibitor resulted in strongly significant increases in apoptotic cells (FIG. 26C), defining a role for LIF signaling in cell survival. Furthermore, LIF actively promotes proliferation, as blocking of either MYC or STAT3 activation greatly reduced incorporation of BrdU and EdU into fetal cartilage explants (FIG. 26D). Interestingly, levels of MYC, but not STAT3, activity directly influenced cellular respiration; glycolysis was unaffected by inhibitors of either protein (FIG. 26E). MYC activity has been documented previously in cancer cell lines to regulate mitochondrial function (Fan et al., 2010). The migratory capacity of fetal chondrocytes is also regulated via LIF/STAT3 and MYC, as their inhibition resulted in a 2- to 4-fold decrease in motile cells (FIG. 26F). Together, these functional data corroborate the MYC transcriptional signature and the enrichment of the STAT3 motif present in the transcriptome of fetal cells (FIG. 25D) and implicate LIF signaling as a major regulator of fetal articular chondrocyte proliferation, survival, metabolism and migration.

Figure 26G:
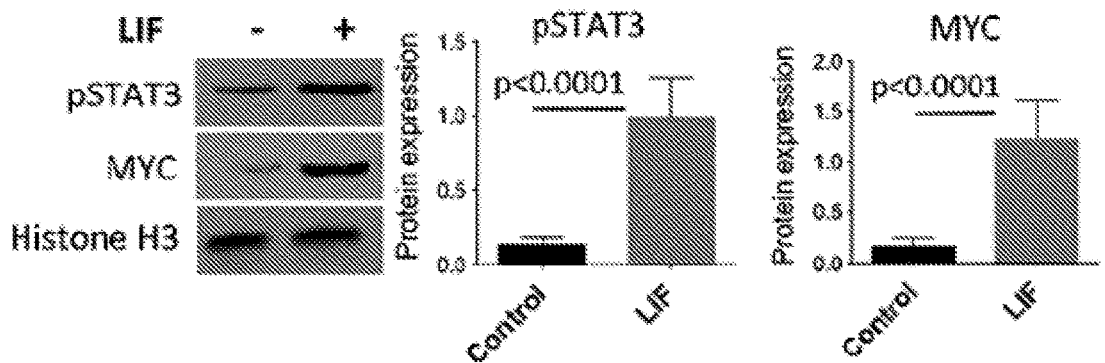
Figure 26H:
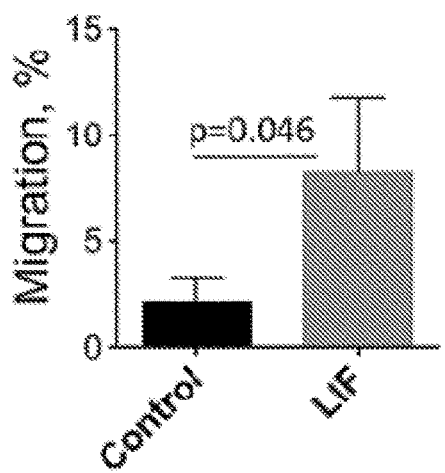
Figure 26I:
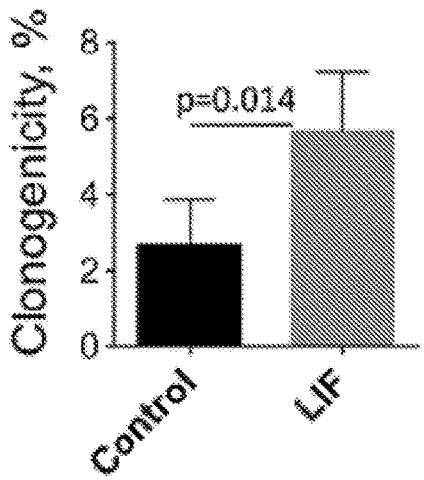
Figure 26J:
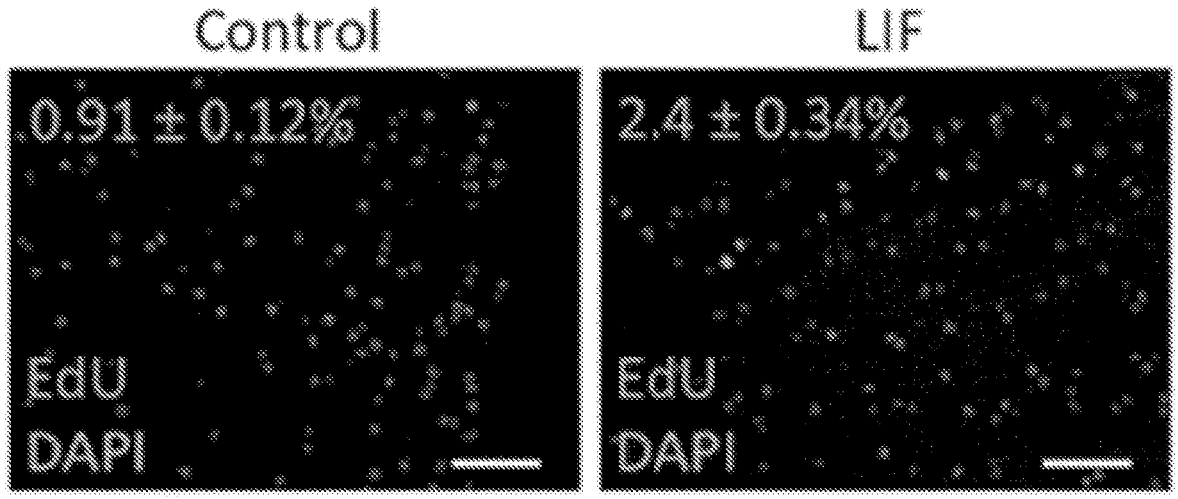

We next wanted to determine if adult articular chondrocytes could respond to LIF stimulation in a similar fashion. Addition of LIF to adult cartilage robustly increased levels of pSTAT3 and MYC (FIG. 26G), as well as increased migration (FIG. 26H) proliferation (FIGS. 26I-26J) and promoted survival (FIGS. 19A-19B). These results suggest that increasing LIF signaling pathway in adult chondrocytes could represent an effective means of promoting cartilage regeneration.

Identification of Novel Small Molecules that Regulate Chondrocyte Differentiation.

Figure 27A:
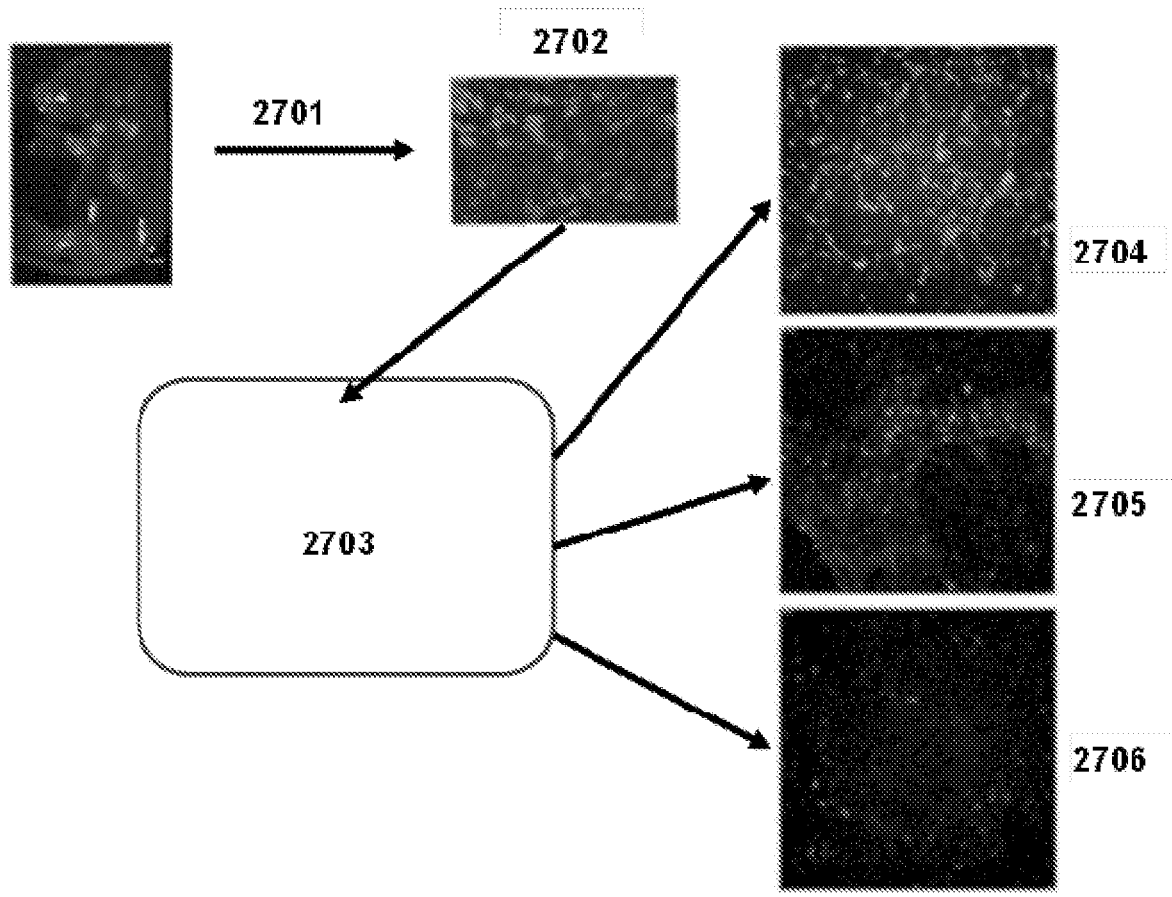
FIGS. 27A-27B. Small molecule screen to identify regulators of cartilage differentiation potential.
Figure 27B:
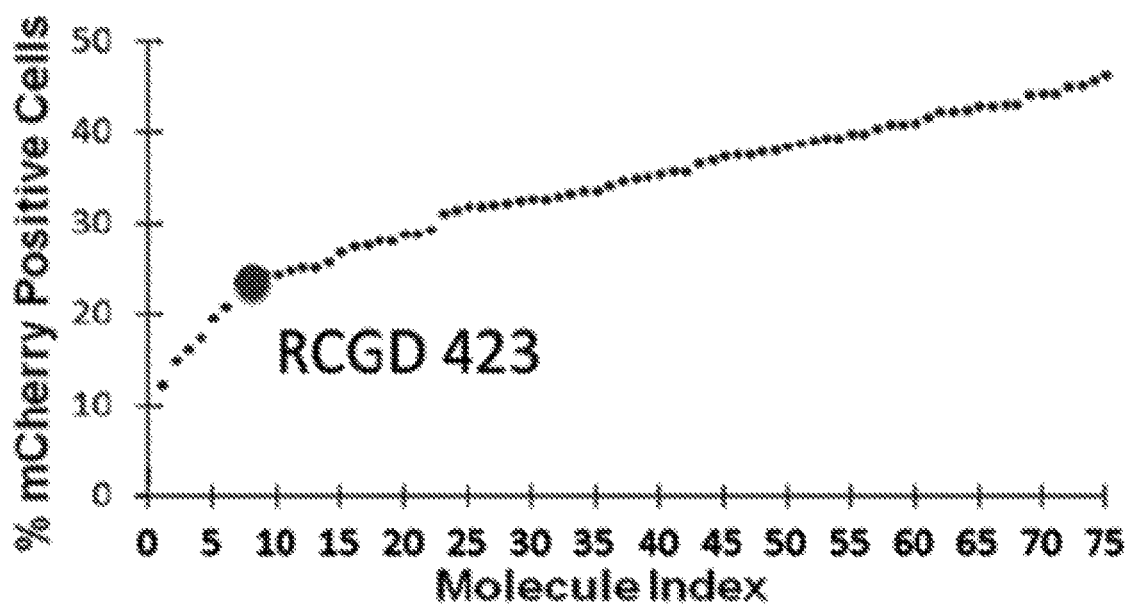
Figure 27C:
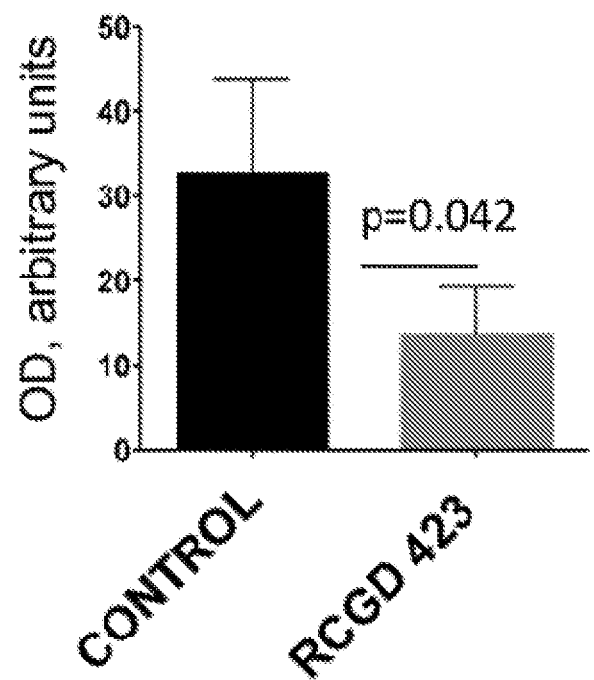
(FIG. 27C) Quantification of alkaline phosphatase levels in human fetal articular chondrocytes treated with BMP-4 in absence (control) or presence of RCGD 423. Data are represented at mean±SD.

From a therapeutic and regulatory standpoint, small molecules represent a highly attractive modality for manipulating cell biology. To this end, we conducted a high throughput screen to discover small molecules that regulate chondrocyte differentiation. As a readout for the screen, we chose mice carrying a transgenic mCherry reporter (Maye et al., 2011) for expression of Col10a1 (COL10). COL10 expression, along with alkaline phosphatase (AP) levels, increases during later stages of chondrocyte differentiation, concomitant with withdrawal from the cell cycle. Moreover, we recently demonstrated that treatment of chondrocytes with LIF inhibits COL10A1 expression. To conduct the screen, total limb cells were isolated from Col10a1-mCherry transgenic embryos and cultured in the presence of BMP-4, a driver of chondrocyte hypertrophy (Wu et al., 2013); 170,000 compounds were assayed for their ability to decrease the mCherry signal in live cells under these conditions (FIG. 27A). Out of this first dataset, 469 molecules were selected for confirmatory screening. This number was further reduced to 75 verified compounds that blocked increases in mCherry signal (FIG. 27B). Additional vetting led to the selection of Regulator of Cartilage Growth and Differentiation (RCGD) 423 as the primary compound for continued characterization. The ability of RCGD 423 to inhibit COL10 expression in human cells was confirmed, and AP activity was employed as a supplemental readout of chondrocyte differentiation. Upon treatment with RCGD 423, AP levels were significantly reduced in fetal cartilage treated with BMP-4, validating that the Col10a1-mCherry screen had successfully identified a small molecule that inhibited chondrocyte differentiation.

RCGD 423 Stimulates Fetal-Like Functional Properties in Adult Chondrocytes.

Figure 28A:
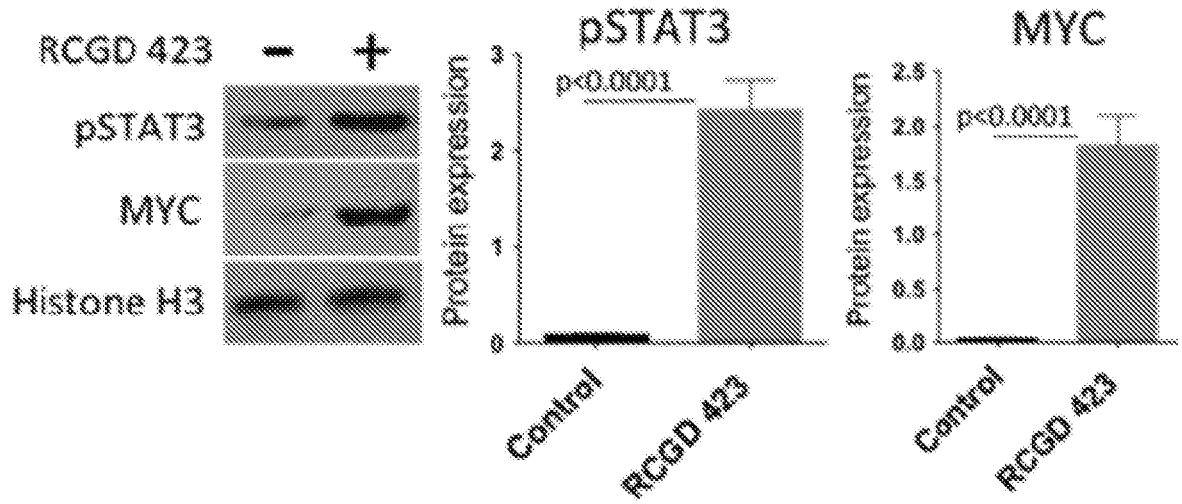
Figures 28G, 28H:
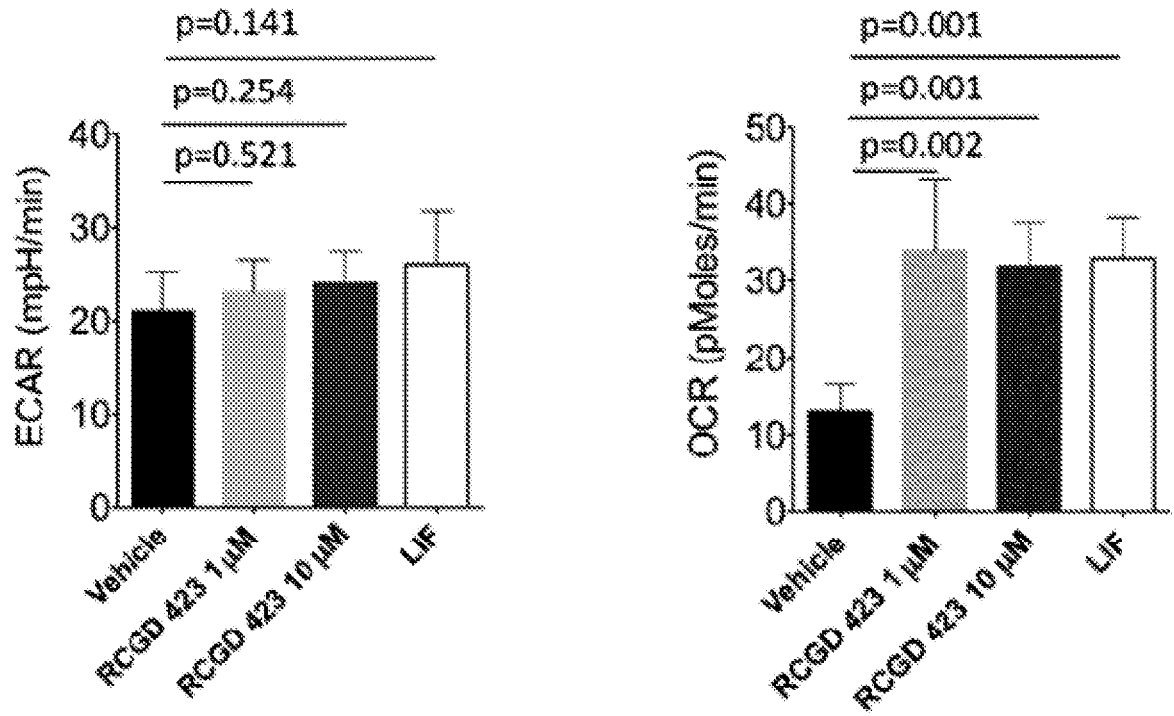
Figure 28I:
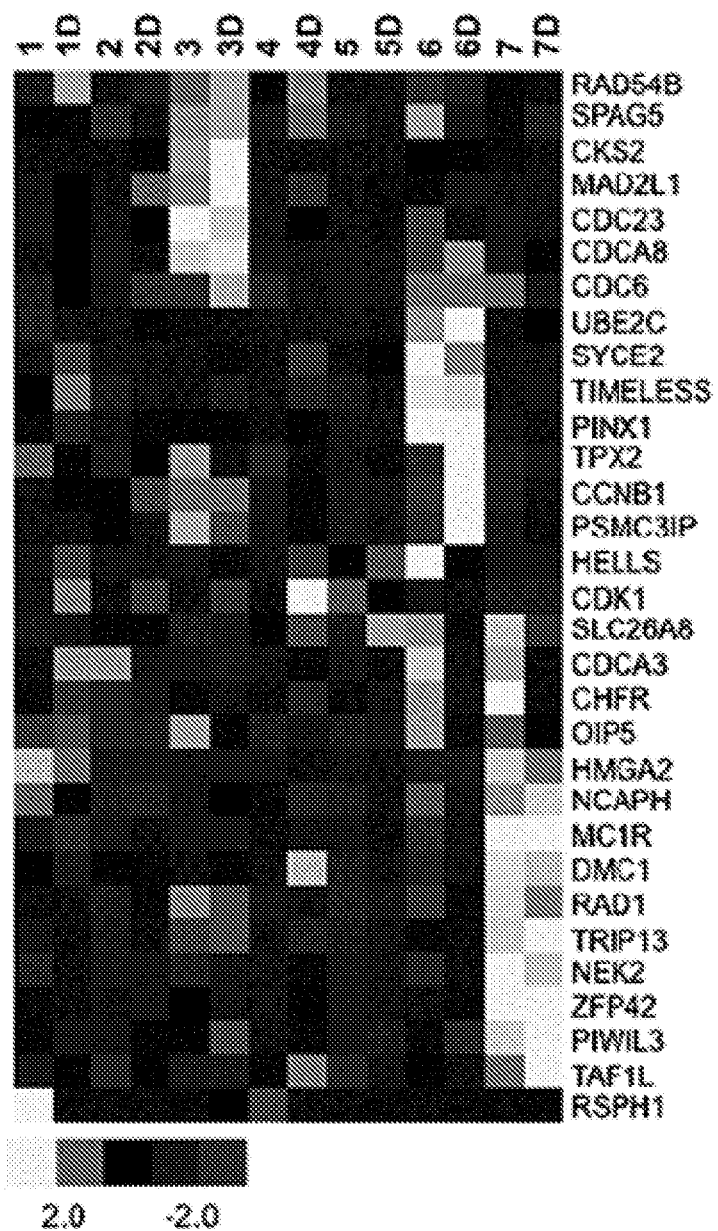
Figure 35:
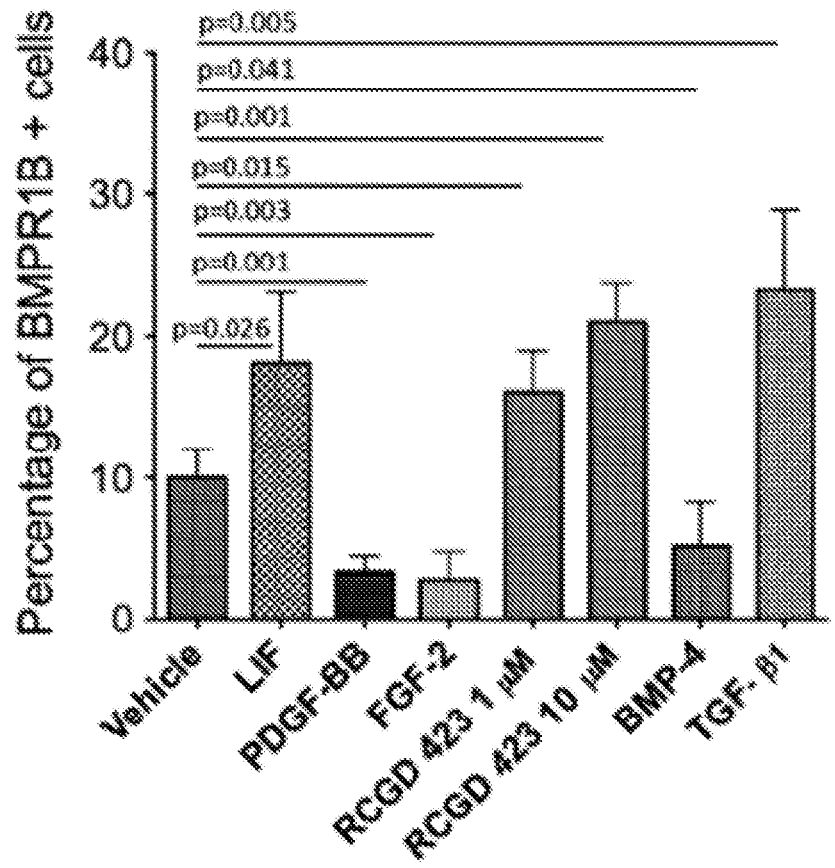
FIG. 35. RCGD 423 Preserves BMPR1B+ Chondrocytes in Culture. Adult pig chondrocytes were cultured in the presence of various cytokines or RCGD 423 and the number of cells expressing BMPR1B were quantitated using flow cytometry. Know mitogens for cartilage, including PDGF-BB and FGF2, promoted dramatic loss of BMPR1B$^+$ cells. In contrast, RCGD 423 and LIF acted to maintain cells with the BMPR1B+ phenotype.
Figure 36:
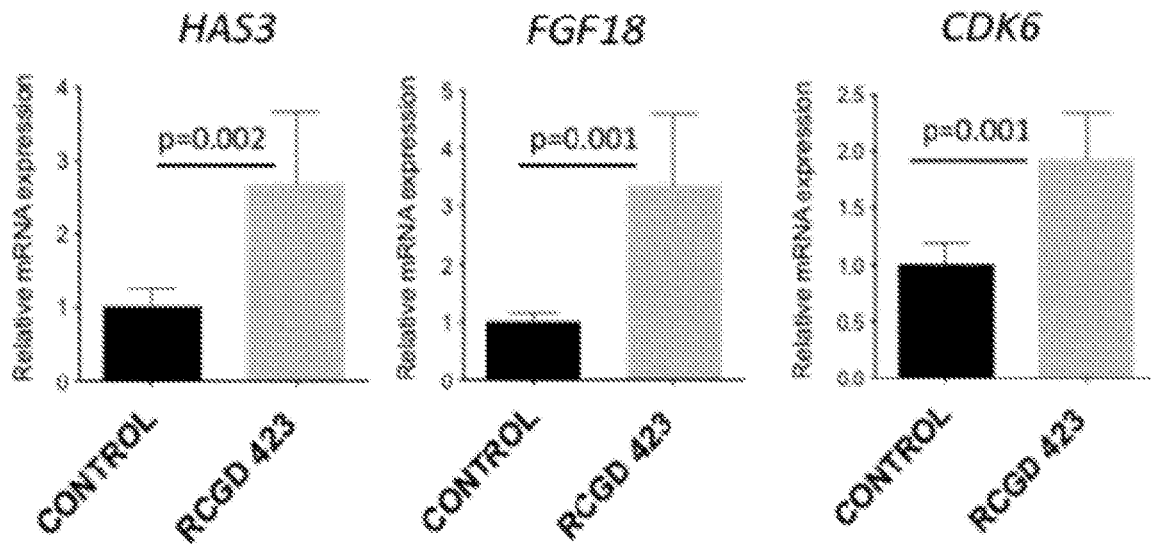
FIG. 36. PCR Validation of Selected Genes Following Treatment with RCGD 423. RNA was isolated from adult human chondrocytes after treatment with RCGD 423. Genes were chosen for validation based on their upregulation in 4 or more adult human cartilage specimens.

Due to its anti-differentiation properties, we hypothesized that RCGD 423 might stimulate the reacquisition of a more primitive phenotype in adult chondrocytes. We first stimulated adult human articular cartilage and quantitated the levels of pSTAT3 and MYC, proteins we have shown to drive proliferation, survival and migration. RCGD 423 robustly increased levels of both proteins in both a dose- and time-dependent manner (FIGS. 28A-28B) and helped maintain BMPR1B+ cells in culture (FIG. 35). Functionally, these increases in pSTAT3 and MYC translated into increased migratory potential (FIG. 28C) as well as decreased apoptosis coupled with increased proliferation (FIGS. 28D-28F). Moreover, treatment with RCGD 423 increased cellular respiration; levels of glycolysis were unchanged (FIG. 28G). We next evaluated the effects of RCGD 423 at the transcriptional level on human adult articular chondrocytes (n=7). As expected, the variability between these samples was high, so we focused our analysis on genes that increased more than 1.5-fold in 4/7 replicates. GO analysis of these 1,244 enriched transcripts revealed categories related to cell cycle, secretion and migration (FIG. 28H); we confirmed upregulation of three of these genes by qPCR (FIG. 36). Based on our data in fetal cells, we hypothesized that RCGD 423 may promote proliferation by acting through MYC. To address this hypothesis, we focused on the 31 genes in the M phase GO category enriched in drug treated cells. Comparison of these 31 genes with MYC targets defined by ChIP-Seq (Zeller et al., 2003) defined a statistically significant overlap (p=0.0062; hypergeometric test), indicating that increased MYC levels mediated by RCGD 432 treatment likely drive cell cycle progression. Together, these data demonstrate that the novel small molecule RCGD 423 stimulates increases in adult chondrocyte proliferation, survival, metabolism and motility, and suggest that these effects may in part result from increased MYC levels.

RCGD 423 and LIF Act Through Similar Molecular Pathways.

Figure 29B:
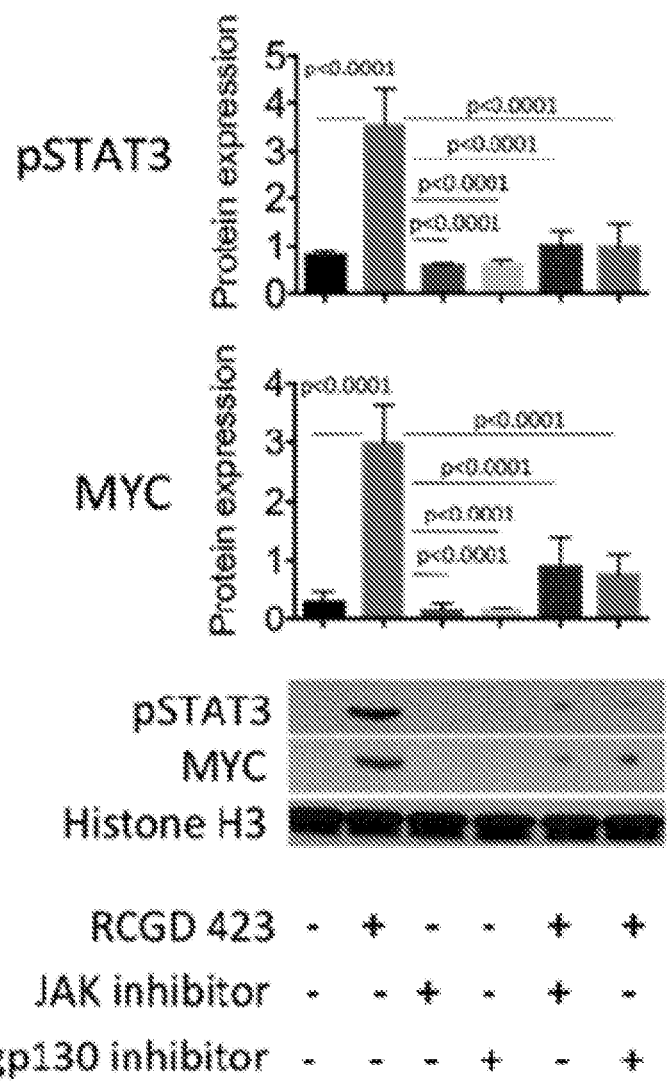

Given the concordance in molecular and functional effects upon stimulation of adult chondrocytes with LIF and RCGD 423, we hypothesized that the latter may act as an agonist within the LIF signaling cascade. To evaluate this, we incubated adult pig articular chondrocytes with inhibitors of various proteins in the LIF pathway in the presence of either LIF or RCGD 423 (FIGS. 29A-29B) and measured levels of pSTAT3 and MYC. Interestingly, inhibitors of both JAK and gp130 greatly reduced the ability of both LIF and RCGD 423 to induce increases in pSTAT3 and MYC. As JAK phosphorylation is required for recruitment and activation of STAT3, these results demonstrated that RCGD 423 acts upstream of JAK. Furthermore, as inhibition of gp130 also prevented increases in pSTAT3 and MYC levels, this strongly suggested that RCGD 423 may directly interact with gp130 to induce signaling in the absence of ligand. To investigate this possibility, we modeled the binding of RCGD 423 to gp130 using the Swissdock and Gold programs. These in silico experiments revealed two potential high affinity binding sites contained within the gp130 extracellular region. One of these sites is within the ligand binding domain of gp130 and closely juxtaposed to where LIF contacts the protein (Boulanger et al., 2003). Moreover, deletion of 4 of the proposed residues interacting with the drug (positions corresponding to positions 173, 174, 175 and 176 in gp130 or residues lysine, alanine, arginine and lysine at positions corresponding to positions 173, 174, 175 and 176, respectively in gp130) has been shown to occur in hepatocellular tumors, and overexpression of this gp130 mutant produced profound changes in gene expression indicative of constitutive gp130/STAT3 signaling (Rebouissou et al., 2009). The other potential site is proximal to the plasma membrane and is comprised of a hydrophobic pocket. Overall these results indicate that RCDG 423 orchestrates gp130/STAT3/MYC signaling in a similar manner to the biological ligand LIF.

Stimulation of Adult Articular Chondrocytes with RCGD 423 does not Result in Matrix Degradation.

Figure 30B:
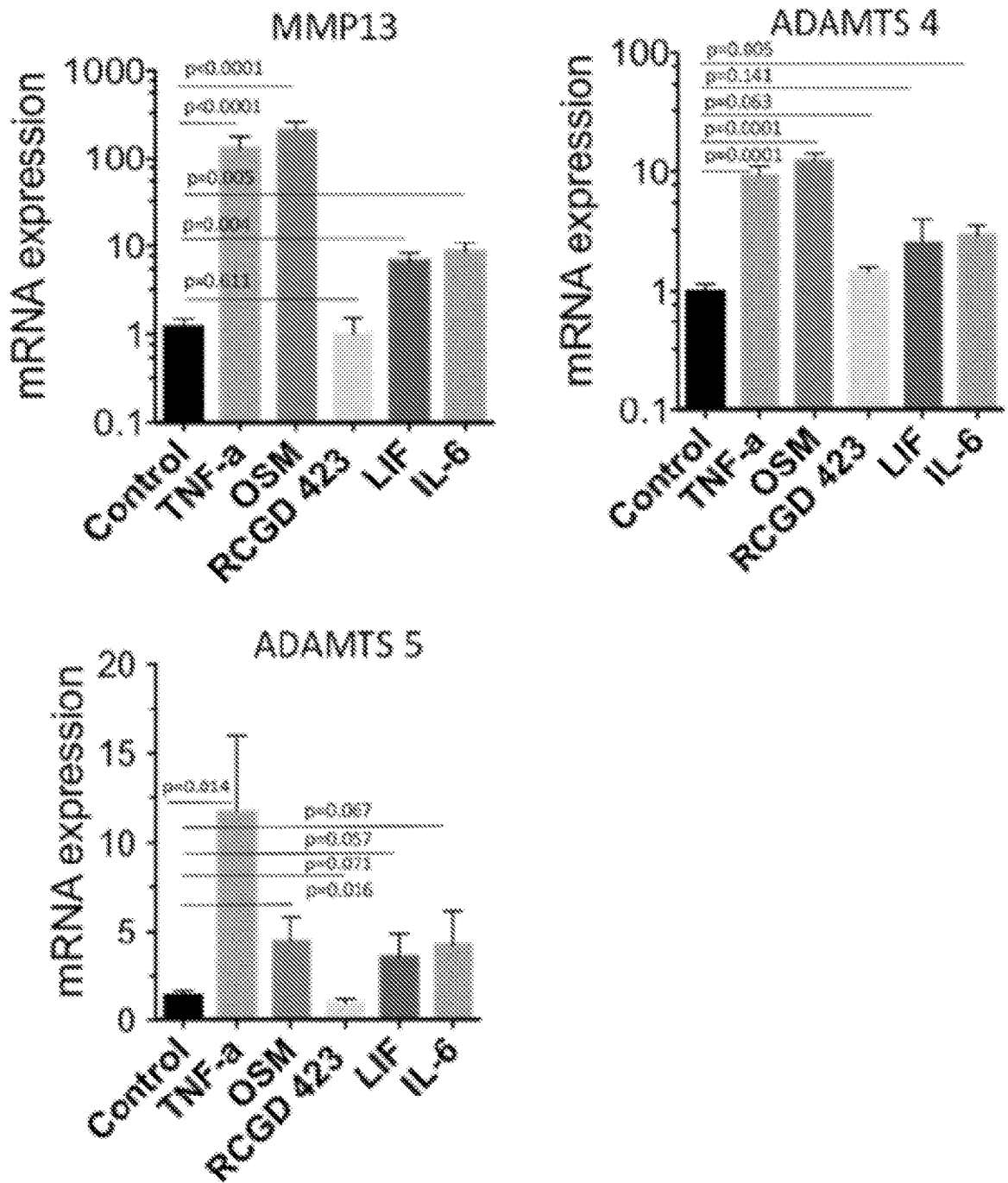
Figure 37:
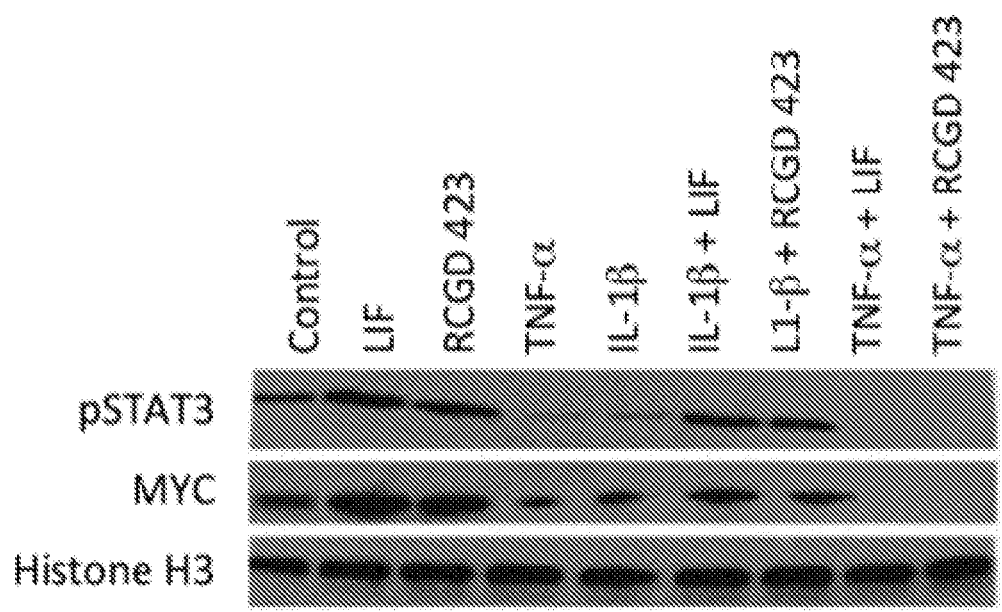
FIG. 37. Exposure to TNF-α Abrogates the Effects of RCGD 423. Adult pig chondrocytes were cultured in the presence of various cytokines and/or RCGD 423. Although both the inflammatory cytokines TNF-α and IL-1a inhibit accumulation of pSTAT3 and MYC proteins, only TNF-α prevents the increases in these proteins in the presence of RCGD 423, suggesting that TNF-α represents a major barrier to improved functional properties in cartilage.

Cartilage degeneration is generally considered a feed-forward process, in which small losses of chondrocytes result in microenvironmental changes including induction of an inflammatory response and other pro-catabolic events (Hunziker, 2002). In turn, these alterations in the joint milieu promote production of matrix degrading proteins including MMPs (collagenases) and proteins of the ADAMTS family (aggrecanases). LIF has been implicated in promoting this cycle of matrix destruction during the pathogenesis of osteoarthritis (Hui et al., 2000; Lotz et al., 1992), although its role in this process has been controversial. In order to better understand the mechanism of action of LIF, RCGD 423 and known pro-inflammatory cytokines in the promotion of degeneration, we stimulated adult pig articular chondrocytes with these molecules and quantitated the levels of activated downstream proteins that mediate the cellular signaling response (FIG. 30A). Furthermore, to coordinate these data with matrix degradation, we assessed the induction of MMP13, ADAMTS4 and ADAMTS5 at the transcriptional level (FIG. 30B). TNF-α, a classic pro-inflammatory cytokine, resulted in strong activation of the MAPK and AKT signaling pathways, culminating in increased NF-κB protein and upregulation of all degradative enzymes. Within the IL-6 family cytokines, OSM acted in a similar fashion to TNF-α, inducing a strong pro-inflammatory response. Interestingly, both LIF and IL-6 stimulated the activation of the MAPK and AKT pathways, although LIF elicited a weaker response in the MAPK pathway. Despite this activation, neither cytokine resulted in substantial transcriptional upregulation of matrix proteases. In parallel with this pro-inflammatory signaling, both cytokines also generated increased levels of pSTAT3 and MYC, suggesting that IL-6 may also be capable of promoting chondrocyte proliferation. RCGD 423 had a unique molecular signaling profile. Akin to LIF, stimulation with RCGD 423 drove strong increases in pSTAT3 and MYC, while concurrently weakly activating the MAPK pathway. Of note, RCGD 423 did not activate AKT or stabilize its downstream effector NF-κB; concordantly, no upregulation of MMP13, ADAMTS4 and ADAMTS5 occurred. However, it should be noted that co-stimulation with TNF-α and RCGD 423 completely suppressed increases in pSTAT3 and MYC (FIG. 37). Together, these data demonstrate that not all members of the IL-6 family elicit similar molecular responses in articular chondrocytes and also demonstrate a potentially critical difference between pro-inflammatory signaling downstream of LIF and RCDG 423.

RCGD 423 Promotes Articular Cartilage Growth and Regeneration.

Figure 31A:
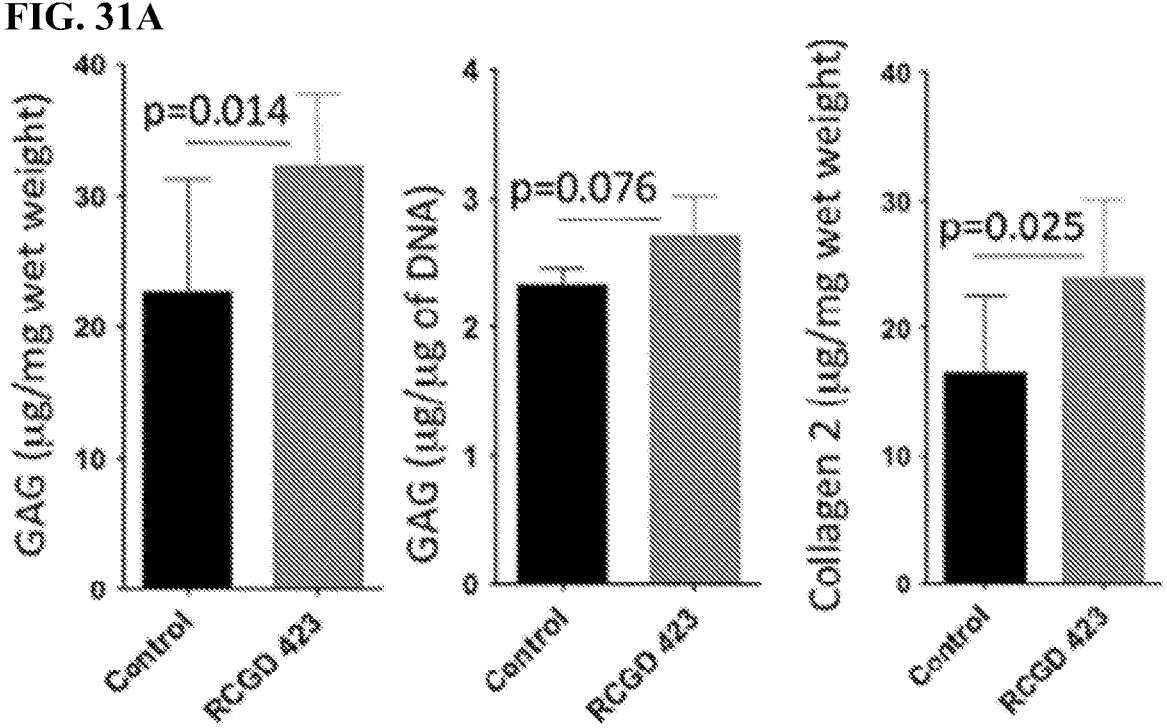
FIGS. 31A-31D. RCGD 423 promotes cartilage repair in a living tissue context.

Mature articular cartilage is comprised of chondrocytes contained within lacunae surrounded by dense extracellular matrix. In order for a regenerative response to occur, proliferation, survival and migration must all proceed in concert. We hypothesized that as RCDG 423 demonstrated the ability to induce all of these properties under specified conditions, it could likely function as regenerative agent in the context of a tissue. We designed two sets of experiments to assess the ability of RCGD 423 to operate in this capacity. First, RCGD 423 or cytokines implicated in the growth and differentiation of articular cartilage were incubated with small plugs of cartilage tissue; after 5 weeks, the amount of COL2 and glycosaminoglycans (GAGs) were determined. As expected, RCGD 423 induced a strong expansion of cartilage tissue at the apical surface, which was coupled with increases in COL2 and GAGs (FIG. 31A). In contrast, other cytokines had little to no effect, although LIF consistently generated small expansions at the apical surface.

Figure 31B:
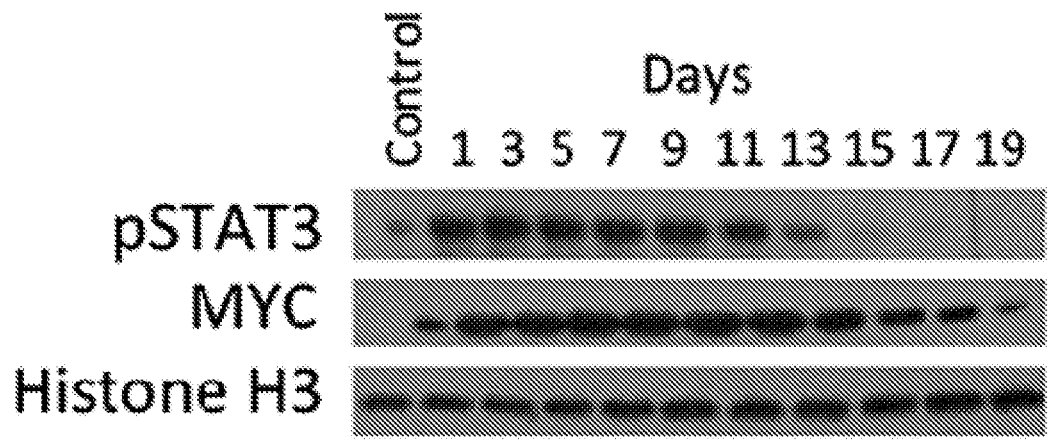
Figure 31C:
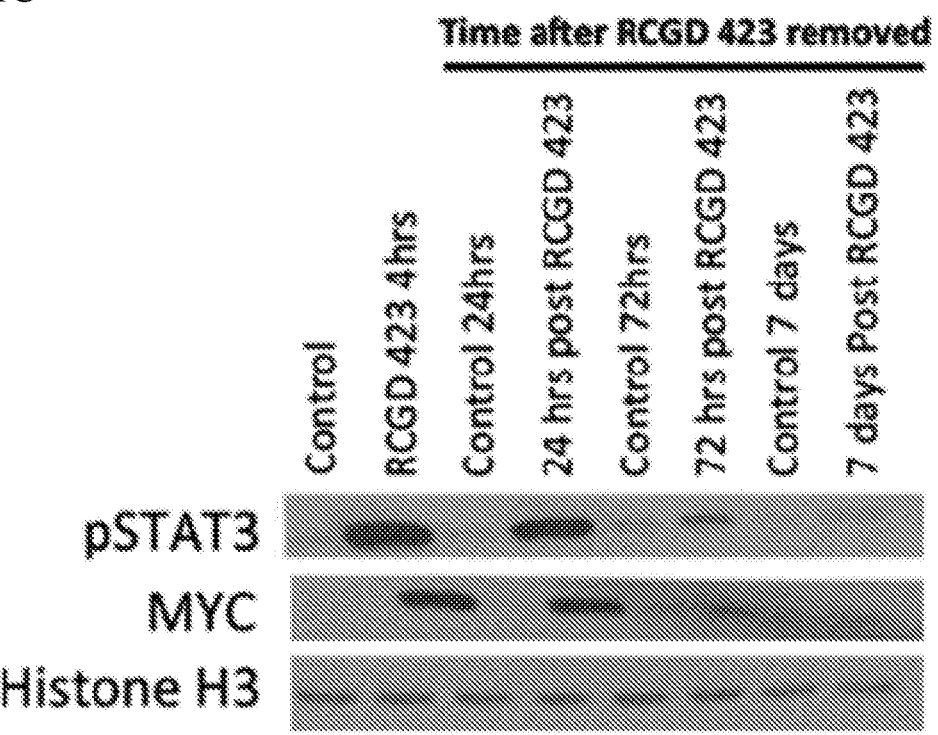
Figure 31D:
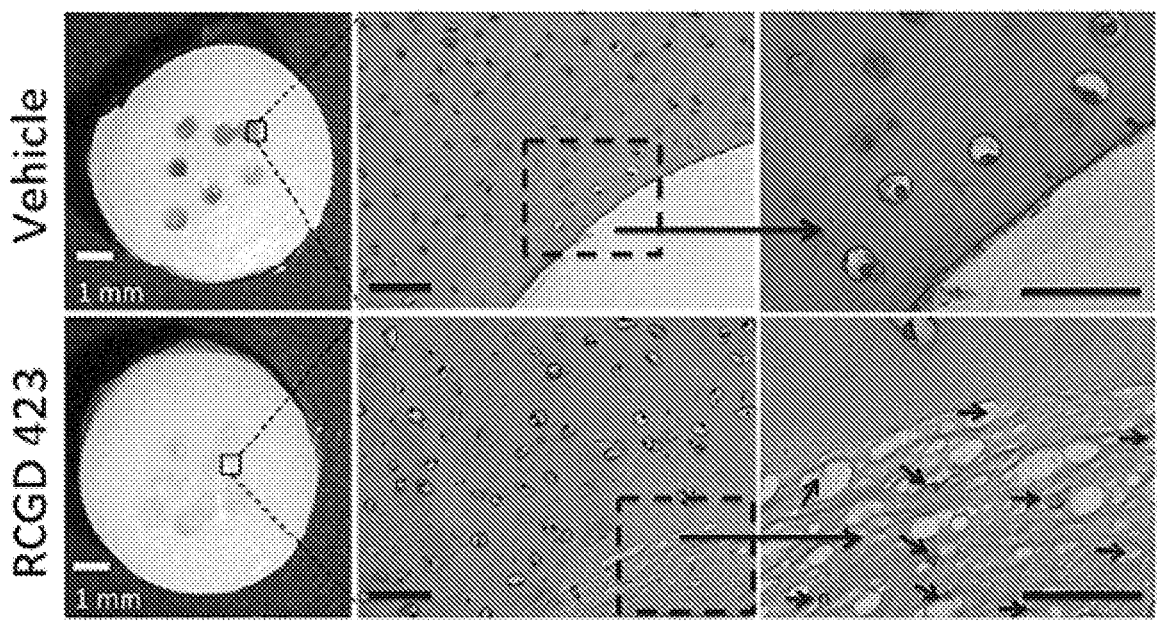

We also tested whether RCGD 423 could initiate healing of small defects generated on the surface of intact articular cartilage. For these experiments, we developed a method to achieve sustained release of RCDG 423 in situ, similar to what would likely be applicable in a clinical situation. As a delivery vehicle, we employed FDA-approved poly(lactic-co-glycolic) acid (PLGA) microspheres loaded with RCGD 423. Initial results demonstrated that drug off-loading from the spheres was sufficient to induce increases in pSTAT3 for 2 weeks and higher MYC levels for 3 weeks (FIG. 31B), while increases in both proteins after drug removal could be observed up to 7 days later (FIG. 31C). Together, these data indicated that a single application of PLGA microspheres loaded with RCGD 423 would induced higher levels of pSTAT3 and MYC for 4-5 weeks. We then applied this delivery system to pig articular cartilage biopsy punches with complete defects in vitro. Defects were filled with Matrigel containing either drug-loaded or unmodified PLGA microspheres and explants were harvested after 5 weeks. At the macroscopic level, defects that contained RCGD 423-loaded microspheres underwent substantial remodeling (FIG. 31D); this was even more evident on sections. These data revealed many chondrocytes that had migrated out of their lacuna and colonized the defect; new extracellular matrix was also present in the area that had formerly comprised the defect. In contrast, control explants evidenced sharp edges between intact tissue and the defect, reflecting the poor intrinsic regenerative capacity of unstimulated cartilage. Collectively, these results demonstrate that RCGD 423 can act as a regenerative agent in the context of articular cartilage tissue and nominate PLGA microspheres as a potential delivery vehicle in future clinical applications.

DISCUSSION

The data presented here unveil LIF/STAT3/MYC signaling as an important regulator of articular chondrocyte biology in humans and define a small molecule partial agonist of this pathway, RCGD 423, as a therapeutic tool for cartilage regeneration. To the best of our knowledge RCGD 423 is the first small molecule agonist of STAT3/MYC signaling reported to date. Molecular and functional analysis of the effects of the drug revealed a mechanism of action very similar to LIF, with the notable exception of a lack of activation of the AKT/NF-κB pathway. We also show that RCGD 423 can stimulate repair of damaged articular cartilage within the context of intact tissue, promoting chondrocyte migration and deposition of new matrix. Collectively, these results define the function of the LIF/STAT3/MYC signaling in human articular chondrocytes and identify a novel therapeutic strategy to achieve cartilage regeneration.

Fetal and adult articular chondrocytes evidence disparate basal levels of metabolism, matrix deposition, proliferation and migration; we show at the transcriptional and protein levels that these properties are enhanced in fetal cells due to high activity of the LIF/STAT3/MYC signaling axis. Although this pathway remains mostly inactive in adult cartilage, it can be activated via the addition of LIF, promoting adult chondrocytes to adopt a fetal-like functional profile. High throughput screening for regulators of chondrocyte differentiation status identified RCGD 423 as a potent agent that promotes the retention of a primitive phenotype; secondary analyses demonstrated that RCDG 423 promotes increased proliferation of articular chondrocytes in their native 3D microenvironment and stimulates cellular respiration, survival and migration in these cells without loss of cartilage commitment marked by the expression of SOX9, COL2A1 and other chondrogenic genes. Importantly, RCGD 423 induces all of these changes without activation of catabolic enzymes including aggrecanases (ADAMTS4/5) and collagenases (MMP13). Several growth factors including FGFs and PDGFs have been shown to induce a proliferative response of adult articular chondrocytes. However, the side effect of this stimulation is excessive catabolic response and chondrocyte de-differentiation to fibroblast-like cells unable to sustain cartilage architecture and functional properties. Our study clearly shows a unique mode of action for RCGD 423, strikingly different from growth factors (FGF-2, PDGF-BB) or morphogens (TGF-β1, BMP-4, GDF5) previously studied in the context of articular cartilage regeneration and/or repair.

LIF and other members of the IL-6 cytokine family have been shown to mediate proliferation and regeneration in a variety of cellular contexts. IL-6 and OSM have both been shown to be important components of the regenerative response in the liver (Cressman et al., 1996; Nakamura et al., 2004), acting upstream of Stat3 to promote proliferation (Li et al., 2002). In mouse embryonic stem cells (mESCs), LIF is sufficient to maintain mESCs in an undifferentiated state in the absence of feeders by activating Stat3 (Niwa et al., 1998; Smith et al., 1988). Moreover, forced homodimerization of gp130 in the absence of LIF can also maintain mESCs in a pluripotent state, suggesting that signaling downstream of gp130 is all that is required for self-renewal (Yoshida et al., 1994). Subsequent work showed that activation of Akt, likely downstream of gp130, is sufficient for mESC self-renewal (Watanabe et al., 2006). LIF is a potent stimulator of MYC in various tissues and here we show marked activation of MYC by LIF in adult articular chondrocytes. Previous studies have shown that MYC, unlike other factors, is alone sufficient to reactivate gene cluster prominent in embryonic stem cells in adult terminally differentiated cells (Wong et al., 2008). As we demonstrate here, levels of MYC are high in rapidly growing fetal tissues; temporary and controlled upregulation of the stem cell-like program by MYC-inducing agents may be beneficial for tissue regeneration and repair, specifically in tissues that lack resident stem cells. However, prolonged upregulation of MYC signaling increases risk of oncogenic transformation, uncontrolled proliferation and eventually cancer.

It is tempting to speculate that LIF could promote proliferation and cell survival in chondrocytes via a mechanism similar to ES cells, as stimulation with LIF elicits strong activation of AKT (FIG. 30A). However, this would clearly not be the case for the response driven by RCGD 423, as no activation of AKT was observed. This difference would suggest that induction of pSTAT3 and MYC are primarily responsible for the proliferative response induced by both LIF and RCGD 423, which is in agreement with our other data. Furthermore, our data suggest that RCGD 423 may bind directly to gp130; how this interaction drives signaling through gp130, via a potential conformational change or dimerization event, remains to be elucidated. Notably, deletion of 4 amino acids that may interact with the drug based on our modeling have been linked with hyperactivity of STAT3 in hepatocellular adenoma (Rebouissou et al., 2009). In other tumors analyzed, deletion of nearby residues promoted homodimerization of gp130 in the absence of ligand; whether RCGD 423 acts to promote a similar molecular result in a reversible fashion will be the subject of additional experiments and could explain the subtle differences in signaling between LIF and RCGD 423.

The function of IL-6 family members in cartilage biology and pathogenesis has been the focus of much study (reviewed in (Kapoor et al., 2011). Both IL-6 and oncostatin M have been implicated as mediators of disease progression in rheumatoid arthritis (Guerne et al., 1989) (Fearon et al., 2006; Manicourt et al., 2000; Nietfeld et al., 1990), with mechanisms of action including promoting proteoglycan degradation and GAG cleavage and recruiting inflammatory cells. Anti-IL-6 receptor therapy has been approved by the FDA in cases of moderate to severe rheumatoid arthritis. Additionally, IL-6 and OSM have also been shown to promote osteoarthritis (Beekhuizen et al., 2013; Ryu et al., 2011; Stannus et al., 2010), either through acting as pro-inflammatory cytokines or directly regulating matrix destruction. LIF has also been shown to promote proteoglycan resorption in vitro (Hui et al., 2000). Consequently, all members of the IL-6 family are often considered to be detrimental to chondrocyte biology and pathogenic. Our data show that individual cytokines activate the MAPK and AKT to different extents and result in varied transcriptional responses in catabolic genes (FIGS. 6A-6B). Moreover, OSM does not elicit any upregulation of pSTAT3 or MYC, while IL-6 and LIF both increase levels of these proteins. This is particularly interesting as OSM and LIF can signal through the same heterodimeric receptor complex (LIFR/gp130). These data suggest that there is great diversity in response to IL-6 family members in chondrocytes and that individual cytokines (e.g. IL-6 and LIF) can have both positive (induction of proliferation) and negative (increase in catabolic gene expression) effects. RCGD 423 represents an interesting new facet of this story, as it uncouples some of the effects downstream of gp130 signaling, such as AKT/NF-κB activation from STAT3/MYC activation. Further study of the molecular output of RCGD 423 stimulation in a hostile environment, i.e. arthritic and/or inflamed cartilage, is warranted and underway.

We have shown that RCGD 423 functions as a partial LIF agonist, mimicking many of the same responses driven by LIF in articular cartilage. LIF has functions in many tissues and systems, including neural stem cell self-renewal (Shimazaki et al., 2001; Wright et al., 2003), maintenance of kidney progenitor cells (Tanigawa et al., 2015), mESC self-renewal (Smith et al., 1988), establishment of naïve pluripotency in human ESCs (Chen et al., 2015) and cardiac regeneration (Zou et al., 2003). Whether RCGD 423 could substitute for LIF in these systems, or perhaps yield a superior molecular signaling profile as we determined in chondrocytes, represents an intriguing set of questions with potentially major clinical applications in stem cell biology and regenerative medicine.

Experimental

Chondrocyte Preparation.

Adult articular chondrocytes were derived from normal cartilage specimens provided by National Disease Research Interchange (NDRI). Fetal articular cartilage was obtained following elective terminations. All human specimens were obtained without any personal identifying information following informed consent. Pig chondrocytes were obtained from articular cartilage of healthy 5-6 month old Yucatan minipigs. Please see Supplemental Experimental Procedures for detailed descriptions of chondrocyte isolation, treatment and analysis.

RNA-Sequencing and Analysis.

RNA libraries were prepared and sequenced by the UCLA Clinical Microarray Core; please see Supplemental Experimental Procedures for details concerning RNA isolation, sequencing and data analysis.

High Throughput Small Molecule Screen.

Total limb cells were isolated from mouse embryos dissected at E13.5 carrying the Col10a1-mCherry transgene (JAX stock number 017465), plated at 2,000 cells per well and cultured for 14 days. Please see Supplemental Experimental Procedures for a detailed description of the screen.

Statistical Analysis.

Descriptive statistics were performed for each data set and the data combined for collective analysis. Data was converted to graphs and statistical analysis was performed with Prizm 6 from GraphPad Software (La Jolla, Calif.). Descriptive statistics, Student T test without or with correction for multiple comparisons using Holm-Sidak method or one-way ANOVA were applied followed by Dunnett or Student-Newman-Keul's test. $p<0.05$ was considered to be significant.

Cell Culture and Treatments.

Only early passages of chondrocytes (passage 0-2) were used for experimentation to avoid de-differentiation and loss of cartilage phenotype (Wu et al., 2014). Cartilage explants were made using 1, 2 or 8 mm biopsy punch and wet weight of each explant determined prior to experimentation. For cell isolation cartilage tissue was digested as described previously (Wu et al., 2015). Postnatal paraffin embedded joint and growth plate specimens were kindly donated by Dr Marcel Karperien from the University of Twente (Netherlands) and Dr Nick Bernthal from University of California Los Angeles. All donated material was anonymous and carried no personal identifiers. Cell culture reagents were purchased from Life Technologies, Inc. (Grand Island, N.Y.). Growth factors LIF, OSM, IL-6, TNF-α, IL-1β were purchased from Life Technologies, Inc (Grand Island, N.Y.). STATTIC, 10058-F4, SC144 hydrochloride, and CP-690550 were purchased from Sigma Aldrich (St. Louis, Mo.). RCGD 423 (N-(4-Bromophenyl)-4-phenyl-1,3-thiazol-2-amine) was synthesized and provided by MolPort (Riga, Latvia). Fetal, adult and pig chondrocytes were cultured in DMEM F12 medium containing 10% (vol/vol) fetal bovine serum and 1% Penicillin-Streptomycin (vol/vol) at 37° C. in a humidified atmosphere of 95% aid and 5% CO2. Media was replenished with DMEM F12 medium containing 1% (vol/vol) fetal bovine serum and 1% Penicillin-Streptomycin (vol/vol) once treatments were added. For 3-dimensional (3D) cell cultures adult human articular chondrocytes were incubated with or without RCGD 423 using 10% solution of Mebiol® hydrogel from Cosmo Bio (Carlsbad, Calif.) in X-vivo 15 serum free medium from Lonza (Walkersville, Md.) as described previously (Wu et al., 2014).

High Throughput Small Molecule Screen.

Total limb cells were isolated from mouse embryos dissected at E13.5 carrying the Col10a1-mCherry transgene. Mice were purchased from JAX (stock number 017465). 2,000 cells per well were deposited in culture media (phenol red-free DMEM/F12, with 1% FBS, 1% Anti-Anti antibiotic, and BMP-4 at 10 ng/mL) per well using a ThermoLabs Multidrop 384 dispenser; each well contained a unique compound, except for first and last two columns of the plate which were used for negative control. The plates were then covered with plastic lids and stored in an incubator at 37° C. for 14 days. Before imaging, Hoechst was added as a nuclear stain and then a Molecular Devices Imagexpress plate reader was used to quantitate mCherry and Hoechst signal. Magnification used was 10×, and each well was imaged in quadrants, totaling 4 images spanning the entire well. Imagexpress software was used to analyze the images and quantify fluorescent signal. A total of 170,000 compounds were screened.

Analysis of Cellular Metabolism.

The mitochondrial assay cellular oxygen consumption and mitochondrial function was carried out to measure basal respiration using XF24 instrument (Seahorse Biosciences) according to manufacturer instructions. Tested cells (100,000 cells per well) we plated into 24-well test plates 48 hours prior to experimentation. Oxygen consumption rates and extracellular acidification rates were measured every 10 minutes for up to 60 minutes (Rate 1-6).

Antibody Staining and Flow Cytometry.

For flow cytometric cell sorting (FACS) analysis, cells were dissociated into a single cell suspension with Collagenase 2 (Worthington) and Tryple Select (Invitrogen) and then incubated with monoclonal antibodies against LIF receptor (LIFR) or BMP receptor 1B (BMPR1B), PE or APC conjugated (obtained from R&D Systems); PE-Cy7 conjugated CD34 antibody was purchased from BD Biosciences or BioLegend, San-Diego, Calif. Isotype control antibodies conjugated with PE, APC or PE-Cy7 were purchased from BD Biosciences. After incubation, cells were washed in PBS containing 1% bovine serum and analyzed using a BD FACSAria or LSRII cytometer (BD Bioscience). FACS files were exported and analyzed using FACSDiva software (BD Biosciences).

SDS-PAGE and Western Blots Analysis.

Treated and non-treated ells were lysed in RIPA Lysis and Extraction Buffer (Pierce, Rockford, Ill.) containing protease inhibitors (Pierce) followed by sonication with a 15-second pulse at a power output of 2 using the VirSonic 100 (SP Industries Company, Warminster, Pa.). Protein concentrations were determined by BCA protein assay (Pierce). Proteins were resolved with SDS-PAGE utilizing 4-15% Mini-PROTEAN TGX Precast Gels and transferred to Trans-Blot Turbo Transfer Packs with a 0.2-µm pore-size nitrocellulose membrane. The SDS-PAGE running buffer, 4-15% Mini-PROTEAN TGX Precast Gels, Trans-Blot Turbo Transfer Packs with a 0.2-µm pore-size nitrocellulose membrane were purchased from Biorad (Hercules, Calif.). Nitrocellulose membranes were blocked in 5% nonfat milk in 0.05% (v/v) Tween 20 (PBST) (Corning, Manassas, Va.). Membranes were then incubated with primary antibodies phospho-STAT3 (#9131), MYC (#5605), NF-κB p65 (#D14E12), pAKT (#9272) Histone 3 (#9715) from Cell Signaling, (Danvers, Mass.); MEK1/2 (ab70613) and p38 (ab795) from Abcam (Cambridge, Mass.) overnight. After washing in PBS containing 0.05% (v/v) Tween 20 (PBST), membranes were incubated with Goat anti-Rabbit IgG (H+L) Secondary Antibody (Thermo Scientific Rockford, Ill.). After washing, membranes were developed with the Clarity Western ECL Blotting Substrate (Hercules, Calif.).

Clonal Assays.

For clonal assays cartilage cells were sorted by FACS and deposited into 96-well culture plates at 1 cell/well in DMEM/F12 culture medium supplemented with 1% FCS with or without LIF or RCGD 423. After 4 weeks clones (colonies with 50 cells or more) were counted using light microscopy in at least 300 wells for each culture condition.

Determination of Apoptosis and Proliferation.

TdT-mediated dUTP nick-end labeling (TUNEL) or EdU assays were performed by using in situ cell death detection kit (TUNEL, Roche Diagnostics GmbH, Germany) or Click-iT® Assay Kit obtained from Invitrogen (Carlsbad, Calif.), respectively, as described in the manufacturer's protocol. For EdU assay, explants were treated with EdU 24 hours prior to fixation. After staining sections were analyzed using fluorescent microscopy. Apoptosis was evaluated by flow cytometry with a Fortessa (BD Biosciences, San Jose, Calif.) cytometer using the Annexin V-FITC (Miltenyi Biotec, San Diego, Calif.) antibody. For proliferation, a BrdU assay (BD Biosciences, San Jose, Calif.) was used according to the manufacturer's protocol.

Assessment of BMPR1B Protein Retention in Culture.

BMPR1B+LIFR+ human adult articular chondrocytes were sorted using FACS and deposited in 96-well culture plates at density 10,000 cells per well in DMEM/F12 culture medium (Invitrogen) supplemented with 1% FBS. Growth factors or RCGD 423 were added at the time of plating. After 1, 3 and 7 days cultures were re-analyzed with FACS using an antibody against BMPR1B.

RNA Isolation and qPCR.

Total RNA was extracted using RNeasy Micro Kit (QIAGEN, Valencia, Calif.) according to the manufacturer's protocol. Quantitative reverse transcription PCR was performed using Bio-Rad T100 Thermal Cycler (Bio-Rad, Hercules, Calif.). Primer sequences are available upon request.

RNA Sequencing and Data Analysis.

RNA libraries were prepared for sequencing by the UCLA Clinical Microarray Core using TruSeq kits (Illumina). Libraries were sequenced on a HiSeq 2000/2500 at 1×50 bp. Transcript levels were estimated using RNA-Seq by Expectation Maximization (RSEM; (Li and Dewey, 2011). Reads were mapped to the human genome (hg19) using RefSeq annotation. Pairwise differential expression assessments were performed using the method EBSeq (Leng et al., 2013); genes were considered to be differentially expressed based on a False Discovery Rate of less than 5% (Posterior Probability of being Differentially Expressed <0.05). Gene Ontology (GO) analysis was performed using DAVID. Gene Set Enrichment Analysis (GSEA) was performed using MSigDB. Ranked lists of genes having a fold change of greater than 1.5 were used as input for GSEA.

Migration Assay.

Cells were plated on Millicell 8 µm Transwell® inserts (Millipore, Billerica, Mass.) in 12-well plates (Fisher Scientific, Pittsburgh, Pa.) and stimulated with 10 µM of RCGD 423, 10 µM MYC inhibitor (10058-F4) or 10 µM STAT3 inhibitor (STATTIC) from Tocris Bioscience (Bristol, UK). Cells that migrated across the membranes were quantified by counting after 48 hours of treatment.

GAG and DNA Assay.

Cartilage explants were washed with PBS and then directly digested or stored at 20° C. For digestion, explants were transferred in digestion buffer composed of 1 mg/mL proteinase K in Tris/Ethylene diamine tetra-acetic acid (EDTA) buffer (pH 7.6) containing 18.5 µg/mL iodoacetamide and 1 µg/mL pepstatin A) for 16-72 h at 56° C. After complete digestion the GAG content was spectrophotometrically determined with 1,9-dimethylmethylene blue chloride staining in the phosphate buffer with ethylene diamine tetra-acetic acid buffer (14.2 g/L $Na_2HPO_4$ and 3.72 g/L Na2EDTA, pH 6.5) using an Infinite M1000 Pro microplate reader (Tecan) at an absorbance of 520 nm with chondroitin sulfate as a standard. Amount of total DNA in explants was determined by a CyQuant DNA Kit (Molecular Probes by Life Technology) using Qubit 1.0 fluorometer (Invitrogen).

Collagen II ELISA.

Cultured explants were first digested in testicular hyaluronidase (0.05% in 50 mM HEPES) for 2 hours at 37° C. 0.5M glacial acetic acid was added to digestion solution to maximize the collagen swelling and provide best pepsin access. Pepsin (250 µg/ml) was then used to further digest the pellets in combination with rotation and occasional gentle vortexing at 4° C. for 18-24 hours. Cold tris base and NaOH were added to the digestion solution to neutralize the acetic acid. Digestion solution was vigorously vortexed immediately, and subsequently rotated at 4° C. overnight to maximize collagen solubility. Tubes were centrifuged to separate undigested tissue and supernatant. Any undigested tissue was subjected to the digestion process again. All supernatants were combined for ELISA. Concentration of collagen II in the supernatant was measured by Type I/II Collagen Detection Kit (Chondrex, Inc, Redmond, Wash.), according to manufacturer's instruction and normalized either to DNA content or wet weight of the explants determined prior to experimentation.

Molecular Modeling.

The docking experiments between RCGD 423 and the extracellular domains of gp130 were performed on the Swiss Dock server (Grosdidier et al., 2011). The PDB structures 1I1R and 3L5I were used (Berman et al., 2000). The structure of RCGD 423 was optimized using PRODRG server (Schuttelkopf and van Aalten, 2004). All rotatable single bonds were allowed to rotate in the ligand and the docking results were screened and analyzed with the Chimera program (Pettersen et al., 2004).

Alkaline Phosphatase Assay.

Cells were fixed with 3.7% formaldehyde and stained for alkaline phosphatase activity with SigmaFast 5-bromo-4-chloro-3-indolyl phosphate/4-nitro blue tetrazolium (BCIP/NBT) (Sigma Aldrich, St. Louis, Mo.) according to the manufacturer's protocol.

Example 19. General Synthetic Procedure for RCGD 423 and Derivatives

General Procedure.

2-Bromo-1-phenylethan-1-one (1.0 equivalent, 0.5 mmol) and 1-(4-fluorophenyl)thiourea (1.0 equivalent, 0.5 mmol) were premixed in 5 mL of ethanol. The mixture was pumped through a preheated glass microfluidic reactor (Syrris Asia Flow Chemistry Module) at a predetermined flow rate to have the desired residence time using Syrris Asia pump. The outcome was collected in a flask and concentrated under reduced pressure. The crude was dissolved in 10 mL ethyl acetate washed with 2×10 mL satd. $NaHCO_3$. The organic phase was combined, dried $MgSO_4$ and concentrated under reduced pressure. The crude product obtained was purified using prepacked silica cartridge on Teledyne CombiFlash $R_f$ 200. Elution with 10:90 Hexaneethyl acetate afforded N-(4-fluorophenyl)-4-phenylthiazol-2-amine (MPA-1/RGCD 423F) in 98% yield. The same methodology was used to synthesize the other compounds disclosed herein.

Although the invention has been described with reference to the above examples, it will be understood that modifications and variations are encompassed within the spirit and scope of the invention. Accordingly, the invention is limited only by the following claims.

What is claimed is:
1. A compound selected from:
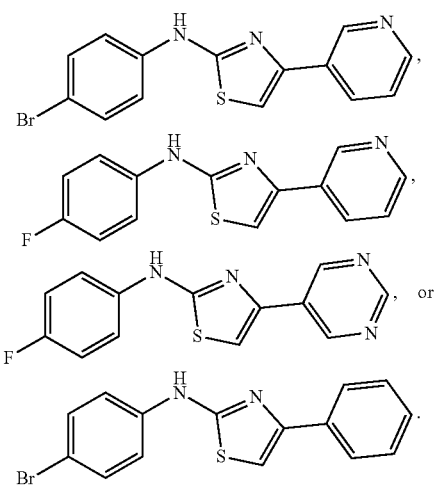
or
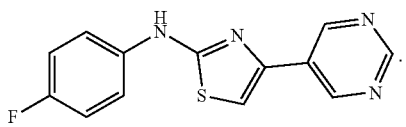 [SMILES: Fc1ccc(Nc2nc(-c3cncnc3)cs2)cc1]
2. The compound of claim 1, wherein the structure is:
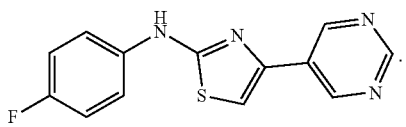 [SMILES: Fc1ccc(Nc2nc(-c3cncnc3)cs2)cc1]
3. The compound of claim 1, wherein the structure is:
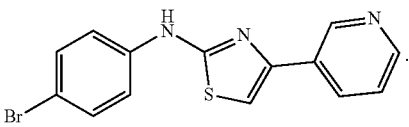 [SMILES: Brc1ccc(Nc2nc(-c3cccnc3)cs2)cc1]
4. The compound of claim 1, wherein the structure is:
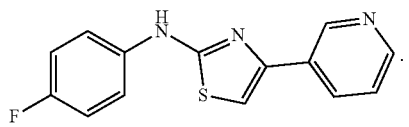
5. The compound of claim 1, wherein the structure is:
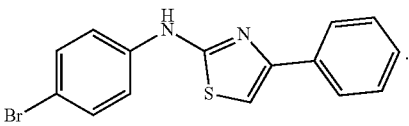 [SMILES: Brc1ccc(Nc2nc(-c3ccccc3)cs2)cc1]
* * * * *